United States Patent [19]
Yoshioka et al.

[11] Patent Number: 5,104,888
[45] Date of Patent: * Apr. 14, 1992

[54] THIAZOLIDINE DERIVATIVES, THEIR PREPARATION AND USE

[75] Inventors: Takao Yoshioka; Eiichi Kitazawa; Yomoyuki Kurumada; Mitsuo Yamazaki; Kazuo Hasegawa; Takashi Fujita, all of Hiromachi, Japan

[73] Assignee: Sankyo Company, Limited, Tokyo, Japan

[*] Notice: The portion of the term of this patent subsequent to Feb. 25, 2003 has been disclaimed.

[21] Appl. No.: 560,466

[22] Filed: Jul. 25, 1990

Related U.S. Application Data

[63] Continuation of Ser. No. 426,533, Oct. 24, 1989, which is a continuation of Ser. No. 311,445, Feb. 19, 1989, abandoned, which is a continuation of Ser. No. 233,984, Aug. 11, 1988, abandoned, which is a continuation of Ser. No. 833,867, Feb. 25, 1986, abandoned.

[30] Foreign Application Priority Data

Feb. 26, 1985 [JP] Japan .................................. 60-35324
Feb. 26, 1985 [JP] Japan .................................. 60-35325

[51] Int. Cl.$^5$ .................. C07D 417/12; A61K 31/425
[52] U.S. Cl. .................................... 514/369; 514/337; 548/183; 546/269
[58] Field of Search ............... 548/183; 514/369, 337; 546/269

[56] References Cited

U.S. PATENT DOCUMENTS 4,572,912 2/1986 Yoshioka .......................... 514/369

FOREIGN PATENT DOCUMENTS 8432559 3/1985 Australia ........................... 548/183
61-36284 2/1986 Japan ................................ 548/183

*Primary Examiner*—Robert Gerstl
*Attorney, Agent, or Firm*—Frishauf, Holtz, Goodman & Woodward

[57] ABSTRACT

Compounds of formula (I):

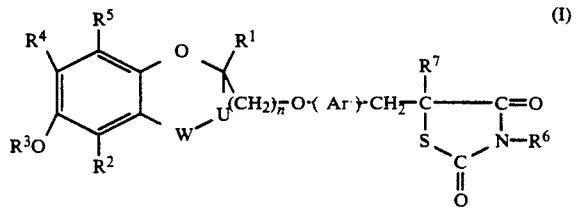

(in which $R^1$-$R^7$ are hydrogen or various organic groups, n is 1-10, Ar is an aromatic group, U is $CH_2$ or a carbon atom doubly bonded to either one of its adjacent carbons, and W is $>CH_2$, $>C=O$, $>CHOH$, $>C=NOH$ or various derivatives thereof) have the ability to lower the levels of blood lipid peroxides and blood sugars and to inhibit the activity of aldose reductase; they may be used therapeutically for these purposes.

37 Claims, No Drawings

THIAZOLIDINE DERIVATIVES, THEIR PREPARATION AND USE

This application is a Continuation, of application Ser. No. 07/426,533, filed Oct. 24, 1989 now abandoned, which is a continuation of Ser. No. 07/311,445 filed Feb. 15, 1989 (abandoned); which is a continuation of Ser. No. 07/233,984 filed Aug. 11, 1988 (abandoned); which is a continuation of Ser. No. 06/833,867 filed Feb. 25, 1986 (abandoned).

BACKGROUND TO THE INVENTION

The present invention relates to a series of novel thiazolidine derivatives containing, on a side chain attached to the 5-position, a chroman ring system. The invention also provides processes for preparing these compounds and compositions and methods for using them, especially for reducing blood lipid and blood sugar levels.

Certain thiazolidine derivatives having the ability to lower blood lipid and blood sugar levels are disclosed in European Patent Publication No. 8203 and in Chem. Pharm. Bull., 30, 3580 (1982). Certain of the thiazolidine derivatives disclosed in these documents have the ability to lower blood lipid and blood sugar levels, although these compounds are rather toxic.

In copending U.S. patent application Ser. No. 644,996, filed Aug. 28, 1984, the disclosure of which is incorporated herein by reference, there are also disclosed some related thiazolidine derivatives having a similar class of activities; some of these prior compounds may also be used as starting materials to prepare the compounds of the invention We have now discovered a series of thiazolidine derivatives which have the ability to improve the metabolism of blood lipids, that is to say they reduce the level of blood lipid peroxides, blood triglycerides, blood cholesterol and blood sugar, whilst having a very low toxicity. The compounds of the invention also have the ability to inhibit the activity of aldose reductase.

BRIEF SUMMARY OF INVENTION

The compounds of the present invention may be represented by the formula (I):

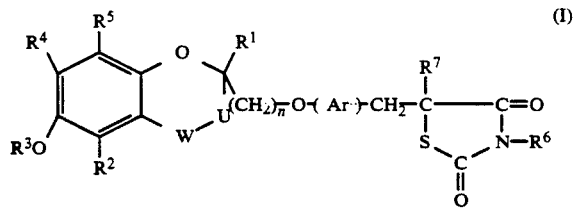

(I)

in which:

$R^1$ represents a hydrogen atom, a $C_1-C_{10}$ alkyl group or a $C_7-C_{13}$ aralkyl group;

$R^2$ represents a hydrogen atom or a $C_1-C_5$ alkyl group;

$R^3$ represents a hydrogen atom, a $C_1-C_{23}$ alkanoyl group, a $C_3-C_{23}$ alkenoyl group, a $C_3-C_{23}$ alkynoyl group, a substituted $C_1-C_{23}$ alkanoyl, $C_3-C_{23}$ alkenoyl or $C_3-C_{23}$ alkynoyl group having at least one substituent selected from the group consisting of substituents (a), an aromatic acyl group, a heterocyclic acyl group, a group of formula $-SO_3R^8$ where $R^8$ represents a hydrogen atom, an aralkyl group where the alkyl part is $C_1-C_3$ alkyl, a $C_1-C_5$ alkyl group or a $C_1-C_5$ alkyl group having at least one substituent selected from the group consisting of hydroxy groups and $C_1-C_5$ alkoxy groups, a $C_1-C_{10}$ alkyl group or a substituted $C_1-C_{10}$ alkyl group having at least one substituent selected from the group consisting of substituents (b);

$R^4$ represents a hydrogen atom, $C_1-C_{10}$ alkyl group or a $C_1-C_5$ alkoxy group;

$R^5$ represents a hydrogen atom, a $C_1-C_5$ alkyl group or a $C_1-C_5$ alkoxy group;

$R^6$ and $R^7$ are independently selected from the group consisting of hydrogen atoms, $C_1-C_{10}$ alkyl groups and substituted $C_1-C_{10}$ alkyl groups having at least one substituent selected from the group consisting of substituents (b);

Ar is a divalent group selected from the group consisting of divalent carbocyclic aromatic groups and divalent heterocyclic aromatic groups;

W represents a $-CH_2-$ group, a $>C=O$ group, a group of formula $>CH-OR^{11}$
wherein $R^{11}$ represents a hydrogen atom, a $C_1-C_{23}$ alkanoyl group, a $C_3-C_{23}$ alkenoyl group, a $C_3-C_{23}$ alkynoyl group, a substituted $C_1-C_{23}$ alkanoyl, $C_3-C_{23}$ alkenoyl or $C_3-C_{23}$ alkynoyl group having at least one substituent selected from the group consisting of substituents (a), an aromatic acyl group, a heterocyclic acyl group, a $C_1-C_{10}$ alkyl group or a substituted $C_1-C_{10}$ alkyl group having at least one substituent selected from the group consisting of substituents (b), or a group of formula $>C=N-O-R^{12}$
in which $R^{12}$ represents a hydrogen atom, a $C_1-C_{10}$ alkyl group, a $C_1-C_{10}$ alkyl group having at least one substituent selected from the group consisting of substituents (b), a $C_1-C_{23}$ alkanoyl group, a $C_3-C_{23}$ alkenoyl group, a $C_3-C_{23}$ alkynoyl group, a substituted $C_1-C_{23}$ alkanoyl, $C_3-C_{23}$ alkenoyl or $C_3-C_{23}$ alkynoyl group having at least one substituent selected from the group consisting of substituents (a), an aromatic acyl group or a heterocyclic acyl group;

U represents a $-CH_2-$ group; or

W and U together represent a group of formula $-CH=CH-$; or when W represents a carbonyl group or said group of formula $>C=N-OR^{12}$, U, $R^1$ and the carbon atom to which $R^1$ is attached together represent a group of formula $-CH=C<$;

n is an integer of from 1 to 3;

said aryl groups and the aryl parts of said aralkyl, aralkyloxycarbonyl, aromatic acyl, aromatic acyloxy and divalent aromatic groups being $C_6-C_{10}$ carbocyclic aryl groups which are unsubstituted or have at least one substituent selected from the group consisting of substituents (c);

said heterocyclic groups, heterocyclic parts of said heterocyclic acyl and acyloxy groups and said divalent heterocyclic aromatic groups have from 5 to 10 ring atoms, of which from 1 to 5 are hetero-atoms selected from the group consisting of nitrogen, oxygen and sulfur hetero-atoms, said heterocyclic groups being unsubstituted or having at least one substituent selected from the group consisting of substituents (d);

said substituents (a) being selected from the group consisting of aryl groups, carboxy groups, $C_2-C_6$ alkoxycarbonyl groups and aralkyloxycarbonyl groups;

said substituents (b) being selected from the group consisting of hydroxy groups, $C_1-C_5$ alkoxy groups, aryl groups, $C_1-C_{23}$ alkanoyloxy groups, $C_3-C_{23}$ alkenoyloxy groups, $C_3$-$C_{23}$ alkynoyloxy groups, substituted $C_1$-$C_{23}$ alkanoyloxy, $C_3$-$C_{23}$ alkenoyloxy or $C_3$-$C_{23}$ alkynoyloxy groups having at least one substituent selected from the group consisting of substituents (a), aromatic acyloxy groups, heterocyclic acyloxy groups, groups of formula —COOR$^8$ where R$^8$ is as defined above and groups of formula —CONR$^9$R$^{10}$ where R$^9$ and R$^{10}$ are independently selected from the group consisting of hydrogen atoms and $C_1$-$C_5$ alkyl groups or R$^9$ and R$^{10}$, together with the nitrogen atom to which they are attached, represent a heterocyclic group having from 5 to 7 ring atoms of which from 1 to 3 atoms, including said nitrogen atom, are heteroatoms selected from the group consisting of nitrogen, oxygen and sulfur hetero-atoms, said heterocyclic group being unsubstituted, or, where said ring atoms include an additional nitrogen hetero-atom, said additional nitrogen atom being unsubstituted or having a single substituent selected from the group consisting of substituents (e);

said substituents (c) being selected from the group consisting of $C_1$-$C_5$ alkyl groups, $C_1$-$C_5$ alkoxy groups, $C_1$-$C_5$ alkyl groups having at least one halogen substituent, halogen atoms, amino groups, $C_1$-$C_5$ alkylamino groups, dialkylamino groups in which each alkyl part is $C_1$-$C_5$, nitro groups, cyano groups, groups of formula —CONR$_2$ where R represents a $C_1$-$C_5$ alkyl group or an aryl group and hydroxy groups; and said substituents (d) being selected from the group consisting of $C_1$-$C_5$ alkyl groups, $C_1$-$C_5$ alkoxy groups and doubly bonded oxygen atoms;

said substituents (e) being selected from the group consisting of $C_1$-$C_5$ alkyl groups, $C_1$-$C_5$ alkanoyl groups, $C_3$-$C_5$ alkenoyl groups and $C_3$-$C_5$ alkynoyl groups; provided that:

($\alpha$) where: R$^3$ represents said hydrogen atom, an unsubstituted $C_1$-$C_6$ alkanoyl group, an unsubstituted $C_3$-$C_6$ alkenoyl group, an unsubstituted $C_3$-$C_6$ alkynoyl group, said aromatic acyl group, said heterocyclic acyl group, an aralkanoyl group or an aralkenoyl group; and R$^6$ and R$^7$ both represent hydrogen atoms; and Ar represents a p-phenylene group; and W represents a group of formula >CH$_2$, >C=O or >CH—OR$^{11x}$ (wherein R$^{11x}$ represents a hydrogen atom, an unsubstituted $C_1$-$C_6$ alkanoyl group, an unsubstituted $C_3$-$C_6$ alkenoyl group, an unsubstituted $C_3$-$C_6$ alkynoyl group, said aromatic acyl group, said heterocyclic acyl group, an aralkanoyl group or an aralkenoyl group); and U represents said group of formula >CH$_2$, then (i) when R$^1$ represents a hydrogen atom or a $C_1$-$C_5$ alkyl group, R$^4$ represents a $C_6$-$C_{10}$ alkyl group, and (ii) when R$^4$ represents a hydrogen atom, a $C_1$-$C_5$ alkyl group or a $C_1$-$C_5$ alkoxy group, R$^1$ represents a $C_6$-$C_{10}$ alkyl group or said $C_7$-$C_{13}$ aralkyl group; or ($\beta$) where: R$^1$ and R$^2$ are independently selected from the group consisting of hydrogen atoms and $C_1$-$C_5$ alkyl groups; and R$^4$ and R$^5$ are independently selected from the group consisting of hydrogen atoms, $C_1$-$C_5$ alkyl groups and $C_1$-$C_5$ alkoxy groups; and Ar represents a p-phenylene group; and W is a group of formula >CH$_2$, >C=O or >CH—OR$^{11x}$ (where R$^{11x}$ is as defined above); and U represents said group of formula >CH$_2$; and n is an integer from 1 to 3, then at least one of R$^3$, R$^6$ and R$^7$ represents said alkyl or substituted alkyl group;

and pharmaceutically acceptable salts thereof.

The invention also provides processes for preparing the compounds of the invention, as described in more detail hereafter.

The invention still further provides a pharmaceutical composition comprising a compound of formula (I) or a pharmaceutically acceptable salt thereof in admixture with a pharmaceutically acceptable carrier or diluent.

The invention still further provides a method of reducing blood lipid and blood sugar levels in an animal, especially a mammal, e.g. a human being, by administering to said animal an effective amount of a compound of formula (I) or a pharmaceutically acceptable salt thereof.

DETAILED DESCRIPTION OF INVENTION

In the compounds of the invention, where R$^1$, R$^3$, R$^6$, R$^7$, R$^{11}$ or R$^{12}$ represents a $C_1$-$C_{10}$ alkyl group, this may be a straight or branched chain group and examples include the methyl, ethyl, propyl, isopropyl, butyl, isobutyl, t-butyl, pentyl, isopentyl, neopentyl, 2-methylbutyl, 1-ethylpropyl, hexyl, isohexyl, neohexyl, 1-methylpentyl, 3-methylpentyl, 1,1-dimethylbutyl, 1,3-dimethylbutyl, 2-ethylbutyl, 1-methyl-1-ethylpropyl, heptyl, 1-methylhexyl, 1-propylbutyl, 4,4-dimethylpentyl, octyl, 1-methylheptyl, 2-ethylhexyl, 5,5-dimethylhexyl, nonyl, decyl, 1-methylnonyl, 3,7-dimethyloctyl and 7,7-dimethyloctyl groups.

Where R$^1$ or R$^8$ represents an aralkyl group, this may be substituted or unsubstituted and is a $C_7$-$C_{13}$ aralkyl group, for example substituted or unsubstituted benzyl, phenethyl, 3-phenylpropyl or 4-phenylbutyl groups. Examples of suitable substituents include: $C_1$-$C_4$ alkyl groups, particularly the methyl, ethyl and propyl groups; $C_1$-$C_4$ alkoxy groups, particularly the methoxy, ethoxy and propoxy groups; and halogen atoms, such as the fluorine, chlorine, bromine and iodine atoms.

Where R$^2$ represents an alkyl group, this may be a $C_1$-$C_5$ alkyl group, for example a methyl, ethyl, propyl, isopropyl, butyl, isobutyl or pentyl group.

Where the acyl group represented by R$^3$, R$^{11}$ or R$^{12}$ is an aliphatic acyl group, this may be a saturated or unsaturated group (the terms "saturated" and "unsaturated" referring to the carbon-carbon bonds) having up to 23 carbon atoms and is thus a $C_1$-$C_{23}$ alkanoyl, $C_3$-$C_{23}$ alkenoyl or $C_3$-$C_{23}$ alkynoyl group, which may be unsubstituted or may have one or more substituents selected from substituents (a), for example selected from the group consisting of aryl groups, carboxy groups, $C_2$-$C_6$ alkoxycarbonyl groups or aralkyloxycarbonyl groups. Examples of such aliphatic acyl groups include the formyl, acetyl, propionyl, propiolyl, butyryl, isobutyryl, pivaloyl, hexanoyl, acryloyl, methacryloyl, crotonoyl, octanoyl, decanoyl, tridecanoyl, pentadecanoyl, hexadecanoyl, heptadecanoyl, octadecanoyl, nonadecanoyl, 2,6,10,14-tetramethylnonadecanoyl and icosanoyl groups. Such groups may be unsubstituted or have one or more (preferably one) substituents as defined above. Suitable aryl substituents include the phenyl and 1- or 2-naphthyl groups, especially the phenyl group, which may themselves be unsubstituted or have one or more substituents selected from substituents (c), especially $C_1$-$C_5$ alkyl groups, $C_1$-$C_5$ alkoxy groups, halogen atoms, hydroxy groups, nitro groups, amino groups and dialkylamino groups where each alkyl part is $C_1$-$C_5$; specific examples of the resulting araliphatic acyl groups are given hereafter. Suitable alkoxycarbonyl groups (as substituents on these acyl groups) include straight or branched chain $C_{C2}-C_6$ groups (i.e. the alkoxy part is $C_1-C_5$), such as the methoxycarbonyl, ethoxycarbonyl, propoxycarbonyl, isopropoxycarbonyl, butoxycarbonyl, isobutoxycarbonyl, sec-butoxycarbonyl, t-butoxycarbonyl, pentyloxycarbonyl and isopentyloxycarbonyl groups. Suitable aralkyloxycarbonyl groups include those where the aralkyl part is as exemplified above in relation to $R^1$.

Examples of the alkanoyl, alkenoyl and alkynoyl groups which may be included in substituents (e) are those unsubstituted acyl groups exemplified above and having up to 5 carbon atoms.

Where $R^3$, $R^{11}$ or $R^{12}$ represents an aromatic acyl group, this is preferably an arylcarbonyl group in which the aryl part is as defined above, but is preferably a phenyl or naphthyl (1- or 2-naphthyl) group, which may be unsubstituted or may have one or more of the substituents (c) defined above. Examples of such aromatic acyl groups include the benzoyl, 4-nitrobenzoyl, 3-fluorobenzoyl, 2-chlorobenzoyl, 4-aminobenzoyl, 3-dimethylaminobenzoyl, 2-methoxybenzoyl, 3,4-dichlorobenzoyl, 3,5-di-t-butyl-4-hydroxybenzoyl and 1-naphthoyl groups.

Where $R^3$, $R^{11}$ or $R^{12}$ represents a heterocyclic acyl group, this is preferably a heterocyclic-carbonyl group, in which the heterocyclic part is as defined above, but is preferably a heterocyclic group having from 5 to 8, and more preferably 5 or 6, ring atoms, of which from 1 to 3, and preferably 1, are hetero-atoms selected from the group consisting of nitrogen, oxygen and sulfur heteroatoms. Such heterocyclic groups may be unsubstituted or may have at least one substituent (d), as defined above. Examples of such heterocyclic acyl groups include the 2-furoyl, 3-thenoyl, 3-pyridinecarbonyl and 4-pyridinecarbonyl groups.

Where $R^3$, $R^{11}$ or $R^{12}$ represents an araliphatic acyl group, this is preferably an aralkanoyl or aralkenoyl group, in which the aryl part is as defined above, but is preferably a phenyl or naphthyl group, more preferably a phenyl group, which may be unsubstituted or may have one or more of the substituents (c) defined above. The alkanoyl or alkenoyl part is preferably a $C_2-C_6$ alkanoyl or $C_3-C_6$ alkenoyl group, more preferably an acetyl, propionyl or acryloyl group. Examples of such araliphatic acyl groups include the phenylacetyl, α-(4-chlorophenyl)acetyl, 3-phenylpropionyl and cinnamoyl groups.

Where $R^3$, $R^6$, $R^7$, $R^{11}$ or $R^{12}$ represents a substituted alkyl group, this is a $C_1-C_{10}$ alkyl group having at least one of the substituents defined above as substituents (b). The parent alkyl group may be any one of those exemplified above. Examples of the substituents include:
hydroxy groups;
alkanoyloxy, alkenoyloxy and alkynoyloxy groups (which may be substituted or unsubstituted), aromatic acyloxy groups and heterocyclic acyloxy groups, examples of which are the acyloxy groups corresponding to the acyl groups exemplified above in relation to $R^3$, $R^{11}$ and $R^{12}$;
carboxy groups (i.e. —COOR$^8$ where R$^8$ is hydrogen);
aralkyloxycarbonyl groups (i.e. —COOR$^8$ where R$^8$ is aralkyl), e.g. where the aralkyl part is as exemplified above in relation to $R^1$;
$C_2-C_6$ alkoxycarbonyl groups (i.e. —COOR$^8$ where R$^8$ is $C_1-C_5$ alkyl) e.g. as exemplified above in relation to substituents on aliphatic acyl groups represented by $R^3$, $R^{11}$ and $R^{12}$;
$C_2-C_6$ hydroxyalkoxycarbonyl groups (i.e. —COOR$^8$ where R$^8$ is $C_1-C_5$ hydroxyalkyl), e.g. hydroxy-substituted analogs of the alkoxycarbonyl groups mentioned above, especially 2-hydroxyethoxycarbonyl, 3-hydroxypropoxycarbonyl and 2-hydroxypropoxycarbonyl groups;
alkoxyalkoxycarbonyl groups (i.e. —COOR$^8$ where R$^8$ is $C_1-C_5$ alkyl having a $C_1-C_5$ alkoxy substituent), e.g. alkoxy-substituted analogs of the alkoxycarbonyl groups mentioned above, especially methoxymethoxycarbonyl, ethoxymethoxycarbonyl, 2-methoxyethoxycarbonyl, 2-ethoxyethoxycarbonyl, 2-propoxyethoxycarbonyl, 1-methoxyethoxycarbonyl, 3-methoxypropoxycarbonyl, 3-ethoxypropoxycarbonyl, 3-propoxypropoxycarbonyl, 3-butoxypropoxycarbonyl, 2-methoxy-1-methylethoxycarbonyl, 2-ethoxy-1-methylethoxycarbonyl, 3-isopropoxypropoxycarbonyl, 4-methoxybutoxycarbonyl, 4-ethoxybutoxycarbonyl, 4-propoxybutoxycarbonyl, 4-butoxybutoxycarbonyl, 4-t-butoxybutoxycarbonyl, 5-methoxypentyloxycarbonyl and 5-ethoxypentyloxycarbonyl groups;
carbamoyl groups (i.e. —CONR$^9$R$^{10}$ where R$^9$=R$^{10}$=H);
mono- and di- alkylcarbamoyl groups (i.e. the groups —CONR$^9$R$^{10}$ where one or both of R$^9$ and R$^{10}$ represents a $C_1-C_5$ alkyl group), e.g. the methylcarbamoyl, ethylcarbamoyl, propylcarbamoyl, isopropylcarbamoyl, butylcarbamoyl, sec-butylcarbamoyl, pentylcarbamoyl, isopentylcarbamoyl, dimethylcarbamoyl, diethylcarbamoyl, dipropylcarbamoyl, dibutylcarbamoyl, dipentylcarbamoyl, N-methyl-N-ethylcarbamoyl, N-methyl-N-propylcarbamoyl and N-ethyl-N-propylcarbamoyl groups; and
nitrogen-containing heterocyclic acyl groups (i.e. —CONR$^9$R$^{10}$ where R$^9$, R$^{10}$ and the nitrogen atom together form an optionally substituted heterocyclic group), for example the 1-pyrrolylcarbonyl, 1-imidazolylcarbonyl, 3-thiazolidinylcarbonyl, 1-pyrrolidinylcarbonyl, 1-pyrrolinylcarbonyl, 1-imidazolinylcarbonyl, 1-imidazolidinylcarbonyl, 3-methyl-1-imidazolidinylcarbonyl, 3-ethyl-1-imidazolidinylcarbonyl, 3-t-butyl-1-imidazolidinylcarbonyl, 3-acetyl-1-imidazolidinylcarbonyl, 3-butyryl-1-imidazolidinylcarbonyl, 3valeryl-1-imidazolidinylcarbonyl, 3-pivaloyl-1-imidazolidinylcarbonyl, piperidinocarbonyl, 1-piperazinylcarbonyl, 4-methyl-1-piperazinylcarbonyl, 4-ethyl-1-piperazinylcarbonyl, 4-propyl-1-piperazinylcarbonyl, 4-butyl-1-piperazinylcarbonyl, 4-pentyl-1-piperazinylcarbonyl, 4-t-butyl-1-piperazinylcarbonyl, 4-acetyl-1-piperazinylcarbonyl, 4-formyl-1-piperazinylcarbonyl, 4-propionyl-1-piperazinylcarbonyl, 4-acryloyl-1-piperazinylcarbonyl, 4-methacryloyl-1-piperazinylcarbonyl, 4-propioloyl-1-piperazinylcarbonyl, 4-butyryl-1-piperazinylcarbonyl, 4-isovaleryl-1-piperazinylcarbonyl and morpholinocarbonyl groups.

Where $R^4$ represents an alkyl group, this has from 1 to 10 carbon atoms and is a straight or branched chain group. Certain examples of such alkyl groups have been given above in relation to such groups which may be represented by $R^1$. However, preferred examples of alkyl groups which may be represented by $R^4$ include the methyl, ethyl, propyl, isopropyl, butyl, isobutyl, t-butyl, pentyl, isopentyl, neopentyl, t-pentyl, hexyl, 1,1-dimethylbutyl, 1,3-dimethylbutyl, heptyl, 1,1-diethylpropyl, octyl, 1-methylheptyl, 2-ethylhexyl, 1,1,3,3-tetramethylbutyl, nonyl, decyl and 3,7-dimethyloctyl groups.

Where $R^4$, $R^5$ or substituent (b) represents an alkoxy group, this may have from 1 to 5 carbon atoms and may be a straight or branched chain group. Examples of such alkoxy groups include the methoxy, ethoxy, propoxy, isopropoxy, butoxy, t-butoxy and pentyloxy groups.

Where $R^5$ or substituent (e) represents an alkyl group, this may have from 1 to 5 carbon atoms and may be a straight or branched chain group. Examples of such alkyl groups which may be represented by $R^5$ are included amongst the alkyl groups which may be represented by $R^1$ or by $R^4$. However, preferred alkyl groups which may be represented by $R^5$ include the methyl, ethyl, propyl, isopropyl, butyl, isobutyl, pentyl and isopentyl groups.

Where Ar represents a divalent carbocyclic aromatic group, this may be substituted or unsubstituted and has from 6 to 10 ring carbon atoms. Examples of such divalent aromatic groups include the p-phenylene, o-phenylene and m-phenylene groups. Where such a group is substituted, it may have at least one of the substituents (c) defined above, but preferably $C_1$-$C_5$ alkyl groups (e.g. the methyl, ethyl, propyl, isopropyl, butyl or pentyl groups) or $C_1$-$C_5$ alkoxy groups (e.g. the methoxy, ethoxy, isopropoxy, t-butoxy or pentyloxy groups).

Where Ar represents a divalent aromatic heterocyclic group, the heterocyclic group is preferably a pyridine, furan, thiophene or pyrrole ring, which may be unsubstituted or have at least one of the substituents (d) defined above, and the two free valences may be in a variety of positions. Specific examples of such groups are as follows, in which the first number given denotes the position of attachment of the heterocyclic group to the group of formula —$(CH_2)_n$—O—, whilst the second number given denotes the position of attachment of the heterocyclic group to the —$CH_2$-thiazolidine group; the pyrid-2,3-diyl, pyrid-2,4-diyl, pyrid-2,5-diyl, pyrid-2,6-diyl, pyrid-3,4-diyl, pyrid-3,5-diyl, pyrid-3,6-diyl, pyrid-3,2-diyl, pyrid-4,3-diyl, pyrid-4,2-diyl, furan-2,3-diyl, furan-2,4-diyl, furan-2,5-diyl, furan-3,2-diyl, furan-4,2-diyl, thien-2,3-diyl, thien-2,4-diyl, thien-2,5-diyl, thien-3,2-diyl, thien-4,2-diyl, pyrrol-2,3-diyl, pyrrol-2,4-diyl, pyrrol-2,5-diyl, pyrrol-3,2-diyl or pyrrol-4,2-diyl groups. Such groups may be unsubstituted or, if desired, may have at least one, and preferably only one, substituted selected from those substituents (d) defined above, but preferably $C_1$-$C_6$ alkyl groups (e.g. the methyl, ethyl, isopropyl, t-butyl or pentyl groups) or $C_1$-$C_6$ alkoxy groups (e.g. the methoxy, ethoxy, isopropoxy, t-butoxy or pentyloxy groups).

W may represent a methylene (—$CH_2$—) group, a carbonyl (>C=O) group, a group of formula >CH—$OR^{11}$ (in which $R^{11}$ is as defined above) or a group of formula >C=$NOR^{12}$ (where $R^{12}$ is as defined above and may be the same as or different from the atom or group represented by $R^3$). Examples of the acyl and alkyl groups which may be represented by $R^{11}$ and $R^{12}$ are as given above. Where $R^{12}$ represents a group of formula —$CONR^9R^{10}$, i.e. a carbamoyl or mono- or di-alkylcarbamoyl group, examples of such groups are as given in relation to the similar groups which may be represented by substituents (b).

Alternatively, W and U may together form a double bond, e.g. as illustrated by the compounds of formula (I-12) described hereafter.

U preferably represents a methylene group. However, as mentioned above, it may form a double bond with W, or, when W represents a carbonyl group or a group of formula >C=N—$OR^{12}$, U may, together with $R^1$ and the carbon atom to which the group represented by $R^1$ is attached, form a group of formula —CH=C>, e.g. as illustrated in the compounds of formulae (I-8) to (I-11), defined hereafter.

Where substituent (c) is a $C_1$-$C_5$ alkyl group having at least one halogen substituent, the alkyl part may be any one of those $C_1$-$C_5$ alkyl groups defined above in relation to $R^5$, both straight and branched chain groups. The resulting haloalkyl group may have one or more halogen atoms (e.g. fluorine, chlorine, bromine or iodine atoms) up to complete perhalogenation. Examples of such groups include the chloromethyl, dichloromethyl, iodomethyl, bromethyl, fluoromethyl, trifluoromethyl, 2-chloroethyl, 2-bromoethyl, 2-iodoethyl, 2-fluoroethyl, 1,2-dibromoethyl, 1,2-dichloroethyl, 2,2-dichloroethyl, 2,2-difluoroethyl, 2,2,2-trichloroethyl, 2,2,2-trifluoroethyl, 2,2,2-tribromoethyl, 1,2,2-trichloroethyl, 1,2,3-trichloropropyl, 4-chlorobutyl and 5-fluoropentyl groups, of which the trifluoromethyl group is preferred.

Where the compounds of the present invention contain an acidic group in their molecule, for example where they contain a carboxy group or where $R^3$ represents a hydrogen atom and the resulting hydroxy group is of an acidic character or where $R^3$ represents a sulfo (—$SO_3H$) group, then the compounds of the invention may form salts with cations. There is no limitation upon the nature of such salts, provided that, where they are to be used for therapeutic purposes, they are pharmaceutically acceptable, which, as is well-known in the art, means that they do not have reduced activity (or unacceptably reduced activity) or increased toxicity (or unacceptably increased toxicity) compared with the free compound of formula (I). Where, however, they are to be used for non-therapeutic purposes, e.g. as intermediates in the preparation of other compounds, even this limitation does not apply. Suitable salts include, for example: alkali metal salts, such as the sodium or potassium salts; alkaline earth metal salts, such as the calcium or magnesium salts; other metal salts, such as the aluminum or iron salts; salts with basic amino acids, such as the lysine or arginine salts; ammonium salts; and salts with organic amines, such as the cyclohexylammonium, diisopropylammonium and triethylammonium salts.

The compounds of the invention may also, depending upon the particular substituents, contain basic groups in their molecules and, in such a case, they can also form acid addition salts. As with the salts mentioned above, there is no particular limitation on the nature of the acid forming such a salt, provided that, where the compound is to be used for therapeutic purposes, the resulting salt is pharmaceutically acceptable. Examples of suitable acids include: inorganic acids, such as hydrochloric acid, sulfuric acid, nitric acid or phosphoric acid; organic carboxylic acids, such as acetic acid, tartaric acid, maleic acid, fumaric acid, malic acid, glutamic acid or aspartic acid; and organic sulfonic acids, such as p-toluenesulfonic acid or methanesulfonic acid.

Preferred classes of compound of the present invention are as follows:

(1) Compounds of formula (I) in which:
$R^1$ represents a hydrogen atom or a $C_1$-$C_{10}$ alkyl group;
$R^2$ represents a hydrogen atom or a $C_1$-$C_3$ alkyl group;

$R^3$ represents a hydrogen atom, a sulfo group, a $C_1$-$C_{10}$ alkanoyl group, a $C_3$-$C_{10}$ alkenoyl group, a substituted $C_1$-$C_{10}$ alkanoyl or $C_3$-$C_{10}$ alkenoyl group having at least one substituent selected from the group consisting of substituents (f), an arylcarbonyl group wherein the aryl part is a $C_6$-$C_{10}$ carbocyclic aryl group which is unsubstituted or has at least one substituent selected from the group consisting of substituents (g), a group of formula $R^{13}$—$(CH_2)_m$—CO—, where $R^{13}$ represents a phenyl group or a phenyl group having at least one substituent selected from the group consisting of substituents (g), and m is an integer from 1 to 5, a group of formula Het—CO—, where Het represents a heterocyclic group having 5 or 6 ring atoms, of which from 1 to 3, and preferably 1, are hetero-atoms selected from the group consisting of nitrogen, oxygen and sulfur hetero-atoms, said heterocyclic group being unsubstituted or having at least one substituent selected from the group consisting of $C_1$-$C_5$ alkyl groups, a $C_1$-$C_5$ alkyl group substituted by a group of formula —COOR$^{8a}$, where $R^{8a}$ represents a hydrogen atom, $C_1$-$C_5$ alkyl group or an alkoxyalkyl group where both the alkoxy part and the alkyl part are $C_1$-$C_5$, a $C_2$-$C_5$ hydroxyalkyl group, an alkoxyalkyl group where both the alkoxy part and the alkyl part are $C_1$-$C_5$, a $C_2$-$C_5$ alkyl group substituted by a group of formula —O—CO—$R^{53}$, where $R^{53}$ represents a $C_1$-$C_{10}$ alkyl group, a phenyl group, a phenyl group having at least one substituent selected from the group consisting of substituents (g) or a heterocyclic group Het, as defined above, or a $C_1$-$C_3$ alkyl group substituted by a single substituent selected from the group consisting of substituents (h);

said substituents (f) are selected from the group consisting of phenyl groups, carboxy groups, $C_2$-$C_6$ alkoxycarbonyl groups and benzyloxycarbonyl groups;

said substituents (g) are selected from the group consisting of $C_1$-$C_5$ alkyl groups, trifluoromethyl groups, $C_1$-$C_5$ alkoxy groups, halogen atoms, nitro groups, amino groups, hydroxy groups and dialkylamino groups where each alkyl part is $C_1$-$C_5$;

said substituents (h) are selected from the group consisting of alkylcarbamoyl groups where the alkyl part is $C_1$-$C_4$, dialkylcarbamoyl groups where each alkyl part is $C_1$-$C_4$, 1-pyrrolidinylcarbonyl groups, piperidinocarbonyl groups and morpholinocarbonyl groups;

$R^4$ represents a $C_1$-$C_{10}$ alkyl group or a methoxy group;

$R^5$ represents a hydrogen atom, a $C_1$-$C_5$ alkyl group or a methoxy group;

$R^6$ and $R^7$ are independently selected from the group consisting of hydrogen atoms, $C_1$-$C_5$ alkyl groups, $C_1$-$C_5$ alkyl groups substituted by a group of formula —COOR$^{8a}$ where $R^{8a}$ is as defined above, $C_2$-$C_5$ hydroxyalkyl groups, $C_1$-$C_5$ alkyl groups substituted by a $C_1$-$C_5$ alkoxy group, $C_2$-$C_5$ alkyl groups substituted by a group of formula —O—CO—$R^{53}$ where $R^{53}$ is as defined above, and $C_1$-$C_3$ alkyl groups having a single substituent selected from the group consisting of substituents (h);

Ar represents a o-phenylene, m-phenylene or p-phenylene group or a pyridine-diyl group which is attached to the part of said compound of formula (I) of formula —$(CH_2)_n$—O— at its 2-position and is attached to the —$CH_2$-thiazolidine group at its 5- or 6-position, said phenylene and pyridine-diyl groups being unsubstituted or having a $C_1$-$C_3$ alkyl substituent;

W represents a group of formula —$CH_2$—, $>C=O$, $>CH$—OR$^{11}$ or $>C=N$—OR$^{12}$ where $R^{11}$ represents a hydrogen atom, a $C_1$-$C_{10}$ alkanoyl group (preferably an acetyl group), a $C_3$-$C_{10}$ alkenoyl group, a substituted $C_1$-$C_{10}$ alkanoyl or $C_3$-$C_{10}$ alkenoyl group having at least one substituent selected from the group consisting of substituents (f), an arylcarbonyl group wherein the aryl part is a $C_6$-$C_{10}$ carbocyclic aryl group which is unsubstituted or has at least one substituent selected from the group consisting of substituents (g), a group of formula $R^{13}$—$(CH_2)_m$—CO— where $R^{13}$ and m are as defined above or a group of formula HET—CO— where Het is as defined above, and $R^{12}$ represents a hydrogen atom, a $C_1$-$C_5$ alkyl group, a $C_1$-$C_{10}$ alkyl group having at least one substituent selected from the group consisting of substituents (j), a $C_1$-$C_{10}$ alkanoyl group, a $C_3$-$C_{10}$ alkenoyl group, a substituted $C_1$-$C_{10}$ alkanoyl or $C_3$-$C_{10}$ alkenoyl group having at least one substituent selected from the group consisting of substituents (f), an arylcarbonyl group wherein the aryl part is a $C_6$-$C_{10}$ carbocyclic aryl group which is unsubstituted or has at least one substituent selected from the group consisting of substituents (g), or said group of formula $R^{13}$—$(CH_2)_m$—CO— or Het—CO—; and said substituents (j) are selected from the group consisting of hydroxy groups, $C_1$-$C_5$ alkoxy groups, phenyl groups, phenyl proups having at least one substituent selected form the group consisting of substituents (g), $C_2$-$C_{11}$ alkanoyloxy groups, $C_2$-$C_{11}$ alkanoyloxy groups substituted by a group of formula —COOR$^{8a}$ where $R^{8a}$ is as defined above, $C_3$-$C_{11}$ alkanoyloxy groups substituted by a group of formula —COOR$^{8a}$ where $R^{8a}$ is as defined above, $C_3$-$C_{11}$ alkenoyloxy groups substituted by a group of formula —COOR$^{8a}$ where $R^{8a}$ is as defined above, phenylalkenoyloxy groups where the alkenyl part is $C_2$-$C_{10}$ and the phenyl part is unsubstituted or has at least one substituent selected from the group consisting of substituents (g), benzoyloxy groups, benzoyloxy groups having at least one substituent selected from the group consisting of substituents (g), groups of formula —COOR$^{8a}$ where $R^{8a}$ is as defined above, benzyloxycarbonyl groups and groups of formula —COR$^9$R$^{10}$ where $R^9$ and $R^{10}$ are as defined above;

U represents (i) where W represents a group of formula —$CH_2$—, $>C=O$, $>CH_2OR^{11}$ or $>C=N$—OR$^{12}$, a group of formula —$CH_2$—, (ii) with W, a group of formula —CH=CH—, or (iii) where W represents a group of formula $>C=O$ or $>C=N$—OR$^{14}$, in which $R^{14}$ represents any one of the acyl groups defined for $R^{12}$, with $R^1$ and the carbon atom to which $R^1$ is attached, a group of formula —CH=C<.

(2) Compounds as defined in (1) above, where:

$R^1$, $R^2$, $R^4$, $R^5$, Ar, W and U are as defined in (1);

$R^6$ and $R^7$ both represent hydrogen atoms;

$R^3$ and $R^{11}$ are independently selected from the group consisting of hydrogen atoms, $C_1$-$C_{10}$ alkanoyl groups, $C_3$-$C_{10}$ alkenoyl groups, $C_1$-$C_{10}$ alkanoyl or $C_3$-$C_{10}$ alkenoyl groups having at least one substituent selected from the group consisting of substituents (f), arylcarbonyl groups as defined in (1) above, and groups of formulae $R^{13}$—$(CH_2)_m$—CO— and Het—CO— where $R^{13}$, m and Het are as defined in (1) above; and $R^{12}$ represents any one of the groups or atoms defined for $R^3$ and $R^{11}$ or a $C_1$-$C_5$ alkyl groups or a $C_1$-$C_3$ alkyl group having at least one substituent selected from the group consisting of substituents (f) defined in (1) above.

(3) Compounds as defined in (1) above, where:
$R^1$, $R^2$, $R^4$, $R^5$, Ar, W and U are as defined in (1);
$R^3$, $R^6$, $R^7$ and $R^{12}$ are independently selected from the group consisting of hydrogen atoms, $C_1$-$C_5$ alkyl groups, $C_1$-$C_5$ alkyl groups substituted by a group of formula —COOR$^{8a}$ where $R^{8a}$ is as defined in (1) above, $C_2$-$C_5$ hydroxyalkyl groups, $C_1$-$C_5$ alkyl groups substituted by a $C_1$-$C_5$ alkoxy group, $C_2$-$C_5$ alkyl groups substituted by a group of formula —O—CO—$R^{53}$ where $R^{53}$ is as defined in (1) above and $C_1$-$C_3$ alkyl groups substituted by a single substituent selected from the group consisting of substituents (h) defined in (1) above; and $R^{11}$ represents a hydrogen atom, an acetyl group or a benzoyl group; or $R^{12}$ represents a hydrogen atom, a $C_1$-$C_5$ alkyl group, a $C_1$-$C_{10}$ alkyl group having at least one substituent selected from the group consisting of substituents (k), a $C_2$-$C_6$ alkanoyl group, a $C_2$-$C_{10}$ alkanoyl group having at least one substituent selected from the group consisting of substituents (l), a $C_3$-$C_5$ alkenoyl group, a $C_3$-$C_5$ alkenoyl group having at least one substituent selected from the group consisting of substituents (l), a benzoyl group, a benzoyl group having at least one substituent selected from the group consisting of substituents (m), a pyridinecarbonyl group, a furoyl group, a thenoyl group or a pyridinecarbonyl, furoyl or thenoyl group having at least one substituent selected from the group consisting of $C_1$-$C_5$ alkyl groups;

said substituents (k) are selected from the group consisting of hydroxy groups, phenyl groups, phenyl groups having at least one substituent selected from the group consisting of substituents (m), $C_2$-$C_5$ alkanoyloxy groups, $C_2$-$C_{10}$ alkanoyloxy or $C_3$-$C_{10}$ alkenoyloxy groups substituted by a group of formula —COOR$^{8a}$ where $R^{8a}$ is as defined in (1) above, $C_3$-$C_{10}$ alkenoyloxy groups substituted by a phenyl group where the phenyl group is unsubstituted or has at least one substituent selected from the group consisting of substituents (m), benzoyloxy groups, benzoyloxy groups having at least one substituent selected from the group consisting of substituents (m), groups of formula —COOR$^{8a}$ where $R^{8a}$ is as defined in (1) above and substituents (h) as defined in (1) above;

said substituents (l) are selected from the group consisting of phenyl groups, carboxy groups, alkoxycarbonyl groups where the alkoxy part is $C_1$-$C_5$ and benzyloxycarbonyl groups; and said substituents (m) are selected from the group consisting of $C_1$-$C_5$ alkyl groups, $C_1$-$C_5$ alkoxy groups, halogen atoms and trifluoromethyl groups.

(4) Compounds of formula (I) in which:
$R^1$ represents an alkyl group selected from the group consisting of methyl, ethyl, isobutyl, pentyl, hexyl, 3,3-dimethylbutyl, heptyl, 4,4-dimethylpentyl, octyl, 5,5-dimethylhexyl, nonyl and 3,7-dimethyloctyl groups;
$R^2$ represents a hydrogen atom or a methyl group;

$R^3$ represents a hydrogen atom, a $C_1$-$C_{10}$ alkanoyl group, a $C_3$-$C_{10}$ alkenoyl group, a substituted $C_1$-$C_{10}$ alkanoyl or $C_3$-$C_{10}$ alkenoyl group having at least one substituent selected from the group consisting of substituents (f) defined in (1) above, a benzoyl group, a benzoyl group having at least one substituent selected from the group consisting of substituents (n), an aralkanoyl group of formula $R^{15}$—$(CH_2)_m$—CO— where $R^{15}$ represents a phenyl group or a phenyl group having at least one substituent selected from the group consisting of substituents (n), and m is an integer from 1 to 5,
a pyridinecarbonyl group, a furoyl group, a thenoyl group, a $C_1$-$C_3$ alkyl group, a $C_1$-$C_3$ alkyl group substituted by a group of formula —COOR$^{8a}$ where $R^{8a}$ is as defined in (1) above, a $C_2$-$C_3$ hydroxyalkyl group, a $C_1$-$C_5$ alkyl group substituted by a $C_1$-$C_5$ alkoxy group, a $C_2$-$C_5$ alkyl group substituted by a $C_2$-$C_4$ alkanoyloxy or a benzoyloxy group or a methyl group having a single substituent selected from the group consisting of substituents (h);

said substituents (n) are selected from the group consisting of $C_1$-$C_5$ alkyl groups, $C_1$-$C_5$ alkoxy groups and halogen atoms;

$R^4$ represents a $C_1$-$C_{10}$ alkyl group;
$R^5$ represents a hydrogen atom or a $C_1$-$C_3$ alkyl group;
$R^6$ and $R^7$ are independently selected from the group consisting of hydrogen atoms, $C_1$-$C_3$ alkyl groups, $C_1$-$C_3$ alkyl groups substituted by a group of formula —COOR$^{8a}$ where $R^{8a}$ is as defined in (1) above, $C_2$-$C_3$ hydroxyalkyl groups, $C_1$-$C_5$ alkyl groups substituted by a $C_1$-$C_5$ alkoxy groups, $C_2$-$C_5$ alkyl groups substituted by a $C_2$-$C_4$ alkanoyloxy or a benzoyloxy group, and methyl groups substituted by a single substituent selected from the group consisting of substituents (h);

Ar represents a o-phenylene, m-phenylene or p-phenylene group or a pyridine-diyl group which is attached to the part of said compound of formula (I) of formula —$(CH_2)_n$—O— at its 2-position and is attached to the —$CH_2$-thiazolidine group at its 5- or 6-position, said phenylene and pyridine-diyl groups being unsubstituted or having a methyl substituent;

W represents a group of formula —$CH_2$—, $>C=O$, $>CH$—$OR^{11}$ or $>C=N$—$OR^{12}$, where:
$R^{11}$ represents a hydrogen atom or any one of the acyl groups defined above for $R^3$; and
$R^{12}$ represents a benzyl group, any one of the groups or atoms defined above for $R^3$, a pyridinecarbonyl group or a pyridinecarbonyl group having at least one substituent selected from the group consisting of $C_1$-$C_5$ alkyl groups;

and U represents
(i) where W represents a group of formula —$CH_2$—, $>C=O$, $>CH$—$OR^{11}$ or $>C=N$—$OR^{12}$, a group of formula —$CH_2$—,
(ii) with W, a group of formula —$CH=CH$—, or
(iii) where W represents a group of formula $>C=O$, with $R^1$ and the carbon atom to which $R^1$ is attached, a group of formula —$CH=C>$.

(5) Compounds as defined in (4) above, where:
$R^1$, $R^2$, $R^4$, $R^5$, Ar, W and U are as defined in (4) above;
$R^6$ and $R^7$ are both hydrogen atoms;
$R^3$ and $R^{11}$ are independently selected from the group consisting of hydrogen atoms, $C_1$-$C_{10}$ alkanoyl groups, $C_3$-$C_{10}$ alkenoyl groups, $C_1$-$C_{10}$ alkanoyl or $C_3$-$C_{10}$ alkenoyl groups having at least one substituent selected from the group consisting of substituents (f) defined above, benzoyl groups, benzoyl groups having at least one substituent selected from the group consisting of substituents (n) defined in (4) above, groups of formula $R^{15}$ —$(CH_2)_m$—CO— where $R^{15}$ and m are as defined in (4) above, pyridinecarbonyl groups, furoyl groups and thenoyl groups; and $R^{12}$ represents a hydrogen atom, a methyl group, a benzyl group, a t-butoxycarbonylmethyl group or any one of the acyl groups defined above for $R^3$ and $R^{11}$.

(6) Compounds as defined in (4) above, where:

$R^1$, $R^2$, $R^4$, $R^5$, Ar, W and U are as defined in (4) above;

$R^3$, $R^6$ and $R^7$ are independently selected from the group consisting of $C_1$-$C_3$ alkyl groups, $C_1$-$C_3$ alkyl groups substituted by a group of formula —$COOR^{8a}$ where $R^{8a}$ is as defined in (1) above, $C_2$-$C_3$ hydroxyalkyl groups, $C_1$-$C_5$ alkyl groups substituted by a $C_1$-$C_5$ alkoxy group, $C_2$-$C_5$ alkyl groups substituted by a $C_2$-$C_4$ alkanoyloxy or a benzoyloxy group, and methyl groups having a single substituent selected from the group consisting of substituents (h) defined in (1) above;

$R^{11}$ represents a hydrogen atom;

$R^{12}$ represents a hydrogen atom, a $C_1$-$C_3$ alkyl group having at least one substituent selected from the group consisting of substituents (o), a $C_2$-$C_4$ alkanoyl group, a $C_2$-$C_4$ alkanoyl group substituted by a group of formula —$COOR^{8a}$ where $R^{8a}$ is as defined in (1) above, an acryloyl group, acryloyl group having a β-substituent selected from the group consisting of substituents (f) defined above, a benzoyl group, a benzoyl group having at least one substituent selected from the group consisting of substituents (q), a pyridinecarbonyl group, a pyridinecarbonyl group having at least one substituent selected from the group consisting of $C_1$-$C_5$ alkyl groups or any one of the groups defined above for $R^3$, $R^6$ and $R^7$;

said substituents (o) are selected from the group consisting of carboxy groups and alkoxycarbonyl groups where the alkoxy part is $C_1$-$C_5$; and said substituents (q) are selected from the group consisting of methyl groups, ethyl groups, methoxy groups and ethoxy groups.

(7) Compounds of formula (I) in which:

$R^1$ represents an alkyl group selected from the group consisting of methyl, isobutyl, hexyl, heptyl, octyl, nonyl and 3,7-dimethyloctyl groups;

$R^2$ represents a hydrogen atom or a methyl group;

$R^3$ represents a hydrogen atom, a $C_1$-$C_5$ alkanoyl group, $C_3$-$C_5$ alkenoyl group, a cinnamoyl group, a group of formula $R^{16}OOC(CH_2)_mCO$—
where $R^{16}$ represents a hydrogen atom or a $C_1$-$C_5$ alkyl group and m is an integer from 1 to 5,
a cis- or trans- group of formula $R^{17}OOC.CH=CH—CO—$
where $R^{17}$ represents a hydrogen atom, a $C_1$-$C_5$ alkyl group or a benzyl group,
2-, 3- or 4-pyridinecarbonyl group or a $C_1$-$C_3$ alkyl group substituted by a group of formula —$COOR^{8a}$ where $R^{8a}$ is as defined in (1) above;

$R^4$ represents an alkyl group selected from the group consisting of methyl, ethyl, propyl, butyl, pentyl, hexyl, heptyl, octyl, 1,1,3,3-tetramethylbutyl, 1,1-dimethylbutyl and 1,1-dimethylpropyl groups;

$R^5$ represents a hydrogen atom or a methyl group;

$R^6$ and $R^7$ are independently selected from the group consisting of hydrogen atoms and $C_1$-$C_3$ alkyl groups substituted by a group of formula —$COOR^{8a}$ where $R^{8a}$ is as defined in (1) above;

Ar represents a p-phenylene group, a m-phenylene group having a methyl group at the position ortho to the position of attachment to the group of formula —$(CH_2)_n$—O— or a pyridine-diyl group attached to said group of formula —$(CH_2)_n$—O— at the 2-position and to the —$CH_2$-thiazolidine group at the 5-position;

W represents a group of formula —$CH_2$—, $>C=O$, $>C=N—OH$, $>C=N—OCH_2COOH$ or $>C=N—OCOR^{18}$
where $R^{18}$ represents a $C_1$-$C_5$ alkyl group; and U represents a group of formula —$CH_2$—.

(7-a) Compounds of formula (I) in which:

$R^1$ represents an alkyl group selected from the group consisting of hexyl, heptyl, octyl, nonyl and 3,7-dimethyloctyl groups;

$R^2$ represents a hydrogen atom or a methyl group;

$R^3$ represents a hydrogen atom, a $C_1$-$C_{C5}$ alkanoyl group, $C_3$-$C_5$ alkenoyl group, a cinnamoyl group, a group of formula $R^{16}OOC(CH_2)_mCO$—
where $R^{16}$ represents a hydrogen atom or a $C_1$-$C_5$ alkyl group and m is an integer from 1 to 5,
a cis- or trans- group of formula $R^{17}OOC.CH=CH—CO—$
where $R^{17}$ represents a hydrogen atom, $C_1$-$C_5$ alkyl group or a benzyl group,
2-, 3- or 4-pyridinecarbonyl group or a $C_1$-$C_3$ alkyl group substituted by a group of formula —$COOR^{8a}$ where $R^{8a}$ is as defined in (1) above;

$R^4$ represents an alkyl group selected from the group consisting of methyl, ethyl, propyl, butyl, pentyl, hexyl, heptyl, octyl, 1,1,3,3-tetramethylbutyl, 1,1-dimethylbutyl and 1,1-dimethylpropyl groups;

$R^5$ represents a hydrogen atom or a methyl group;

$R^6$ and $R^7$ are independently selected from the group consisting of hydrogen atoms and $C_1$-$C_3$ alkyl groups substituted by a group of formula —$COOR^{8a}$ where $R^{8a}$ is as defined in (1) above;

Ar represents a p-phenylene group, a m-phenylene group having a methyl group at the position ortho to the position of attachment to the group of formula —$(CH_2)_n$—O— or a pyridine-diyl group attached to said group of formula —$(CH_2)_n$—O— at the 2-position and to the —$CH_2$-thiazolidine group at the 5-position;

W represents a group of formula —$CH_2$—, $>C=O$ or $>C=N—OR^{12}$
where $R^{12}$ is as defined in (9) below or represents a $C_1$-$C_5$ alkyl group or a $C_1$-$C_5$ alkyl group substituted by a phenyl group where the phenyl group is unsubstituted or has at least one substituent selected from the group consisting of substituents (n) as defined in (4) above; and U represents a group of formula —$CH_2$—.

(7-b) Compounds of formula (I) in which:

$R^1$ represents an alkyl group selected from the group consisting of methyl, isobutyl, hexyl, heptyl, octyl, nonyl and 3,7-dimethyloctyl groups;

$R^2$ represents a hydrogen atom or a methyl group;

$R^3$ represents a hydrogen atom, a $C_1$-$C_5$ alkanoyl group, $C_3$-$C_5$ alkenoyl group, a cinnamoyl group, a group of formula $R^{16}OOC(CH_2)_mCO$—
where $R^{16}$ represents a hydrogen atom or a $C_1$-$C_5$ alkyl group and m is an integer from 1 to 5,
a cis- or trans- group of formula $R^{17}OOC.CH=CH—CO—$ where $R^{17}$ represents a hydrogen atom, a $C_1$-$C_5$ alkyl group or a benzyl group,
a 2-, 3- or 4-pyridinecarbonyl group or a $C_1$-$C_3$ alkyl group substituted by a group of formula —COOR$^{8a}$ where $R^{8a}$ is as defined in (1) above;

$R^4$ represents an alkyl group selected from the group consisting of hexyl, heptyl, octyl, 1,1,3,3-tetramethylbutyl, 1,1-dimethylbutyl and 1,1-dimethylpropyl groups;

$R^5$ represents a hydrogen atom or a methyl group;

$R^6$ and $R^7$ are independently selected from the group consisting of hydrogen atoms and $C_1$-$C_3$ alkyl groups substituted by a group of formula —COOR$^{8a}$ where $R^{8a}$ is as defined in (1) above;

Ar represents a p-phenylene group, a m-phenylene group having a methyl group at the position ortho to the position of attachment to the group of formula —(CH$_2$)$_n$—O— or a pyridine-diyl group attached to said group of formula —(CH$_2$)$_n$—O— at the 2-position and to the —CH$_2$-thiazolidine group at the 5-position;

W represents a group of formula —CH$_2$—, >C=O or >C=N—OR$^{12}$ where $R^{12}$ is as defined in (9) below or represents a $C_1$-$C_5$ alkyl group or a $C_1$-$C_5$ alkyl group substituted by a phenyl group where the phenyl group is unsubstituted or has at least one substituent selected from the group consisting of substituents (n) as defined in (4) above; and U represents a group of formula —CH$_2$—.

(7-c) Compounds of formula (I) in which:

$R^1$ represents an alkyl group selected from the group consisting of methyl, isobutyl, hexyl, heptyl, octyl, nonyl and 3,7-dimethyloctyl groups;

$R^2$ represents a hydrogen atom or a methyl group;

$R^3$ represents $C_1$-$C_3$ alkyl group substituted by a group of formula —COOR$^{8a}$ where $R^{8a}$ is as defined in (1) above;

$R^4$ represents an alkyl group selected from the group consisting of methyl, ethyl, propyl, butyl, pentyl, hexyl, heptyl, octyl, 1,1,3,3-tetramethylbutyl, 1,1-dimethylbutyl and 1,1-dimethylpropyl groups;

$R^5$ represents a hydrogen atom or a methyl group;

$R^6$ and $R^7$ are both hydrogen atoms;

Ar represents a p-phenylene group, a m-phenylene group having a methyl group at the position ortho to the position of attachment to the group of formula —(CH$_2$)$_n$—O— or a pyridine-diyl group attached to said group of formula —(CH$_2$)$_n$—O— at the 2-position and to the —CH$_2$-thiazolidine group at the 5-position;

W represents a group of formula —CH$_2$—, >C=O, >C=N—OH, or >C=N—O—(C$_1$-C$_3$ alkyl)—COOR$^{8a}$ where $R^{8a}$ is as defined in (1) above;

U represents a group of formula —CH$_2$—; and n is 1 or 2.

(7-d) Compounds of formula (I) in which:

$R^1$ represents an alkyl group selected from the group consisting of methyl, isobutyl, hexyl, heptyl, octyl, nonyl and 3,7-dimethyloctyl groups;

$R^2$ represents a hydrogen atom or a methyl group;

$R^3$ represents —CH$_2$—COO(C$_1$-C$_5$ alkyl) group;

$R^4$ represents an alkyl group selected from the group consisting of methyl, ethyl, propyl, butyl, pentyl, hexyl, heptyl, octyl, 1,1,3,3-tetramethylbutyl, 1,1-dimethylbutyl and 1,1-dimethylpropyl groups;

$R^5$ represents a hydrogen atom or a methyl group;

$R^6$ and $R^7$ are both hydrogen atoms;

Ar represents a p-phenylene group, a m-phenylene group having a methyl group at the position ortho to the position of attachment to the group of formula —(CH$_2$)$_n$—O— or a pyridine-diyl group attached to said group of formula —(CH$_2$)$_n$—O— at the 2-position and to the —CH$_2$-thiazolidine group at the 5-position;

W represents a group of formula —CH$_2$—, >C=O, >C=N—OH, or >C=N—O—(C$_1$-C$_3$ alkyl)—COO(C$_1$-C$_5$ alkyl);

U represents a group of formula —CH$_2$—; and n is 2 or 2.

(8) Compounds as defined in (7) above, where:

$R^1$, $R^2$, $R^4$, $R^5$, Ar and U are as defined in (7) above;

$R^3$ represents a hydrogen atom, a $C_1$-$C_5$ alkanoyl group, a $C_3$-$C_5$ alkenoyl group, a cinnamoyl group, a group of formula $R^{16}$OOC(CH$_2$)$_m$CO— where $R^{16}$ and m are as defined in (7) above, a cis or trans- group of formula $R^{17}$OOC.CH=CH—CO— where $R^{17}$ is as defined in (7) above, or a 2-, 3- or 4-pyridinecarbonyl group;

$R^6$ and $R^7$ are both hydrogen atoms;

W represents a group of formula >C=NOR$^{12}$ where $R^{12}$ is as defined in (9) below; and n is 1 or 2.

(9) Compounds as defined in (7) above, where:

$R^1$, $R^2$, $R^4$, $R^5$, Ar and U are as defined in (7) above;

$R^3$, $R^6$ and $R^7$ are independently selected from the group consisting of $C_1$-$C_3$ alkyl groups substituted by a group of formula —COOR$^{8a}$ where $R^{8a}$ is as defined in (1) above;

W represents a group of formula >CH$_2$, >C=O or >C=NOR$^{12}$;

$R^{12}$ represents a hydrogen atom, a group of formula —(CH$_2$)$_3$COOR$^{8a}$, —CH$_2$COOR$^{8a}$, —C(CH$_3$)$_2$COOR$^{8a}$, —COCH$_2$CH$_2$COOR$^{8a}$ or —CO—CH=CH—COOR$^{8a}$ where $R^{8a}$ is as defined in (1) above, an acetyl group, a cinnamoyl group, a benzoyl group, a pyridinecarbonyl group or any one of the groups defined above for $R^3$, $R^6$ and $R^7$; and n is 1 or 2.

(9-a) Compounds as defined in (7) above, where:

$R^1$, $R^2$, $R^4$, $R^5$, Ar and U are as defined in (7) above;

$R^3$ represents a hydrogen atom, a $C_1$-$C_{10}$ alkanoyl group, a $C_3$-$C_{10}$ alkenoyl group, a $C_1$-$C_{10}$ alkanoyl or $C_3$-$C_{10}$ alkenoyl group having at least one substituent selected from the group consisting of substituents (f), an arylcarbonyl group as defined in (1) above, a group of formula $R^{13}$—(CH$_2$)$_m$—CO— or Het—CO— where $R^{13}$, m and Het are as defined in (1) above or a $C_1$-$C_3$ alkyl group substituted by a group of formula —COOR$^{8a}$ where $R^{8a}$ is as defined in (1) above;

$R^6$ represents a $C_1$-$C_3$ alkyl group substituted by a group of formula —COOR$^{8a}$ where $R^{8a}$ is as defined in (1) above;

$R^7$ represents a hydrogen atom or a $C_1$-$C_3$ alkyl group substituted by a group of formula —COOR$^{8a}$ where $R^{8a}$ is as defined in (1) above;

W represents a group of formula >CH$_2$, >C=O or >C=NOR$^{12}$, where $R^{12}$ represents a hydrogen atom, a group of formula —(CH$_2$)$_3$COOR$^{8a}$, —CH$_2$COOR$^{8a}$, —C(CH$_3$)$_2$COOR$^{8a}$, —COCH$_2$CH$_2$COOR$^{8a}$ or —CO—CH=CH —COOR$^{8a}$ where $R^{8a}$ is as defined in (1) above, an acetyl group, a cinnamoyl group, a benzoyl group, a pyridinecarbonyl group or a $C_1$-$C_3$ alkyl group substituted by a group of formula —COOR$^{8a}$ where R$^{8a}$ is as defined in (1) above; and n is 1 or 2.

Specific examples of compounds of the invention are given in the following Tables 1–26, referring to the formula (I-1) to (I-26). In the Tables, the following abbreviations are used:

| | |
|---|---|
| Ac | acetyl |
| Boz | benzoyl |
| Bu | butyl |
| iBu | isobutyl |
| tBu | t-butyl |
| Bz | benzyl |
| Dc | decyl |
| 3,3-DMB | 3,3-dimethylbutyl |
| 5,5-DMH | 5,5-dimethylhexyl |
| 3,7-DMO | 3,7-dimethyloctyl |
| 7,7-DMO | 7,7-dimethyloctyl |
| Et | ethyl |
| Hp | heptyl |
| Hx | hexyl |
| Hxd | hexadecyl |
| Ic | icosyl |
| Me | methyl |
| Mor | morpholino |
| Nn | nonyl |
| Oc | octyl |
| Ocd | octadecyl |
| Ph | phenyl |
| Phn | phenylene |
| Pip | piperidino |
| Piz | piperazinyl |

-continued

| | |
|---|---|
| Pn | pentyl |
| iPn | isopentyl |
| nPn | neopentyl |
| Pr | propyl |
| iPr | isopropyl |
| Pydi | pyridine-diyl |
| Pyl | pyrrolidinyl |
| Pyr | pyridyl |
| TMB | 1,1,3,3-tetramethylbutyl |
| Trd | tridecyl |

In the case of the divalent group represented by Ar, where appropriate, the number given first is the position of attachment of that group to the group represented by —(CH$_2$)$_n$—O— in the compound of formula (I), whilst the number given second is the position of attachment of that group to the —CH$_2$-thiazolidine group.

Compounds of formula (I-1):

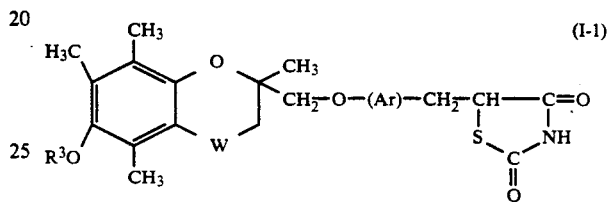

are as defined in Table 1:

TABLE 1

| Cpd. No. | R$^3$ | W | Ar |
|---|---|---|---|
| 1 | H | >CH$_2$ | 6-Me-1,3-Phn |
| 2 | Ac | >CH$_2$ | 6-Me-1,3-Phn |
| 3 | H | >C=O | 6-Me-1,3-Phn |
| 4 | H | >C=NOH | 6-Me-1,3-Phn |
| 5 | H | >CH$_2$ | 2,5-Pydi |
| 6 | H | >C=O | 2,5-Pydi |
| 7 | Ac | >C=O | 2,5-Pydi |
| 8 | H | >C=NOH | 2,5-Pydi |
| 9 | H | >C=NOH (anti) | p-Phn |
| 10 | H | >C=NOH (syn) | p-Phn |
| 11 | Ac | >C=NOAc | p-Phn |

TABLE 1-continued

| Cpd. No. | R³ | W | Ar |
|---|---|---|---|
| 12 | Boz | >C=NOBoz | p-Phn |
| 13 | 3-PyrCO | >C=NO(3-PyrCO) | p-Phn |
| 14 | H | >C=NOMe | p-Phn |
| 15 | H | >C=NOBz | p-Phn |
| 16 | H | >C=NO(4-MeBz) | p-Phn |
| 17 | H | >C=NOCH₂COOH | p-Phn |
| 18 | Ac | >C=NOCH₂COOMe | p-Phn |
| 19 | H | >C=NOCH₂COOEt | p-Phn |
| 20 | H | >C=NOCH₂COOiPr | p-Phn |
| 21 | H | >C=NOCH₂COOtBu | p-Phn |
| 22 | Me(CH₂)₁₄CO— | >CH₂ | p-Phn |
| 23 | HOOC(CH₂)₂CO— | >CH₂ | p-Phn |
| 24 | HOOCCH=CHCO-(cis) | >CH₂ | p-Phn |
| 25 | HOOC(CH₂)₂CO— | >C=O | p-Phn |
| 26 | HOOC(CH₂)₃CO— | >CH—OH | p-Phn |
| 27 | HOOC(CH₂)₂CO— | >C=NOH | p-Phn |
| 28 | HOOC(CH₂)₂CO— | >CH₂ | 2,5-Pydi |
| 29 | HOOC(CH₂)₂CO— | >C=NOCH₂COOH | p-Phn |
| 30 | HOOC(CH₂)₂CO— | >C=NOCH₂COOH | 2,5-Pydi |

Compounds of formula (I-2):

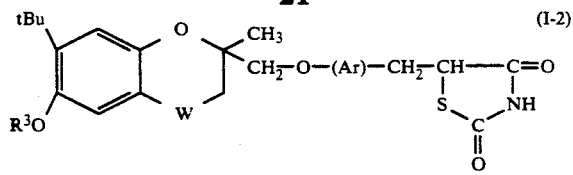
(I-2)

are as defined in Table 2:

TABLE 2

| Cpd. No. | R³ | W | Ar |
|---|---|---|---|
| 31 | H | >CH₂ | 6-Me-1,3-Phn |
| 32 | H | >C=O | 6-Me-1,3-Phn |
| 33 | H | >C=NOH | 6-Me-1,3-Phn |
| 34 | H | >CH₂ | 2,5-Pydi |
| 35 | Ac | >CH₂ | 2,5-Pydi |
| 36 | H | >C=O | 2,5-Pydi |
| 37 | Ac | >C=O | 2,5-Pydi |
| 38 | H | >C=NOH | 2,5-Pydi |
| 39 | H | >C=NOH (anti) | p-Phn |
| 40 | Ac | >C=NOAc | p-Phn |
| 41 | Boz | >C=NOBoz | p-Phn |
| 42 | 3-PyrCO | >C=NO(3-PyrCO) | p-Phn |
| 43 | H | >C=NOMe | p-Phn |
| 44 | H | >C=NOBz | p-Phn |
| 45 | H | >C=NO(2-OMeBz) | p-Phn |
| 46 | H | >C=NOCH₂COOH | p-Phn |
| 47 | H | >C=NOCH₂COOEt | p-Phn |
| 48 | H | >C=NOCH₂COOiPr | p-Phn |
| 49 | H | >C=NOCH₂COOtBu | p-Phn |
| 50 | HOOC(CH₂)₆CO— | >CH₂ | m-Phn |

Compounds of formula (I-3):

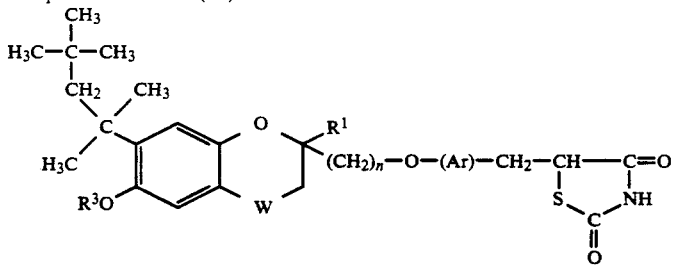
(I-3)

are as defined in Table 3:

TABLE 3

| Cpd. No. | R¹ | R³ | n | W | Ar |
|---|---|---|---|---|---|
| 51 | me | H | 1 | >CH₂ | p-Phn |
| 52 | Me | H | 1 | >C=O | p-Phn |
| 53 | Me | H | 1 | >C=NOH | p-Phn |

TABLE 3-continued

| Cpd. No. | R¹ | R³ | n | W | Ar |
|---|---|---|---|---|---|
| 54 | Me | H | 2 | >CH₂ | p-Phn |
| 55 | Me | H | 1 | >CH₂ | 6-Me-1,3-Phn |
| 56 | Me | Ac | 1 | >CH₂ | p-Phn |
| 57 | Me | Ac | 1 | >C=O | p-Phn |
| 58 | Me | H | 1 | >C=NOH | 6-Me-1,3-Phn |
| 59 | Me | H | 2 | >CH₂ | 6-Me-1,3-Phn |
| 60 | Me | H | 1 | >CH₂ | 2,5-Pydi |
| 61 | Me | H | 1 | >C=O | 2,5-Pydi |
| 62 | Me | H | 1 | >C=NOH | 2,5-Pydi |
| 63 | iPr | H | 1 | >C=O | p-Phn |
| 64 | Bz | H | 1 | >CH₂ | p-Phn |
| 65 | Bz | H | 1 | >C=NOH | p-Phn |
| 66 | Bz | H | 1 | >C=NOH | 2,5-Pydi |
| 67 | Hx | H | 1 | >CH₂ | p-Phn |
| 68 | Hx | H | 1 | >C=O | p-Phn |
| 69 | Hx | H | 1 | >C=NOH | p-Phn |
| 70 | Hx | H | 1 | >CH₂ | 2,5-Pydi |
| 71 | 3,3-DMB | H | 1 | >CH₂ | p-Phn |
| 72 | Hp | H | 1 | >CH₂ | p-Phn |
| 73 | Oc | H | 1 | >CH₂ | p-Phn |

TABLE 3-continued

| Cpd. No. | R¹ | R³ | n | W | Ar |
|---|---|---|---|---|---|
| 74 | Oc | H | 1 | >C=O | p-Phn |
| 75 | Oc | H | 1 | >C=NOH | p-Phn |
| 76 | Oc | H | 1 | >CH₂ | 2,5-Pydi |
| 77 | 5,5-DMH | H | 1 | >CH₂ | p-Phn |
| 78 | 5,5-DMH | H | 1 | >C=O | p-Phn |
| 79 | 5,5-DMH | H | 1 | >C=NOH | p-Phn |
| 80 | Dc | H | 1 | >CH₂ | p-Phn |
| 81 | Me | HOOCCH=CHCO— (trans) | 1 | >CH₂ | p-Phn |

Compounds of formula (I-4):

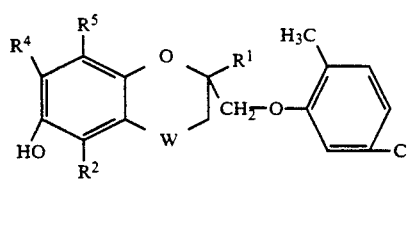

are as defined in Table 4:

TABLE 4

| Cpd. No. | R¹ | R² | R⁴ | R⁵ | W |
|---|---|---|---|---|---|
| 82 | Me | iPr | iPr | Me | >C=NOH |
| 83 | Et | Me | Me | Me | >CH₂ |
| 84 | Et | H | tBu | H | >CH₂ |
| 85 | Pr | Me | Me | Me | >CH₂ |
| 86 | iBu | Me | Me | Me | >CH₂ |
| 87 | Bz | Me | Me | Me | >CH₂ |
| 88 | 1-MeHx | H | tBu | H | >C=NOH |
| 89 | Oc | Me | Me | Me | >CH₂ |
| 90 | Oc | Me | Me | Me | >C=O |
| 91 | Oc | Me | Me | Me | >C=NOH |
| 92 | Oc | H | tBu | H | >CH₂ |
| 93 | 5,5-DMH | Me | Me | Me | >CH₂ |
| 94 | Dc | Me | Me | Me | >C=O |

Compounds of formula (I-5):

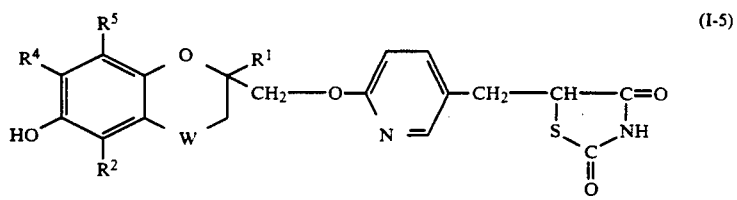

(I-5)

are as defined in Table 5:

TABLE 5

| Cpd. No. | R¹ | R² | R⁴ | R⁵ | W |
|---|---|---|---|---|---|
| 95 | Et | iPr | iPr | H | >C=O |
| 96 | Bz | Me | Me | Me | >CH₂ |
| 97 | Bz | Me | Me | Me | >C=NOH |
| 98 | 2-OMeBz | H | tBu | H | >C=NOH |
| 99 | Hx | Me | Me | Me | >CH₂ |
| 100 | Hx | Me | Me | Me | >C=O |
| 101 | Hx | Me | Me | Me | >C=NOH |
| 102 | Hx | H | tBu | H | >CH₂ |
| 103 | Hx | H | tBu | H | >C=O |
| 104 | Hx | H | tBu | H | >C=NOH |
| 105 | 3,3-DMB | H | tBu | H | >CH₂ |
| 106 | Hp | Me | Me | Me | >CH₂ |
| 107 | Hp | H | tBu | H | >CH₂ |
| 108 | Oc | Me | Me | Me | >CH₂ |
| 109 | Oc | Me | Me | Me | >C=O |
| 110 | Oc | Me | Me | Me | >C=NOH |
| 111 | 5,5-DMH | Me | Me | Me | >CH₂ |
| 112 | 5,5-DMH | Me | Me | Me | >C=NOH |
| 113 | 5,5-DMH | H | tBu | H | >CH₂ |
| 114 | Dc | Me | Me | Me | >C=NOH |

Compounds of formula (I-6):

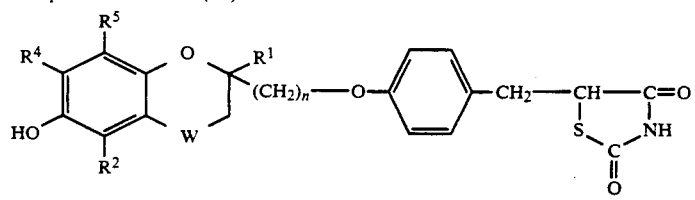

(I-6)

are as defined in Table 6:

TABLE 6

| Cpd. No. | R¹ | R² | R⁴ | R⁵ | W | n |
|---|---|---|---|---|---|---|
| 115 | iPr | H | tBu | H | >C=NOH | 1 |
| 116 | Bz | Me | Me | Me | >CH₂ | 1 |
| 117 | Bz | Me | Me | Me | >C=O | 1 |
| 118 | iBu | Me | Me | Me | >C=NOH | 1 |

TABLE 6-continued

| Cpd. No. | R¹ | R² | R⁴ | R⁵ | W | n |
|---|---|---|---|---|---|---|
| 119 | Bz | H | tBu | H | >CH₂ | 1 |
| 120 | 4-MeBz | H | Me | H | >CH—OH | 1 |
| 121 | 3-ClBz | iPr | iPr | H | >C=NOH | 1 |
| 122 | 2-PhEt | Me | Me | Me | >CH₂ | 2 |
| 123 | Hx | Me | Me | Me | >CH₂ | 1 |
| 124 | Hx | Me | Me | Me | >C=O | 1 |
| 125 | Hx | Me | Me | Me | >C=NOH | 1 |
| 126 | Hx | H | tBu | H | >CH₂ | 1 |
| 127 | Hx | H | tBu | H | >C=O | 1 |
| 128 | Hx | H | tBu | H | >C=NOH | 1 |
| 129 | 1-MePn | Me | Me | Me | >CH₂ | 1 |
| 130 | 3,3-DMB | Me | Me | Me | >CH₂ | 1 |
| 131 | 3,3-DMB | Me | Me | Me | >C=O | 1 |
| 132 | 3,3-DMB | Me | Me | Me | >C=NOH | 1 |
| 133 | 3,3-DMB | H | tBu | H | >CH₂ | 1 |
| 134 | 1-EtBu | Me | Me | Me | >CH₂ | 2 |
| 135 | 3-MePn | iPr | iPr | H | >CH—OH | 1 |
| 136 | Hp | Me | Me | Me | >CH₂ | 1 |
| 137 | Hp | Me | Me | Me | >C=O | 1 |
| 138 | Hp | Me | Me | Me | >C=NOH | 1 |
| 139 | Hp | H | tBu | H | >CH₂ | 1 |
| 140 | Hp | H | tBu | H | >C=O | 1 |
| 141 | 4,4-diMePn | Me | Me | Me | >CH₂ | 1 |
| 142 | Oc | Me | Me | Me | >CH₂ | 1 |
| 143 | Oc | Me | Me | Me | >C=O | 1 |
| 144 | Oc | Me | Me | Me | >C=NOH | 1 |
| 145 | Oc | H | tBu | H | >CH₂ | 1 |
| 146 | Oc | H | tBu | H | >C=O | 1 |
| 147 | Oc | H | tBu | H | >C=NOH | 1 |
| 148 | 5,5-DMH | Me | Me | Me | >CH₂ | 1 |
| 149 | 5,5-DMH | Me | Me | Me | >C=O | 1 |
| 150 | 5,5-DMH | Me | Me | Me | >C=NOH | 1 |
| 151 | 5,5-DMH | H | tBu | H | >CH₂ | 1 |
| 152 | 5,5-DMH | H | tBu | H | >C=O | 1 |
| 153 | 5,5-DMH | H | tBu | H | >C=NOH | 1 |
| 154 | Nn | Me | Me | Me | >CH₂ | 1 |
| 155 | Dc | Me | Me | Me | >CH₂ | 1 |
| 156 | Dc | H | tBu | H | >CH₂ | 1 |
| 157 | 1-MeNn | Me | Me | H | >CH₂ | 1 |
| 158 | 3,7-DMO | Me | Me | Me | >CH₂ | 1 |

TABLE 6-continued

| Cpd. No. | R$^1$ | R$^2$ | R$^4$ | R$^5$ | W | n |
|---|---|---|---|---|---|---|
| 159 | 3,7-DMO | Me | Me | Me | >C=O | 1 |
| 160 | 3,7-DMO | Me | Me | Me | >C=NOH | 1 |
| 161 | 3,7-DMO | H | tBu | H | >CH$_2$ | 1 |

TABLE 6-continued

| Cpd. No. | R$^1$ | R$^2$ | R$^4$ | R$^5$ | W | n |
|---|---|---|---|---|---|---|
| 162 | 3,7-DMO | H | tBu | H | >C=O | 1 |
| 163 | 7,7-DMO | Me | Me | Me | >CH$_2$ | 1 |
| 164 | 7,7-DMO | Me | Me | Me | >C=O | 1 |

Compounds of formula (I-7):

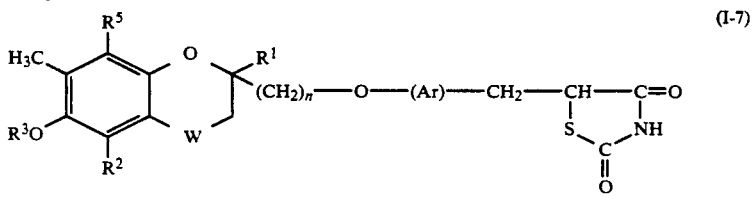

(I-7)

are as defined in Table 7:

TABLE 7

| Cpd. No. | R$^1$ | R$^2$ | R$^3$ | R$^5$ | W | Ar | n |
|---|---|---|---|---|---|---|---|
| 165 | 2-(3-OEtPh)Et | H | H | H | >C=O | 2-Me-1,4-Phn | 1 |
| 166 | Hx | Me | H | H | >CHOH | 3-Me-1,4-Phn | 1 |
| 167 | Oc | Me | Ac | Me | >CH$_2$ | p-Phn | 1 |
| 168 | Oc | Me | Ac | Me | >C=O | p-Phn | 1 |
| 169 | 5,5-DMH | Me | Ac | Me | >CH$_2$ | 2,5-Pydi | 1 |
| 170 | 3,7-DMO | Me | Ac | Me | >C=O | p-Phn | 1 |
| 171 | 7,7-DMO | Me | Ac | Me | >C=O | p-Phn | 1 |
| 172 | Pr | Me | EtOOC(CH$_2$)$_2$CO— | Me | >CH$_2$ | p-Phn | 1 |
| 173 | Oc | Me | HOOC(CH$_2$)$_4$CO— | Me | >CH$_2$ | p-Phn | 2 |

Compounds of formula (I-8):

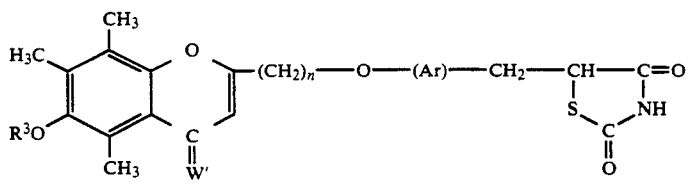

are as defined in Table 8:

TABLE 8

| Cpd. No. | R³ | W' | Ar | n |
|---|---|---|---|---|
| 174 | H | O | p-Phn | 1 |
| 175 | Ac | O | p-Phn | 1 |
| 176 | H | O | p-Phn | 2 |
| 177 | Ac | O | p-Phn | 2 |
| 178 | H | O | p-Phn | 3 |
| 179 | Ac | O | p-Phn | 3 |
| 180 | Boz | O | p-Phn | 1 |
| 181 | H | NOH | p-Phn | 1 |
| 182 | Ac | NOAc | p-Phn | 1 |
| 183 | H | NOH | p-Phn | 2 |
| 184 | H | NOH | p-Phn | 3 |
| 185 | H | O | 6-Me-1,3-Phn | 1 |
| 186 | Ac | O | 6-Me-1,3-Phn | 1 |
| 187 | H | O | 6-Me-1,3-Phn | 2 |
| 188 | H | NOH | 6-Me-1,3-Phn | 1 |
| 189 | Ac | NOAc | 6-Me-1,3-Phn | 1 |
| 190 | H | O | 2,5-Pydi | 1 |
| 191 | Ac | O | 2,5-Pydi | 1 |
| 192 | H | O | 2,5-Pydi | 2 |
| 193 | H | NOH | 2,5-Pydi | 1 |
| 194 | HOOC(CH₂)₂CO— | O | p-Phn | 1 |
| 195 | HOOCCH=CHCO-(cis) | O | p-Phn | 1 |
| 196 | HOOCCH=CHCO-(trans) | O | 2,5-Pydi | 1 |
| 197 | HOOC(CH₂)₂CO— | O | p-Phn | 2 |
| 198 | HOOC(CH₂)₂CO— | NOH | p-Phn | 1 |
| 199 | HOOC(CH₂)₂CO— | NOCH₂COOH | p-Phn | 1 |
| 200 | HOOC(CH₂)₂CO— | NOCH₂COOH | 2,5-Pydi | 1 |
| 201 | HOOC(CH₂)₂CO— | NOCH₂COOtBu | p-Phn | 1 |
| 202 | EtOOC(CH₂)₆CO— | NOCH₂COOEt | p-Phn | 1 |

Compounds of formula (I-9):

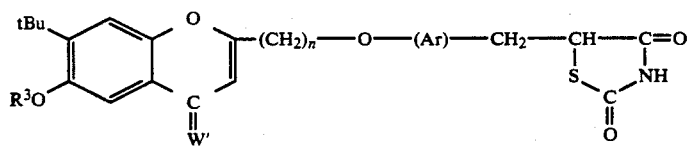

are as defined in Table 9:

TABLE 9

| Cpd. No. | R³ | W' | Ar | n |
|---|---|---|---|---|
| 203 | H | O | p-Phn | 1 |
| 204 | Ac | O | p-Phn | 1 |
| 205 | H | O | p-Phn | 2 |
| 206 | Ac | O | p-Phn | 2 |
| 207 | H | NOH | p-Phn | 1 |
| 208 | H | O | 6-Me-1,3-Phn | 1 |
| 209 | Ac | O | 6-Me-1,3-Phn | 1 |
| 210 | H | O | 2,5-Pydi | 1 |
| 211 | Ac | O | 2,5-Pydi | 1 |
| 212 | Ac | NOH | 2,5-Pydi | 1 |
| 213 | HOOC(CH₂)₂CO— | O | p-Phn | 1 |

Compounds of formula (I-10):

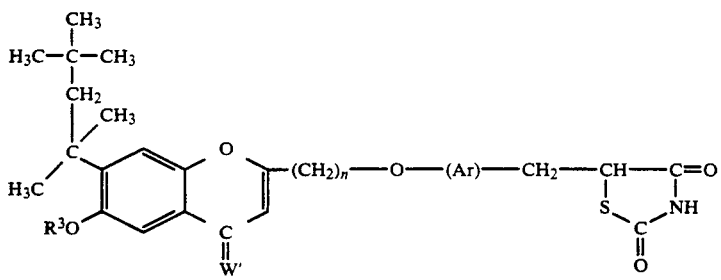
(I-10)

are as defined in Table 10:

TABLE 10

| Cpd. No. | $R^3$ | W' | Ar | $n$ |
|---|---|---|---|---|
| 214 | H | O | p-Phn | 1 |
| 215 | Ac | O | p-Phn | 1 |
| 216 | Ac | NOH | p-Phn | 1 |
| 217 | H | NOH | p-Phn | 2 |
| 218 | H | O | 6-Me-1,3-Phn | 1 |
| 219 | Ac | O | 6-Me-1,3-Phn | 1 |
| 220 | H | O | 6-Me-1,3-Phn | 2 |
| 221 | H | NOH | 6-Me-1,3-Phn | 1 |
| 222 | H | O | 2,5-Pydi | 1 |
| 223 | HOOC(CH$_2$)$_2$CO— | O | p-Phn | 1 |
| 224 | HOOC(CH$_2$)$_2$CO— | NOCH$_2$COOH | 2,5-Pydi | 1 |

Compounds of formula (I-11):

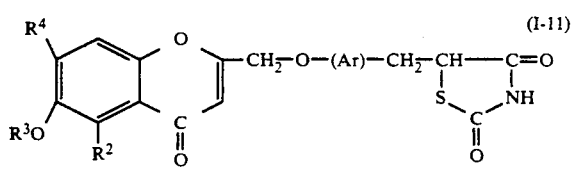
(I-11)

are as defined in Table 11:

TABLE 11

| Cpd. No. | $R^2$ | $R^3$ | $R^4$ | Ar |
|---|---|---|---|---|
| 225 | iPr | H | iPr | p-Phn |
| 226 | Me | EtOOC(CH$_2$)$_4$CO— | Me | 6-Me-1,3-Phn |

Compounds of formula (I-12):

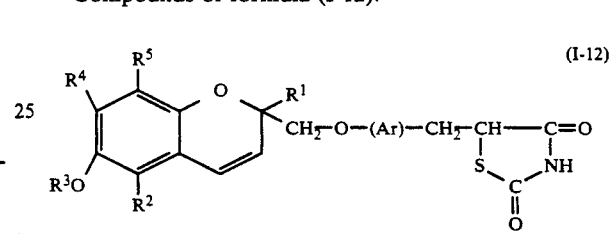
(I-12)

are as defined in Table 12:

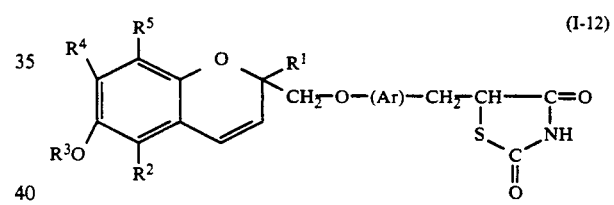
(I-12)

TABLE 12

| Cpd. No. | $R^1$ | $R^2$ | $R^3$ | $R^4$ | $R^5$ | Ar |
|---|---|---|---|---|---|---|
| 227 | Me | Me | H | Me | Me | p-Phn |
| 228 | Me | Me | Ac | Me | Me | p-Phn |
| 229 | Me | Me | Boz | Me | Me | p-Phn |
| 230 | Me | Me | H | Me | Me | 6-Me-1,3-Phn |
| 231 | Me | Me | Ac | Me | Me | 6-Me-1,3-Phn |
| 232 | Me | Me | H | Me | Me | 2,5-Pydi |
| 233 | Me | Me | Ac | Me | Me | 2,5-Pydi |
| 234 | Me | H | H | tBu | H | p-Phn |
| 235 | Me | H | Ac | tBu | H | p-Phn |
| 236 | Me | H | H | tBu | H | 6-Me-1,3-Phn |
| 237 | Me | H | Ac | tBu | H | 6-Me-1,3-Phn |
| 238 | Me | H | H | tBu | H | 2,5-Pydi |
| 239 | Me | H | Ac | tBu | H | 2,5-Pydi |
| 240 | Me | iPr | H | iPr | H | p-Phn |
| 241 | Me | H | H | TMB | H | p-Phn |
| 242 | Me | H | H | TMB | H | 6-Me-1,3-Phn |
| 243 | Me | H | H | TMB | H | 2,5-Pydi |
| 244 | Et | Me | H | Me | Me | p-Phn |
| 245 | Pr | H | H | tBu | H | p-Phn |
| 246 | Pr | H | Ac | tBu | H | p-Phn |
| 247 | iPr | H | H | TMB | H | p-Phn |
| 248 | iBu | Me | H | Me | Me | p-Phn |
| 249 | iBu | Me | Ac | Me | Me | p-Phn |
| 250 | Bu | H | H | tBu | H | p-Phn |
| 251 | iBu | H | H | TMB | H | p-Phn |
| 252 | nPn | Me | H | Me | Me | p-Phn |
| 253 | iPn | H | H | tBu | H | p-Phn |
| 254 | Pn | H | H | TMB | H | 2,5-Pydi |
| 255 | Hx | Me | H | Me | Me | p-Phn |

TABLE 12-continued

| Cpd. No. | R¹ | R² | R³ | R⁴ | R⁵ | Ar |
|---|---|---|---|---|---|---|
| 256 | Oc | Me | H | Me | Me | p-Phn |
| 257 | Dc | Me | H | Me | Me | p-Phn |
| 258 | 3,7-DMO | H | H | tBu | H | p-Phn |
| 259 | 7,7-DMO | H | H | tBu | H | 6-Me-1,3-Phn |
| 260 | 3,7-DMO | H | H | tBu | H | 2,5-Pydi |
| 261 | 7,7-DMO | H | H | TMB | H | p-Phn |
| 262 | Bz | H | H | TMB | H | p-Phn |
| 263 | Me | Me | HOOC(CH₂)₂CO— | Me | Me | p-Phn |
| 264 | Me | H | HOOC(CH₂)₂CO— | tBu | H | p-Phn |
| 265 | Me | H | HOOC(CH₂)₂CO— | TMB | H | p-Phn |

Compounds of formula (I-13):

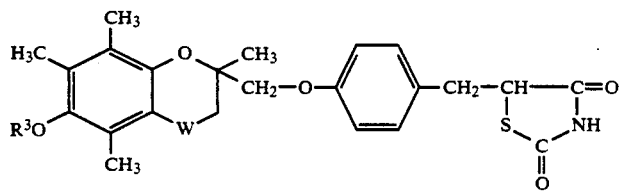

(I-13)

are as defined in Table 13:

TABLE 13

| Cpd. No. | R³ | W |
|---|---|---|
| 266 | Et | >CH₂ |
| 267 | iPr | >C=NOH |
| 268 | Me | >C=NOCMe₂COOH |
| 269 | Pn | >C=NOCH₂COOH |

TABLE 13-continued

| Cpd. No. | R³ | W |
|---|---|---|
| 270 | 2-HOEt | >CH₂ |
| 271 | 2-HOEt | >C=NOCMe₂COOH |
| 272 | 5-AcOPn | >C=NOH |
| 273 | 2-HOEt | >C=NOCH₂COOH |

Compounds of formulae (I-14), (I-15), (I-16) and (I-17):

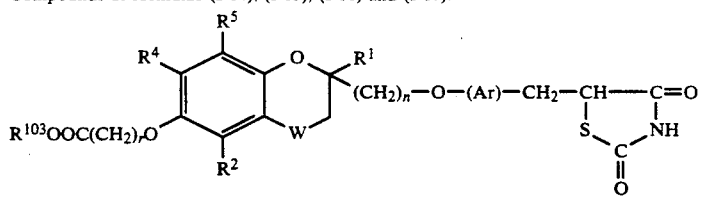

(I-14)

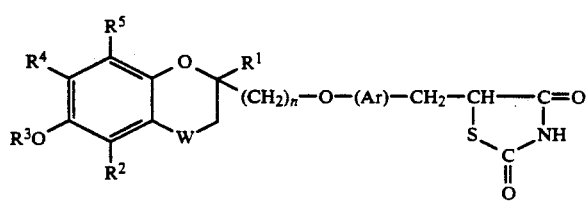

(I-15)

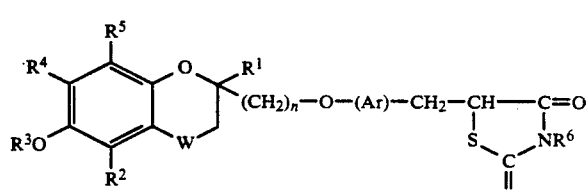

(I-16)

-continued

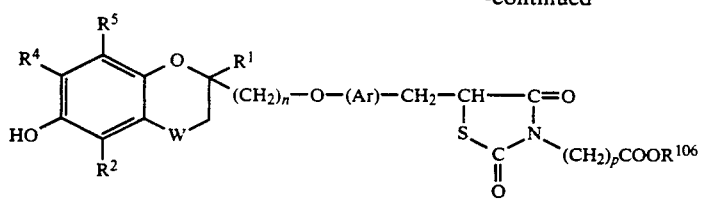
(I-17)

are as defined in Tables 14, 15, 16 and 17, respectively:

TABLE 14

| Cpd. No. | $R^1$ | $R^2$ | $R^4$ | $R^5$ | $R^{103}$ | W | Ar | n | r |
|---|---|---|---|---|---|---|---|---|---|
| 274 | Me | Me | Me | Me | H | >CH$_2$ | p-Phn | 1 | 1 |
| 275 | Me | Me | Me | Me | Me | >CH$_2$ | p-Phn | 1 | 1 |
| 276 | Me | Me | Me | Me | Et | >CH$_2$ | p-Phn | 1 | 1 |
| 277 | Me | Me | Me | Me | tBu | >CH$_2$ | p-Phn | 1 | 1 |
| 278 | Me | Me | Me | Me | H | >C=O | p-Phn | 1 | 1 |
| 279 | Me | Me | Me | Me | Me | >C=O | p-Phn | 1 | 1 |
| 280 | Me | Me | Me | Me | Et | >C=O | p-Phn | 1 | 1 |
| 281 | Me | Me | Me | Me | iPr | >C=O | p-Phn | 1 | 1 |
| 282 | Me | Me | Me | Me | tBu | >C=O | p-Phn | 1 | 1 |
| 283 | Me | Me | Me | Me | H | >CH—OH | p-Phn | 1 | 1 |
| 284 | Me | Me | Me | Me | H | >C=NOH | p-Phn | 1 | 1 |
| 285 | Me | Me | Me | Me | Et | >C=NOH | p-Phn | 1 | 1 |
| 286 | Me | Me | Me | Me | tBu | >C=NOH | p-Phn | 1 | 1 |
| 287 | Me | Me | Me | Me | H | >C=NOCH$_2$COOH | p-Phn | 1 | 1 |
| 288 | Me | Me | Me | Me | Et | >C=NOCH$_2$COOEt | p-Phn | 1 | 1 |
| 289 | Me | Me | Me | Me | tBu | >C=NOCH$_2$COOtBu | p-Phn | 1 | 1 |

TABLE 14-continued

| Cpd. No. | R¹ | R² | R⁴ | R⁵ | R¹⁰³ | W | Ar | n | r |
|---|---|---|---|---|---|---|---|---|---|
| 290 | Me | Me | Me | Me | H | >C=NOCMe₂COOH | p-Phn | 1 | 1 |
| 291 | Me | Me | Me | Me | H | >C=NOH | p-Phn | 2 | 1 |
| 292 | Me | Me | Me | Me | H | >CH₂ | p-Phn | 1 | 2 |
| 293 | Me | Me | Me | Me | H | >CH₂ | m-Phn | 1 | 1 |
| 294 | Me | Me | Me | Me | H | >CH₂ | 2,5-Pydi | 1 | 1 |
| 295 | Me | Me | Me | Me | H | >C=O | 2,5-Pydi | 1 | 2 |
| 296 | Me | Me | Me | Me | H | >C=NOCH₂COOH | p-Phn | 2 | 2 |
| 297 | Me | Me | Me | Me | H | >C=NOH | 2,5-Pydi | 1 | 1 |
| 298 | Me | Me | Me | Me | H | >CH—OH | 2,5-Pydi | 3 | 3 |
| 299 | Me | Me | Me | Me | H | >C=NO(CH₂)₂COOH | p-Phn | 1 | 1 |
| 300 | Me | Me | Me | Me | H | >C=NO(CH₂)₃COOH | p-Phn | 1 | 1 |
| 301 | Me | H | tBu | H | H | >CH₂ | p-Phn | 1 | 1 |
| 302 | Me | H | tBu | H | Et | >CH₂ | p-Phn | 1 | 1 |
| 303 | Me | H | tBu | H | t-Bu | >CH₂ | p-Phn | 1 | 1 |
| 304 | Me | H | tBu | H | H | >C=O | p-Phn | 1 | 1 |
| 305 | Me | H | tBu | H | H | >C=NOH | p-Phn | 1 | 1 |
| 306 | Me | H | tBu | H | Et | >C=NOH | p-Phn | 1 | 1 |
| 307 | Me | H | tBu | H | H | >C=NOCH₂COOH | p-Phn | 1 | 1 |
| 308 | Me | H | tBu | H | H | >C=NOCMe₂COOH | p-Phn | 1 | 1 |
| 309 | Me | H | tBu | H | H | >CH₂ | 2,5-Pydi | 1 | 1 |

TABLE 14-continued

| Cpd. No. | R$^1$ | R$^2$ | R$^4$ | R$^5$ | R$^{103}$ | W | Ar | n | r |
|---|---|---|---|---|---|---|---|---|---|
| 310 | Me | H | tBu | H | H | >C=NOH | 2,5-Pydi | 1 | 1 |
| 311 | Me | H | tBu | H | H | >C=NOCH$_2$COOH | 2,5-Pydi | 1 | 1 |
| 312 | Et | iPr | iPr | H | Me | >C=NO(CH$_2$)$_3$COOH | p-Phn | 1 | 1 |
| 313 | Pr | H | Me | H | H | >CH$_2$ | p-Phn | 1 | 1 |
| 314 | iPr | H | tBu | H | H | >C=NOH | m-Phn | 1 | 1 |
| 315 | iBu | Me | Me | Me | H | >CH$_2$ | p-Phn | 1 | 1 |
| 316 | iBu | Me | Me | Me | H | >C=NOH | p-Phn | 1 | 1 |
| 317 | Oc | Me | Me | Me | H | >CH$_2$ | p-Phn | 1 | 1 |
| 318 | Oc | Me | Me | Me | H | >C=NOCH$_2$COOH | 2,5-Pydi | 2 | 1 |
| 319 | Me | Me | MeO | MeO | H | >CH$_2$ | p-Phn | 1 | 1 |
| 320 | Me | Me | MeO | MeO | H | >C=NOH | p-Phn | 1 | 1 |
| 321 | Me | H | TMB | H | H | >CH$_2$ | p-Phn | 1 | 1 |
| 322 | Me | H | TMB | H | H | >C=O | p-Phn | 1 | 1 |
| 323 | Me | H | TMB | H | H | >C=NOH | p-Phn | 1 | 1 |
| 324 | Me | H | TMB | H | H | >C=NOCH$_2$COOH | p-Phn | 1 | 1 |
| 325 | Bu | H | TMB | H | H | >CH$_2$ | 2,5-Pydi | 1 | 3 |
| 326 | 5,5-DMH | Me | Me | Me | H | >CH$_2$ | p-Phn | 1 | 1 |
| 327 | Me | Me | Me | Me | Et | >CH$_2$ | p-Phn | 1 | 5 |
| 328 | Me | Me | Me | Me | H | >C=NOBz | p-Phn | 1 | 1 |

TABLE 14

| Cpd. No. | R$^1$ | R$^2$ | R$^4$ | R$^5$ | R$^{103}$ | W | Ar | n | r |
|---|---|---|---|---|---|---|---|---|---|
| 274 | Me | Me | Me | Me | H | >CH$_2$ | p-Phn | 1 | 1 |
| 275 | Me | Me | Me | Me | Me | >CH$_2$ | p-Phn | 1 | 1 |
| 276 | Me | Me | Me | Me | Et | >CH$_2$ | p-Phn | 1 | 1 |
| 277 | Me | Me | Me | Me | tBu | >CH$_2$ | p-Phn | 1 | 1 |
| 278 | Me | Me | Me | Me | H | >C=O | p-Phn | 1 | 1 |
| 279 | Me | Me | Me | Me | Me | >C=O | p-Phn | 1 | 1 |
| 280 | Me | Me | Me | Me | Et | >C=O | p-Phn | 1 | 1 |
| 281 | Me | Me | Me | Me | iPr | >C=O | p-Phn | 1 | 1 |
| 282 | Me | Me | Me | Me | tBu | >C=O | p-Phn | 1 | 1 |
| 283 | Me | Me | Me | Me | H | >CH—OH | p-Phn | 1 | 1 |
| 284 | Me | Me | Me | Me | H | >C=NOH | p-Phn | 1 | 1 |
| 285 | Me | Me | Me | Me | Et | >C=NOH | p-Phn | 1 | 1 |
| 286 | Me | Me | Me | Me | tBu | >C=NOH | p-Phn | 1 | 1 |
| 287 | Me | Me | Me | Me | H | >C=NOCH$_2$COOH | p-Phn | 1 | 1 |
| 288 | Me | Me | Me | Me | Et | >C=NOCH$_2$COOEt | p-Phn | 1 | 1 |
| 289 | Me | Me | Me | Me | tBu | >C=NOCH$_2$COOtBu | p-Phn | 1 | 1 |
| 290 | Me | Me | Me | Me | H | >C=NOCMe$_2$COOH | p-Phn | 1 | 1 |
| 291 | Me | Me | Me | Me | H | >C=NOH | p-Phn | 2 | 1 |
| 292 | Me | Me | Me | Me | H | >CH$_2$ | p-Phn | 1 | 2 |
| 293 | Me | Me | Me | Me | H | >CH$_2$ | m-Phn | 1 | 1 |

TABLE 14-continued

| Cpd. No. | R¹ | R² | R⁴ | R⁵ | R¹⁰³ | W | Ar | n | r |
|---|---|---|---|---|---|---|---|---|---|
| 294 | Me | Me | Me | Me | H | >CH₂ | 2,5-Pydi | 1 | 1 |
| 295 | Me | Me | Me | Me | H | >C=O | 2,5-Pydi | 1 | 2 |
| 296 | Me | Me | Me | Me | H | >C=NOCH₂COOH | p-Phn | 2 | 2 |
| 297 | Me | Me | Me | Me | H | >C=NOH | 2,5-Pydi | 1 | 1 |
| 298 | Me | Me | Me | Me | H | >CH—OH | 2,5-Pydi | 3 | 3 |
| 299 | Me | Me | Me | Me | H | >C=NO(CH₂)₂COOH | p-Phn | 1 | 1 |
| 300 | Me | Me | Me | Me | H | >C=NO(CH₂)₃COOH | p-Phn | 1 | 1 |
| 301 | Me | H | tBu | H | H | >CH₂ | p-Phn | 1 | 1 |
| 302 | Me | H | tBu | H | Et | >CH₂ | p-Phn | 1 | 1 |
| 303 | Me | H | tBu | H | t-Bu | >CH₂ | p-Phn | 1 | 1 |
| 304 | Me | H | tBu | H | H | >C=O | p-Phn | 1 | 1 |
| 305 | Me | H | tBu | H | H | >C=NOH | p-Phn | 1 | 1 |
| 306 | Me | H | tBu | H | Et | >C=NOH | p-Phn | 1 | 1 |
| 307 | Me | H | tBu | H | H | >C=NOCH₂COOH | p-Phn | 1 | 1 |
| 308 | Me | H | tBu | H | H | >C=NOCMe₂COOH | p-Phn | 1 | 1 |
| 309 | Me | H | tBu | H | H | >CH₂ | 2,5-Pydi | 1 | 1 |
| 310 | Me | H | tBu | H | H | >C=NOH | 2,5-Pydi | 1 | 1 |
| 311 | Me | H | tBu | H | H | >C=NOCH₂COOH | 2,5-Pydi | 1 | 1 |
| 312 | Et | iPr | iPr | H | Me | >C=NO(CH₂)₃COOH | p-Phn | 1 | 1 |
| 313 | Pr | H | Me | H | H | >CH₂ | p-Phn | 1 | 1 |

TABLE 14-continued

| Cpd. No. | R$^1$ | R$^2$ | R$^4$ | R$^5$ | R$^{103}$ | W | Ar | n | r |
|---|---|---|---|---|---|---|---|---|---|
| 314 | iPr | H | tBu | H | H | >C=NOH | m-Phn | 1 | 1 |
| 315 | iBu | Me | Me | Me | H | >CH$_2$ | p-Phn | 1 | 1 |
| 316 | iBu | Me | Me | Me | H | >C=NOH | p-Phn | 1 | 1 |
| 317 | Oc | Me | Me | Me | H | >CH$_2$ | p-Phn | 1 | 1 |
| 318 | Oc | Me | Me | Me | H | >C=NOCH$_2$COOH | 2,5-Pydi | 2 | 1 |
| 319 | Me | Me | MeO | MeO | H | >CH$_2$ | p-Phn | 1 | 1 |
| 320 | Me | Me | MeO | MeO | H | >C=NOH | p-Phn | 1 | 1 |
| 321 | Me | H | TMB | H | H | >CH$_2$ | p-Phn | 1 | 1 |
| 322 | Me | H | TMB | H | H | >C=O | p-Phn | 1 | 1 |
| 323 | Me | H | TMB | H | H | >C=NOH | p-Phn | 1 | 1 |
| 324 | Me | H | TMB | H | H | >C=NOCH$_2$COOH | p-Phn | 1 | 1 |
| 325 | Bu | H | TMB | H | H | >CH$_2$ | 2,5-Pydi | 1 | 3 |
| 326 | 5,5-DMH | Me | Me | Me | H | >CH$_2$ | p-Phn | 1 | 1 |
| 327 | Me | Me | Me | Me | Et | >CH$_2$ | p-Phn | 1 | 5 |
| 328 | Me | Me | Me | Me | H | >C=NOBz | p-Phn | 1 | 1 |

TABLE 15

| Cpd. No. | R$^1$ | R$^2$ | R$^3$ | R$^4$ | R$^5$ | W | Ar | n |
|---|---|---|---|---|---|---|---|---|
| 329 | Me | H | HO(CH$_2$)$_2$OCOCH$_2$— | TMB | H | >CH$_2$ | p-Phn | 1 |
| 330 | Pr | H | HO(CH$_2$)$_2$OCOCH$_2$— | tBu | H | >C=O | p-Phn | 1 |
| 331 | Et | H | HO(CH$_2$)$_3$OCOCH$_2$— | Me | H | >C=NOH | p-Phn | 1 |

TABLE 15-continued

| Cpd. No. | R¹ | R² | R³ | R⁴ | R⁵ | W | Ar | n |
|---|---|---|---|---|---|---|---|---|
| 332 | Me | Me | HO(CH₂)₅OCOCH₂— | Me | Me | >C=NOCH₂COOH | p-Phn | 1 |
| 333 | Me | Me | MeO(CH₂)₂OCOCH₂— | Me | Me | >CH₂ | p-Phn | 1 |
| 334 | Me | Me | MeO(CH₂)₂OCOCH₂— | Me | Me | >C=O | p-Phn | 1 |
| 335 | Me | Me | MeO(CH₂)₂OCOCH₂— | Me | Me | >C=NOH | p-Phn | 1 |
| 336 | Me | Me | MeO(CH₂)₂OCOCH₂— | Me | Me | >C=NOCH₂COOH | p-Phn | 1 |
| 337 | Me | H | MeO(CH₂)₂OCOCH₂— | tBu | H | >CH₂ | p-Phn | 1 |
| 338 | Me | H | MeO(CH₂)₂OCOCH₂— | tBu | H | >C=O | p-Phn | 1 |
| 339 | Me | H | MeO(CH₂)₂OCOCH₂— | TMB | H | >CH₂ | p-Phn | 1 |
| 340 | Me | H | MeO(CH₂)₂OCOCH₂— | TMB | H | >C=O | p-Phn | 1 |
| 341 | Me | Me | MeO(CH₂)₂OCOCH₂— | Me | Me | >CH—OH | p-Phn | 1 |
| 342 | Me | Me | MeO(CH₂)₂OCOCH₂— | Me | Me | >C=NOH | 6-Me-1,3-Phn | 1 |
| 343 | 3,3-DMB | Me | EtO(CH₂)₂OCOCH₂— | Me | Me | >CHOAc | p-Phn | 1 |
| 344 | Me | H | iPrO(CH₂)₃OCOCH₂— | Me | H | >C=NOCH₂COOEt | p-Phn | 1 |
| 345 | 5,5-DMH | H | MeO—(CH₂)₅OCOCH₂— | iPr | H | >C=NOCH₂COOH | p-Phn | 1 |
| 346 | Me | Me | AcO—(CH₂)₂O—CO—CH₂— | Me | Me | >CH₂ | 2,5-Pydi | 2 |
| 347 | Bz | Me | BozO(CH₂)₂OCOCH₂— | Me | Me | >C=O | p-Phn | 1 |
| 348 | Me | Me | MeO(CH₂)₂OCO(CH₂)₂— | MeO | MeO | >CH₂ | p-Phn | 1 |
| 349 | 7,7-DMO | Me | MeO(CH₂)₂OCO(CH₂)₃— | Me | Me | >C=O | 6-Me-1,3-Phn | 1 |
| 350 | Me | Me | MeO(CH₂)₂OCO(CH₂)₅— | Me | Me | >CH₂ | p-Phn | 3 |
| 351 | Me | Me | MeOOC—CH(Me)— | Me | Me | >CH₂ | p-Phn | 1 |

TABLE 15-continued

| Cpd. No. | R¹ | R² | R³ | R⁴ | R⁵ | W | Ar | n |
|---|---|---|---|---|---|---|---|---|
| 352 | Me | Me | MeOOC—CH(Me)CH₂— | Me | Me | >C=NOH | p-Phn | 1 |
| 353 | Me | Me | MeOOC—CMe₂— | Me | Me | >CH₂ | p-Phn | 1 |
| 354 | Me | Me | EtOOC—CMe₂— | Me | Me | >CH₂ | p-Phn | 1 |
| 355 | Me | Me | EtOOC—CMe₂— | Me | Me | >C=O | p-Phn | 1 |
| 356 | Me | Me | EtOOC—CMe₂— | Me | Me | >C=NOH | p-Phn | 1 |
| 357 | Me | Me | EtOOC—CMe₂— | Me | Me | >C=NOCH₂COOH | p-Phn | 1 |
| 358 | Me | Me | EtOOC—CMe₂— | Me | Me | >C=NOCH₂COOEt | p-Phn | 1 |
| 359 | Me | H | EtOOC—CMe₂— | tBu | H | >CH₂ | p-Phn | 1 |
| 360 | Me | H | EtOOC—CMe₂— | tBu | H | >C=O | p-Phn | 1 |
| 361 | Me | H | EtOOC—CMe₂— | tBu | H | >C=NOH | p-Phn | 1 |
| 362 | Me | H | EtOOC—CMe₂— | tBu | H | >C=NOCH₂COOH | p-Phn | 1 |
| 363 | Me | H | EtOOC—CMe₂— | tBu | H | >C=NOCH₂COOEt | p-Phn | 1 |
| 364 | Me | Me | EtOOC—CMe₂— | Me | Me | >C=NOCMe₂COOEt | p-Phn | 1 |
| 365 | Me | Me | HOOC—CMe₂— | Me | Me | >CH₂ | p-Phn | 1 |
| 366 | Me | Me | HOOC—CMe₂— | Me | Me | >C=O | p-Phn | 1 |
| 367 | Me | Me | HOOC—CMe₂— | Me | Me | >C=NOH | p-Phn | 1 |
| 368 | Me | Me | HOOC—CMe₂— | Me | Me | >C=NOCH₂COOH | p-Phn | 1 |
| 369 | Me | Me | HOOC—CMe₂— | Me | Me | >C=NO(CH₂)₂COOH | p-Phn | 1 |
| 370 | Me | Me | HOOC—CMe₂— | Me | Me | >C=NOCMe₂COOH | p-Phn | 1 |
| 371 | Me | H | HOOC—CMe₂— | tBu | H | >CH₂ | p-Phn | 1 |

TABLE 15-continued

| Cpd. No. | R¹ | R² | R³ | R⁴ | R⁵ | W | Ar | n |
|---|---|---|---|---|---|---|---|---|
| 372 | Me | H | HOOC—CMe$_2$— | tBu | H | >C=O | p-Phn | 1 |
| 373 | Me | H | HOOC—CMe$_2$— | tBu | H | >C=NOH | p-Phn | 1 |
| 374 | Me | H | HOOC—CMe$_2$— | TMB | H | >CH$_2$ | p-Phn | 1 |
| 375 | Me | H | HOOC—CMe$_2$— | TMB | H | >C=NOCH$_2$COOH | p-Phn | 1 |
| 376 | Me | Me | H$_2$NCOCH$_2$— | Me | Me | >C=O | p-Phn | 1 |
| 377 | Me | Me | MeNHCOCH$_2$— | Me | Me | >C=NOH | p-Phn | 1 |
| 378 | Me | H | Me$_2$NCOCH$_2$— | tBu | H | >CH$_2$ | p-Phn | 1 |
| 379 | Me | Me | Et(Me)NCOCH$_2$— | Me | Me | >C=NOBoz | p-Phn | 1 |
| 380 | Me | Me | MorCOCH$_2$— | Me | Me | >C=NOCMe$_2$COOH | p-Phn | 1 |
| 381 | Me | Me | 1-PipCOCH$_2$— | Me | Me | >C=NOCH$_2$COOH | p-Phn | 1 |
| 382 | Me | Me | 1-PylCOCH$_2$— | Me | Me | >C=NOBz | 6-Me-1,3-Phn | 1 |
| 383 | Me | H | 1-PizCOCH$_2$— | TMB | H | >CH$_2$ | p-Phn | 1 |
| 384 | Me | Me | 4-Me-1-PizCOCH$_2$— | Me | Me | >CH$_2$ | p-Phn | 1 |
| 385 | Me | Me | Me$_2$NCOCH$_2$CH$_2$— | Me | Me | >CH$_2$ | p-Phn | 2 |
| 386 | Me | Me | Me$_2$NCO—CMe$_2$— | Me | Me | >C=O | p-Phn | 1 |
| 387 | Me | Me | Me$_2$NCO(CH$_2$)$_5$— | Me | Me | >C=NOH | p-Phn | 1 |

TABLE 16

| Cpd. No. | R¹ | R² | R³ | R⁴ | R⁵ | R⁶ | W | Ar | n |
|---|---|---|---|---|---|---|---|---|---|
| 388 | Me | Me | HOOC—CH$_2$— | Me | Me | Oc | >C=NOH | p-Phn | 1 |
| 389 | Me | H | EtOOC—CH$_2$— | Me | H | 5,5-DMH | >C=O | p-Phn | 3 |

TABLE 16-continued

| Cpd. No. | R¹ | R² | R³ | R⁴ | R⁵ | R⁶ | W | Ar | n |
|---|---|---|---|---|---|---|---|---|---|
| 390 | Me | Me | MeOCH₂CH₂OCOCH₂— | Me | Me | Me | >C=NOCH₂COOH | p-Phn | 1 |
| 391 | Me | Me | AcOCH₂CH₂OCOCH₂— | MeO | MeO | 2-MeOEt | >C=NOH | 2,5-Pydi | 2 |
| 392 | Me | Me | HOOC—CMe₂ | Me | Me | Bu | >CH₂ | 5-Me-1,3-Phn | 1 |
| 393 | Me | H | HOOC—CH₂CH₂— | TMB | H | 3,3-DMB | >C=NOCMe₂COOH | p-Phn | 1 |
| 394 | Me | Me | H₂NCOCH₂— | Me | Me | Dc | >CH₂ | p-Phn | 1 |
| 395 | 7,7-DMO | H | Et(Me)NCOCH₂— | tBu | H | iBu | >C=NOCH₂COOEt | p-Phn | 1 |
| 396 | Me | Me | H | Me | Me | Et | >CH₂ | p-Phn | 1 |
| 397 | 3,3-DMB | H | Me | TMB | H | Pr | >C=NOCMe₂COOH | p-Phn | 1 |
| 398 | Me | Me | Ac | Me | Me | iPr | >C=NOH | p-Phn | 1 |
| 399 | Me | H | Me | tBu | H | Bu | >C=NOCH₂COOH | p-Phn | 1 |
| 400 | Me | Me | H | Me | Me | 2-OHEt | >CH₂ | p-Phn | 1 |

TABLE 17

| Cpd. No. | R¹ | R² | R⁴ | R⁵ | R¹⁰⁶ | W | Ar | n | p |
|---|---|---|---|---|---|---|---|---|---|
| 401 | Me | Me | Me | Me | H | >CH₂ | p-Phn | 1 | 1 |
| 402 | Me | Me | Me | Me | Me | >CH₂ | p-Phn | 1 | 1 |
| 403 | Me | Me | Me | Me | Et | >CH₂ | p-Phn | 1 | 1 |
| 404 | Me | Me | Me | Me | tBu | >CH₂ | p-Phn | 1 | 1 |
| 405 | Me | Me | Me | Me | H | >C=O | p-Phn | 1 | 1 |
| 406 | Me | Me | Me | Me | Me | >C=O | p-Phn | 1 | 1 |
| 407 | Me | Me | Me | Me | iPr | >C=O | p-Phn | 1 | 1 |

TABLE 17-continued

| Cpd No. | R¹ | R² | R⁴ | R⁵ | R¹⁰⁶ | W | Ar | n | p |
|---|---|---|---|---|---|---|---|---|---|
| 408 | Me | Me | Me | Me | tBu | >C=O | p-Phn | 1 | 1 |
| 409 | Me | Me | Me | Me | H | >CHOH | p-Phn | 1 | 1 |
| 410 | Me | Me | Me | Me | H | >C=NOH | p-Phn | 1 | 1 |
| 411 | Me | Me | Me | Me | tBu | >C=NOH | p-Phn | 1 | 1 |
| 412 | Me | Me | Me | Me | H | >C=NOCH₂COOH | p-Phn | 1 | 1 |
| 413 | Me | Me | Me | Me | H | >C=NOCH₂COOEt | p-Phn | 1 | 1 |
| 414 | Me | Me | Me | Me | tBu | >C=NOCH₂COOt-Bu | p-Phn | 1 | 1 |
| 415 | Me | Me | Me | Me | H | >C=NOH | p-Phn | 2 | 1 |
| 416 | Me | Me | Me | Me | H | >CH₂ | p-Phn | 1 | 2 |
| 417 | Me | Me | Me | Me | H | >CH₂ | m-Phn | 1 | 1 |
| 418 | Me | Me | Me | Me | H | >CH₂ | 2,5-Pydi | 1 | 1 |
| 419 | Me | Me | Me | Me | H | >C=O | 2,5-Pydi | 1 | 2 |
| 420 | Me | Me | Me | Me | H | >C=NOCH₂COOH | p-Phn | 2 | 2 |
| 421 | Me | Me | Me | Me | H | >C=NOH | 2,5-Pydi | 1 | 1 |
| 422 | Me | Me | Me | Me | H | >CHOH | 2,5-Pydi | 3 | 3 |
| 423 | Me | Me | Me | Me | H | >C=NO(CH₂)₂COOH | p-Phn | 1 | 1 |
| 424 | Me | Me | Me | Me | H | >C=NO(CH₂)₃COOH | p-Phn | 1 | 1 |
| 425 | Me | H | tBu | H | H | >CH₂ | p-Phn | 1 | 1 |
| 426 | Me | H | tBu | H | tBu | >CH₂ | p-Phn | 1 | 1 |
| 427 | Me | H | tBu | H | H | >C=O | p-Phn | 1 | 1 |

TABLE 17-continued

| Cpd No. | R¹ | R² | R⁴ | R⁵ | R¹⁰⁶ | W | Ar | n | p |
|---|---|---|---|---|---|---|---|---|---|
| 428 | Me | H | tBu | H | H | >C=NOH | p-Phn | 1 | 1 |
| 429 | Me | H | tBu | H | H | >C=NOCH₂COOH | p-Phn | 1 | 1 |
| 430 | Me | H | tBu | H | H | >CH₂ | 2,5-Pydi | 1 | 1 |
| 431 | Me | H | tBu | H | H | >C=NOH | 2,5-Pydi | 1 | 1 |
| 432 | Me | H | tBu | H | H | >C=NOCH₂COOH | 2,5-Pydi | 1 | 1 |
| 433 | Et | iPr | iPr | H | Me | >C=NO(CH₂)₃COOH | p-Phn | 1 | 1 |
| 434 | Pr | H | Me | H | H | >CH₂ | p-Phn | 1 | 1 |
| 435 | iPr | H | tBu | H | H | >C=NOH | m-Phn | 1 | 1 |
| 436 | iBu | Me | Me | Me | H | >CH₂ | p-Phn | 1 | 1 |
| 437 | iBu | Me | Me | Me | H | >C=NOH | p-Phn | 1 | 1 |
| 438 | Oc | Me | Me | Me | H | >CH₂ | p-Phn | 1 | 1 |
| 439 | Oc | Me | Me | Me | H | >C=NOCH₂COOH | 2,5-Pydi | 2 | 1 |
| 440 | Me | Me | MeO | MeO | H | >CH₂ | p-Phn | 1 | 1 |
| 441 | Me | Me | MeO | MeO | H | >C=NOH | p-Phn | 1 | 1 |
| 442 | Me | H | TMB | H | H | >CH₂ | p-Phn | 1 | 1 |
| 443 | Me | H | TMB | H | H | >C=O | p-Phn | 1 | 1 |
| 444 | Me | H | TMB | H | H | >C=NOH | p-Phn | 1 | 1 |
| 445 | Me | H | TMB | H | H | >C=NOCH₂COOH | p-Phn | 1 | 1 |
| 446 | Bu | H | TMB | H | H | >CH₂ | 2,5-Pydi | 1 | 3 |

Compounds of formula (I-18):

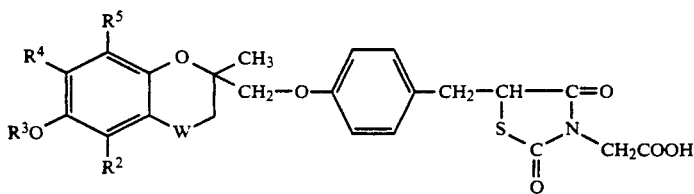

(I-18)

are as defined in Table 18:

TABLE 18

| Cpd No. | R² | R³ | R⁴ | R⁵ | W |
|---|---|---|---|---|---|
| 447 | Me | Me | Me | Me | >C=NOCH₂COOH |
| 448 | Me | Ac | Me | Me | >C=NOCH₂COOH |
| 449 | Me | MeOCH₂— | Me | Me | >CH₂ |

TABLE 18-continued

| Cpd No. | R² | R³ | R⁴ | R⁵ | W |
|---|---|---|---|---|---|
| 450 | H | Boz | tBu | H | >C=NOH |
| 451 | Me | EtOOCCH₂— | Me | Me | >C=N—O(4-MeBz) |

Compounds of formula (I-19):

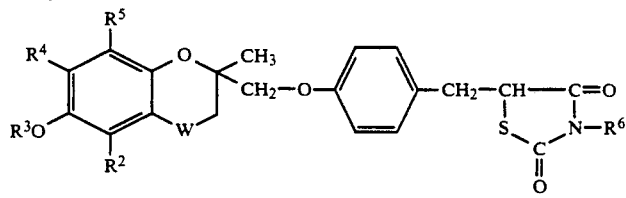

(I-19)

are as defined in Table 19:

TABLE 19

| Cpd No. | R² | R³ | R⁴ | R⁵ | R⁶ | W |
|---|---|---|---|---|---|---|
| 452 | Me | Ac | Me | Me | —CH₂COOH | >CH₂ |
| 453 | Me | Ac | Me | Me | —CH₂COOMe | >CH₂ |
| 454 | Me | Ac | Me | Me | —CH₂COOt-Bu | >CH₂ |
| 455 | Me | H | Me | Me | —CMe₂COOH | >C=NOCMe₂CO |
| 456 | H | Ac | tBu | H | —CMe₂COOH | >C=NOCH₂COO |
| 457 | Me | H | Me | Me | —CMe₂COOEt | >CH₂ |
| 458 | Me | H | Me | Me | —CH₂CONMe₂ | >CH₂ |
| 459 | Me | H | Me | Me | —CH₂C)(4-Me-1-Piz) | >CH₂ |

TABLE 19-continued
| Cpd No. | R² | R³ | R⁴ | R⁵ | R⁶ | W |
|---|---|---|---|---|---|---|
| 460 | Me | HOOCCMe₂— | Me | Me | —CH₂COOH | >C=NOBz |
Compounds of formulae (I-20), (I-21), (I-22), (I-23) and (I-24):
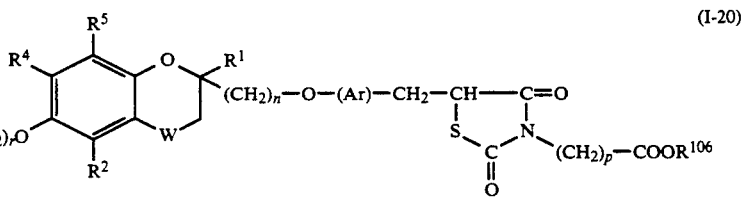
(I-20)
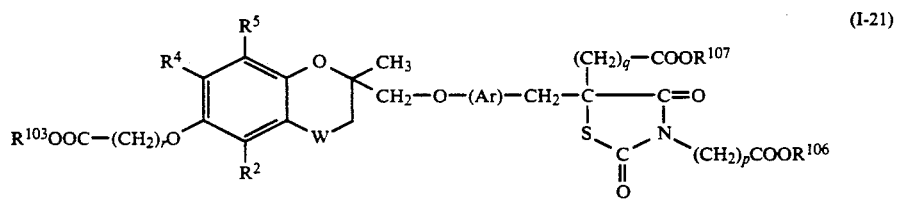
(I-21)
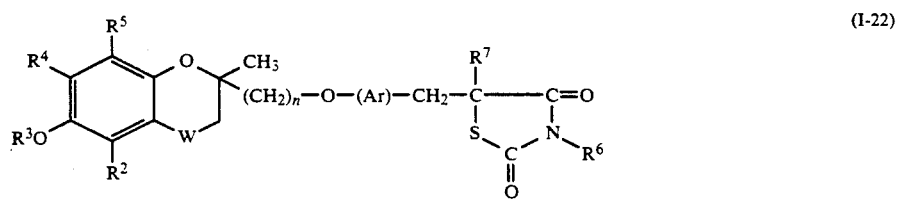
(I-22)
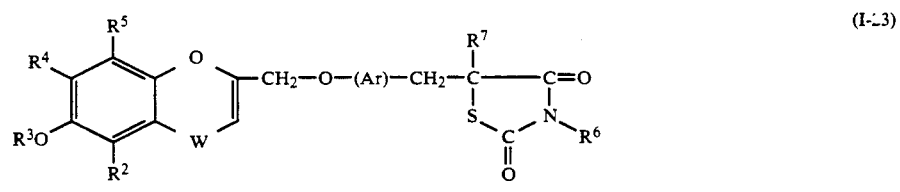
(I-23)
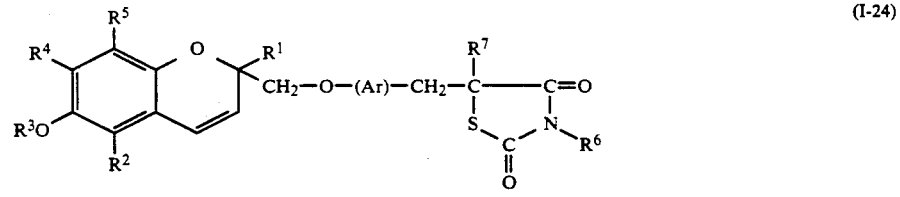
(I-24) are as defined in Tables 20, 21, 22, 23 and 24, respectively:
TABLE 20
| Cpd No. | R¹ | R² | R⁴ | R⁵ | R¹⁰³ | R¹⁰⁶ | W | Ar | n | r | p |
|---|---|---|---|---|---|---|---|---|---|---|---|
| 461 | Me | Me | Me | Me | H | H | >CH₂ | p-Phn | 1 | 1 | 1 |
| 462 | Me | Me | Me | Me | Et | Et | >CH₂ | p-Phn | 1 | 1 | 1 |
| 463 | Me | Me | Me | Me | tBu | tBu | >CH₂ | p-Phn | 1 | 1 | 1 |
| 464 | Me | Me | Me | Me | H | H | >C=O | p-Phn | 1 | 1 | 1 |

TABLE 20-continued

| Cpd No. | R¹ | R² | R⁴ | R⁵ | R¹⁰³ | R¹⁰⁶ | W | Ar | n | r | p |
|---|---|---|---|---|---|---|---|---|---|---|---|
| 465 | Me | Me | Me | Me | Me | Me | >C=O | p-Phn | 1 | 1 | 1 |
| 466 | Me | Me | Me | Me | tBu | tBu | >C=O | p-Phn | 1 | 1 | 1 |
| 467 | Me | Me | Me | Me | H | H | >C=NOH | p-Phn | 1 | 1 | 1 |
| 468 | Me | Me | Me | Me | tBu | tBu | >C=NOH | p-Phn | 1 | 1 | 1 |
| 469 | Me | Me | Me | Me | H | H | >C=NOCH₂COOH | p-Phn | 1 | 1 | 1 |
| 470 | Me | Me | Me | Me | H | H | >C=NOCH₂COOEt | p-Phn | 1 | 1 | 1 |
| 471 | Me | Me | Me | Me | tBu | tBu | >C=NOCH₂COOt—Bu | p-Phn | 1 | 1 | 1 |
| 472 | Me | Me | Me | Me | H | H | >CH₂ | p-Phn | 1 | 2 | 2 |
| 473 | Me | Me | Me | Me | H | H | >CH₂ | p-Phn | 2 | 1 | 1 |
| 474 | Me | Me | Me | Me | H | H | >C=O | p-Phn | 1 | 2 | 1 |
| 475 | Me | Me | Me | Me | H | H | >C=NOH | p-Phn | 2 | 1 | 2 |
| 476 | Me | Me | Me | Me | H | H | >CH₂ | m-Phn | 1 | 3 | 3 |
| 477 | Me | Me | Me | Me | H | H | >CH₂ | 2,5-Pydi | 1 | 1 | 1 |
| 478 | Me | Me | Me | Me | H | H | >C=O | 2,5-Pydi | 1 | 1 | 1 |
| 479 | Me | Me | Me | Me | H | H | >C=NOH | 2,5-Pydi | 1 | 1 | 1 |
| 480 | Me | Me | Me | Me | H | H | >C=NOCH₂COOH | 2,5-Pydi | 1 | 1 | 1 |
| 481 | Me | Me | Me | Me | Et | iPr | >C=NOCH₂COOtBu | 2,5-Pydi | 1 | 1 | 1 |
| 482 | Me | Me | Me | Me | H | H | >CH₂ | 2,5-Pydi | 3 | 2 | 2 |
| 483 | Me | Me | Me | Me | H | H | >C=NO(CH₂)₂COOH | 2,5-Pydi | 1 | 2 | 2 |
| 484 | Me | H | tBu | H | H | H | >CH₂ | p-Phn | 1 | 1 | 1 |

TABLE 20-continued

| Cpd No. | R$^1$ | R$^2$ | R$^4$ | R$^5$ | R$^{103}$ | R$^{106}$ | W | Ar | n | r | p |
|---|---|---|---|---|---|---|---|---|---|---|---|
| 485 | Me | H | tBu | H | Et | Et | >CH$_2$ | p-Phn | 1 | 1 | 1 |
| 486 | Me | H | tBu | H | tBu | tBu | >CH$_2$ | p-Phn | 1 | 1 | 1 |
| 487 | Me | H | tBu | H | H | H | >C=O | p-Phn | 1 | 1 | 1 |
| 488 | Me | H | tBu | H | tBu | tBu | >C=O | p-Phn | 1 | 1 | 1 |
| 489 | Me | H | tBu | H | H | H | >C=NOH | p-Phn | 1 | 1 | 1 |
| 490 | Me | H | tBu | H | H | H | >C=NOCH$_2$COOH | p-Phn | 1 | 1 | 1 |
| 491 | Me | H | tBu | H | tBu | tBu | >C=NOCH$_2$COOt—Bu | p-Phn | 1 | 1 | 1 |
| 492 | Me | H | tBu | H | H | H | >C=NOCH$_2$COOH | 2,5-Pydi | 1 | 1 | 1 |
| 493 | Et | Me | Me | Me | H | H | >C=NO(CH$_2$)$_2$COOH | p-Phn | 1 | 2 | 2 |
| 494 | Pr | Me | Me | Me | H | H | >C=O | m-Phn | 2 | 1 | 1 |
| 495 | iPr | H | Me | H | H | H | >CH$_2$ | p-Phn | 2 | 3 | 3 |
| 496 | iBu | Me | Me | Me | H | H | >C=NOCH$_2$COOH | 2,5-Pydi | 1 | 1 | 1 |
| 497 | Oc | Me | Me | Me | H | H | >C=O | p-Phn | 1 | 1 | 1 |
| 498 | Me | Me | MeO | MeO | H | H | >CH$_2$ | p-Phn | 1 | 1 | 1 |
| 499 | Me | Me | MeO | MeO | H | H | >C=O | p-Phn | 1 | 1 | 1 |
| 500 | Me | H | TMB | H | H | H | >CH$_2$ | p-Phn | 1 | 1 | 1 |
| 501 | Me | H | TMB | H | H | H | >C=O | p-Phn | 1 | 1 | 1 |
| 502 | Me | H | TMB | H | H | H | >C=NOH | p-Phn | 1 | 1 | 1 |
| 503 | Me | H | TMB | H | H | H | >C=NOCH$_2$COOH | p-Phn | 1 | 1 | 1 |

TABLE 20-continued

| Cpd No. | R¹ | R² | R⁴ | R⁵ | R¹⁰³ | R¹⁰⁶ | W | Ar | n | r | p |
|---|---|---|---|---|---|---|---|---|---|---|---|
| 504 | Me | H | TMB | H | H | H | >C=NOCH₂COOH | 2,5-Pydi | 1 | 1 | 1 |

TABLE 21

| Cpd No. | R² | R⁴ | R⁵ | R¹⁰³ | R¹⁰⁶ | R¹⁰⁷ | W | Ar | r | p | q |
|---|---|---|---|---|---|---|---|---|---|---|---|
| 505 | Me | Me | Me | H | H | H | >CH₂ | p-Phn | 1 | 1 | 1 |
| 506 | Me | Me | Me | Et | Et | Et | >CH₂ | p-Phn | 1 | 1 | 1 |
| 507 | Me | Me | Me | tBu | tBu | tBu | >CH₂ | p-Phn | 1 | 1 | 1 |
| 508 | Me | Me | Me | H | H | H | >C=O | p-Phn | 1 | 1 | 1 |
| 509 | Me | Me | Me | tBu | tBu | tBu | >C=O | p-Phn | 1 | 1 | 1 |
| 510 | Me | Me | Me | H | H | H | >C=NOH | p-Phn | 1 | 1 | 1 |
| 511 | Me | Me | Me | tBu | tBu | tBu | >C=NOH | p-Phn | 1 | 1 | 1 |
| 512 | Me | Me | Me | H | H | H | >C=NOCH₂COOH | p-Phn | 1 | 1 | 1 |
| 513 | Me | Me | Me | Et | Et | Et | >C=NOCH₂COOEt | p-Phn | 1 | 1 | 1 |
| 514 | Me | Me | Me | H | H | H | >CH₂ | p-Phn | 2 | 3 | 4 |
| 515 | Me | Me | Me | H | H | H | >C=NOH | 2,5-Pydi | 1 | 1 | 1 |
| 516 | Me | Me | Me | H | H | H | >C=NOCH₂COOH | 2,5-Pydi | 1 | 1 | 1 |
| 517 | Me | Me | Me | Et | Et | Et | >C=NOCH₂COOEt | 2,5-Pydi | 1 | 1 | 1 |
| 518 | H | t-Bu | H | H | H | H | >CH₂ | p-Phn | 1 | 1 | 1 |
| 519 | H | t-Bu | H | H | H | H | >C=O | p-Phn | 1 | 1 | 1 |
| 520 | H | t-Bu | H | H | H | H | >C=NOH | p-Phn | 1 | 1 | 1 |
| 521 | H | t-Bu | H | H | H | H | >C=NOCH₂COOH | 2,5-Pydi | 1 | 1 | 1 |

TABLE 21-continued

| Cpd No. | R² | R⁴ | R⁵ | R¹⁰³ | R¹⁰⁶ | R¹⁰⁷ | W | Ar | r | p | q |
|---|---|---|---|---|---|---|---|---|---|---|---|
| 522 | H | TMB | H | H | H | H | >C=NOH | p-Phn | 1 | 1 | 1 |
| 523 | H | TMB | H | H | H | H | >C=NOCH₂COOH | p-Phn | 1 | 1 | 1 |

TABLE 22

| Cpd No. | R² | R³ | R⁴ | R⁵ | R⁶ | R⁷ | W | Ar | n |
|---|---|---|---|---|---|---|---|---|---|
| 524 | Me | HOOCCMe₂— | Me | Me | —CMe₂COOH | —CMe₂COOH | >C=NOCMe₂COOH | p-Phn | 1 |
| 525 | Me | HOOCCMe₂— | Me | Me | —CMe₂COOH | —CMe₂COOH | >C=NOCMe₂COOH | 2,5-Pydi | 1 |
| 526 | Me | HOOCCMe₂— | Me | Me | —CMe₂COOH | —CMe₂COOH | >C=NOH | p-Phn | 1 |
| 527 | Me | HOOCCMe₂— | Me | Me | —CMe₂COOH | —CMe₂COOH | >CH₂ | p-Phn | 1 |
| 528 | H | HOOCCMe₂— | tBu | H | —CMe₂COOH | —CMe₂COOH | >CH₂ | 6-Me-1,3-Phn | 2 |
| 529 | Me | H₂NCOCH₂— | Me | Me | —CH₂CONH₂ | —CH₂CONH₂ | >CH₂ | p-Phn | 1 |
| 530 | Me | MorCOCH₂— | Me | Me | —CH₂COMor | —CH₂COMor | >C=NOCH₂COMor | p-Phn | 1 |
| 531 | Me | HOOCCH₃— | Me | Me | —CH₂CONH₂ | —CH₂CONH₂ | >CH₂ | p-Phn | 1 |
| 532 | Me | HOOCCMe₂— | Me | Me | —CH₂COMor | —CH₂COMor | >C=NOCH₂COMor | p-Phn | 1 |

TABLE 23

| Cpd No. | R² | R³ | R⁴ | R⁵ | R⁶ | R⁷ | W₁ | Ar |
|---|---|---|---|---|---|---|---|---|
| 533 | Me | HOOCCH₂— | Me | Me | H | H | >C=O | p-Phn |
| 534 | Me | HOOCCH₂— | Me | Me | —CH₂COOH | H | >C=N—OH | p-Phn |
| 535 | Me | EtOOCCH₂— | Me | Me | CH₂COOEt | —CH₂COOEt | >C=NOCH₂COOEt | p-Phn |
| 536 | Me | H | Me | Me | —CH₂COOH | H | >C=NOCH₂COOH | p-Phn |
| 537 | Me | HOOCCMe₂— | Me | Me | H | H | >C=O | p-Phn |
| 538 | H | PipCOCH₂— | t-Bu | H | —CH₂COPip | H | >C=O | 2,5-Pydi |

TABLE 24

| Cpd. No. | R¹ | R² | R³ | R⁴ | R⁵ | R⁶ | R⁷ | Ar |
|---|---|---|---|---|---|---|---|---|
| 539 | Me | Me | MeOCH₂CH₂OOCCH₂— | Me | Me | H | H | p-Phn |
| 540 | Me | Me | HOOCCH₂— | Me | Me | H | H | p-Phn |
| 541 | 7,7-DMO | H | HOOCCMe₂— | tBu | H | —CMe₂COOH | —CMe₂COOH | 2,5-Pydi |
| 542 | Me | Me | MeOOCCH₂— | Me | Me | H | H | p-Phn |
| 543 | Me | Me | 2-HOEt | Me | Me | H | H | p-Phn |
| 544 | Bz | H | CH₃OCH₂— | TMB | H | —CMe₂COOEt | —CH₂COOt-Bu | 6-Me-1,3-Phn |
| 545 | Me | Me | H | Me | Me | —CH₂COOH | —CH₂COOH | p-Phn |

Compounds of formula (I-25):

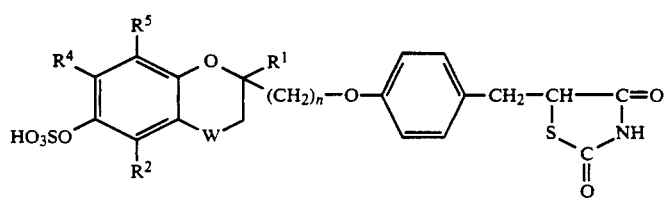

(I-25)

are as defined in Table 25:

TABLE 25

| Cpd No. | R¹ | R² | R⁴ | R⁵ | n | W |
|---|---|---|---|---|---|---|
| 546 | Me | Me | Me | Me | 1 | >CH₂ |
| 547 | Me | Me | Me | Me | 1 | >C=O |
| 548 | Me | H | tBu | H | 1 | >CH₂ |
| 549 | Me | H | tBu | H | 1 | >C=O |
| 550 | Me | Me | Me | Me | 2 | >CH₂ |
| 551 | Me | H | tBu | H | 2 | >CH₂ |
| 552 | Et | Me | Me | Me | 1 | >CH₂ |
| 553 | iBu | Me | Me | Me | 1 | >CH₂ |
| 554 | iBu | Me | Me | Me | 1 | >C=O |
| 555 | Pn | Me | Me | Me | 1 | >CH₂ |
| 556 | H | Me | Me | Me | 1 | >CH₂ |
| 557 | Me | H | iPr | H | 1 | >CH₂ |
| 558 | iBu | H | tBu | H | 1 | >CH₂ |
| 559 | Oc | Me | Me | Me | 1 | >CH₂ |
| 560 | Oc | Me | Me | Me | 1 | >C=O |
| 561 | Oc | H | tBu | H | 1 | >CH₂ |
| 562 | Oc | H | tBu | H | 1 | >C=O |
| 563 | Me | H | TMB | H | 1 | >CH₂ |
| 564 | Me | H | TMB | H | 2 | >CH₂ |
| 565 | iBu | H | TMB | H | 1 | >CH₂ |
| 566 | Oc | H | TMB | H | 1 | >CH₂ |

Compounds of formula (I-26):

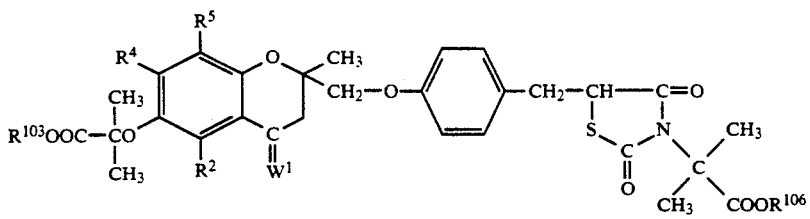

(I-26)

are as defined in Table 26:

TABLE 26

| Cpd. No. | R² | R¹⁰³ | R⁴ | R⁵ | R¹⁰⁶ | W' |
|---|---|---|---|---|---|---|
| 546 | Me | H | Me | Me | H | =NOCMe₂COOH |
| 547 | H | H | tBu | H | H | =NOCH₂COOH |
| 548 | Me | H | Me | Me | H | =NOH |
| 549 | Me | H | Me | Me | H | =H₂ |
| 550 | Me | Et | Me | Me | Et | =H₂ |

Of the compounds listed above, preferred compounds are Compounds Nos. 5, 9, 10, 11, 12, 14, 15, 17, 23, 32, 39, 51, 52, 53, 56, 57, 118, 142, 159, 160, 174, 227, 274, 276, 278, 279, 280, 282, 284, 285, 287, 288, 301, 302, 305, 307, 401, 403, 405, 410, 412, 425, 428, 429, 461, 462, 464, 465, 467, 469, 484, 485, 487, 489, 490, 492, 505, 506, 508, 510, 512, 513, 518, 519, 520, 521, and 546. The more preferred compounds are Compounds Nos. 9, 10, 11, 12, 17, 23, 51, 52, 53, 56, 57, 118, 142, 159, 160, 174, 274, 284, 401, 405, 410, 461, 464, 467, 508 and 510, and the most preferred compounds are Compounds Nos. 9, 11, 142, 464, 467 and 510.

Also preferred are pharmaceutically acceptable salts of the above compounds.

The compounds of the invention, which include those compounds having no proviso, may be prepared by reacting a compound of formula (II):

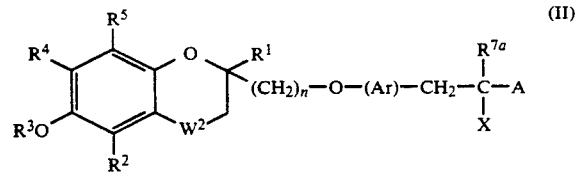

(II)

[in which:
R¹, R², R³, R⁴, R⁵, n and Ar are as defined above;
A represents a cyano group, a carboxy group, a C₂-C₆ alkoxycarbonyl group, a carbamoyl group or a group of formula -COOM where M represents a cation;
X represents a halogen atom;
R⁷ᵃ represents a hydrogen atom or an unsubstituted C₁-C₁₀ alkyl group; and
W² represents a methylene (—CH₂—) group or a carbonyl (>C=O) group] with thiourea, which has the formula (III):

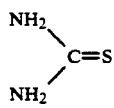

(III)

to give a compound of formula (V):

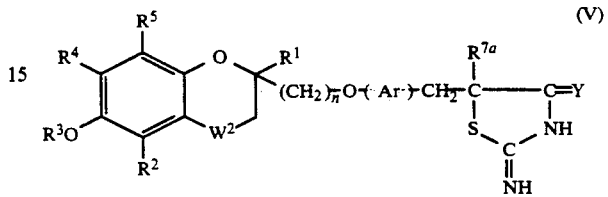

(V)

(in which:
R¹, R², R³, R⁴, R⁵, R⁷¹, n, Ar and W² are as defined above; and
Y represents an oxygen atom or an imino group).

This compound may immediately be hydrolized under the prevailing reaction conditions; if it is not, then a separate hydrolysis step is required, to hydrolize the imino group at the 2-position of the thiazolidine ring and, where Y represents an imino group, hydrolize that imino group also, to an oxygen atom, thereby giving the compound of formula (IV):

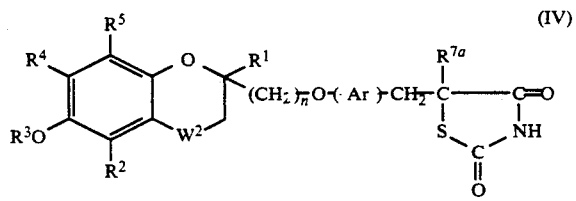

(IV)

(in which R¹, R², R³, R⁴, R⁵, R⁷ᵃ, n, Ar and W² are as defined above).

If necessary, subsequent steps may be carried out to replace various of the substituent groups by other groups within the definitions given above, employing the reactions described in more detail hereafter.

Where A represents a C₂-C⁶ alkoxycarbonyl group (i.e. the alkoxy part has from 1 to 5 carbon atoms), examples of such groups include the methoxycarbonyl, ethoxycarbonyl, propoxycarbonyl, isopropoxycarbonyl and butoxycarbonyl groups. Where A represents a group of formula -COOM and M represents a cation, the nature of the cation is not critical to the invention, since it is eliminated in the course of the reaction. Preferably the cation is a metal ion, such as a sodium, potassium, calcium or aluminum ion, but it may also be an ammonium ion and other ions, including ions derived from organic bases, are possible, although not presently preferred.

X represents a halogen atom and, again, the nature of this is not critical, since the atom is eliminated in the course of the reaction. Most suitably, the halogen atom represented by X is a chlorine, bromine or iodine atom.

The reaction of the compound of formula (II) with the thiourea is preferably effected in the presence of a solvent. The nature of the solvent is not critical, provided that it has no adverse effect upon the reaction.

Suitable solvents include, for example: alcohols, such as methanol, ethanol, propanol, butanol and ethylene glycol monomethyl ether; ethers, such as tetrahydrofuran or dioxane; ketones, such as acetone; dimethyl sulfoxide; sulfones, such as sulfolane; and amides, such as dimethylformamide.

There is no criticality as to the molar ratio of the compound of formula (II) to the thiourea and so conventional criteria apply to determine the most suitable proportions. Preferably the two reagents are employed in equimolar amounts or the thiourea is employed in excess, preferably a slight excess. The most suitable ratio of thiourea to compound of formula (II) is from 1:1 to 2:1.

The reaction temperature is not critical to the invention, although the optimum temperature will vary, depending upon the nature of the reagents and the solvent employed. In general, we prefer to carry out the reaction at the boiling point of the solvent or at a temperature within the range from 80° to 150° C. The time required for the reaction will vary, depending upon many factors, notably the reaction temperature and the nature of the reagents, but a period of from 1 to 20 hours will normally suffice.

Where hydrolysis of the resulting compound of formula (V) is required, this may be effected by heating the compound of formula (V) in a suitable solvent in the presence of water and of an acid. The nature of the solvent is not critical, provided that it has no adverse effect upon the reaction and examples of suitable solvents include: sulfolane; and alcohols, such as methanol, ethanol or ethylene glycol monomethyl ether. Suitable acids include such organic acids as acetic acid and such mineral acids as sulfuric acid or hydrochloric acid. The amount of acid added is preferably from 0.1 to 10 moles, more preferably from 0.2 to 3 moles, per mole of the compound of formula (V). The water or aqueous solvent employed in this hydrolysis is preferably added in stoichiometric excess with respect of the compound of formula (V), preferably a large excess. The reaction temperature is not particularly critical, although we prefer to carry out the reaction at a temperature of from 50° to 100° C., at which temperature the reaction will normally be essentially complete within a period of from 2 to 20 hours.

Where $R^3$ in the compound of formula (V) represents an acyl group, the hydrolysis step will often hydrolize this to a hydrogen atom, giving a compound of formula (IVH):

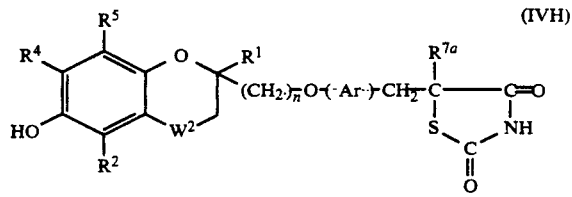

(in which $R^1$, $R^2$, $R^4$, $R^5$, $R^{7a}$n, Ar and $W^2$ are as defined above); however, depending upon the precise reaction conditions and the nature of the acyl group represented by $R^3$, this hydrolysis may not take place or may take place to a limited extent only, so that the acyl group is kept intact. Similarly, other acyl groups within the compound of formula (V) may or may not also be hydrolized.

Compounds of formula (IV) can exist in the following tautomeric forms:

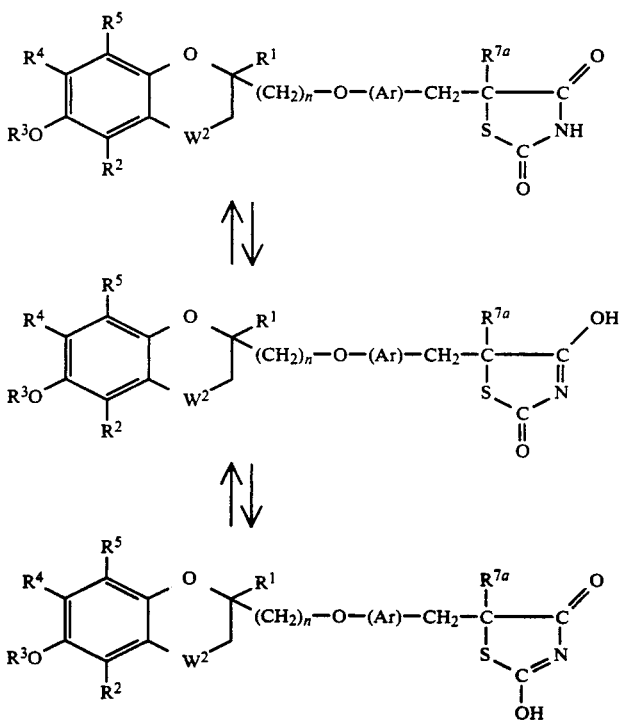

although, for convenience, these are represented by a single formula (IV) herein. It will be appreciated that similar tautomeric forms exist in relation to the imino compound of formula (V) and these likewise are shown herein by means of a single formula only.

Those compounds of the invention which contain one or more carboxy groups or which contain a phenolic hydroxy group [e.g. where $R^3$ represents a hydrogen atom, as in the compounds of formula (IVH)] can form salts, in a conventional manner, with cations. There is no particular restriction on the nature of the cations employed to form such salts, except that, where the compounds of the invention are to be used for therapeutic purposes, the resulting salts should be pharmaceutically acceptable, which, as is well-known in the art, means that the resulting salts should not have a reduced activity (or unacceptably reduced activity) or an increased toxicity (or unacceptably increased toxicity) as compared with the parent compound. On the other hand, where the compounds are to be used for non-therapeutic purposes, e.g. where they are to be used as intermediates in the preparation of other compounds, even this restriction does not apply. Suitable salts include, for example: alkali metal salts, such as the sodium, potassium or lithium salts; alkaline earth metal salts, such as the calcium or magnesium salts; salts with other metals, especially trivalent metals, for example salts with aluminum, iron, cobalt, nickel or zinc; ammonium salts; salts with organic amines, for example the triethylamine or cyclohexylamine salts; and salts with basic amino acids, for example lysine or arginine.

Likewise, where the compounds of the invention contain a basic group, they can form acid addition salts. As with the salts mentioned above, where the compounds are to be used for therapeutic purposes, the salts should be pharmaceutically acceptable but, where they are to be used for non-therapeutic purposes, this restriction dces not apply. Suitable acids for use in producing such salts include: inorganic acids, such as hydrochloric acid, sulfuric acid, nitric acid or phosphoric acid; organic carboxylic acids, such as acetic acid, tartaric acid, maleic acid, fumaric acid, malic acid, glutamic acid or aspartic acid; and organic sulfonic acids, such as p-toluenesulfonic acid or methanesulfonic acid.

Furthermore, compounds of formula (IVH) can be converted into a corresponding ester by reaction with an acylating agent, normally an organic acid or reactive derivative thereof. Suitable reactive derivatives include the acid halides and acid anhydrides, especially the acid anhydrides. Where an acid itself is employed, we prefer to carry out the reaction in the presence, as catalyst, of a strong acid, for example a mineral acid such as hydrochloric acid or sulfuric acid or an organic sulfonic acid such as p-toluenesulfonic acid.

Otherwise, the nature of the acylating agent employed depends upon the nature of the acyl group which it is desired to introduce, and these are defined above as the acyl groups which may be represented by $R^3$.

The reaction is preferably effected in the presence of an solvent, the nature of which is not critical, provided that it has no adverse effect upon the reaction. Suitable solvents include, for example: ethers, such as diethyl ether, tetrahydrofuran or dioxane; aromatic hydrocarbons, such as benzene or toluene; aliphatic hydrocarbons, such as hexane, cyclohexane or heptane; halogenated hydrocarbons, especially halogenated aliphatic hydrocarbons, such as methylene chloride or chloroform; ketones, such as acetone or methyl ethyl ketone; amides, such as dimethylformamide or dimethylacetamide; organic bases, such as pyridine or triethylamine; sulfoxides, such as dimethyl sulfoxide; sulfones, such as sulfolane; water; and mixtures of any two or more thereof. There is no particular restriction on the ratio of the compound of formula (IVH) to the acylating agent, but we generally prefer to employ an excess, suitably a slight excess, of the acylating agent or an equimolar amount of the two reagents. In general, we would employ a molar ratio of acylating agent to compound of formula (IVH) of from 1:1 to 10:1.

The reaction temperature is not critical and the reaction will take place over a wide range of temperatures; however, we generally prefer to carry out the reaction at a temperature of from 0° C. to 100° C. The time required for the reaction will vary widely, depending upon many factors, notably the nature of the reagents and the reaction temperature, but, at a temperature within the recommended range, a period of from 5 minutes to 20 hours will normally suffice.

Compounds of the invention in which W represents a hydroxymethylene group, that is to say compounds of formula (VI):

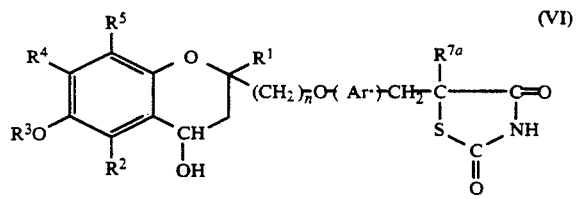

(in which $R^1$, $R^2$, $R^3$, $R^4$, $R^5$, $R^{7a}$, n and Ar are as defined above), can be prepared by reacting a compound of formula (IV) or (IVH) in which $W^2$ represents a carbonyl group, that is to say a compound of formula (VII):

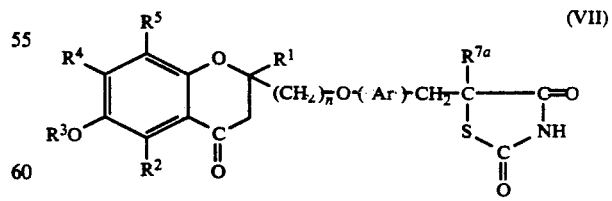

(in which $R^1$, $R^2$, $R^3$, $R^4$, $R^5 R^{7a}$, n and Ar are as defined above) with a reducing agent, such as sodium borohydride or K-selectride, preferably sodium borohydride. The resulting compound of formula (VI) can exist in the following tautomeric forms:

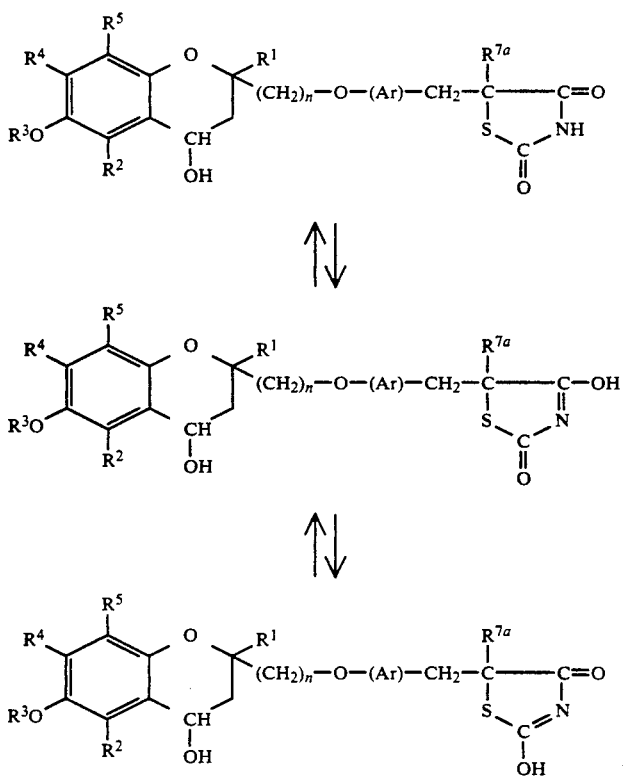

but, for convenience, these are all represented herein by the single formula (VI).

Reaction of the compound of formula (VII) with the reducing agent is preferably effected in the presence of a solvent. The nature of the solvent is not critical, provided that it has no adverse effect upon the reaction. Suitable solvents include, for example: alcohols, such as methanol, ethanol, propanol, butanol or ethylene glycol monomethyl ether; and ethers, such as tetrahydrofuran or dioxane. There is also no criticality as to the ratio of the compound of formula (VII) to the reducing agent, although an excess of the reducing agent is generally preferred. In general, we prefer to employ a molar ratio of reducing agent to compound of formula (VII) of from 1:1 to 20:1.

The reaction will take place over a wide range of temperatures and the particular reaction temperature chosen is not particularly critical. We generally prefer to carry out the reaction at a temperature of from 0° C. to 100° C. The time required for the reaction will vary widely, depending upon many factors, notably the reaction temperature and the nature of the reducing agent, but a period of from 1 to 20 hours will normally suffice.

The resulting compounds of formula (VI) can, if desired, be converted to the corresponding acyl derivatives of formula (VIII):

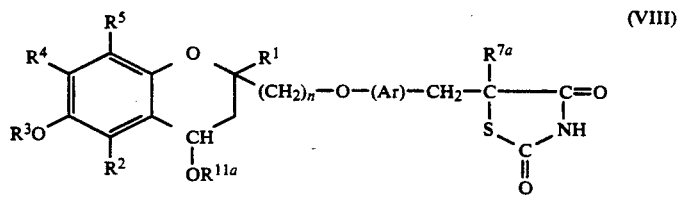

(VIII)

(in which $R^1$, $R^2$, $R^3$, $R^4$, $R^5$, $R^{7a}$, n and Ar are as defined above, and $R^{11a}$ represents any one of the acyl groups included within the definition of $R^{11}$). These compounds can exist in the following tautomeric forms:

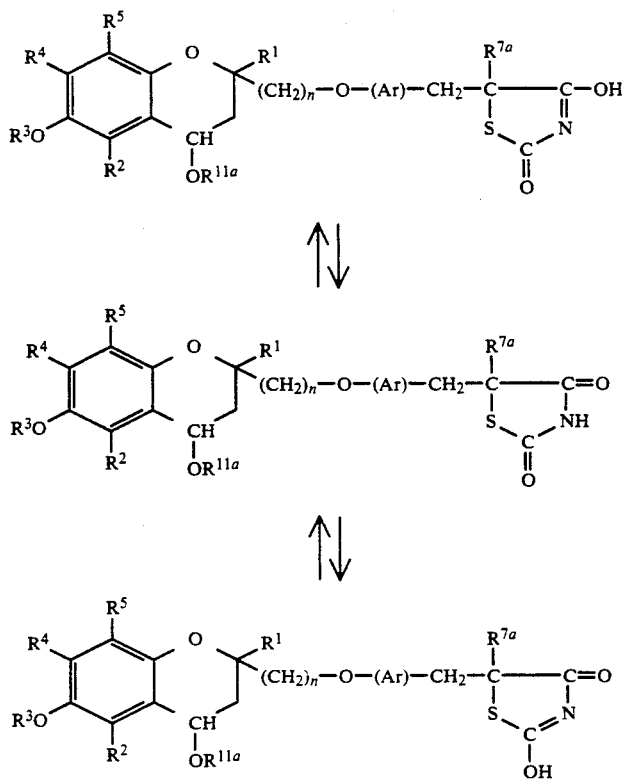

but, for convenience, they are all represented herein by a single formula only.

The nature of the reagents, solvent, proportions of reagents and reaction conditions such as temperature and reaction time, are as described above in relation to the acylation of a compound of formula (IVH) to give the corresponding ester. In view of this, depending upon the precise reaction conditions, where the compound of formula (VI) used as starting material is a compound in which $R^3$ represents a hydrogen atom, then that hydrogen atom may simultaneously be replaced by an acyl group to give a compound of formula (VIII) in which both $R^3$ and $R^{11a}$ represent the same acyl group.

Compounds of the invention in which W and U together form a carbon-carbon double bond, that is to say compounds of formula (IX):

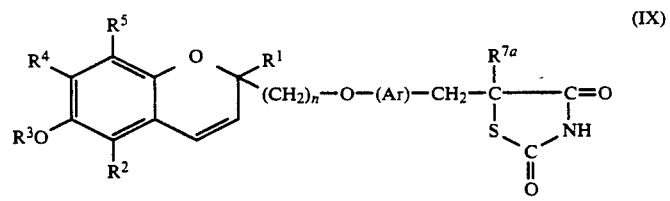

(IX)

(in which $R^1$, $R^2$, $R^3$, $R^4$, $R^5$, $R^{7a}$, n and Ar are as defined above) can be prepared by eliminating water from the above compound of formula (VI) or eliminating an acid $R^{11a}OH$ from the aforementioned compound of formula (VII). The compounds of formula (IX) can exist in various tautomeric forms, as illustrated below:

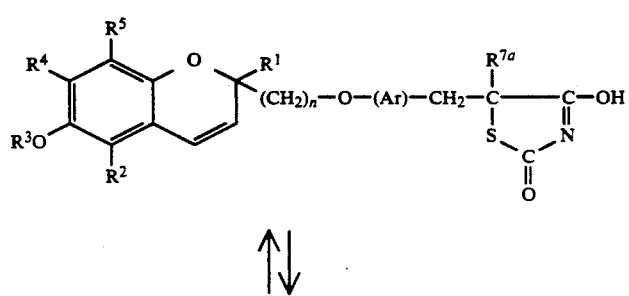

-continued

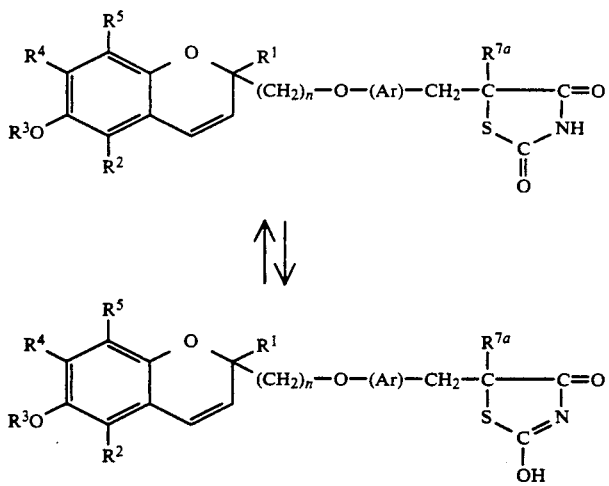

Elimination of water or of the acid R^{11a}OH from the compound of formula (VI) or (VIII) may be effected by contacting in the compound with an acid catalyst in a solvent; alternatively, if an acidic solvent is employed, then no additional acid catalyst is required.

Suitable acid catalysts include: inorganic acids, such as hydrochloric acid or sulfuric acid; organic carboxylic acids, such as acetic acid; and organic sulfonic acids, such as p-toluenesulfonic acid. The nature of the solvent employed is not critical, provided that it has no adverse effect upon the reaction. Suitable solvents include, for example: ethers, such as diethyl ether, tetrahydrofuran or dioxane; aromatic hydrocarbons, such as benzene, toluene or xylene; aliphatic hydrocarbons, such as hexane, cyclohexane or heptane; halogenated hydrocarbons, especially halogenated aliphatic hydrocarbons, such as methylene chloride or chloroform; ketones, such as acetone or methyl ethyl ketone; water; and mixtures of any two or more thereof.

There is no particular restriction on the ratio of the compound of formula (VI) or (VIII) to the acidic catalyst. However, we generally prefer to employ a molar ratio of said compound to said catalyst of from 1:0.001 to 1:1, more preferably from 1:0.01 to 1:0.1.

Where an acidic solvent is to be employed, we prefer to use an organic acid, particularly an organic carboxylic acid, such as acetic acid.

The reaction will take place over a wide range of temperatures, although we generally prefer to employ a temperature of from 0° C. to 100° C. The time required for the reaction may vary widely, depending upon many factors, notably the nature of the reagents and the reaction temperature, but a period of from 5 minutes to 20 hours will normally suffice.

Compounds of formula (IX) may also be prepared by hydrolysis of the corresponding imino compound of formula (X):

(in which $R^1$, $R^2$, $R^3$, $R^4$, $R^5$, $R^{7a}$, n and Ar are as defined above; and Y is also as defined above, i.e. it is an oxygen atom or an imino group).

The compound of formula (X) may be prepared from the compound of formula (V) by a series of reactions analogous to those employed to prepare the compound of formula (IX) from the compound of formula (VII), employing the same reagents and reaction conditions.

The hydrolysis reaction employed is the same as that employed to convert the compound of formula (V) into the compound of formula (IV) and may be carried out under the same conditions and employing the same reagents as described in the context of that reaction. As with that reaction, the hydrolysis in this reaction may lead to removal of any acyl group represented by $R^3$ and its replacement by a hydrogen atom, to give a compound of formula (IXH):

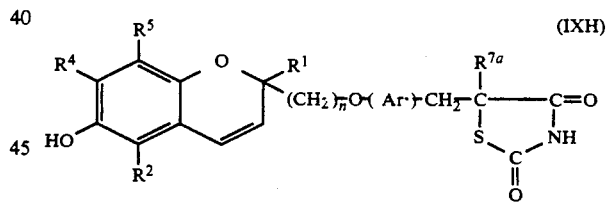

(IXH)

(in which $R^1$, $R^2$, $R^4$, $R^5$, $R^{7a}$, n and Ar are as defined above). However, the acyl group may be kept intact by selecting suitable reaction conditions. Also, if desired, the acyl group may be reinstated by an acylation reaction, as described above in relation to acylation of the compound of formula (IVH).

Compounds of formula (I) in which W represents a methylene group, that is to say compounds of formula (XI):

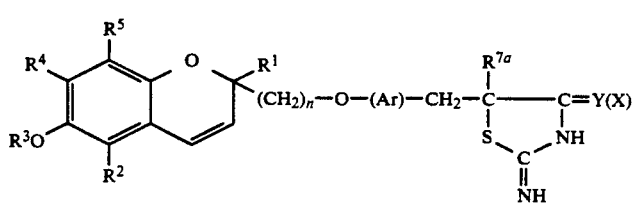

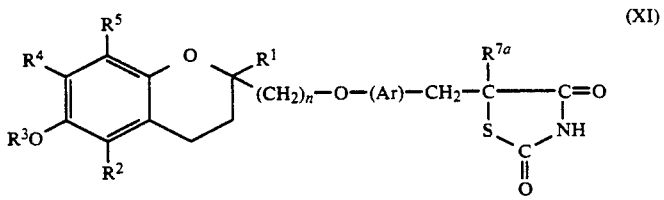

(XI)

(in which $R^1$, $R^2$, $R^3$, $R^4$, $R^5$, $R^{7a}$, n and Ar are as defined above), may be prepared by hydrogenation of a compound of formula (IX).

This hydrogenation is preferably effected in the presence of a catalyst, for example palladium-on-carbon, Raney nickel or platinum oxide, of which palladium-on-carbon is preferred. The partial pressure of hydrogen is preferably from 1 to 100 atmospheres (about 1 to 101 bars), more preferably from 1 to 6 atmospheres (about 1 to 6 bars). The reaction is preferably effected in the presence of a solvent, the nature of which is not critical, provided that it has no adverse effect upon the reaction. Suitable solvents include, for example: alcohols, such as methanol or ethanol; aromatic hydrocarbons, such as benzene or toluene; ethers, such as tetrahydrofuran; organic acids, such as acetic acid; amides, such as dimethylformamide or dimethylacetamide; water; and mixtures of any two or more thereof. The reaction will take place over a wide range of temperatures, but we normally find it convenient to carry out the reaction at a temperature within the range from room temperature to 50° C. The time required for the reaction will vary widely, depending upon many factors, notably the nature of the reagents and the reaction temperature, but a period of from 5 minutes to 20 hours will normally suffice, where a temperature within the recommended range is employed.

Compounds of formula (I) in which W represents a carbonyl group and U, $R^1$ and the carbon atom to which $R^1$ is attached together represent a group of formula —CH=C<, that is to say a compound of formula (XII):

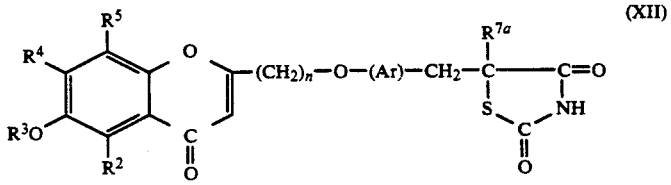

(XII)

(in which $R^2$, $R^3 R^4$, $R^5$, $R^{7a}$, n and Ar are as defined above), can be prepared by reacting a compound of formula (XIII):

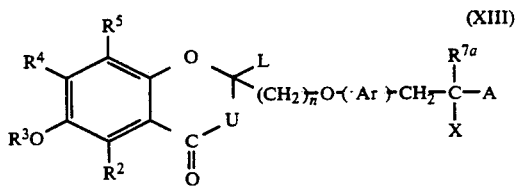

(XIII)

(in which $R^2$, $R^3$, $R^4$, $R^5 R^{7a}$, A, X, n and Ar are as defined above and L and U are as defined below) with thiourea, to give a compound of formula (XIV):

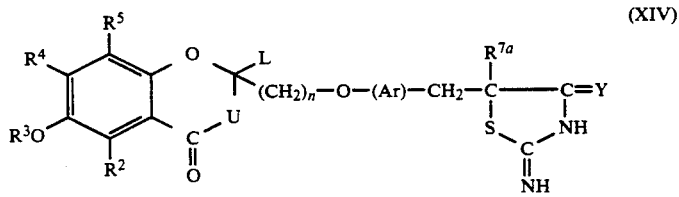

(XIV)

(in which $R^2$, $R^3$, $R^4$, $R^5$, $R^{7a}$, Y, n and Ar are as defined above and L and U are as defined below) and then hydrolizing this compound in the presence of an acid to give said compound of formula (XII).

In the above formulae, L represents a group of formula -$OR^3$, in which $R^3$ is as defined above, and U represents a methylene group; alternatively, U, L and the carbon atom to which the group represented by l is attached, together form a group of formula —CH=C<.

The reactions of the compound of formula (XIII) with thiourea and the hydrolysis of the compound of formula (XIV) thus produced to give the desired compound of formula (XII) are similar to the reactions of the compound of formula (II) with thiourea to give the compound of formula (V) and the hydrolysis of this to give the compound of formula (IV) and may be carried out employing the same reagents and under the same reaction conditions.

Compounds of formulae (X), (IXH), (XI), (XII) and (XIV) exist as tautomeric forms, analogous to those already described above in relation to compounds of formulae (IV), (VI), (VIII) and (IX), although all such tautomers are represented herein by a single formula only, for convenience.

Compounds of formula (I) in which W represents a group of formula >C=N-OR$^{12a}$, that is to say compounds of formula (XV):

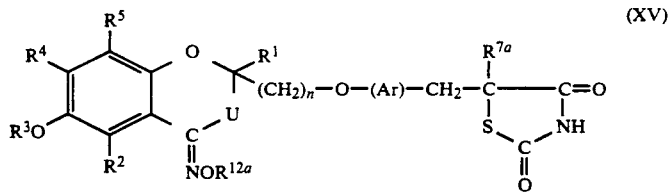

(XV)

The compounds of formulae (XV) and (XVI) can exist in tautomeric forms, for example as follows in relation to the compound of formula (XV):

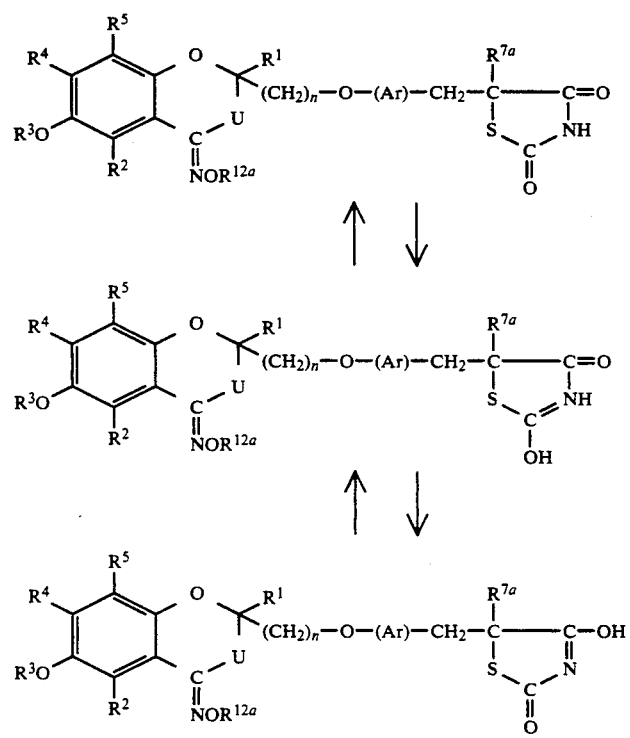

(in which: R$^1$, R$^2$, R$^3$, R$^4$, R$^5$, R$^{7a}$, U, n and Ar are as defined above; and R$^{12a}$ represents a hydrogen atom, a C$_1$–C$_{10}$ alkyl group or a substituted C$_1$–C$_{10}$ alkyl group, as defined for R$^{12}$), can be prepared by reacting the corresponding compound in which W represents a carbonyl group, that is to say a compound of formula (XVI):

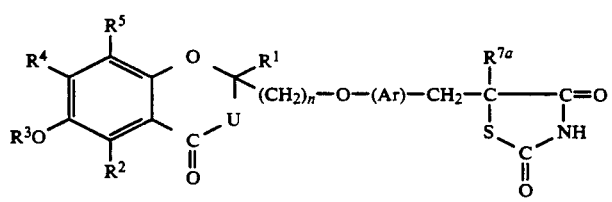

(XVI)

(in which R$^1$, R$^2$, R$^3$, R$^4$, R$^5$, R$^{7a}$, U, n and Ar are as defined above) with a hydroxylamine derivative of formula (XVII):

  (XVII)

(in which R$^{12a}$ is as defined above) or a salt thereof.

however, for convenience, these are represented herein by a single formula only.

The nature of the hydroxylamine derivative of formula (XVII) depends upon the nature of the group =NOR$^{12a}$ which it is desired to introduce into the compound. The hydroxylamine derivative may be employed in the form of a salt thereof, for example a salt with a mineral acid, such as hydrochloric acid or sulfuric acid.

The reaction may be effected in the presence of an acid-binding agent. Where an acid-binding agent is employed, it is preferably an alkali metal hydroxide (such as potassium hydroxide) or an alkali metal carbonate (such as sodium carbonate or potassium carbonate).

The reaction is preferably effected in the presence of a solvent, the nature of which is not critical, provided that it has no adverse effect upon the reaction. Examples of suitable solvents include: alcohols, such as methanol, ethanol, propanol, butanol or ethylene glycol monomethyl ether; ethers, such as tetrahydrofuran or dioxane; amides, such as dimethylformamide or dimethylacetamide; sulfoxides, such as dimethyl sulfoxide; sulfones, such as sulfolane; organic bases, such as triethylamine or pyridine; water; and mixtures of any two or more thereof.

There is no particular limitation on the molar ratio of the hydroxylamine derivative of formula (XVII) to the compound of formula (XVI) and the reaction will take place at any molar ratio. However, we generally prefer to employ an excess of the hydroxylamine derivative, preferably a large excess, with respect to the compound of formula (XVI). A preferred molar ratio of the hydroxylamine derivative (XVII) to the compound of formula (XVI) is from 1:1 to 50:1.

If an acid addition salt of the hydroxylamine derivative (XVII) is employed, then we prefer to carry out the reaction in the presence of an acid-binding agent. The amount of acid-binding agent is not critical and an amount less than equimolar with respect to the salt of the hydroxylamine derivative can be employed.

The reaction will take place over a wide range of temperatures and the particular temperature chosen is not critical. We prefer to carry out the reaction at a temperature within the range from 0° C. to 100° C. The time required for the reaction will vary widely, depending upon many factors, notably the nature of the reagents and the reaction temperature, but, at temperatures within the preferred range given above, a period of from 5 minutes to 10 days will normally suffice.

Compounds of formula (I) in which W represents a group of formula $>C=N-O-R^{12b}$ (in which $R^{12b}$ represents any one of the acyl groups defined for $R^{12}$), that is to say compounds of formula (XVIII):

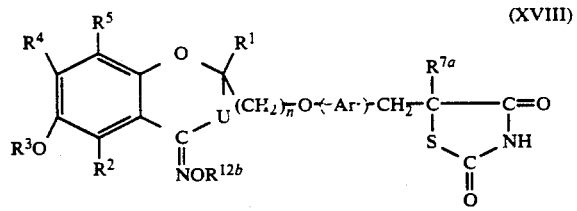

(XVIII)

(in which $R^1$, $R^2$, $R^3$, $R^4$, $R^5$, $R^{7a}$, $R^{12b}$, U, n and Ar are as defined above), may be prepared by reacting the corresponding compound of formula (XV) in which $R^{12a}$ represents a hydrogen atom, that is to say a compound of formula (XIX):

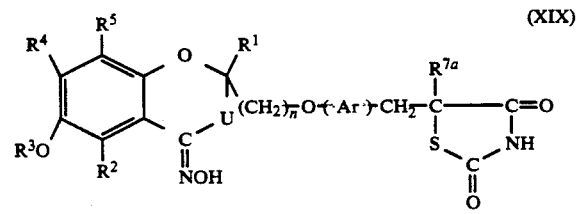

(XIX)

(in which $R^1$, $R^2$, $R^3$, $R^4$, $R^5$, $R^{7a}$, U, n and Ar are as defined above) with an acylating agent, preferably an acid halide or acid anhydride, especially an acid anhydride.

The compounds of formula (XVIII) can exist in the form of tautomers, analogous to those defined above in relation to the other similar compounds. However, for convenience, these tautomers are all represented herein by a single formula (XVIII).

The acylation reaction of this compound of formula (XIX) to give the compound of formula (XVIII) is essentially the same as the reaction employed to acylate the compound of formula (IVH) and may be carried out under the same conditions and employing the same reagents, solvents etc as described heretofore in relation to that acylation reaction.

The compounds of the invention in which W represents a group of formula $>C=N-OR^{12}$ (in which $R^{12}$ is as defined above), that is to say the oxime, oxime ether and oxime ester compounds, i.e. compounds of formulae (XV), (XVIII) and (XIX), can exist in both the syn and anti forms, and both forms are included within the scope of the present invention. These oxime, oxime ether and oxime ester compounds can be converted into their salts by conventional means. As with the salts described previously, there is no particular limitation on the nature of the salt, provided that, where the salt is to be employed for therapeutic purposes, it should be pharmaceutically acceptable. Suitable salts include: alkali metal salts, such as the sodium or potassium salt; alkaline earth metal salts, such as the calcium salt; and salts with trivalent metals, such as the aluminum salt. However, other salts, including those other ones described above can also be formed.

Compounds of the invention in which $R^6$ and/or $R^7$ represents an alkyl group or substituted alkyl group, i.e. compounds of formula (XX):

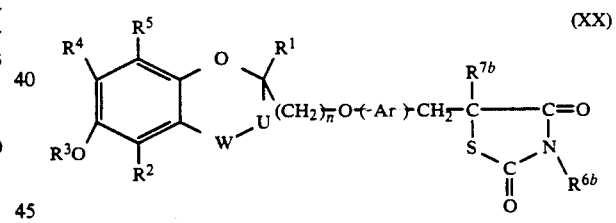

(XX)

(in which $R^1$, $R^2$, $R^3$, $R^4$, $R^5$, W, U, n and Ar are as defined above; and $R^{6b}$ and $R^{7b}$ are the same or different and each represents a hydrogen atom, a $C_1$–$C_{10}$ alkyl group or a substituted $C_1$–$C_{10}$ alkyl group, as defined in relation to $R^6$ and $R^7$, provided that $R^{6b}$ and $R^{7b}$ do not both represent hydrogen atoms), can be prepared by reacting a compound of formula (XXI):

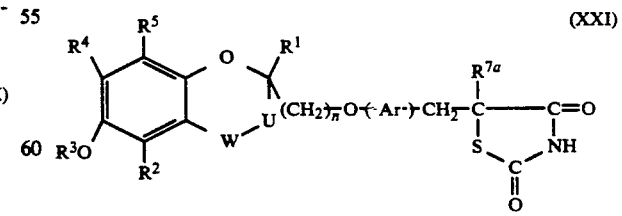

(XXI)

(in which $R^1$, $R^2$, $R^3$, $R^4$, $R^5$, $R^{7a}$, W, U, n and Ar are as defined above) with an alkyl halide or substituted alkyl halide of formula (XXII):

$$R^{20}X \qquad \text{(XXII)}$$

(in which $R^{20}$ represents $R^{6b}$ or $R^{7b}$ and X represents a halogen atom, for example a fluorine, chlorine, bormine or iodine atom, preferably a chlorine or bromine atom.

The reaction is preferably effected in the presence of an acid-binding agent. The purpose of the acid-binding agent is to remove from the reaction system the hydrogen halide HX produced by the reaction and any compound capable of doing this may be employed. Examples of suitable acid-binding agents include: alkali metal carbonates, such as sodium carbonate or potassium carbonate; alkali metal hydroxides, such as sodium hydroxide or potassium hydroxide; alkali metal bicarbonates, such as sodium bicarbonate or potassium bicarbonate; alkaline earth metal hydroxides, such as calcium hydroxide; alkali metal hydrides, such as sodium hydride or potassium hydride; alkali metal alkoxides, such as sodium methoxide or sodium ethoxide; organic lithium compounds, such as butyllithium or t-butyllithium; lithium dialkylamides, such as lithium diisopropylamide or lithium dicyclohexylamide; and organic bases, such as pyridine or triethylamine. Of these, the alkali metal carbonates, especially potassium carbonate, are preferred.

The relative proportions of the base and the compound of formula (XXI) are not particularly critical and may vary over a wide range. For example, a molar ratio of base to compound (XXI) of from 0.5:1 to 20:1 is preferred, more preferably from 1:1 to 10:1.

The reaction is preferably effected in the presence of a solvent, the nature of which is not critical, provided that it has no adverse effect upon the reaction. Suitable solvents include, for example: ketones, such as acetone or methyl ethyl ketone; ethers, such as diethyl ether, tetrahydrofuran or dioxane; aromatic hydrocarbons, such as benzene, toluene or xylene; aliphatic hydrocarbons, such as hexane, heptane or cyclohexane; amides, such as dimethylformamide or dimethylacetamide; sulfoxides, such as dimethyl sulfoxide; sulfones, such as sulfolane; halogenated hydrocarbons, especially halogenated aliphatic hydrocarbons, such as methylene chloride, chloroform or (1,2-dichloroethane; organic bases, such as pyridine or triethylamine; water; and mixtures of any two or more thereof.

The molar ratio of the compound of formula (XXI) to the alkyl halide of formula (XXII) is not particularly critical but, in order to ensure that the reaction goes to completion, we prefer to employ an excess of the alkyl halide. In general, the molar ratio of the alkyl halide to the compound of formula (XXI) is from 0.5:1 to 20:1, more preferably from 1;1 to 10:1. Where only a group $R^{6b}$ is to be introduced into the compound, a still more preferred molar ratio is from 1:1 to 5:1, most preferably from 1:1 to 3:1. Where both groups $R^{6b}$ and $R^{7b}$ are to be introduced, the more preferred ratio is from 1:1 to 10:1 and the most preferred ratio is from 3:1 to 6:1.

The reaction will take place over a wide range of temperatures and the particular reaction temperature is not particularly critical. We generally prefer to carry out the reaction at a temperature of from $-10°$ C. to $+100°$ C., more preferably from 15° to 40° C. The time required for the reaction may vary widely, depending upon many factors, notably the reaction temperature and the nature of the reagents, however, at a temperature within the preferred range, a period of from 10 minutes to several days, more commonly from 1 hour to 4 days, will normally suffice.

Where only $R^{6b}$ is to be introduced, a preferred reaction temperature is from 0° to 100° C., more preferably from 15° to 40° C. At such a temperature, the reaction time will normally be from 10 minutes to several hours, commonly from 30 minutes to 3 hours.

Where both $R^{6b}$ and $R^{7b}$ are to be introduced, a preferred reaction temperature is from 0° to 100° C., more preferably from 15° to 40° C. At such a temperature, the reaction time will normally be from 10 minutes to several days, commonly from 5 hours to 2 days.

The reaction normally takes place preferentially at the nitrogen atom at the 3-position of the thiazolidine ring and, accordingly, where the quantity of alkyl halide (XXII) is restricted, the principal product will normally be a compound in which the alkyl or substituted alkyl group has been introduced at that position. Where $R^{7a}$ represents a hydrogen atom in the compound of formula (XXI), it is possible to replace this by an alkyl or substituted alkyl group by this reaction and, provided sufficient alkyl halide (XXII) is employed, disubstitution will take place.

Where a compound in which $R^6$ and/or $R^7$ represents a carboxyalkyl group is required, we prefer to employ a compound of formula (XXII) in which $R^{20}$ represents an alkoxycarbonylalkyl or substituted alkoxycarbonylalkyl group, to give the corresponding compound of formula (XX) where $R^{6b}$ and/or $R^{7b}$ represents that alkoxycarbonylalkyl or substituted alkoxycarbonylalkyl group. The resulting compound of formula (XX) may then be hydrolized to remove the alkoxy or substituted alkoxy part of this alkoxycarbonylalkyl group and give a free carboxyalkyl group. In general, particularly where W is $>CH_2$ or $>C=O$, the hydrolysis reaction employed is similar to the hydrolysis employed to convert the compound of formula (V) to a compound of formula (IV) and may be carried out under the same reaction conditions and employing the same reagents. In the case of lower alkyl, e.g. ethyl or t-butyl, esters, the free acid may be formed at a relatively low temperature, e.g. from 0° to 5° C., by treatment with an aqueous alkali, e.g. alkali metal hydroxide, such as sodium hydroxide. In the case of alkoxyalkyl esters, e.g. the 2-methoxyethyl esters, the reaction is preferably effected at a higher temperature in the presence of an acid. As with the previously described hydrolysis reaction, there is a possibility that the hydrolysis may also hydrolize any acyl group represented by $R^3$ in the compound of formula (XX) to give a compound (XXI) in which $R^3$ represents a hydrogen atom. However, this may be avoided by appropriate choice of reagents and reaction conditions.

Compounds of the invention in which $R^3$ represents a sulfo ($HSO_3-$) group or an esterified sulfo group of formula $-SO_3R^8$, i.e. compounds of formula (XXIII):

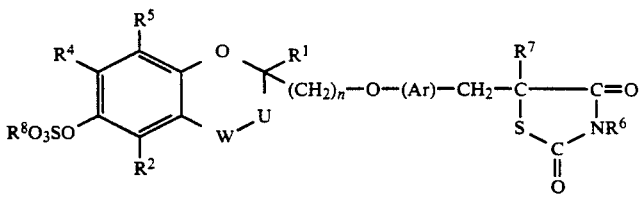
(XXIII)

(in which $R^1$, $R^2$, $R^4$, $R^5$, $R^6$, $R^7$, $R^8$, W, U, n and Ar are as defined above), may be prepared by reacting the corresponding compound of formula (I) in which $R^3$ represents a hydrogen atom, e.g. a compound of formula (IVH) or (IXH), with a corresponding halosulfonic acid or halosulfonate of formula (XXIV):

$$XSO_2OR^8 \qquad (XXIV)$$

(in which $R^8$ and X are as defined above).

The reaction is similar to the reaction to introduce an alkyl or substituted alkyl group $R^{6b}$ or $R^{7b}$ into a compound of formula (XXI) and may be carried out under the same conditions and employing the same solvents and acid-binding agents.

In all of the compounds of the invention, the carbon atom at the 5-position of the thiazolidine ring is asymmetric. Moreover, when $R^1$ represents an atom of a group (i.e. it does not, together with U, form a double bond), the carbon atom at the 2-position of the chroman ring is asymmetric. When W represents a group of formula >CH-$OR^{11}$, then the carbon atom at the 4-position of the chroman ring is also asymmetric. It will, therefore, be appreciated that a variety of isomers of the compounds of the invention are possible, as a result of different configurations of substituent groups about these asymmetric carbon atoms. Although all such isomers are represented herein by a single formula only, the present invention envisages both the individual isolated isomers and mixtures thereof. The compounds of the invention may be produced in the form of individual isomers by using an isolated isomer as the starting material or by stereospecific synthesis techniques. Alternatively, the compounds may be produced as a mixture of such isomers, in which case they may be employed in the form of such a mixture or the individual isomers may be separated by conventional resolution techniques.

The compounds of the invention obtained by any of the reactions discussed above may be isolated and purified by conventional techniques, including any one or more of the following: concentration; evaporation of solvent under reduced pressure; extraction with a solvent; crystallization and recrystallization; solvent transfer; chromatography techniques, especially column chromatography and thin layer chromatography; and optical resolution.

The α-halocarboxylic acid derivatives of formula (II) employed as starting materials in the processes of the present invention can be prepared by a variety of methods, for example as follows.

Method A

Method A is the method described in more detail in copending U.S. patent application Ser. No. 644,996 and prepares compounds where W and U both represent methylene groups, that is to say compounds of formula (XXX), as illustrated in the following reaction scheme:

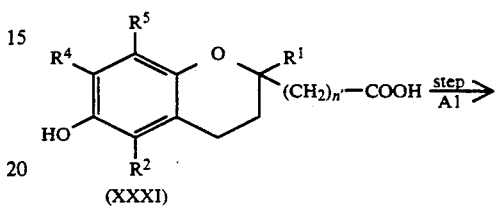
(XXXI)

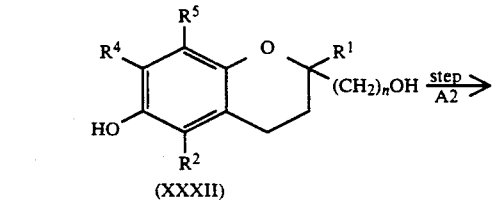
(XXXII)

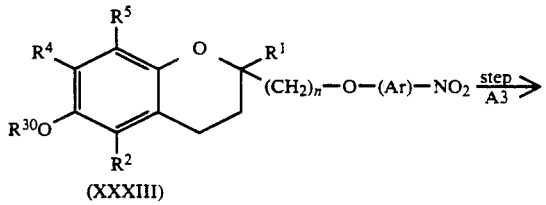
(XXXIII)

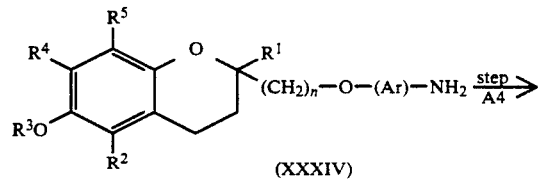
(XXXIV)

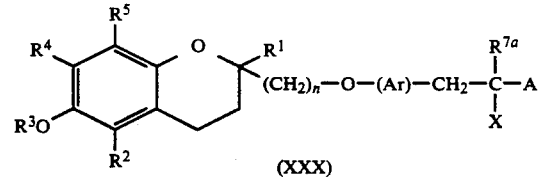
(XXX)

In the above formulae, $R^1$-$R^5$, $R^{7a}$, Ar, n, A and X are as defined above, n'=(n-1); and $R^{30}$ represents a hydroxy-protecting group.

Step A1

The chroman carboxylic acid homologs (XXXI), which are the starting materials for this Method, may be prepared as described, for example, in the Journal of the American Oil Chemists Society, 51, 200 (1974).

These acids (XXXI) are reduced with a reducing agent, such as lithium aluminum hydride or Vitride [sodium bis(2-methoxyethoxy)aluminum hydride], to give the corresponding chroman alcohol homolog (XXXII). This reaction is preferably effected in the presence of a solvent, the nature of which is not critical, provided that it does not interfere with the reaction. Suitable solvents include: ethers, such as diethyl ether, tetrahydrofuran or ethylene glycol dimethyl ether; aromatic hydrocarbons, such as benzene, toluene or xylene; and aliphatic hydrocarbons, such as hexane, heptane, cyclohexane, petroleum ether, ligroin or ethylcyclohexane.

The ratio of the amount of acid (XXXI) to reducing agent is not particularly critical, but we generally prefer to use a slight molar excess of reducing agent. Preferably the amount of reducing agent is from 1 to 2 moles per mole of acid (XXXI). The reaction conditions, particularly the reaction temperature and time, will vary depending upon many factors, such as the nature of the starting material, the reducing agent and the solvent, but the reaction is generally carried out at a temperature of from 0° to 100° C. At such a temperature, a reaction period of from 10 minutes to 20 hours will normally suffice.

Alternatively, the chroman alcohol homolog (XXXII) may be prepared by reacting a hydroquinone with a compound of formula (XXXV):

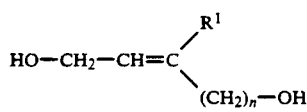
(XXXV)

(in which n and $R^1$ are as defined above), especially the compound of formula (XXXV) where $R^1$ represents a methyl group, in the presence of aluminum chloride, as described in West German Patent No. 3,010,504.

Step A2

The chroman alcohol homologs of formula (XXXII) obtained in Step A1 may be converted to the corresponding nitrophenoxyalkyl chroman compounds (XXXIII). However, before carrying out this reaction, we prefer that the phenolic hydroxy group should be protected by a hydroxy-protecting group $R^{30}$.

The nature of the hydroxy-protecting group is not critical and any such group commonly used in this type of reaction and compound may be employed. Suitable groups include: alkoxyalkyl groups, such as the methoxymethyl group; alkoxycarbonylalkyl groups, such as the ethoxycarbonylmethyl, t-butoxycarbonylmethyl, 1-methoxycarbonyl-1-methylethyl and 1-(t-butoxycarbonyl)-1-methylethyl groups; aralkyl groups, such as the benzyl group; the 2-tetrahydropyranyl group; and acyl groups, such as the acetyl or benzoyl groups. The alkoxyalkyl, alkoxycarbonylalkyl and 2-tetrahydropyranyl groups are preferred. The reaction is normally effected by contacting a compound $R^{30}X$ (in which $R^{30}$ is as defined above and X represents a halogen atom, preferably a chlorine atom), such as methoxymethyl chloride, ethoxycarbonylmethyl bromide, 1-(t-butoxycarbonyl)-1-methylethyl bromide, benzoyl chloride or benzyl chloride, more preferably methoxymethyl chloride or benzoyl chloride, with the compound of formula (XXXII) in the presence of a base such as an alkali metal or alkaline earth metal hydride (e.g. sodium hydride or calcium hydride) or an alkali metal alkoxide (e.g. sodium methoxide, sodium ethoxide or potassium t-butoxide). The reaction is normally carried out in the presence of a solvent, for example: an ether, such as diethyl ether, tetrahydrofuran or dioxane; an aromatic hydrocarbon, such as benzene, toluene or xylene; an aliphatic hydrocarbon, such as hexane or heptane; an amide, such as dimethylformamide or dimethylacetamide; a sulfoxide, such as dimethyl sulfoxide; or a sulfone, such as sulfolane. There is no particular limitation on the molar ratio of compound (XXXII) to the compound $R^{30}X$. In general, we prefer to employ from about 0.8 to 1.2 mole of the compound $R^{30}X$ per mole of the compound (XXXII). The reaction conditions, particularly the reaction temperature and time, may vary depending upon a number of factors, especially the natures of the starting material, the compound $R^{30}X$ and the solvent, but we normally prefer a reaction temperature of from 0° to 50° C. and a time of from several minutes to several tens of minutes.

The protection chroman alcohol produced by this reaction can, if desired, be isolated and purified, but it may be, and preferably is, converted to the nitrophenoxyalkylchroman compound of formula (XXXIII) without intermediate isolation.

Conversion to the compound of formula (XXXIII) is effected by reacting the protected compound (XXXII) with a halonitroaryl compound, e.g. a 4- or 3-halonitrobenzene, of formula $X$-(AR)-$NO_2$ (in which X and Ar are as defined above) in the presence of a base, such as sodium hydride, in a solvent, such as dimethyl sulfoxide or dimethylformamide. The amount of halonitroaryl compound employed is preferably about 2 moles per mole of protected compound (XXXII). The reaction temperature is preferably from 30° to 100° C. and the time required for the reaction is usually from several minutes to several hours.

Sept A3

The nitro compound of formula (XXXIII) thus obtained is reduced in this step to the corresponding amino compound of formula (XXXIV). In the course of or before or after this reduction, the protecting groups $R^{30}$ may be allowed to remain as it is, removed or converted to another group (particularly an acyl group, such as an acetyl or benzoyl group).

When deprotection of the compound (XXXIII) is desired, this can easily be achieved by reacting the compound (XXXIII) with a dilute aqueous acid (such as hydrochloric acid, sulfuric acid or nitric acid) to hydrolyse the protecting group. The reaction is normally carried out in the presence of a solvent, for example: an alcohol, such as methanol, ethanol or propanol; an ether, such as tetrahydrofuran or dioxane; a ketone, such as acetone or methyl ethyl ketone; an organic acid, such as acetic acid or propionic acid; dimethyl sulfoxide; dimethylformamide; or water. Of these, water or an organic acid is preferred. The amount of acid used for hydrolysis is preferably from 0.01 to 5 moles, more preferably from 0.01 to 1 mole, per mole of the compound (XXXIII). We prefer to carry out the reaction in the presence of a large molar excess of water or of acetic acid as the solvent. The reaction temperature is preferably from ambient temperature to 100° C. and the time required for the reaction is normally from several minutes to about 20 hours.

If it is desired to convert the protecting group $R^{30}$ to another group, particularly an acyl group, this may be achieved by acylation of the deprotected compound obtained as described above. The acylating agent may be an acid halide, such as acetyl chloride or benzoyl chloride, or an acid anhydride, such as acetic anhydride. This reaction is preferably carried out in the presence of an organic amine (such as pyridine or triethylamine) or in the presence of an inorganic base (for example an alkali metal hydroxide, such as sodium hydroxide or potassium hydroxide, or an alkali metal carbonate or bicarbonate, such as sodium carbonate, potassium carbonate or sodium bicarbonate). The acylating reaction is preferably carried out in the presence of a solvent, for example: an aliphatic hydrocarbon, such as hexane, cyclohexane, heptane, ligroin or ethylcyclohexane; an aromatic hydrocarbon, such as benzene, toluene or xylene; an organic amine, such as pyridine or triethylamine; a ketone, such as acetone or methyl ethyl ketone; an amide, such as dimethylformamide; a sulfoxide, such as dimethyl sulfoxide; or water. The ratio of the amount of deprotected compound (XXXIII) to acylating agent is not particularly critical, however, a slight molar excess of acylating agent is usually preferred, for example from 1 to 1.5 moles of acylating agent per mole of deprotected compound (XXXIII). Where an organic amine is employed as the acid-binding agent, it may be employed in any amount from 1 mole to a large molar excess per mole of the compound of formula (XXXIII). Where an inorganic base is employed as the acid-binding agent, it is preferably employed in an amount of from 1 to 10 moles per mole of the compound of formula (XXXIII). The reaction conditions, particularly the reaction temperature and time, may vary depending upon a number of factors, particularly the natures of the starting material and solvent employed, but the reaction is preferably effected at a temperature of from 0° to 100° C. for a period of from several minutes to 20 hours.

The nitro compound of formula (XXXIII) (which may optionally have been subjected to any of the processes described above) is then reduced to the amino compound of formula (XXXIV). The reduction may be a catalytic reduction process employing hydrogen, or reduction with a metal (Such as zinc or iron) and an acid (which may be a mineral acid such as hydrochloric acid or sulfuric acid or an organic acid such as acetic acid). Preferably a catalytic reduction process is employed. The catalyst employed for this catalytic reduction is preferably palladium-on-carbon, Raney nickel or platinum oxide, of which palladium-on-carbon is particularly preferred. The hydrogen pressure is preferably from 1 to 100 atmospheres (about 1 to 101 bars), more preferably from 1 to 6 atmospheres (about 1 to 6 bars). The reaction is preferably effected in the presence of a solvent, the nature of which is not critical, provided that it has no adverse effect upon the reaction. Suitable solvents include: alcohols, such as methanol or ethanol; aromatic hydrocarbons, such as benzene or toluene; ethers, such as tetrahydrofuran; organic acids, such as acetic acid; water; or mixtures of any two or more thereof. The reaction conditions, particularly the reaction temperature and time, may vary depending upon a number of factors, particularly the nature of the starting material, the method employed for reduction and the solvent, but the reaction is normally effected at a temperature from ambient temperature to 50° C. and the period required for the reaction is generally from several minutes to about 20 hours.

Step A4

The chroman derivative of formula (XXXIV), prepared as described in step A3 above, is diazotized and then subjected to a Meerwein arylation, to give the desired α-halocarboxylic acid compound of formula (XXX). The two reactions are preferably effected sequentially in the same reaction system.

The diazotization reaction comprises reacting the amino compound of formula (XXXIV) with a nitrite (such as sodium nitrite) in the presence of an acid, such as hydrochloric acid or hydrobromic acid.

The Meerwein arylation reaction comprises reacting the resulting diazonium compound with an acrylic compound of formula $CH_2=CR^{7a}A$ (in which $R^{7a}$ and A are as defined above), e.g. acrylic acid, an acrylic or methacrylic acid ester (such as methyl acrylate, ethyl acrylate or ethyl methacrylate) or another acrylic acid derivative (such as acrylonitrile, acrylamide, methacrylonitrile or methacrylamide), in the presence of a catalytic amount of a cuprous compound (which may be a salt, such as cuprous chloride, or another cuprous compound such as cuprous oxide). The acrylic and methacrylic acid esters are preferred and the preferred cuprous compound is cuprous oxide.

The reactions are preferably effected in the presence of a solvent, the nature of which is not critical, provided that it does not interfere with the reactions. Suitable solvents include: alcohols, such as methanol or ethanol; ketones, such as acetone or methyl ethyl ketone; water; or a mixture of any two or more thereof. The molar ratio of the amino compound of formula (XXXIV) to the acrylic acid or derivative thereof of formula $CH_2=CR^{7a}A$ is preferably from 1:1 to 1:15, more preferably from 1:5 to 1:10. The molar ratio of the amino compound (XXXIV) to the cuprous compound is preferably from 1:0.01 to 1:1, more preferably from 1:0.03 to 1:0.3. The reaction conditions, particularly the reaction temperature and time, may vary depending upon a number of factors, especially the natures of the starting materials and the solvent employed, but the reaction is normally carried out at a temperature from ambient temperature to 100° C., preferably from 30° to 60° C., and the period required for the reaction is normally from about 20 minutes to about 20 hours, more preferably from 30 minutes to 2 hours.

Method B

This method may also be used to prepare compounds of formula (II) in which both W and U represent methylene groups and is especially useful for preparing compounds in which n is 2. The reactions involved are illustrated in the following reaction scheme:

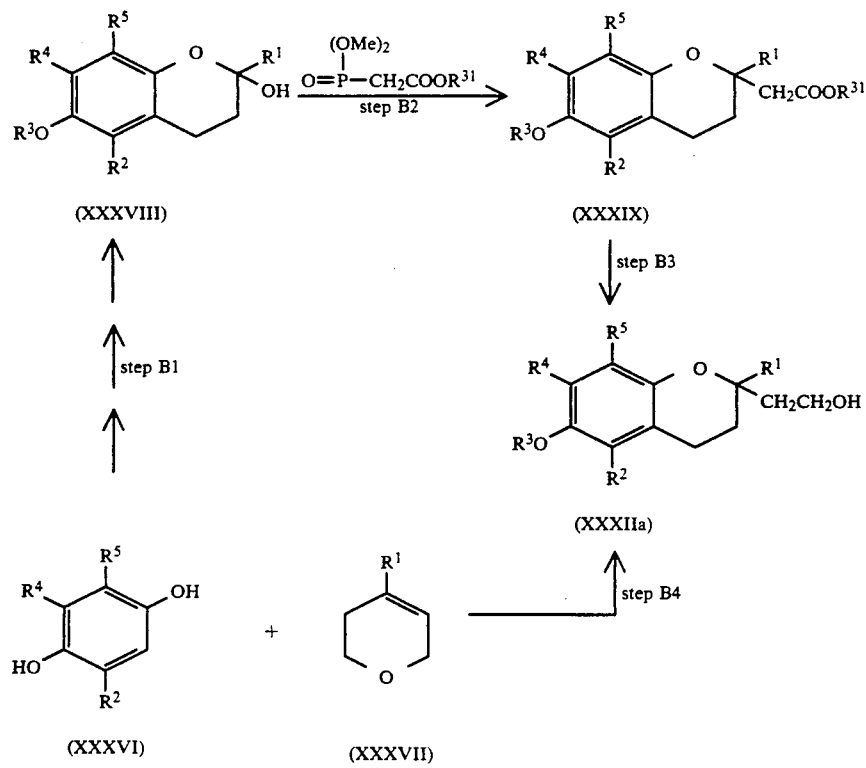

(XXXVI) (XXXVII)

In the above reaction scheme, $R^1$-$R^5$ are as defined above, $R^{31}$ represents an alkyl group and Me represents the methyl group.

In this reaction, the chroman alcohol of formula (XXXIIa) or its analogs in which n is an integer other than 2, may be prepared from the hydroquinone derivative of formula (XXXVI) via the sequence of steps indicated as steps B1, to give the compound of formula (XXXVIII), followed by step B2, and then step B3 (analogous to step A1 1 of Method A), according to the method described in the Journal of the American Oil Chemists Society, 51, 200 (1974). Alternatively, it can be synthesized in a single step by reacting the hydroquinone derivative (XXXVI) with the dihydropyran derivative of formula (XXXVII), as illustrated in step B4 by the method described in Japanese Patent Application Kokai No. 201775/83. Subsequently, the resulting compound of formula (XXXIIa) may be subjected to steps A2, A3 and A4, to give the desired compound of formula (XXX).

Method C

This method is also useful for synthesizing compounds of formula (II) in which both W and U represent methylene groups. This method may be carried out as illustrated by the following reaction scheme:

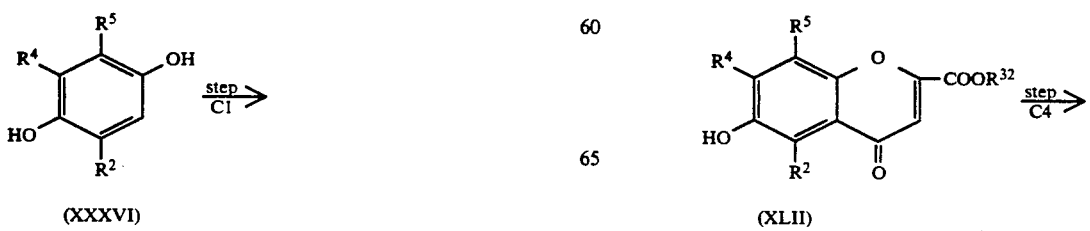

-continued

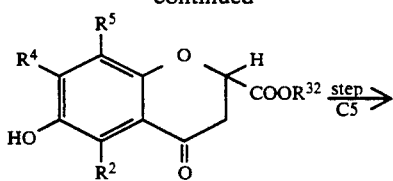

(XLIII)

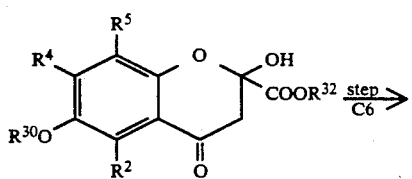

(XLIV)

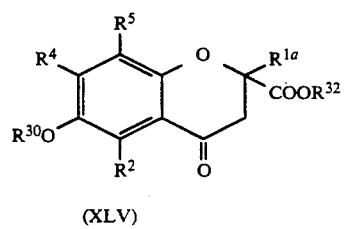

(XLV)

In the above formulae, $R^2$, $R^4$, $R^5$ and $R^{30}$ are as defined above; $R^{1a}$ represents any one of the groups heretofore defined for $R^1$, other than the hydrogen atom; and $R^{32}$ represents a hydrogen atom or a carboxy-protecting group, preferably an alkyl, alkenyl, alkynyl, aralkyl or optionally substituted phenyl group, more preferably a $C_1$-$C_4$ alkyl group.

Steps C1–C4

These steps are carried out essentially as described in the Journal of Medicinal Chemistry, 18, 934 (1975).

Step C5

In this step, the phenolic hydroxy group is, if required, protected. We prefer that this hydroxy group should be protected prior to step C6. Examples of protecting groups $R^{30}$ have been given above in relation to Method A and the method of introducing the protecting group is also as described above in relation to step A2. However, in this step, we prefer to employ the compound $R^{30}X$ in excess, preferably a molar ratio of the compound $R^{30}X$ to the compound of formula (XLIII) of from 1:1 to 2:1. The reaction is preferably effected at a temperature of from 0° to 50° C., more preferably from 10° to 25° C. The time required for the reaction will vary, depending upon many factors, but a period of from several minutes to several hours will normally suffice. The resulting compound of formula (XLIV) may then be used in step C6 without intermediate isolation.

Step C6

In this step, a chromancarboxylic acid derivative of formula (XLV) having a protected hydroxy group at the 6-position and a group $R^{1a}$ at the 2-position is prepared. This may be achieved by reacting the compound of formula (XLIV) with a base in an inert solvent in order to generate a carbanion and then reacting this carbanion with a compound of formula $R^{1a}X^1$ (in which $R^{1a}$ is as defined above and $X^1$ represents a halogen atom, for example a chlorine, bromine or iodine atom, or a sulfonyloxy group, for example a methanesulfonyloxy, ethanesulfonyloxy, benzenesulfonyloxy or p-toluenesulfonyloxy group).

Any base may be employed in the reaction to generate the carbanion, and examples of such bases include: organic lithium compounds, such as methyllithium, butyllithium, t-butyllithium or phenyllithium; lithium dialkylamides, such as lithium diisopropylamide, lithium dicyclohexylamide or lithium N-isopropyl-N-cyclohexylamide; and alkali metal hydrides, such as lithium hydride, sodium hydride or potassium hydride. Of these, we prefer the organic lithium compounds and lithium dialkylamides.

The reaction is preferably effected in the presence of a solvent, the nature of which is not critical, provided that it has no adverse effect upon the reaction. Suitable solvents include, for example, ethers, such as diethyl ether, tetrahydrofuran or dioxane.

The reaction temperature employed for generation of the carbanion is preferably relatively low, e.g. from −78° C. to room temperature. The temperature employed for reaction of this anion with the compound of formula $R^{1a}X^1$ is preferably somewhat higher, e.g. from 0° C. to 60° C. The time required for these reactions will vary widely, depending upon many factors, notably the nature of the reagents and the reaction temperature, but a period of from 30 minutes to 2 hours will normally suffice for generation of the carbanion, whilst a period of from 1 to 24 hours will normally suffice for the subsequent reaction with the compound $R^{1a}X^1$.

Thereafter, the resulting compound of formula (XLV) may be subjected to the same reactions as described in Method A, to give the resulting compound of formula (XXX).

If desired, Step C6 may be omitted, to prepare a compound in which $R^1$ is a hydrogen atom.

Method D

This method is also described in copending U.S. patent application Ser. No. 644,996 and prepares compounds of formula (II) in which U represents a methylene group and W represents a carbonyl group, that is to say compounds of formula (LI), by the reactions summarized in the following reaction scheme:

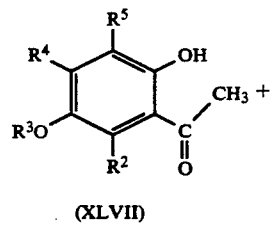

(XLVII)

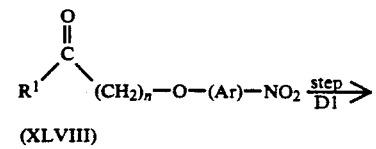

(XLVIII)

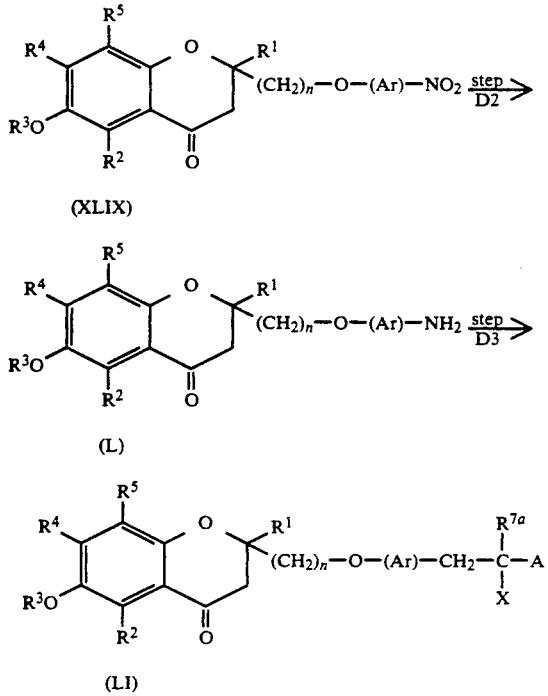

(XLIX)

(L)

(LI)

In the above formulae, $R^1$-$R^5$, $R^{7a}$, Ar, n, A and X are as defined above. The reaction sequence comprises the following steps:

Step D1

The acetophenone derivative of formula (XLVII) which is one of the starting materials for this step may be prepared, for example, as described in Chem. Berichte, 95, 1413. The other starting material, the nitroaryloxyalkyl alkyl ketone of formula (XLVIII), may be prepared, for example, as described in J. Med. Chem., 21, 386 (1978) and J. Am. Chem. Soc., 99, 7653 (1977).

In this step, the compounds (XLVII) and (XLVIII) are reacted together in the presence of a secondary amine, as described, for example, in Japanese Patent Application Kokai No. 19670/77.

The reaction is preferably effected in the presence of a solvent, the nature of which is not critical, provided that it has no adverse effect upon the reaction. Suitable solvents include: aliphatic and aromatic hydrocarbons, such as petroleum ether, benzene, toluene, xylene, hexane and cyclohexane; halogenated aliphatic and aromatic hydrocarbons, such as carbon tetrachloride, methylene chloride, chloroform, chlorobenzene and dichlorobenzene; ethers, such as diethyl ether, tetrahydrofuran and dioxane; amides, such as dimethylformamide, dimethylacetamide and N-methylpyrrolidone; alcohols, such as methanol, ethanol and ethylene glycol monomethyl ether; esters, such as ethyl acetate; nitriles, such as acetonitrile; and sulfoxides, such as dimethyl sulfoxide.

The secondary amine employed in this reaction is preferably a compound of formula $R^a$-NH-$R^b$, in which $R^a$ and $R^b$ may be the same or different and each represents an alkyl group, or $R^a$ and $R^b$, together with the nitrogen atom to which they are attached, represent a nitrogen-containing heterocyclic ring system. Examples of such secondary amines include diethylamine, dimethylamine, N-methylpiperazine, pyrrolidine, piperidine or morpholine, of which pyrrolidine is particularly preferred.

The molar ratio of the compound of formula (XLVII) to the compound of formula (XLVIII) is not particularly critical, but, to avoid waste, roughly equimolar amounts of the two compounds are used. In general, the amount of secondary amine is preferably from 0.05 to 1.5 moles, more preferably from 0.1 to 1 mole, per mole of the compound of formula (XLVII) or (XLVIII).

The reaction conditions particularly reaction temperature and time, may vary depending upon a number of factors, especially the nature of the staring materials and of the solvent, but, in general, we prefer to carry out the reaction at a temperature of from −30° C. to +150° C., more preferably from 10° to 120° C., for a period of from 30 minutes to 3 days.

Step D2

In this step, the nitro compound of formula (XLIX) prepared as in step D1 is reduced t the corresponding amino compound of formula (L). This reaction is precisely the same as step A3 of Method A, employing the same reaction conditions and reagents.

Step D3

In this step, the amino compound of formula (L), obtained as described in step D2, is diazotized and then subjected to a Meerwein arylation, to give the desired α-halocarboxylic acid derivative of formula (LI). These reactions are precisely the same as those described in step A4 of Method A and may be carried out employing the same reagents and reaction conditions.

Method E

This method may be used for preparing compounds of formula (II) in which W represents a carbonyl group and U represents a methylene group, and where there is a group $R^{1a}$ (as defined above) at the 2-position of the chroman ring. The reactions involved are summarized in the following reaction scheme:

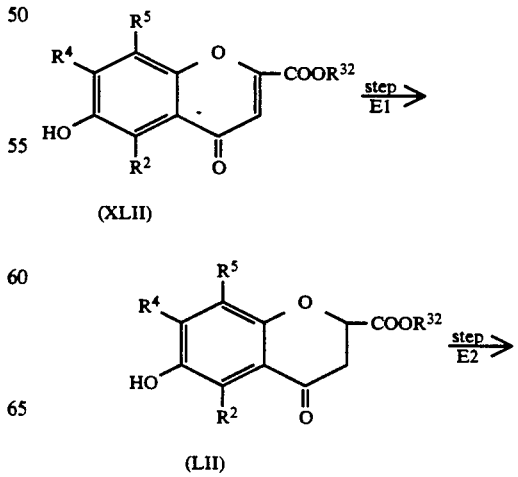

(XLII)

(LII)

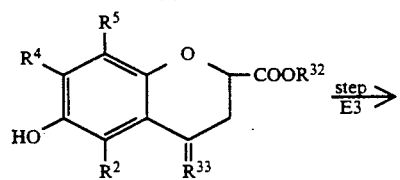

(LIII)

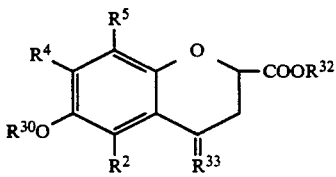

(LIV)

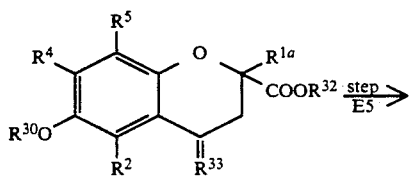

(LV)

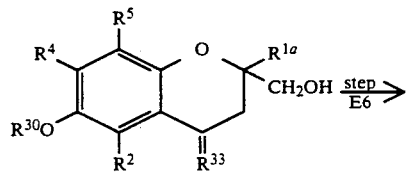

(LVI)

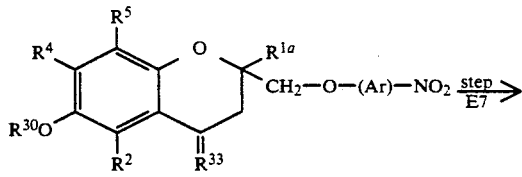

(LVII)

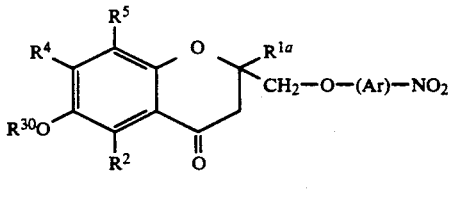

(LVIII)

In the above formulae, $R^{1a}$, $R^2$, $R^4$, $R^5$, $R^{30}$, $R^{32}$ and Ar are as defined above. $R^{33}$ represents a carbonyl-protecting group, examples of which are described in more detail below.

Step E1

In this step, the starting material of formula (XLII), which may have been prepared as described in step C3 of Method C, is subjected to reduction, but under milder conditions than employed in step C4, so that only the double bond between the 2- and 3-positions is hydrogenated.

The reaction is preferably effected by catalytic hydrogenation. Suitable catalysts include palladium-on-carbon, Raney nickel and platinum oxide, of which palladium-on-carbon is preferred. The reaction is preferably effected employing a partial pressure of hydrogen of from 1 to 100 atmospheres (about 1 to 101 bars), more preferably from 1 to 6 atmospheres (about 1 to 6 bars). The reaction is preferably effected in the presence of a solvent, the nature of which is not critical, provided that it has no adverse effect upon the reaction. Suitable solvents include, for example: alcohols, such as methanol or ethanol; aromatic hydrocarbons, such as benzene or toluene; ethers, such as tetrahydrofuran; amides, such as dimethylformamide or dimethylacetamide; organic carboxylic acids, such as acetic acid; water; and mixtures of any two or more thereof.

The reaction will take place over a wide range of temperatures, but we prefer to employ a temperature of from room temperature to 50° C., more preferably from room temperature to 40° C. The time required for the reaction will vary widely, depending upon many factors, notably the nature of the reagents and the reaction temperature; however, at a temperature within the preferred range described above, the reaction will normally be complete within a period of from several minutes to several days, commonly from 30 minutes to 20 hours.

Step E2

In this step, the carbonyl group at the 4-position of the chroman compound of formula (LII) prepared in step E1 is protected; it is desirable that this protection should be carried out prior to the alkylation reaction of step E4.

There is no particular limitation on the nature of the protecting group employed and any such group commonly used for protecting carbonyl groups may equally well be used in the present invention. For example, the oxo compound may be converted into a protected enol compound, such as an enol ether or enol ester. Alternatively, it may be converted into a ketone acetal having cyclic or non-cyclic side chains or into a ketone dithioacetal. Conversion into a ketone dithioacetal is preferred.

Preferably, $R^{33}$ represents a group of formula -$B^1$-$B^2$-$B^1$-, where $B^1$ represents an oxygen or sulfur atom (preferably a sulfur atom) and $B^2$ represents a group of formula —$(CH_2)_2$—, —$(CH_2)_3$—, —$(CH_2)_4$— or —$CH_2$—$CH$=$CH$—$CH_2$-(cis), preferably —$(CH_2)_2$— or —$(CH_2)_3$— and more preferably —$(CH_2)_3$—. Such a protected compound may be prepared by reacting the compound of formula (LII) with a compound of formula H-$B^1$-$B^2$-$B^1$-H (in which $B^1$ and $B^2$ are as defined above), for example ethylene glycol, 1,3-propanediol, 1,2-ethanedithiol, 1,3-propanedithiol or cis-2-butene-1,4-diol, preferably 1,3-propanedithiol, under dehydrating conditions. The reaction may take place in the presence or absence of a catalyst. Where a catalyst is employed, suitable catalysts include, for example: Lewis acids, such as boron trifluoride and diethyl ether and acetic acid complexes thereof, or aluminum chloride; inorganic acids, such as hydrogen chloride or sulfuric acid; organic carboxylic acids, such as acetic acid, tartaric acid, fumaric acid or maleic acid; and organic sulfonic acids, such as p-toluenesulfonic acid or methanesulfonic acid. We prefer to use a Lewis acid, more preferably a boron trifluoride acetic acid complex salt.

The reaction does not always require a solvent; however, if a solvent is employed, its nature is not critical, provided that it has no adverse effect upon the reaction. Examples of suitable solvents include: aromatic hydrocarbons, such as benzene or xylene; and halogenated hydrocarbons, especially halogenated aliphatic hydrocarbons, such as chloroform or methylene chloride. Of these, we prefer halogenated hydrocarbons, such as chloroform.

There is no particular limitation on the proportions of the compound of formula (LII) to the compound of formula $H-B^1-B^2-B^1-H$; however, a small excess of $H-B^1-B^2-B^1-H$ is preferred, preferably a molar ratio of the compound $H-B^1-B^2-B^1-H$ to the compound of formula (LII) of from 1:1 to 2:1. Equally, there is no particular limitation on the proportions of catalyst employed. However, a molar ratio of catalyst to compound of formula (LII) of from 1:1 to 1:4 is preferred.

The reaction will take place over a wide range of temperatures, but we generally prefer to carry out the reaction at a temperature of from 0° to 100° C., more preferably from 10° C. to 40° C. The time required for the reaction may vary widely, depending upon the nature of the reagents and the reaction temperature, but a period of from several minutes to several days, more commonly from 1 hour to 30 hours, will normally suffice.

Step E3

In this step, the phenolic hydroxy group at the 6-position of the chroman ring is protected, typically by reaction with a compound of formula $R^{30}X$ (in which $R^{30}$ and X are as defined above). This reaction is similar to the reactions described in steps A2 and C5 and is preferably carried out employing the same reagents and under the reaction conditions described in relation to step C5. The resulting compound of formula (LIV) may be isolated from the reaction mixture or may be used without intermediate isolation directly in step E4.

Step E4

In this step, the compound of formula (LIV) is converted to a carbanion and then reacted with a compound of formula $R^{1a}X^1$ (in which $R^{1a}$ and $X^1$ are as defined above). This reaction is similar to that described above in relation to step C6 and may be carried out employing the same reagents and under the same reaction conditions as employed in step C6.

If it is desired to prepare a compound in which $R^1$ represents a hydrogen atom, step E4 may be omitted, and the product of step E3—the compound of formula (LIV)—may be employed directly in step E5.

Step E5

In this step, the chroman-2-carboxylic acid derivative of formula (LV) is reduced to the corresponding alcohol of formula (LVI). This reaction is essentially the same as that described above in step A1 of the Method A and may be carried out under the same conditions and employing the same reagents. However, in this case, we prefer to employ a temperature within the range from $-50°$ C. to $+120°$ C.

Step E6

In this step, a group of formula $-(Ar)-NO_2$ (Ar being as defined above) is introduced into the compound of formula (LVI) prepared as described in step E5. This reaction may be effected by reacting the compound of formula (LVI) with a base to convert it to the corresponding alkoxide, and then reacting this with a compound of formula $X-(Ar)-NO_2$ (in which X and Ar are as defined above).

Any base capable of forming an alkoxide with the compound of formula (LVI) may be employed. Examples include: alkali metal and alkaline earth metal hydrides, such as sodium hydride or calcium hydride; and alkali metal alkoxides, such as sodium methoxide, sodium ethoxide or potassium t-butoxide. Of these, we prefer sodium hydride or sodium ethoxide. The proportions of the compound of formula (LVI) and the base are not particularly critical; however, we prefer to employ a slight excess of the base, preferably a molar ratio of base to compound of formula (LVI) of from 1:1 to 2:1.

The reactions are preferably effected in the presence of a solvent, the nature of which is not critical, provided that it has no adverse effect upon the reaction. Suitable solvents include, for example: ethers, such as diethyl ether, tetrahydrofuran or dioxane; aromatic hydrocarbons, such as benzene, toluene or xylene; aliphatic hydrocarbons, such as hexane or heptane; amides, such as dimethylformamide or dimethylacetamide; sulfoxides, such as dimethyl sulfoxide; and sulfones, such as sulfolane. Of these, the amides are preferred. The relative proportions of the compound of formula $X-(Ar)-NO_2$ to the compound of formula (LVI) are not particularly critical to the present invention, however, we prefer to employ a slight excess of the compound of formula $X-(Ar)-NO_2$, preferably a molar ratio of said compound of formula $X-(Ar)-NO_2$ to compound of formula (LVI) of from 1:1 to 10:1.

The reaction will take place over a wide range of temperatures, but we generally prefer to employ a temperature of from 30° C. to 100° C. The time required for the reaction may vary widely, depending upon many factors, notably the nature of the reagents and the reaction temperature. A period of from several minutes to several hours will normally suffice.

The nitro compound of formula (LVII) thus obtained may then be converted to the desired compound of formula (XXX) by following steps A3 and A4 as described in Method A. At some stage in the course of this, the protected carbonyl group at the 4-position of the chroman system is deprotected and this may be carried out as described hereafter in Step E7.

Step E7

In this step, the protected carbonyl group is deprotected. Any conventional reaction employed to deprotect a protected carbonyl group may be employed in this step. For example, the protected compound may be reacted with: a protonic acid, such as hydrochloric acid or sulfuric acid; a Lewis acid, such as boron trifluoride or an ether, e.g. diethyl ether, or acetic acid complex thereof, or aluminum chloride; when $B^1$ represents a sulfur atom, a heavy metal salt, heavy metal oxide, heavy metal peroxide or a mixture of any two or three of these, for example a silver, cadmium, mercurous, mercuric, cuprous or thallic chloride, bromide, iodide, nitrate, perchlorate, oxide or peroxide; iodine; a sulfuryl halide, such as sulfuryl chloride; or an N-haloimide, such as N-chlorosuccinimide or N-bromosuccinimide. Of these, we prefer mercuric chloride, mercuric oxide or a mixture thereof, more preferably a mixture of mercuric chloride and mercuric oxide.

The reaction is preferably effected in the presence of a solvent, the nature of which is not critical, provided that it has no adverse effect upon the reaction. Suitable solvents include, for example: alcohols, such as methanol, ethanol, propanol or isopropanol; ketones, such as acetone or methyl ethyl ketone; halogenated hydrocarbons, especially halogenated aliphatic hydrocarbons, such as chloroform, methylene chloride or 1,2-dichloroethane; ethers, such as tetrahydrofuran or dioxane; organic carboxylic acids, such as acetic acid; nitriles, such as acetonitrile; water; and mixtures of any two or more thereof.

The proportions of the compound of formula (LVII) or other protected compound to the deprotecting agent are not critical. However, we prefer to employ a slight excess of the deprotecting agent, e.g. a molar ratio of deprotecting agent to compound of formula (LII) or other protected compound of from 1:1 to 10:1, more preferably from 1:1 to 4:1.

The reaction will take place over a wide range of temperatures, but we generally find it convenient to carry out the reaction at a temperature within the range from room temperature to 100° C., more preferably from 40° C. to 80° C. The time required for the reaction will vary, depending upon many factors, notably the nature of the reagents and the reaction temperature; however, at a temperature within the ranges mentioned above, a period of from several minutes to several hours, more commonly from 30 minutes to 4 hours, will normally suffice.

Thereafter, the compound of formula (LVIII) may be subjected to steps A3 and A4 to give the desired compound of formula (XXX). Alternatively, the deprotection step E7 may take place after or between these steps A3 and A4.

Method F

A particularly preferred process for preparing compounds of formula (II) in which both W and U represent methylene groups is illustrated in the following reaction scheme:

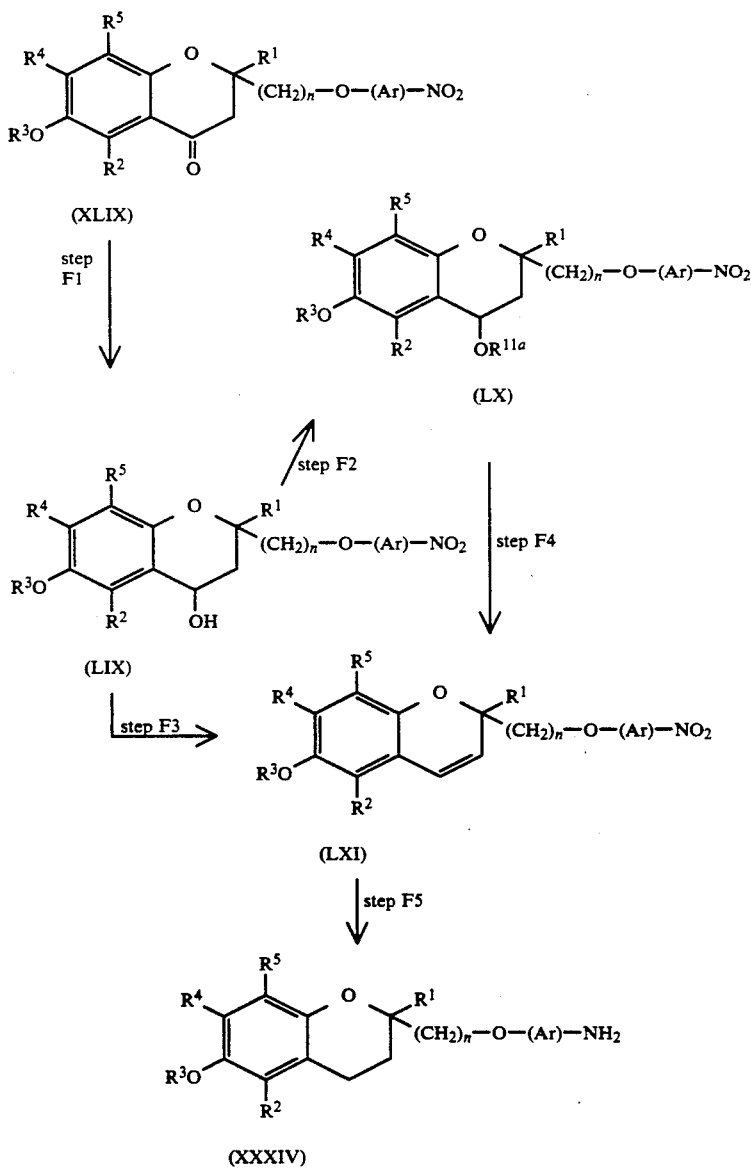

In the above formulae, $R^1$–$R^5$, n and Ar are as defined above and $R^{11a}$ represents any one of the acyl groups defined above in relation to $R^{11}$.

STEP F1

In this step, a 4-oxochroman derivative of formula (XLIX), which may have been prepared by a variety of the methods described above, including, for example step E7 of Method E or step D1 of Method D, is reduced to the corresponding 4-hydroxy compound of formula (LIX). Any reducing agent capable of reducing an oxo group on a saturated ring system to a hydroxy group may be employed. We generally prefer to employ sodium borohydride or K-selectride, of which sodium borohydride is particularly preferred.

The reaction is preferably effected in the presence of a solvent, the nature of which is not critical, provided that it has no adverse effect upon the reaction. Suitable solvents include, for example: alcohols, such as methanol, ethanol, propanol, butanol or ethylene glycol monomethyl ether; and ethers, such as tetrahydrofuran or dioxane.

There is no particular limitation on the relative proportions of the compound of formula (XLIX) to the reducing agent, e.g. sodium borohydride, but we generally prefer to employ an excess, preferably a slight excess, of the reducing agent. In general, we would use a molar ratio of reducing agent to compound of formula (XLIX) of from 1:1 to 20:1.

The reaction will take place over a wide range of temperatures and the exact temperature chosen is not particularly critical. A temperature within the range from 0° C. to 100° C. is generally preferred. The time required for the reaction may vary widely, depending upon many factors, notably the nature of the reagents and the reaction temperature. However, a period of from 1 to 20 hours will normally suffice.

Step F2

In this optional step, the compound of formula (LIX) prepared as described in step F1 is acylated. The acylating agent employed is preferably an acid halide or acid anhydride.

The reaction is preferably carried out in the presence of a solvent, the nature of which is not critical, provided that it does not interfere with the reaction. Suitable solvents include, for example: ethers, such as diethyl ether, tetrahydrofuran or dioxane; aromatic hydrocarbons, such as benzene, toluene or xylene; aliphatic hydrocarbons, such as hexane, cyclohexane or heptane; halogenated hydrocarbons, especially halogenated aliphatic hydrocarbons, such as methylene chloride or chloroform; organic bases, such as pyridine or triethylamine; amides, such as dimethylformamide or dimethylacetamide; sulfoxides, such as dimethyl sulfoxide; and sulfones, such as sulfolane.

There is no particular limitation on the proportions of compound of formula (LIX) to the acylating agent, but we generally prefer to use equimolar amounts or a slight excess of acylating agent. In general, a molar ratio of acylating agent to compound of formula (LIX) of from 1:1 to 10:1 is preferred. Where $R^3$ in the compound of formula (LIX) is a hydrogen atom, the group $R^3O$ may also be acylated in the course of this reaction.

The reaction will take place over a wide range of temperatures and the particular temperature chosen is not critical. We generally prefer to carry out the acylation reaction at a temperature within the range from 0° C. to 100° C. The time required for the reaction may vary over a wide range, depending upon many factors, notably the nature of the reagents and the reaction temperature; however, at a temperature within the preferred range, a period of from 5 minutes to 20 hours will normally suffice.

Step F3

In this step, which is an alternative to step F2, a 2H-chromene compound of formula (LXI) is prepared by dehydrating the 4-hydroxychroman (LIX).

The dehydration reaction may be achieved in the presence or absence of a dehydrating agent or dehydrating catalyst. Suitable dehydrating agents and catalysts include, for example: inorganic acids, such as hydrochloric acid, sulfuric acid, nitric acid or phosphoric acid; organic carboxylic acids, such as acetic acid, tartaric acid or maleic acid; organic sulfonic acids, such as p-toluenesulfonic acid, naphthalenesulfonic acid or methanesulfonic acid; inorganic salts, such as ammonium chloride or calcium chloride; phosphorus pentoxide; polyphosphoric acid; silica gel; and alumina. Of these, we prefer an organic carboxylic acid such as acetic acid or an organic sulfonic acid, such as p-toluenesulfonic acid.

It is not always necessary to employ a solvent in this reaction; however, where a solvent is used, its nature is not particular critical, provided that is does not interfere with the reaction. Examples of suitable solvents include: alcohols, such as methanol, ethanol or isopropanol; ketones, such as acetone or methyl ethyl ketone; ethers, such as diethyl ether, tetrahydrofuran or dioxane; aromatic hydrocarbons, such as benzene, toluene or xylene; aliphatic hydrocarbons, such as hexane, cyclohexane or heptane; halogenated hydrocarbons, especially halogenated aliphatic hydrocarbons, such as methylene chloride or chloroform; organic carboxylic acids, such as acetic acid or propionic acid; organic bases, such as pyridine or triethylamine; amides, such as dimethylformamide or dimethylacetamide; sulfoxides, such as dimethyl sulfoxide; sulfones, such as sulfolane; water; and mixtures of any two or more thereof. Of these, we prefer aromatic hydrocarbons, such as benzene, or organic acids, such as acetic acid.

If a dehydrating agent or catalyst is employed, the relative proportion of such agent or catalyst to the compound of formula (LIX) is not critical, but we prefer to employ a molar ratio of said agent or catalyst to said compound of formula (LIX) of from 0.01:1 to 10:1, more preferably from 0.1:1 to 3:1.

The reaction will take place over a wide range of temperatures and the exact temperature chose is not particularly critical; however, we generally prefer to carry out the reaction at a temperature in the range from 20° C. to 100° C. The time required for the reaction will vary, depending upon many factors, notably the nature of the reagents and the reaction temperature; however, at temperatures within the preferred range indicated above, a period of from several minutes to 20 hours will normally suffice.

Step F4

In this step, the 2H-chromene compound of formula (LXI) is prepared from the 4-acyloxychroman of formula (LX) by elimination of an acid of formula $R^{11a}OH$ (in which $R^{11a}$ is as defined above).

This elimination reaction can be carried out in the presence or absence of an acid-binding agent or catalyst. Examples of suitable such agents and catalysts include: inorganic acids, such as hydrochloric acid, sulfuric acid, nitric acid or phosphoric acid; organic carboxylic acids, such as acetic acid, tartaric acid or maleic acid; organic sulfonic acids, such as p-toluenesulfonic acid; naphthalenesulfonic acid or methanesulfonic acid; inorganic salts, such as ammonium chloride or calcium chloride; organic bases, such as pyridine or triethylamine; silica gel; and alumina. Of these, we prefer an organic carboxylic or sulfonic acid, such as acetic acid or p-toluenesulfonic acid.

It is not always necessary to employ a solvent for this elimination reaction and, where a solvent is employed, its nature is not critical, provided that it has no adverse effect on the reaction. Suitable solvents include, for example: alcohols, such as methanol, ethanol or isopropanol; ketones, such as acetone or methyl ethyl ketone; ethers, such as deithyl ether, tetrahydrofuran or dioxane; aromatic hydrocarbons, such as benzene, toluene or xylene; aliphatic hydrocarbons, such as hexane, cyclohexane or heptane; halogenated hydrocarbons, such as methylene chloride or chloroform; organic acids, such as acetic acid or propionic acid; organic bases, such as pyridine or triethylamine; amides, such as dimethylformamide or dimethylacetamide; sulfoxides, such as dimethyl sulfoxide; sulfones, such as sulfolane; and water. Of these, we prefer aromatic hydrocarbons (such as benzene) or organic acids (such as acetic acid).

Where an acid-binding agent or catalyst is employed, the relative proportions of such agent or catalyst and the compound of formula (LX) are not particularly critical. We generally prefer to employ the agent or catalyst and the compound of formula (LX) in a molar ratio of from 0.01:1 to 10:1, more preferably from 0.1:1 to 3:1.

The reaction will take place over a wide range of temperatures and the exact temperature chosen is not particularly critical. In general, we prefer to carry out the reaction at a temperature within the range from 0° C. to 120° C., more preferably from 40° C. to 100° C. The time required for the reaction may vary widely, depending upon many factors, notably the nature of the reagents and the reaction temperature; however, at a temperature within the preferred ranges indicated above, a period of from several minutes to several days, commonly from 10 minutes to 10 hours, will normally suffice.

Step F5

In this step, the chroman derivative of formula (XXXIV) is prepared by the reductive hydrogenation of the 2H-chromene derivative of formula (LXI).

Catalytic hydrogenation is preferably employed. Suitable catalysts include, for example palladium-on-carbon, Raney nickel or platinum oxide, of which palladium-on-carbon is preferred. The partial pressure of hydrogen may vary widely, for example from 1 to 100 atmospheres (about 1 to 101 bars), more preferably from 1 to 6 atmospheres (about 1 to 6 bars). The reaction is preferably effected in the presence of a solvent, the nature of which is not critical, provided that it does not interfere with the reaction. Suitable solvents include, for example: alcohols, such as methanol or ethanol; aromatic hydrocarbons, such as benzene or toluene; ethers, such as tetrahydrofuran; organic acids, such as acetic acid; water; or a mixture of any two or more thereof.

The reaction will take place over a wide range of temperatures and the exact temperature chosen is not particularly critical; however, we generally prefer to carry out the reaction at a temperature from room temperature to 50° C. The time required for the reaction may vary widely, depending upon many factors, notably the nature of the reagents and the reaction temperature; however, at a temperature within the indicated range, a period of from several minutes to 20 hours will normally suffice.

The α-halocarboxylic acid derivative of formula (XXX) may then be prepared as described in step A4 from this compound of formula (XXXIV).

Steps F1, F3 (or F2+F4), F5, A4 and the final step for reacting the α-halocarboxylic acid derivative (XXX) with thiourea to give the desired thiazolidine derivative of the invention can, if desired, be carried out in succession without intermediate isolation of the products of any of these steps.

Moreover, these steps are not necessarily carried out in the sequence described above and they may be carried out in any appropriate order. For example, one suitable alternative sequence would comprise: first, reducing the nitro group in the compound of formula (XLIX) by a step analogous to step F5 to give the corresponding amino compound; reducing the carbonyl group at the 4-position of the chroman ring by a step analogous to step F1 to give a 4-hydroxychroman compound; dehydrating this 4-hydroxychroman compound by a step analogous to step F3 (or acylating and then eliminating the acid by steps analogous to steps F2 and F4), to give a 2H-chromene compound; and finally hydrogenating the 2H-chromene compound by a step analogous to step F5.

Method G

This process is useful for converting a chroman derivative, such as those prepared in steps E5 and E6 of Method E, having a carbonyl group as W at the 4-position to the corresponding compound where W is a methylene group. The compounds prepared as described in steps E5 and E6 are first, if necessary, deprotected, to remove the protecting group $R^{30}$ at the 6-position. The resulting free hydroxy group is then acylated.

The resulting compound then has its carbonyl group protected, as described in step E2, to give a compound of formula (LXIII) or (LXV). These compounds are then hydrogenated, to give the corresponding compounds of formulae (LXIV) or (LXVI), as shown below:

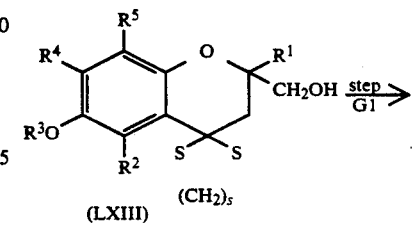

(LXIII)

-continued

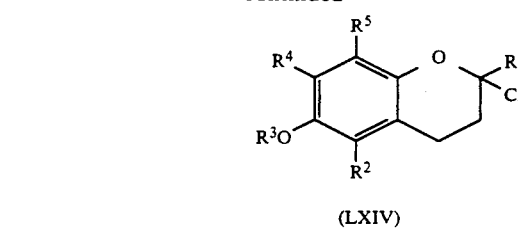
(LXIV)

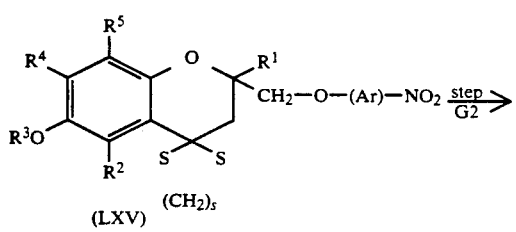
(LXV)

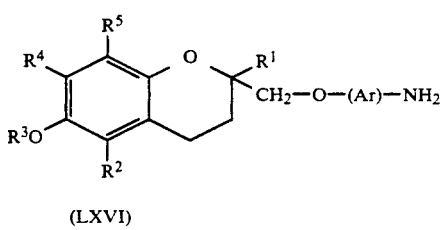
(LXVI)

In the above formulae, $R^1$-$R^5$ and Ar are as defined above; s is 2, 3 or 4.

The hydrogenation is preferably effected in the presence of a catalyst, preferably a nickel catalyst, such as Raney nickel.

The hydrogen partial pressure may vary widely, for example from 1 to 100 atmospheres (about 1 to 101 bars), more preferably from 1 to 6 atmospheres (about 1 to 6 bars).

The reaction is preferably effected in the presence of a solvent, the nature of which is not critical, provided that it has no adverse effect upon the reaction. Suitable solvents include, for example: alcohols, such as methanol or ethanol; aromatic hydrocarbons, such as benzene or toluene; ethers, such as tetrahydrofuran; organic acids, such as acetic acid; water; and mixtures of any two or more thereof.

The reaction will take place over a wide range of temperatures, for example from room temperature to 50° C. The time required for the reaction will vary, depending upon many factors, notably the nature of the reagents and the reaction temperature, but a period of from several minutes to 20 hours will normally suffice.

The resulting compounds of formulae (LXIV) and (LXVI) may thereafter be treated by any of the appropriate processes described above to give the desired compounds of formula (II).

Method H

This method can be used to prepare compounds of formula (XIII), having a group L at the 2-position of the chroman ring and where W is a carbonyl group, as illustrated in the following reaction scheme:

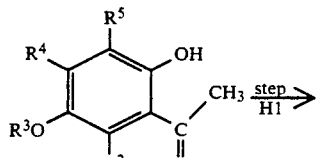
(XLVII)

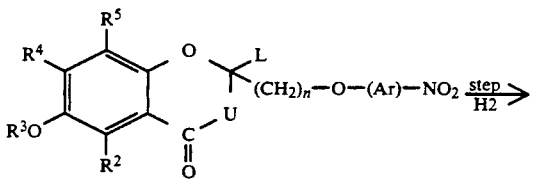
(LXVIII)

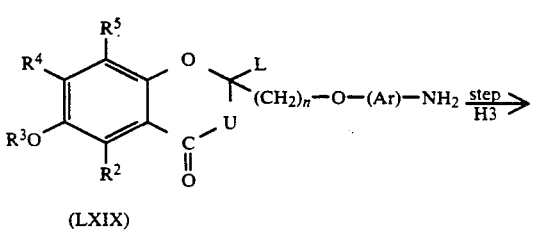
(LXIX)

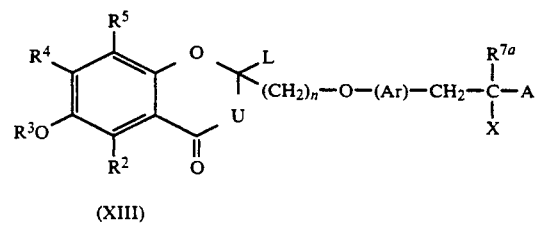
(XIII)

In the above formulae, $R^2$-$R^5$, U, L, n, Ar, $R^{7a}$, X and A are as defined above.

Preferably, L represents a group of formula -$OR^3$ and U represents a methylene group. However, if desired, L, the carbon atom to which it is attached and U may together represent a double bond.

Step H1

In this step, the compound of formula (XLVII) is reacted with a compound of formula (LXX):

$$O_2N—(Ar)—O—(CH_2)_n—COX \qquad (LXX)$$

(in which Ar, n and X are as defined above), followed by treatment with an organic base, such as sodium ethoxide or potassium t-butoxide. The reaction is otherwise similar to that of step C2 of Method C and may be carried out under the same reaction conditions.

Step H2

This is equivalent to step A3 and may be carried out using the same reagents and under the same reaction conditions.

Step H3

This is equivalent to step A4 of Method A and may be carried out using the same reagents under the same reaction conditions.

Of Methods A-H, Methods A, B, C, D, E, F and H are preferred, Methods A, C, D, E, F and H being more preferred and a combination of Methods D, F and A being most preferred. A particularly preferred combination of reactions comprises steps F1, F3 or F2 plus F4), F5, A4 and finally reaction with thiourea to give a compound of formula (I) in which $R^7$ is $R^{7a}$ and $R^6$ is a hydrogen atom. In particular, we prefer this sequence of steps where Ar represents a p-phenylene group.

In the compounds of formula (II), the carbon atom at the 2-position of the chroman ring and the carbon atom to which the substituents X, A and $R^{7a}$ are attached are both asymmetric and accordingly a number of isomers are possible. The present invention envisages both the individual isolated isomers as well as mixtures thereof. Individual isomers may be prepared by stereospecific synthesis techniques or by separation of mixtures of isomers. Alternatively, the mixtures of isomers may be employed as such.

We have found that the α-halocarboxylic acid derivatives of formula (II) have the ability to lower the levels of blood lipid peroxides, blood triglycerides and blood cholesterol, indicating that, in addition to their use as intermediates in the preparation of the compounds of the invention, they may also have in themselves therapeutic value in the treatment of hyperlipemia.

The compounds of formula (II) prepared as described above can, if desired, be converted to various of their hydrolysis products or may be transesterified or converted to salts, for example such metal salts as the sodium, potassium, calcium or aluminum salts. Alternatively, they can be converted from metal salts or from compounds having free hdyroxyphenyl groups or free carboxy groups to derivatives thereof, for example as follows:

Compounds in which $R^3$ represents a hydrogen atom and A represents a carboxy group can be prepared by hydrolysis of the corresponding compound of formula (II) in which, for example, $R^3$ represents an acyl group and A represents an alkoxycarbonyl group. This reaction is preferably effected in the presence of a base, for example: an inorganic base, such as an alkali metal carbonate (e.g. sodium carbonate or potassium carbonate) or an alkali metal hydroxide (e.g. sodium hydroxide or potassium hydroxide); or an organic base, such as an alkali metal alkoxide (e.g. sodium methoxide, sodium ethoxide or potassium t-butoxide). The reaction is preferably effected in the presence of a solvent, the nature of which is not critical, provided that it has no adverse effect upon the reaction. Suitable solvents include: lower alcohols, such as methanol or ethanol; ethers, such as tetrahydrofuran or dioxane; water; or mixtures of any two or more thereof.

The molar ratio of the compound of formula (II) to the base is preferably from 1:1 to 1:5, more preferably from 1:2 to 1:3. Although the reaction conditions, particularly the reaction temperature and time, may vary depending upon a number of factors, particularly the natures of the starting material, base and solvent employed, the reaction is generally carried out at a temperature of from $-10°$ C. to $+30$ C., more preferably from $0°$ C. to $10°$ C., and the reaction time is generally from several minutes to several tens of hours.

The compound of formula (II) in which $R^3$ represents a hydrogen atom and A represents an alkoxycarbonyl group can be prepared by solvolysis of the corresponding compound in which $R^3$ represents an acyl group and A represents an alkoxycarbonyl group. This is carried out in the presence of a base, preferably an alkali metal alkoxide, such as sodium methoxide, sodium ethoxide or potassium t-butoxide. The reaction is preferably effected in the presence of a solvent, for example: an alcohol, such as methanol, ethanol, propanol, isopropanol or t-butanol; an ether, such as tetrahydrofuran or dioxane; or a mixture of any two or more thereof. It the alkoxycarbonyl group represented by A in the starting material is to be kept intact, it is preferred that the alkali metal alkoxide should be the alkoxide corresponding to this alkoxycarbonyl group and that the solvent should be an alcohol, which likewise corresponds to the alkoxycarbonyl group. However, the alkoxycarbonyl group in the starting material may, if desired, be converted into any other alkoxycarbonyl group by suitable choice of the alkali metal alkoxide and the alcohol solvent.

The molar ratio of the compound of formula (II) to the base is preferably from 1:1 to 1:3, more preferably from 1:1 to 1:2. The reaction conditions, especially the reaction temperature and reaction time, may vary, depending upon a number of factors, particularly the natures of the starting materials, bases and solvents employed, but the reaction is preferably carried out at a temperature of from $-10°$ C. to $+30°$ C., more preferably from $0°$ to $10°$ C., for a period of from several minutes to several tens of hours.

Compounds of formula (II) in which $R^3$ represents an acyl group and A represents a carboxy group may be prepared by hydrolysis of the corresponding compound of formula (II) in which $R^3$ represents an acyl group and A represents an alkoxycarbonyl group. In this case, the hydrolysis is effected in the presence of an inorganic base (for example an alkali metal carbonate, such as sodium carbonate or potassium carbonate, or an alkali metal hydroxide, such as sodium hydroxide or potassium hydroxide) or in the presence of another base such as an alkali metal alkoxide (for example sodium methoxide, sodium ethoxide or potassium t-butoxide). This reaction is preferably effected in the presence of a solvent, for example: a lower alcohol, such as methanol or ethanol; an ether, such as tetrahydrofuran or dioxane; water; or a mixture of any two or more thereof. The molar ratio of the compound of formula (II) to the base is preferably from 1:1 to 1:5, more preferably from 1:1 to 1:2. The reaction conditions, particularly the reaction temperature and time, may vary depending upon a number of factors, especially the natures of the starting materials, bases and solvents employed, but the reaction is normally effected at a temperature of from $-10°$ C. to $+30°$ C., more preferably from $0°$ to $10°$ C. for a period of from several minutes to several tens of hours.

Of the compounds of formula (II) which exhibit the therapeutic effects mentioned above and which also form part of the present invention, preferred compounds are those listed below in Table 27.

In this Table, the abbreviations used are as previously defined in relation to Tables 1-26.

Compounds of formula (II-27):

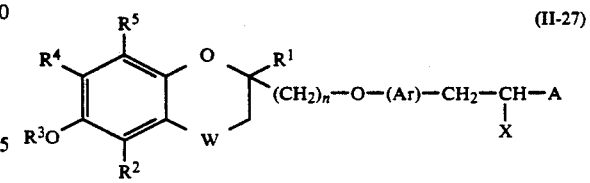

are as defined in Table 27:

TABLE 27

| Cpd. No. | R¹ | R² | R³ | R⁴ | R⁵ | W | n | Ar | X | A |
|---|---|---|---|---|---|---|---|---|---|---|
| 1001 | Me | Me | H | Me | Me | >CH₂ | 1 | 6-Me-1,3-Phn | Cl | —COOEt |
| 1002 | Me | Me | Ac | Me | Me | >CH₂ | 1 | 6-Me-1,3-Phn | Cl | —COOEt |
| 1003 | Me | Me | H | Me | Me | >C=O | 1 | 6-Me-1,3-Phn | Cl | —COOEt |
| 1004 | Me | Me | Ac | Me | Me | >C=O | 1 | 6-Me-1,3-Phn | Cl | —COOEt |
| 1005 | Me | Me | H | Me | Me | >CH₂ | 1 | 2,5-Pydi | Cl | —COOEt |
| 1006 | Me | Me | Ac | Me | Me | >CH₂ | 1 | 2,5-Pydi | Cl | —COOEt |
| 1007 | Me | Me | H | Me | Me | >C=O | 1 | 2,5-Pydi | Cl | —COOEt |
| 1008 | Me | Me | Ac | Me | Me | >C=O | 1 | 2,5-Pydi | Cl | —COOEt |
| 1009 | Me | H | H | t-Bu | H | >CH₂ | 1 | 6-Me-1,3-Phn | Cl | —COOEt |
| 1010 | Me | H | Ac | t-Bu | H | >CH₂ | 1 | 6-Me-1,3-Phn | Cl | —COOEt |
| 1011 | Me | H | H | t-Bu | H | >C=O | 1 | 6-Me-1,3-Phn | Cl | —COOEt |
| 1012 | Me | H | Ac | t-Bu | H | >C=O | 1 | 6-Me-1,3-Phn | Cl | —COOEt |
| 1013 | Me | H | H | t-Bu | H | >CH₂ | 1 | 2,5-Pydi | Cl | —COOEt |
| 1014 | Me | H | Ac | t-Bu | H | >CH₂ | 1 | 2,5-Pydi | Cl | —COOEt |
| 1015 | Me | H | H | t-Bu | H | >C=O | 1 | 2,5-Pydi | Cl | —COOEt |
| 1016 | Me | H | Ac | t-Bu | H | >C=O | 1 | 2,5-Pydi | Cl | —COOEt |
| 1017 | Me | H | Ac | TMB | H | >CH₂ | 1 | p-Phn | Cl | —COOEt |
| 1018 | Me | H | Ac | TMB | H | >C=O | 1 | p-Phn | Cl | —COOEt |
| 1019 | Me | H | Ac | TMB | H | >CH₂ | 1 | 6-Me-1,3-Phn | Cl | —COOEt |
| 1020 | Me | H | Ac | TMB | H | >C=O | 1 | 6-Me-1,3-Phn | Cl | —COOEt |

TABLE 27-continued

| Cpd. No. | R¹ | R² | R³ | R⁴ | R⁵ | W | n | Ar | X | A |
|---|---|---|---|---|---|---|---|---|---|---|
| 1021 | Me | H | Ac | TMB | H | >CH₂ | 1 | 2,5-Pydi | Cl | —COOEt |
| 1022 | Me | H | Ac | TMB | H | >CH₂ | 2 | p-Phn | Cl | —COOMe |
| 1023 | Et | Me | Boz | Me | Me | >C=O | 1 | 5-Me-1,3-Phn | Cl | —COOH |
| 1024 | iBu | Me | 4-MeBoz | Me | H | >C=O | 1 | 2,5-Pydi | Cl | —COOHN₄ |
| 1025 | nPn | Me | Ac | Me | Me | >CH₂ | 1 | 2,5-Pydi | Cl | —COOMe |
| 1026 | Hx | Me | Ac | Me | Me | >CH₂ | 1 | p-Phn | Cl | —COOEt |
| 1027 | iHx | Me | Ac | Me | Me | >C=O | 1 | p-Phn | Cl | —COOMe |
| 1028 | Hx | Me | Ac | Me | Me | >CH₂ | 1 | 6-Me-1,3-Phn | Cl | —COOH |
| 1029 | Hp | H | H | tBu | H | >CH₂ | 1 | 2,5-Pydi | Cl | —COOEt |
| 1030 | Oc | Me | Ac | Me | Me | >CH₂ | 1 | p-Phn | Cl | —COOEt |
| 1031 | Oc | Me | Ac | Me | Me | >C=O | 1 | p-Phn | Cl | —COOEt |
| 1032 | Oc | Me | Ac | Me | Me | >CH₂ | 1 | 6-Me-1,3-Phn | Cl | —COOEt |
| 1033 | Oc | Me | Ac | Me | Me | >C=O | 1 | 6-Me-1,3-Phn | Cl | —COOEt |
| 1034 | Oc | Me | Ac | Me | Me | >CH₂ | 1 | 2,5-Pydi | Cl | —COOEt |
| 1035 | Oc | Me | Ac | Me | Me | >C=O | 1 | 2,5-Pydi | Cl | —COOEt |
| 1036 | Oc | H | Ac | t-Bu | H | >CH₂ | 1 | p-Phn | Cl | —COOEt |
| 1037 | Oc | H | Ac | t-Bu | H | >C=O | 1 | p-Phn | Cl | —COOEt |
| 1038 | Oc | H | Ac | t-Bu | H | >CH₂ | 1 | 6-Me-1,3-Phn | Cl | —COOEt |
| 1039 | Oc | H | Ac | t-Bu | H | >C=O | 1 | 6-Me-1,3-Phn | Cl | —COOEt |
| 1040 | Oc | H | Ac | t-Bu | H | >CH₂ | 1 | 2,5-Pydi | Cl | —COOEt |

TABLE 27-continued

| Cpd. No. | R¹ | R² | R³ | R⁴ | R⁵ | W | n | Ar | X | A |
|---|---|---|---|---|---|---|---|---|---|---|
| 1041 | Oc | H | Ac | t-Bu | H | >C=O | 1 | 2,5-Pydi | Cl | —COOEt |
| 1042 | Oc | H | Ac | TMB | H | >CH₂ | 1 | p-Phn | Cl | —COOEt |
| 1043 | Oc | H | Ac | TMB | H | >C=O | 1 | p-Phn | Cl | —COOEt |
| 1044 | Oc | H | Ac | TMB | H | >CH₂ | 1 | 6-Me-1,3-Phn | Cl | —COOEt |
| 1045 | Oc | H | Ac | TMB | H | >C=O | 1 | 6-Me-1,3-Phn | Cl | —COOEt |
| 1046 | Oc | H | Ac | TMB | H | >CH₂ | 1 | 2,5-Pydi | Cl | —COOEt |
| 1047 | Oc | H | Ac | TMB | H | >C=O | 1 | 2,5-Pydi | Cl | —COOEt |
| 1048 | 5,5-DMH | Me | Ac | Me | Me | >CH₂ | 1 | p-Phn | Cl | —COOEt |
| 1049 | Bz | iPr | H | iPr | H | >CH₂ | 1 | p-Phn | Cl | —COOEt |
| 1050 | Nn | Me | H | Me | H | >CH₂ | 1 | p-Phn | Cl | —COOEt |
| 1051 | Dc | Me | Ac | MeO | MeO | >CH₂ | 1 | p-Phn | Cl | —COOEt |
| 1052 | 3,7-DMO | Me | H | Me | Me | >CH₂ | 1 | p-Phn | Cl | —COOEt |
| 1053 | 3,7-DMO | Me | Ac | Me | Me | >CH₂ | 1 | p-Phn | Cl | —COOEt |
| 1054 | 3,7-DMO | Me | Ac | Me | Me | >C=O | 1 | p-Phn | Cl | —COOEt |
| 1055 | 3,7-DMO | Me | Ac | Me | Me | >CH₂ | 1 | 6-Me-1,3-Phn | Cl | —COOEt |
| 1056 | 3,7-DMO | Me | Ac | Me | Me | >C=O | 1 | 6-Me-1,3-Phn | Cl | —COOEt |
| 1057 | 3,7-DMO | Me | Ac | Me | Me | >CH₂ | 1 | 2,5-Pydi | Cl | —COOEt |
| 1058 | 3,7-DMO | Me | Ac | Me | Me | >C=O | 1 | 2,5-Pydi | Cl | —COOEt |
| 1059 | 3,7-DMO | H | H | tBu | H | >CH₂ | 1 | p-Phn | Cl | —COOEt |
| 1060 | 3,7-DMO | H | Ac | tBu | H | >CH₂ | 1 | p-Phn | Cl | —COOEt |

TABLE 27-continued

| Cpd. No. | R¹ | R² | R³ | R⁴ | R⁵ | W | n | Ar | X | A |
|---|---|---|---|---|---|---|---|---|---|---|
| 1061 | 3,7-DMO | H | H | tBu | H | >C=O | 1 | p-Phn | Cl | —COOEt |
| 1062 | 3,7-DMO | H | Ac | tBu | H | >C=O | 1 | p-Phn | Cl | —COOEt |
| 1063 | 3,7-DMO | H | H | tBu | H | >CH₂ | 1 | 6-Me-1,3-Phn | Cl | —COOEt |
| 1064 | 3,7-DMO | H | Ac | tBu | H | >CH₂ | 1 | 6-Me-1,3-Phn | Cl | —COOEt |
| 1065 | 3,7-DMO | H | H | tBu | H | >C=O | 1 | 6-Me-1,3-Phn | Cl | —COOEt |
| 1066 | 3,7-DMO | H | Ac | tBu | H | >C=O | 1 | 6-Me-1,3-Phn | Cl | —COOEt |
| 1067 | 3,7-DMO | H | Ac | tBu | H | >CH₂ | 1 | 2,5-Pydi | Cl | —COOEt |
| 1068 | 3,7-DMO | H | Ac | tBu | H | >C=O | 1 | 2,5-Pydi | Cl | —COOEt |
| 1069 | 3,7-DMO | H | Ac | TMB | H | >CH₂ | 1 | p-Phn | Cl | —COOEt |
| 1070 | 3,7-DMO | H | Ac | TMB | H | >C=O | 1 | p-Phn | Cl | —COOEt |
| 1071 | 3,7-DMO | H | Ac | TMB | H | >CH₂ | 1 | 6-Me-1,3-Phn | Cl | —COOEt |
| 1072 | 3,7-DMO | H | Ac | TMB | H | >C=O | 1 | 6-Me-1,3-Phn | Cl | —COOEt |
| 1073 | 3,7-DMO | H | AC | TMB | H | >CH₂ | 1 | 2,5-Pydi | Cl | —COOEt |
| 1074 | 3,7-DMO | H | Ac | TMB | H | >C=O | 1 | 2,5-Pydi | Cl | —COOEt |
| 1075 | 3,7-DMO | H | Boz | TMB | H | >CH₂ | 1 | p-Phn | Cl | —COOEt |
| 1076 | 3,7-DMO | H | Ac | Me | H | >CH₂ | 1 | p-Phn | Cl | —COOH |
| 1077 | 7,7-DMO | Me | H | Me | Me | >CH₂ | 1 | p-Phn | Cl | —COOEt |
| 1078 | 7,7-DMO | Me | Ac | Me | Me | >CH₂ | 1 | p-Phn | Cl | —COOEt |
| 1079 | 7,7-DMO | Me | H | Me | Me | >C=O | 1 | p-Phn | Cl | —COOEt |
| 1080 | 7,7-DMO | Me | Ac | Me | Me | >C=O | 1 | p-Phn | Cl | —COOEt |

TABLE 27-continued

| Cpd. No. | R¹ | R² | R³ | R⁴ | R⁵ | W | n | Ar | X | A |
|---|---|---|---|---|---|---|---|---|---|---|
| 1081 | 7,7-DMO | Me | Ac | Me | Me | >CH₂ | 1 | 6-Me-1,3-Phn | Cl | —COOEt |
| 1082 | 7,7-DMO | Me | Ac | Me | H | >C=O | 1 | 6-Me-1,3-Phn | Cl | —COOEt |
| 1083 | 7,7-DMO | Me | Ac | Me | H | >CH₂ | 1 | 2,5-Pydi | Cl | —COOEt |
| 1084 | 7,7-DMO | Me | Ac | Me | H | >C=O | 1 | 2,5-Pydi | Cl | —COOEt |
| 1085 | 7,7-DMO | H | Ac | tBu | H | >CH₂ | 1 | p-Phn | Cl | —COOEt |
| 1086 | 7,7-DMO | H | Ac | tBu | H | >C=O | 1 | p-Phn | Cl | —COOEt |
| 1087 | 7,7-DMO | H | Ac | TMB | H | >CH₂ | 1 | p-Phn | Cl | —COOEt |
| 1088 | Bz | Me | H | Me | Me | >CH₂ | 1 | p-Phn | Cl | —COOEt |
| 1089 | Bz | Me | Ac | Me | Me | >CH₂ | 1 | p-Phn | Cl | —COOEt |
| 1090 | Bz | Me | H | Me | Me | >C=O | 1 | p-Phn | Cl | —COOEt |
| 1091 | Bz | Me | Ac | Me | Me | >C=O | 1 | p-Phn | Cl | —COOEt |
| 1092 | Bz | H | H | tBu | H | >CH₂ | 1 | p-Phn | Cl | —COOEt |
| 1093 | Bz | H | H | TMB | H | >CH₂ | 1 | p-Phn | Cl | —COOEt |
| 1094 | Me | Me | HOOCCH₂— | Me | Me | >CH₂ | 1 | p-Phn | Cl | —COOEt |
| 1095 | Me | Me | EtOOCCH₂— | Me | Me | >C=O | 1 | p-Phn | Cl | —COOEt |
| 1096 | Me | H | HOOCCH₂— | tBu | H | >CH₂ | 1 | 2,5-Pydi | Cl | —COOH |
| 1097 | 3,7-DMO | H | HOOC(CH₂)₂— | tBu | H | >CH₂ | 2 | p-Phn | Br | —COOH |
| 1098 | Me | H | HOOCCMe₂— | TMB | H | >C=O | 1 | 6-Me-1,3-Phn | Cl | —COOPr |

In addition, other compounds useful as intermediates are shown in Tables 28 and 29, the abbreviations used again being as defined in relation to Tables 1-26.

Compounds of formulae (XIII-28) and (XIII-29):

-continued

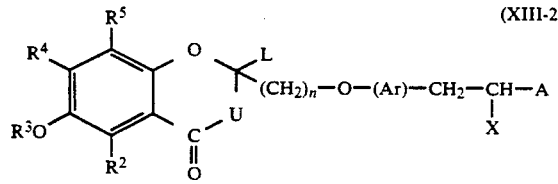

(XIII-28)

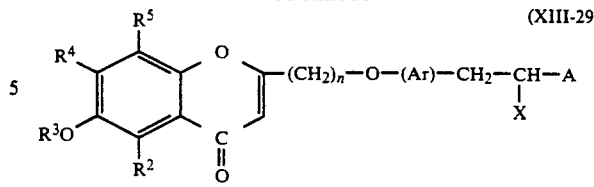

(XIII-29)

are as defined in Table 27 and 28, respectively:

TABLE 28

| Cpd. No. | L | U | R² | R³ | R⁴ | R⁵ | n | Ar | X | A |
|---|---|---|---|---|---|---|---|---|---|---|
| 2001 | —OH | >CH₂ | Me | H | Me | Me | 1 | p-Phn | Cl | —COOH |
| 2002 | —OH | >CH₂ | Me | Ac | Me | Me | 1 | p-Phn | Cl | —COOEt |
| 2003 | —OH | >CH₂ | Me | H | Me | Me | 2 | p-Phn | Cl | —COOH |
| 2004 | —OH | >CH₂ | Me | H | Me | Me | 1 | 6-Me-1,3-Phn | Cl | —COOMe |
| 2005 | —OH | >CH₂ | Me | Ac | Me | Me | 1 | 6-Me-1,3-Phn | Cl | —COOEt |
| 2006 | —OH | >CH₂ | Me | H | Me | Me | 1 | 2,5-Pydi | Cl | —COOH |
| 2007 | —OH | >CH₂ | Me | Ac | Me | Me | 1 | 2,5-Pydi | Cl | —COOiPr |
| 2008 | —OH | >CH₂ | H | H | tBu | H | 1 | p-Phn | Cl | —COOH |
| 2009 | —OH | >CH₂ | H | Ac | tBu | H | 1 | p-Phn | Cl | —COOEt |
| 2010 | —OH | >CH₂ | H | H | tBu | H | 1 | 6-Me-1,3-Phn | Cl | —COOH |
| 2011 | —OAc | >CH₂ | H | Ac | tBu | H | 1 | 6-Me-1,3-Phn | Cl | —COO-tBu |
| 2012 | —OH | >CH₂ | H | H | tBu | H | 1 | 2,5-Pydi | Cl | —COOH |
| 2013 | —OH | >CH₂ | H | Ac | tBu | H | 1 | 2,5-Pydi | Cl | —COOPh |
| 2014 | —OH | >CH₂ | H | H | TMB | H | 1 | p-Phn | Cl | —COOH |
| 2015 | —OH | >CH₂ | H | H | TMB | H | 1 | 6-Me-1,3-Phn | Cl | —COOH |
| 2016 | —OH | >CH₂ | H | H | TMB | H | 1 | 2,5-Pydi | Cl | —COOH |

TABLE 29

| Cpd. No. | R² | R³ | R⁴ | R⁵ | n | Ar | X | A |
|---|---|---|---|---|---|---|---|---|
| 2017 | Me | H | Me | Me | 1 | p-Phn | Cl | —COOH |
| 2018 | Me | Ac | Me | Me | 1 | p-Phn | Cl | —COOEt |
| 2019 | Me | H | Me | Me | 1 | 6-Me-1,3-Phn | Cl | —COOH |
| 2020 | Me | Ac | Me | Me | 1 | 6-Me-1,3-Phn | Cl | —COOMe |
| 2021 | Me | H | Me | Me | 1 | 2,5-Pydi | Cl | —COOH |
| 2022 | Me | Ac | Me | Me | 1 | 2,5-Pydi | Cl | —COOEt |
| 2023 | H | H | tBu | H | 1 | p-Phn | Cl | —COOH |
| 2024 | H | H | tBu | H | 1 | 6-Me-1,3-Phn | Cl | —COOH |
| 2025 | H | H | tBu | H | 1 | 2,5-Pydi | Cl | —COOH |

TABLE 29-continued

| Cpd. No. | R² | R³ | R⁴ | R⁵ | n | Ar | X | A |
|---|---|---|---|---|---|---|---|---|
| 2026 | H | H | TMB | H | 1 | p-Phn | Cl | —COOH |
| 2027 | H | H | TMB | H | 1 | p-Phn | Cl | —COOiBu |
| 2028 | Me | HOOC—CH₂— | Me | Me | 1 | p-Phn | Cl | —COOH |
| 2029 | Me | EtOOC—CH₂— | Me | Me | 1 | p-Phn | Cl | —COOEt |
| 2030 | Me | EtOOC—CH₂— | Me | Me | 1 | 2,5-Pydi | Cl | —COOEt |
| 2031 | H | HOOC—CH₂— | tBu | H | 1 | p-Phn | Cl | —COOH |
| 2032 | H | EtOOC—CH₂— | tBu | H | 1 | 6-Me-1,3-Phn | Cl | —COOEt |
| 2033 | H | HOOC—CH₂— | TMB | H | 1 | p-Phn | Cl | —COOH |
| 2034 | H | BuOOC—CH₂— | TMB | H | 1 | p-Phn | Cl | COOBu |
| 2035 | H | HOOC—CH₂— | TMB | H | 1 | p-Phn | Br | —COOH |
| 2036 | Me | HOOCCMe₂— | Me | Me | 1 | p-Phn | Cl | —COOH |
| 2037 | H | HOOCCMe₂— | tBu | H | 1 | p-Phn | Cl | —COOH |
| 2038 | H | HOOCCMe₂— | TMB | H | 1 | p-Phn | Cl | —COOH |
| 2039 | H | EtOOCCMe₂— | Me | H | 1 | p-Phn | Cl | —COOEt |

The compounds of the invention have shown a very strong ability to inhibit the oxidation of unsaturated fatty acids and their esters (such as linolic acid and ethyl linolate) and, accordingly, it is expected that these compounds will be able to prevent the oxidation of phospholipids containing a high content of unsaturated fatty acids from oxidation, even in vivo.

The compounds of the invention have been shown to have a very strong ability to lower the level of lipid peroxides, as demonstrated, inter alia, by the test against rat liver microsomal lipid peroxidation described in Biochem. Biphys. Res. Commun., 95, 734 (1980). In addition, in experiments using alloxan-induced hyperlipaemic ice, the compounds have demonstrated the ability to lower blood lipid peroxide, triglyceride and cholesterol levels. The compounds have also shown the ability to lower blood sugar levels in a test using genetically diabetic mice of the KK strain. Moreover, the compounds of the invention are less toxic than many known compounds to experimental animals such as rats or mice and result in little anorexia, inhibition of body weight increase and liver hypertrophy.

Accordingly, it is considered that the compounds of the present invention will be useful for the therapeutic treatment of human hyperlipaemia, diabetes and complications thereof, especially diabetes mellitus. The compounds of the invention may be administered orally, for example in the form of tablets, capsules, powders or granules, or parenterally, for example by injection or in the form of a suppository. The recommended dosage will, of course, vary depending upon the age and body weight of the patient as well as the nature and severity of the disease. However, for an adult human patient, a daily dose of from 50 mg to 5 g (which may be administered in a single dose or in divided doses) is recommended in the treatment of hyperlipaemia, diabetes mellitus and complications thereof.

The following Examples illustrate the preparation of various of the compounds of the present invention. Preparation of various of the starting materials employed in the Examples is illustrated in the subsequent Preparations. The subsequent Test Examples illustrate the valuable biological properties of these compounds.

In the nuclear magnetic resonance spectra reported in the Examples and Preparations, the abbreviation "nd" means that precise identification of the signal was not possible because of overlap by other signals or the absorption of the solvent.

EXAMPLE 1

59]4-(6-Hydroxy-2-isobutyl-5,7,8-trimethyl-4-oxochroman-2-ylmethoxy)benzyl]thiazolidine -2,4-dione (Step D4)

A mixture of 0.5 g of ethyl 3-[4-(6-acetoxy-2-isobutyl-5,7,8-trimethyl-4-oxochroman-2-ylmethoxy)phenyl]-2-chloropropionate (prepared as described in Preparation 9), 0.2 g of thiourea and 0.8 g of sulfolane was heated at 120°-135° C. for 4 hours under a nitrogen stream. A mixture of 1 ml of concentrated hydrochloric acid, 1 ml of water and 5 ml of ethylene glycol monomethyl ether was then added to the reaction mixture, and the mixture was heated under reflux for 6 hours. The reaction mixture was then poured into water and extracted with ethyl acetate. The ethyl acetate extract was dried over anhydrous sodium sulfate. The solvent was distilled off and the residue was purified by preparative silica gel thin layer chromatography using a 1:1 by volume mixture of hexane and ethyl acetate as developing solvent, to give the title compound, softening at 70°-78° C.

Nuclear Magnetic Resonance Spectrum (CDCl₃) δ ppm:
0.97 (6H, doublet, J+6 Hz);
1.5-2.1 (3H, nd);
2.12 (3H, singlet);
2.21 (3H, singlet);
2.53 (3H, singlet);
2.77 δ 2.99 (2H, AB type, J=16 Hz);
2.8-3.2 (1H, nd);
3.41 (1H, doublet of doublets, J=4 δ 14 Hz);
4.06 (2H, AB type, J=10 Hz);

4.43 (1H, doublet of doublets, j=4 δ 9 Hz);
4.6–5.3 (1H, broad singlet, disappeared on adding heavy water);
6.81 (2H, doublet, J=9 Hz);
7.12 (2H, doublet, J=9 Hz);
8.7–9.3 (1H, broad singlet, disappeared on adding heavy water).

EXAMPLE 2

5-[4-(6-Acetoxy-5,7,8-trimethyl-2-octylchroman-2-ylmethoxy)benzyl]thiazolidine-2,4-dione A mixture of 2.1 g of ethyl 3-[4-(6-acetoxy-5,7,8-trimethyl-2-octylchroman-2-ylmethoxy)phenyl]-2-chloropropionate (prepared as described in Preparation 18), 0.35 g of thiourea and 2.5 ml of sulfolane was heated for 7 hours at 120°–130° C. under a nitrogen atmosphere. The reaction mixture was then dissolved in benzene. The benzene solution was washed with water and dried over anhydrous sodium sulfate. The solvent was distilled off under reduced pressure. The residue was purified by silica gel column chromatography, eluted with a 10:1 by volume mixture of benzene and ethyl acetate, to give the title compound as a slightly yellow, foamy solid.

Rf value on silica gel thin layer chromatography=0.55 (developing solvent, benzene:ethyl acetate=4:1 by volume).

Nuclear Magnetic Resonance Spectrum (CDCl$_3$) δ ppm:
0.7–1.0 (3H, multiplet);
1.1–2.0 (16H, multiplet);
1.97 (3H, singlet);
2.03 (3H, singlet);
2.08 (3H, singlet);
2.31 (3H, singlet);
2.60 (2H, broad triplet, J=6 Hz);
3.03 (1H, doublet of doublets, J=10 δ 15 Hz);
3.44 (1H, doublet of doublets, J=3 δ 15 Hz);
3.92 (2H, singlet);
4.45 (1H, doublet of doublets, J=3 δ 10 Hz);
6.85 (2H, doublet, J=9 Hz);
7.13 (2H, doublet, J=9 Hz);
8.0–8.9 (1H, broad, disappeared on adding heavy water).

EXAMPLE 3

5-[4-(6-Hydroxy-5,7,8-trimethyl-2-octylchroman-2-ylmethoxy)benzyl]thiazolidine-2,4-dione A mixture of 2.1 g of ethyl 3-[4-(6-acetoxy-5,7,8-trimethyl-2-octylchroman-2-ylmethoxy)phenyl]-2-chloropropionate (prepared as described in Preparation 18), 0.35 g of thiourea and 2.5 ml of sulfolane was heated for 7 hours at 120°–130° C. under a nitrogen atmosphere. A mixture of 3.6 ml of 2N aqueous hydrochloric acid and 5 ml of ethylene glycol monomethyl ether was then added to the reaction mixture, after which it was heated for a further 5 hours at 85°–90° C. The reaction mixture was then poured into water and extracted with benzene. The benzene extract was washed with water and dried over anhydrous sodium sulfate. The solvent was distilled off under reduced pressure and the residue was purified by silica gel column chromatography, using a 10:1 by volume mixture of benzene and ethyl acetate as eluent, to give the title compound as a slightly yellow, foamy solid.

Rf value on silica gel thin layer chromatography=0.43 (trailing) (developing solvent, benzene:ethyl acetate=4:1 by volume).

Nuclear Magnetic Resonance Spectrum (CDCl$_3$) δ ppm:
0.7–1.0 (3H, multiplet);
1.1–2.1 (16H, multiplet);
2.10 (6H, singlet);
2.15 (3H, singlet);
2.61 (2H, broad triplet, J=6 Hz);
3.05 (1H, doublet of doublets, J=10 δ 15 Hz);
3.42 (1H, doublet of doublets, J=3 δ 15 Hz);
3.92 (2H, singlet);
4.22 (1H, singlet, disappeared on adding heavy water);
4.47 (1H, doublet of doublets, J=3 δ 10 Hz);
6.85 (2H, doublet, J=9 Hz);
7.13 (2H, doublet, J=9 Hz);
8.33 (1H, broad singlet, disappeared on adding heavy water).

EXAMPLE 4

5-[4-(6-Acetoxy-2-methyl-7-(1,1,3,3-tetramethylbutyl)-chroman-2-ylmethoxy)benzyl]thiazolidine -2,4dione The procedure described in Example 2 was repeated, but using 7.0 g of ethyl 3-{4-[6-acetoxy-2-methyl-7-(1,1,3,3-tetramethylbutyl)chroman-2-ylmethoxy]-phenyl}-2-chloropropionate (prepared as described in Preparation 23), 1.2 g of thiourea and 9 ml of sulfolane, to give the title compound as slightly yellow glassy solid, softening at 75°–80° C.

Nuclear Magnetic Resonance Spectrum (CDCl$_3$) δ ppm:
0.79 (9H, singlet);
1.36 (6H, singlet);
1.45 (3H, singlet);
1.66–2.28 (2H, nd);
1.80 (2H, singlet);
2.29 (3H, singlet);
2.73 (2H, broad triplet, J=6 Hz);
3.28 (1H, doublet of doublets, J=9 δ 14 Hz);
3.45 (1H, doublet of doublets, J=4 δ 14 Hz);
3.93 (2H, AB type, J=9 Hz);
4.49 (1H, doublet of doublets, J=4 δ 9 Hz);
6.75 (1H, singlet);
6.86 (1H, singlet);
6.90 (2H, doublet, J=9 Hz);
7.13 (2H, doublet, J=9 Hz);
8.1–8.7 (1H, broad, disappeared on adding heavy water).

EXAMPLE 5

5-{4-[6Hydroxy-2-methyl-7-(1,1,3,3-tetramethylbutyl)-chroman-2-ylmethoxy]benzyl}thiazolidine-2,4-dione The procedure described in Example 3 was repeated, but using 7.0 g of ethyl 3-{4-[6-acetoxy-2-methyl-7-(1,1,3,3-tetramethylbutyl)chroman-2-ylmethoxy]-phenyl}-2-chloropropionate (prepared as described in Preparation 23), 1.2 g of thiourea, 9 ml of sulfolane, 13 ml of 2N hydrochloric acid and 20 ml of ethylene glycol monomethyl ether, to give the title compound as a slightly yellow glassy solid, softening at 80°–85° C.

Nuclear Magnetic Resonance Spectrum (CDCl$_3$) δ ppm:
0.78 (9H, singlet);
1.41 (9 H, singlet);
1.60–2.30 (2H, nd);

1.91 (2H, singlet);
2.67 (2H, broad triplet, J=6.5 Hz);
3.07 (1H, doublet of doublets, J=10 δ 14 Hz);
3.45 (1H, doublet of doublets, J=4 and 14 Hz);
3.93 (2H, AB type, J=9 Hz);
4.45 (1H, singlet, disappeared on adding heavy water);
4.49 (1H, doublet of doublets, J=4 δ 10 Hz);
6.34 (1H, singlet);
6.77 (1H, singlet);
6.88 (2H, doublet, J=9 Hz);
7.17 (2H, doublet, J=9 Hz);
8.4 (1H, broad singlet, disappeared on adding heavy water).

EXAMPLE 6

5-{4-[6-Acetoxy-2-methyl-4-oxo-7-(1,1,3,3-tetramethylbutyl)chroman-2-ylmethoxy]benzyl}thiazolidine-2,4-dione The procedure described in Example 2 was repeated, but using 7.3 g of ethyl 3-{4-[6-acetoxy-2-methyl-4-oxo-7-(1,1,3,3-tetramethylbutyl) chroman-2-ylmethoxy]phenyl}-2-chloropropionate (prepared as described in Preparation 25), 1.3 g of thiourea and 8 ml of sulfolane, to give the title compound as a slightly yellow powder, softening at 80°–88° C.

Nuclear Magnetic Resonance Spectrum (CDCl$_3$) δ ppm:
0.78 (9H, singlet);
1.37 (6H, singlet);
1.53 (3H, singlet);
1.83 (2H, singlet);
2.30 (3H, singlet);
2.70 (1H, doublet, J=17 Hz);
2.8–3.2 (1H, nd);
3.10 (1H, doublet, J=17 Hz);
3.45 (1H, doublet of doublets, J=4 δ 15 Hz);
4.00 δ 4.12 (2H, AB type, J=9 Hz);
4.48 (1H, doublet of doublets, J=4 δ 9 Hz);
6.85 (2H, doublet, J=9 Hz);
7.02 (1H, singlet);
7.17 (2H, doublet, J=9 Hz);
7.51 (1H, singlet);
8.3–9.0 (1H, broad, disappeared on adding heavy water).

EXAMPLE 7

5-{4-[6-Hydroxy-2-methyl-4-oxo-7-(1,1,3,3-tetramethylbutyl)chroman-2-ylmethoxy]benzyl}thiazolidine-2,4-dione A mixture of 5.2 g of 5-{4-[6-acetoxy-2-methyl-4-oxo-7-(1,1,3,3-tetramethylbutyl) chroman-2-ylmethoxy]benzyl}-2-iminothiazolidin-4-one prepared as described in Preparation 26), 16 ml of 2N hydrochloric acid and 25 ml of ethylene glycol monomethyl ether was heated for 6 hours at 85°–90° C. under a nitrogen atmosphere. The reaction mixture was then poured into water and extracted with benzene. The benzene extract was washed with water and dried over anhydrous sodium sulfate. The solvent was distilled off under reduced pressure and the residue was purified by silica gel column chromatography, eluted with a 4:1 by volume mixture of benzene and ethyl acetate, to give the title compound as a slightly yellow foamy solid, softening at 100°–105° C.

Nuclear Magnetic Resonance Spectrum (CDCl$_3$) δ ppm:
0.77 (9H, singlet);
1.43 (6H, singlet);
1.52 (3H, singlet);
2.00 (2H, singlet);
2.70 (1H, doublet, J=17 Hz);
2.8–3.2 (1H, nd);
3.12 (1H, doublet, J=17 Hz);
3.43 (1H, doublet of doublets, J=4 δ 15 Hz);
4.00 δ 4.10 (2H, AB type, J=9 Hz);
4.49 (1H, doublet of doublets, J=4 δ 9 Hz);
6.1 (1H, broad singlet, disappeared on adding heavy water);
6.85 (2H, doublet, J=9 Hz);
6.93 (1H, singlet);
7.15 (2H, doublet, J=9 Hz);
7.30 (1H, singlet);
8.2–9.3 (1H, broad, disappeared on adding heavy water).

EXAMPLE 8

5-{4-[2-(3,7-Dimethyloctyl)-6-hydroxy-5,7,8-trimethyl-4-oxochroman-2-ylmethoxy]benzyl}thiazolidine-2,4-dione The procedure described in Example 3 was repeated, but using 1.1 g of ethyl 3-{4-[6-acetoxy-2-(3,7-dimethyloctyl)-5,7,8-trimethyl-4-oxochroman-2-ylmethoxy]phenyl}-2-chloropropionate (prepared as described in Preparation 33), 0.2 g of thiourea, 1.5 ml of sulfolane, 5 ml of 2N aqueous hydrochloric acid and 10 ml of ethylene glycol monomethyl ether, to give the title compound, as a slightly yellow powder, softening at 41°–45° C.

Nuclear Magnetic Resonance Spectrum (CDCl$_3$) δ ppm:
0.85 (9H, doublet, J=7 Hz);
1.0–2.0 (12H, multiplet);
2.13 (3H, singlet);
2.22 (3H, singlet);
2.55 (3H, singlet);
2.65–3.2 (3H, multiplet);
3.43 (1H, doublet of doublets, J=4 δ -Hz);
4.05 (2H, singlet);
4.35–5.3 (1H, broad, disappeared on adding heavy water);
4.46 (1H, doublet of doublets, J=4 δ 10 Hz);
6.83 (2H, doublet, J=9 Hz);
7.15 (2H, doublet, J=9 Hz);
8.0–9.5 (1H, broad, disappeared on adding heavy water).

EXAMPLE 9

5-[2-(6-Hydroxy-2,5,7,8-tetramethylchroman-2-ylmethoxy)pyridin-5-ylmethyl]thiazolidine-2,4-dione The procedure described in Example 3 was repeated, but using 3.8 g of ethyl 3-[2-(6-acetoxy-2,5,7,8-tetramethylchroman-2-ylmethoxy)pyridin-5-yl]-2-chloropropionate (prepared as described in Preparation 38), 0.77 g of thiourea, 5.0 ml of sulfolane, 4.5 ml of ethylene glycol monomethyl ether, 1.5 ml of concentrated hydrochloric acid and 4.5 ml of water, to give the title compound, softening at 87°–94° C.

Nuclear Magnetic Resonance Spectrum (CDCl$_3$) δ ppm:
1.38 (3H, singlet);
1.7–2.3 (2H, multiplet);
2.06 (3H, singlet);
2 09 (3H, singlet);

2.14 (3H, singlet);
2.63 (2H, broad triplet, J=6 Hz);
3.10 (1H, doublet of doublets, J=15 δ 7.5 Hz);
3.33 (1H, doublet of doublets, J=15 δ 4.5 Hz);
4.0–5.0 (1H, broad, disappeared on adding heavy water);
4.32 (3H, singlet);
4.47 (1H, doublet of doublets, J=7.5 δ 4.5 Hz);
6.75 (1H, doublet, J=9 Hz);
7.46 (1H, doublet of doublets, J=9 δ 3 Hz);
8.02 (1H, doublet, J=3 Hz).

EXAMPLE 10

5-[3-(7-t-Butyl-6-hydroxy-2-methyl-4-oxochroman-2-ylmethoxy)-4-methylbenzyl]thiazolidine-2,4-dione the procedure described in Example 3 was repeated, but using 2,4 g of ethyl 3-[3-(6-acetoxy-7-t-butyl-2-methyl-4-oxochroman-2-ylmethoxy) -4-methylphenyl]-2-chloropropionate (prepared as described in Preparation 42), 0.7 g of thiourea, 5 ml of sulfolane, 10 ml of 2N aqueous hydrochloric acid and 15 ml of ethylene glycol monomethyl ether, to give the title compound.

Rf value on silica gel thin layer chromatography=0.44 (developing solvent, benzene:ethyl acetate=1:1 by volume).

Nuclear Magnetic Resonance Spectrum (CDCl$_3$) δ ppm:
1.40 (9H, singlet);
1.57 (3H, singlet);
2.14 (3H, singlet;
2.77 (1H, doublet, J=16 Hz);
3.01 (1H, doublet of doublets, J=10 δ 14 Hz);
3.07 (1H, doublet, J=16 Hz);
3.44 (1H, doublet of doublets, J=4 δ 14 Hz);
3.99 δ 4.13 (2H, AB type, J=10 Hz);
4.50 (1H, doublet of doublets, J=4 δ 10 Hz);
5.84 (1H, broad singlet, disappeared on adding heavy water);
6.6–6.85 (2H, nd);
6.91 (1H, singlet);
7.08 (1H, doublet, J=7.5 Hz);
7.32 (1H, singlet);
8.3–9.0 (1H, broad, disappeared on adding heavy water).

EXAMPLE 11

5-[4-(6-Hydroxy-5,7,8-trimethyl-4-oxochroman-2-ylmethoxy)benzyl]thiazolidine-2,4-dione The procedure described in Example 3 was repeated, but using 2.2 g of ethyl 3-[4-(6-acetoxy-2-hydroxy-5,7,8-trimethyl-4-oxochroman-2-ylmethoxy) phenyl]-2-chloropropionate (prepared as described in Preparation 45), 0.8 g of thiourea, 4.5 g of sulfolane, 70 ml of ethylene glycol monomethyl ether, 8 ml of water and 4 ml of 35% w/v aqueous hydrochloric acid, to give the title compound, melting at 249°–252° C.

Nuclear Magnetic Resonance Spectrum [(CD$_3$)$_2$SO] δppm:
2.25 (6H, singlet);
2.63 (3H, singlet);
2.7–3.8 (2H, nd);
4.88 (1H, doublet of doublets, J=4 δ 9 Hz);
5.11 (2H, singlet);
6.28 (1H, singlet);
7.05 (2H, doublet, J=9 Hz);
7.24 (2H, doublet, J=9 Hz);
8.3–8.7 (1H, broad singlet, disappeared on adding heavy water).

EXAMPLE 12

5-[4-(6-Hydroxy-2,5,7,8-tetramethylchroman-2-ylmethoxy)benzyl]-5-methylthiazolidine-2,4-dione The procedure described in Example 3 was repeated, but using 1.17 g of ethyl 3-[4-(6-acetoxy-2,5,7,8-tetramethylchroman-2-ylmethoxy)phenyl]-2-chloro -2-methylpropionate (prepared as described in Preparation 46), 0.63 g of thiourea, 3 g of sulfolane, 10 ml of ethylene glycol monomethyl ether, 3 ml of water and 2 ml of 35% w/v aqueous hydrochloric acid, to give the title compound, softening at 69°–72° C.

Nuclear Magnetic Resonance Spectrum (CDCl$_3$) δ ppm:
1.40 (3H, singlet);
1.72 (3H, singlet);
1.6–2.3 (2H, nd);
2.10 (6H, singlet);
2.16 (3H, singlet);
2.62 (2H, broad triplet, J=7 Hz);
2.94 (1H, doublet, J=14 Hz);
3.24 (1H, doublet, J=14 Hz);
3.84 and 3.97 (2H, AB type, J=9 Hz);
4.40 (1H, broad singlet, disappeared on adding heavy water);
6.84 (2H, doublet, J=9 Hz);
7.13 (2H, doublet, J=9 Hz);
8.4–8.9 (1H, broad singlet, disappeared on adding heavy water).

EXAMPLE 13

5-{4-[6-Hydroxy-4-(E)-hydroxyimino-2,5,7,8-tetramethylchroman-2-ylmethoxy]benzyl}thiazolidine-2,4-dione A mixture of 5 g of 5-[4-(6hydroxy-2,5,7,8-tetramethyl-4-oxochroman-2-ylmethoxy)benzyl]thiazolidine-2,4-dione (prepared as described in Example 22 of copending U.S. Ser. No. 644,996), 3 g of hydroxylamine hydrochloride, 50 g of methanol and 3 g of pyridine was stirred for 1 week at room temperature. At the end of this time, ethyl acetate and an aqueous solution of potassium carbonate were added. The organic layer was separated and dried over anhydrous sodium sulfate. The solvent was distilled off and the residue was purified by silica gel column chromatography, eluted with a 1:1 by volume mixture of hexane and ethyl acetate, to give the title compound, softening at 84°–100° C.

Nuclear Magnetic Resonance Spectrum [(CD$_3$)$_2$CO] δppm:
1.42 (3H, singlet);
2.09 (3H, singlet);
2.18 (3H, singlet);
2.48 (3H, singlet);
3.03 (1H, doublet of doublets, J=9 δ 14 Hz);
3.07 (2H, singlet);
3.43 (1H, doublet of doublets, J=4 δ 14 Hz);
4.05 (2H, singlet);
4.72 (1H, doublet of doublets, J=4 δ 9 Hz);
6.92 (2H, doublet, J=9 Hz);
7.21 (2H, doublet, J=9 Hz);
9.7–10.5 (1H, broad singlet, disappeared on adding heavy water).

EXAMPLE 14

5-{4-[6-Hydroxy-4-(Z)-hydroxylimino-2,5,7,8-tetramethylchroman-2-ylmethoxy]benzyl}thiazolidine-2,4-dione The title compound, softening at 100°-105° C., was obtained from the fraction that was eluted following the reaction containing the compound of Example 13 in the column chromatography conducted in Example 13 and using the same eluent.

Nuclear Magnetic Resonance Spectrum [$(CD_3)_2CO$] δ ppm:
- 1.46 (3H, singlet);
- 2.04 (3H, singlet);
- 2.18 (6H, singlet);
- 2.58 (1H, doublet, J=13 Hz);
- 2.87 (1H, doublet, J=13 Hz);
- 3.10 (1H, doublet of doublets, J=9 δ 14 Hz);
- 3.43 (1H, doublet of doublets, J=4 δ 14 Hz);
- 4.01 (2H, singlet);
- 4.74 (1H, doublet of doublets, J=4 δ 9 Hz);
- 6.92 (2H, doublet, J=9 Hz);
- 7.22 (2H, doublet, J=9 Hz);
- 9.4-10.6 (1H, broad singlet, disappeared on adding heavy water).

EXAMPLE 15

5-{4-[6-Hydroxy-4-(Z)-hydroxyimino-2,5,7,8-tetramethylchroman-2-ylmethoxy]benzyl}thiazolidine-2,4-dione 27 mg of 59{4-[6-hydroxy-4-(E)-hydroxyimino-2,5,7,8-tetramethylchroman-2-ylmethoxy]-benzyl}thiazolidine-2,4-dione (prepared as described in Example 13) was heated on an oil bath for 5 hours at 140°±5° C. The reaction mixture was then subjected to high pressure liquid chromatography, which confirmed the presence of the title compound (the same compound as in Example 14).

EXAMPLE 16

5-{4-[6Hydroxy-4-(E)-hydroxyimino-2,5,7,8-tetramethylchroman-2-ylmethoxy]benzyl}thiazolidine-2,4-dione 62 mg of 5-{4-[6-hydroxy-4-(Z)-hydroxyimino-2,5,7,8-tetramethylchroman-2-ylmethoxy]benzyl}-thiazolidine-2,4-dione (prepared as described in Example 14) were heated in an oil bath for 5 hours at 140°±5° C. The reaction mixture was subjected to high pressure liquid chromatography, to confirm the presence of the title compound (the same compound as described in Example 13).

EXAMPLE 17

5-{4-[6-Acetoxy-4-(E)-acetoxyimino-2,5,7,8-tetramethylchroman-2-ylmethoxy]benzyl}thiazolidine-2,4-dione A mixture of 1 g of 5-{4-[6-hydroxy-4-(E)-hydroxyimino-2,5,7,8tetramethylchroman-2-ylmethoxy ]benzyl}thiazolidine-2,4-dione (prepared as described in Example 13), 1.3 g of acetic anhydride and 10 ml of pyridine was allowed to stand for 8 days at room temperature, after which it was heated for 8 hours at 60°-80° C. An aqueous solution of potassium carbonate and ethyl acetate were then added to the reaction mixture. The organic layer was separated and dried over anhydrous sodium sulfate. The solvent was distilled off and the residue was purified by silica gel column chromatography, eluted with a 4:1 by volume mixture of hexane and ethyl acetate, to give the title compound, softening at 93°-97° C.

Nuclear Magnetic Resonance Spectrum ($CDCl_3$) δ ppm:
- 1.48 (3H, singlet);
- 2.07 (3H, singlet);
- 2.10 (3H, singlet);
- 2.22 (3H, singlet);
- 2.33 (3H, singlet);
- 2.42 (3H, singlet);
- 3.00 (1H, doublet, J=17 Hz);
- 3.26 (1H, doublet, J=17 Hz);
- 3.0-3.3 (1H, nd);
- 3.41 (1H, doublet of doublets, J=4 δ 14 Hz);
- 3.91 and 4.06 (2H, AB type, J=9 Hz);
- 4.47 (1H, doublet of doublets, J=4 δ 9 Hz);
- 6.84 (2H, doublet, J=9 Hz);
- 7.14 (2H, doublet, J=9 Hz).

EXAMPLE 18

5-{4-[6-Benzoyloxy-4-(E)-benzoyloxyimino-2,5,7,8tetramethylchroman-2-ylmethoxy]benzyl}thiazolidine-2,4-dione A mixture of 1 g of 5-{4-[6-hydroxy-4-(E)-hydroxyimino-2,5,7,8tetramethylchroman-2-ylmethoxy ]benzyl}-thiazolidine-2,4-dione (prepared as described in Example 13), 1.7 g of benzoyl bromide, 10 ml of pyridine and 5 ml of dimethylformamide was allowed to stand for 6 days at room temperature, after which it was heated for 8 hours at 60°-80° C. An aqueous solution of potassium carbonate and ethyl acetate were then added to the reaction mixture. The organic layer was separated and dried over anhydrous sodium sulfate. The solvent was distilled off and the residue was purified by silica gel column chromatography eluted with a 4:3 by volume mixture of hexane and ethyl acetate, to give the title compound, softening at 101°-107° C.

Nuclear Magnetic Resonance Spectrum ($CDCl_3$) δ ppm:
- 1.55 (3H, singlet);
- 2.14 (6H, singlet);
- 2.58 (3H, singlet);
- 2.8-3.7 (4H, nd);
- 3.98 and 4.12 (2H, AB type, J=9 Hz);
- 4.45 (1H, doublet of doublets, J=4 δ 9 Hz);
- 6.84 (2H, doublet, J=9 Hz);
- 7.14 (2H, doublet, J=9 Hz);
- 7.3-7.8 (6H, multiplet);
- 7.9-8.5 (4H, multiplet).

EXAMPLE 19

5-{4-[2,5,7,8-Tetramethyl-6-nicotinoyloxy-4-(E)-nicotinoyloxyiminochroman-2-ylmethoxy]benzyl}-thiazolidine-2,4-dione A mixture of 1 g of 5-{4-[6-hydroxy-4-(E)-hydroxyimino-2,5,7,8-tetramethylchroman-2-ylmethoxy ]benzyl}thiazolidine-2,4-dione (prepared as described in Example 13), 1.1 g of nicotinoyl chloride hydrochloride, 12 ml of pyridine and 12 ml of dimethylformamide was allowed to stand for 6 days at room temperature, after which it was heated for 8 hours at 60°-80° C. An aqueous solution of potassium carbonate and ethyl acetate were added to the reaction mixture. The organic layer was separated and dried over anhydrous sodium sulfate. The solvent was distilled off, and the residue was purified by silica gel column chromatography eluted with a 2:3 by volume mixture of hexane and ethyl acetate, followed by preparative thin layer silica gel chromatography (developing solvent, hexane:ethyl acetate=1:10 by volume), to give the title compound, softening at 123°–130° C.

Nuclear Magnetic Resonance Spectrum (CDCl$_3$) δ ppm:

1.56 (3H, singlet);
2.13 (3H, singlet);
2.17 (3H, singlet);
2.57 (3H, singlet);
2.8–3.7 (4H, nd);
3.99 and 4.16 (2H, AB type, J=9 Hz);
4.45 (1H, doublet of doublets, J=4 δ 9 Hz);
6.84 (2H, doublet, J=9 Hz);
7.15 (2H, doublet, J=9 Hz);
7.4–7.7 (2H, multiplet);
8.3–8.7 (2H, multiplet);
8.7–9.0 (2H, multiplet);
9.2–9.6 (2H, multiplet);
10.0–11.0 (1H, broad, disappeared on adding heavy water).

EXAMPLE 20

5-{4-[7-t-Butyl-6hydroxy-4-(E)-hydroxyimino-2methyl-chroman-2-ylmethoxy]benzyl}thiazolidine-2,4-dione The procedure described in Example 13 was repeated, but using 1.32 g of 5-[4-(7-t-butyl-6-hydroxy-2-methyl-4-oxochroman-2-ylmethoxy)benzyl]thiazolidine-2,4-dione (prepared as described in Example 24 of copending U.S. Ser. No. 644,996), 2.0 g of hydroxylamine hydrochloride, 0.5 ml of pyridine and 20 ml of methanol, to give the title compound as colorless crystals, melting at 235°–237° C. (with decomposition).

Nuclear Magnetic Resonance Spectrum [(CD$_3$)$_2$CO]δ ppm:

1.40 (12H, singlet);
2.6–4.0 (1H, broad, disappeared on adding heavy water);
2.98 (2H, singlet);
3.10 (1H, doublet of doublets, J=9 δ 14 Hz);
3.43 (1H, doublet of doublets, J=4 δ 14 Hz);
4.05 (2H, singlet);
4.74 (1H, doublet of doublets, J=4 δ 9 Hz);
6.73 (1H, singlet);
6.95 (2H, doublet, J=9 Hz);
7.2–8.5 (1H, broad, disappeared on adding heavy water);
7.25 (2H, doublet, J=9 Hz);
7.30 (1H, singlet);
9.7–10.6 (1H, broad, disappeared on adding heavy water).

EXAMPLE 21

5-{4-[6-Hydroxy-4-(E)-hydroxyimino-2-methyl-7-(1,1,3,3-tetramethylbutyl)chroman-2-ylmethoxy]benzyl)thiazolidine-2,4-dione The procedure described in Example 13 was repeated, but using 1.0 g of 5-{4-[6-hydroxy-2-methyl-4-oxo-7-(1,1,3,3-tetramethylbutyl)chroman -2-ylmethoxy]benzyl}thiazolidine-2,4-dione (prepared as described in Example 7), 0.26 g of hydroxylamine hydrochloride, 0.3 g of pyridine and 10 ml of methanol, to give the title compound as a white powder, softening at 115°–120° C.

Nuclear Magnetic Resonance spectrum [(CD$_3$)$_2$CO] δppm:

0.76 (9H, singlet);
1.40 (9H, singlet);
2.00 (2H, singlet);
2.5–3.6 (1H, broad, disappeared on adding heavy water);
2.98 (2H, singlet);
3.09 (1H, doublet of doublets, J=9 δ 15 Hz);
3.44 (1H, doublet of doublets, J=4 δ 15 Hz);
4.03 (2H, singlet);
4.76 (1H, doublet of doublets, J=4 δ 0 Hz);
6.75 (1H, singlet);
6.93 (2H, doublet, J=9 Hz);
7.22 (2H, doublet, J=9 Hz);
7.25 (1H, singlet);
7.5–8.4 (1H, broad, disappeared on adding heavy water).

EXAMPLE 22

5-{4-[6-Hydroxy-4-(E)-hydroxyimino-2-isobutyl-5,7,8-trimethylchroman-b 2-ylmethoxy]benzyl}thiazolidine-2,4-dione The procedure described in Example 13 was repeated, but using 155 mg of 5-[4-(6-hydroxy-2-isobutyl-5,7,8-trimethyl-4-oxochroman-2-ylmethoxy) benzyl]-thiazolidine-2,4-dione (prepared as described in Example 1), 600 mg of hydroxylamine hydrochloride, 4 ml of ethanol and 6 ml of pyridine, to give the title compound, softening at 77°–80° C.

Nuclear Magnetic Resonance Spectrum [(CD$_3$)$_2$CO] δppm:

0.97 (6H, doublet, J=6 Hz);
1.6–2.3 (1H, nd);
1.78 (2H, doublet, J=6 Hz);
2.11 (3H, singlet);
2.18 (3H, singlet);
2.46 (3H, singlet);
2.7–3.7 (1H, broad, disappeared on adding heavy water);
2.8–3.2 (1H, nd);
3.09 (2H, singlet);
3.43 (1H, doublet of doublets, J=4 δ 14 Hz);
4.05 (2H, AB type, J=10 Hz);
4.72 (1H, doublet of doublets, J=4 δ 9 Hz);
6.91 (2H, doublet, J=9 Hz);
7.22 (2H, doublet, J=9 Hz);
9.8–10.5 (1H, broad singlet, disappeared on adding heavy water).

EXAMPLE 23

5-{4-[2-(3,7-Dimethyloctyl)-6-hydroxy-4-(E)-hydroxyimino-5,7,8-trimethylchroman-2-trimethylchroman-2ylmethoxy]benzyl}thiazolidine-2,4-dione The procedure described in Example 13 was repeated, but using 150 mg of 5-{4-[2-(3,7-dimethyloctyl)-6-hydroxy-5,7,8-trimethyl-4-oxochroman -2-ylmethoxy]benzyl}thiazolidine-2,4-dione (prepared as described in Example 8), 36 mg of hydroxylamine hydrochloride, 41 mg of pyridine and 2 ml of methanol, to give the title compound as a slightly yellow powder, softening at 55°–60 ° C.

Nuclear Magnetic Resonance Spectrum (CDCl$_3$) δ ppm:

0.83 (9H, doublet, J=7 Hz);
1.0–2.0 (12H, multiplet);
2.10 (3H, singlet);
2.18 (3H, singlet);
2.41 (3H, singlet);

2.9–3.2 (1H, nd);
2.92 (1H, doublet, J=17 Hz);
3.2–3.55 (1H, nd);
3.23 (1H, doublet, J=17 Hz);
3.94 (2H, singlet);
4.3–4.8 (1H, nd);
4.46 (1H, doublet of doublets, J=4 δ 10 Hz);
6.83 (2H, doublet, J=9 Hz);
7.15 (2H, doublet, J=9 Hz);
7.8–8.9 (2H, broad, disappeared on adding heavy water).

EXAMPLE 24

5-[4-(6-Hydroxy-2,5,7,8-tetramethyl-4-(E)-methoxyiminochroman-2-ylmethoxy)benzyl]thiazolidine-2,4dione A mixture of 1 g of 5-[4-(6-hydroxy-2,5,7,8-tetramethyl-4-oxochroman-2-ylmethoxy)benzyl]thiazolidine-2,4-dione (prepared as described in Example 22 of copending U.S. Ser. No. 644,996), 0.6 g of methoxyamine hydrochloride and 5 g of methanol was allowed to stand for 10 days at room temperature. At the end of this time, ethyl acetate and an aqueous solution of potassium carbonate were added. The organic layer was separated and dried over anhydrous sodium sulfate. The solvent was distilled off and the residue was purified by silica gel column chromatography eluted with a 3:1 by volume mixture of hexane and ethyl acetate, to give the title compound softening at 72°–76° C.

Nuclear Magnetic Resonance Spectrum (CDCl₃) δ ppm:

1.41 (3H, singlet);
2.08 (3H, singlet);
2.17 (3H, singlet);
2.50 (3H, singlet);
2.88 δ 3.08 (2H, AB type, J=17 Hz);
3.00 (1H, doublet of doublets, J=9 δ 14 Hz);
3.42 (1H, doublet of doublets, J=4 δ 14 Hz);
3.92 (2H, singlet);
3.96 (3H, singlet);
4.2–4.9 (1broad);
4.45 (1H, doublet of doublets, J=4 δ 9 Hz);
6.83 (2H, doublet, J=9 Hz);
7.12 (2H, doublet, J=9 Hz).

EXAMPLE 25

5-{4-[4-(E)-Benzyloxyimino-6-hydroxy-2,5,7,8-tetramethylchroman-2-ylmethoxy]benzyl}thiazolidine-2,4-dione A mixture of 1 g of 5-[4-(6-hydroxy-2,5,7,8-tetramethyl-4-oxochroman-2-ylmethoxy)benzyl]thiazolidine-2,4-dione (prepared as described in Example 22 of copending U.S. Ser. No. 644,996), 1.2 g of benzyloxylamine hydrochloride and 10 g of methanol was allowed to stand for 7 days at room temperature. At the end of this time, ethyl acetate and an aqueous solution of potassium carbonate were added. The organic layer was separated and dried over anhydrous sodium sulfate. The solvent was distilled off and the residue was purified by silica gel column chromatography eluted with a 3:1 by volume mixture of hexane and ethyl acetate, to give the title compound, softening at 64°–69° C.

Nuclear Magnetic Resonance Spectrum (CDCl₃) δ ppm:

1.40 (3H, singlet);
2.06 (3H, singlet);
2.16 (3H, singlet);
2.41 (3H, singlet);
2.92 δ 3.18 (2H, AB type, J=17 Hz);
3.02 (1H, doublet of doublets, J=9 δ 14 Hz);
3.42 (1H, doublet of doublets, J=4 δ 14 Hz);
3.90 (2H, singlet);
4.43 (b 1H, doublet of doublets, J=4 δ 9 Hz);
5.19 (2H, singlet);
6.82 (2H, doublet, J=9 Hz);
7.11 (2H, doublet, J=9 Hz);
7.2–7.5 (5H, multiplet).

EXAMPLE 26

5-{4-84-(E)-t-Butoxycarbonylmethoxyimino-6-hydroxy-2,5,7,8-tetramethylchroman-2-ylmethoxy]benzyl }thiazolidine-2,4-dione A mixture of 1 g of 5-[4-(6-hydroxy-2,5,7,8-tetramethyl-4-oxochroman-2-ylmethoxy)benzyl]thiazolidine-2,4-dione (prepared as described in Example 22 of copending U.S. Ser. No. 644,996), 2.1 g of t-butoxycarbonylmethoxylammonium p-toluenesulfonate, 5 g of methanol and 0.6 g of pyridine was allowed to stand for 7 days at room temperature. At the end of this time, ethyl acetate and an aqueous solution of potassium carbonate were added. The organic layer was separated and dried over anhydrous sodium sulfate. The solvent was distilled off and the residue was purified by silica gel column chromatography eluted with a 3:1 by volume mixture of hexane and ethyl acetate, to give the title compound, softening at 76°–80° C.

Nuclear Magnetic Resonance Spectrum (CDCl₃) δ ppm:

1.44 (3H, singlet);
1.49 (9H, singlet);
2.07 (3H, singlet);
2.17 (3H, singlet);
2.43 (3H, singlet);
3.02 (1H, doublet of doublets, J=9 δ 14 Hz);
3.08 (2H, AB type, J=17 Hz);
3.42 (1H, doublet of doublets, J=4 δ 14 Hz);
3.96 (2H, singlet);
4.43 (1H, doublet of doublets, J=4 δ 9 Hz);
4.57 (2H, singlet);
4.9–6.1 (2H, broad, disappeared on adding heavy water);
6.84 (2H, doublet, J=9 Hz);
7.10 (2H, doublet, J=9 Hz).

EXAMPLE 27

(a)
5-[4-(6-Hydroxy-2,5,7,8-tetramethylchroman-2ylmethoxy)benzyl]-2-iminothiazolidin-4-one and (b)
5-[4-(6-hydroxy-2,5,7,8-tetramethylchroman-2-ylmethoxy)benzyl]thiazolidine-2,4-dione (Step A5)

A mixture of 9.6 g of ethyl 3-[4-(6-acetoxy-2,5,7,8-tetramethylchroman-2-ylmethoxy)phenyl]-2-chloropropionate (prepared as described in Preparation 51), 1.8 g of thiourea and 11 ml of sulfolane was heated at 115°–120° C. for 80 minutes under a stream of nitrogen. A mixture of 90 ml of acetic acid, 30 ml of concentrated hydrochloric acid and 15 ml of water was then added to the reaction mixture, which was then heated at 85°–90° C. for a further 12 hours. 27 g of sodium bicarbonate were added to the reaction mixture, and, after the generation of carbon dioxide gas had ceased, the solvent was distilled off. A mixture of 10 parts by volume of benzene and 1 part of ethyl acetate was added to the crude residue, and the resulting solution was washed with a 1:1 by volume mixture of a saturated aqueous solution of sodium bicarbonate and water. A white powdery product was collected by filtration, washed with water and recrystallized from acetone to give the title compound (a), melting at 205°–207° C.

Nuclear Magnetic Resonance Spectrum [DCON(CD$_3$)$_2$+D$_2$O] δ ppm:
1.37 (3H, singlet);
about 2 (2H, multiplet);
2.02 (3H, singlet);
2.14 (6H, singlet);
2.3–3.1 (adsorption signal of solvent);
3.42 (1H, doublet of doublets, J=15 δ 4.5 Hz);
4.60 (1H, doublet of doublets, J=9 δ 4.5 Hz);
6.93 (2H, doublet, J=9 Hz);
7.23 (2H, doublet, J=9 Hz).

The organic layer which was obtained after removal of the above white powder was washed with water and dried over anhydrous sodium sulfate. The solvent was distilled off and the resulting crude residue was purified by silica gel column chromatography. After elution with a 10:1 by volume mixture of benzene and ethyl acetate, the title compound (b) was obtained as a powder, melting at 184°–186° C., from the next elution with a 10:1.4 by volume mixture of benzene and ethyl acetate.

Nuclear Magnetic Resonance Spectrum [(CD$_3$)$_2$CO] δ ppm:
1.39 (3H, singlet);
about 2 (2H, multiplet);
2.02 (3H, singlet);
2.09 (3H, singlet);
2.13 (3H, singlet);
2.63 (2H, broad triplet, J=6 Hz);
3.07 (1H, doublet of doublets, J=15 δ 9 Hz);
3.41 (1H, doublet of doublets, J=15 δ 4.5 Hz);
3.97 (2H, AB type, J=9 Hz);
4.70 (2H, doublet of doublets, J=9 δ 4.5 Hz);
6.90 (2H, doublet, J=9 Hz);
7.21 (2H, doublet, J=9 Hz).

EXAMPLE 28

5-[4-(6-Hydroxy-2,5,7,8-tetramethylchroman-2-ylmethoxy)benzyl]thiazolidine-2,4-dione (Step A5)

A mixture of 9.6 g of ethyl 3-[4-(6-acetoxy-2,5,7,8-tetramethylchroman-2-ylmethoxy)phenyl]-2-chloropropionate (prepared as described in Preparation 51), 1.8 g of thiourea and 11 ml of sulfolane was heated for 3.5 hours at 120° C. under a nitrogen stream. 100 ml of ethylene glycol monomethyl ether and 70 ml of 10% w/v aqueous hydrochloric acid were then added to the reaction mixture, after which it was heated under reflux for 12 hours. The product was then purified as described in Example 27, to give the title compound. The melting point and nuclear magnetic resonance spectrum of this compound accorded with those of the compound obtained in Example 27(b).

EXAMPLE 29

5-[4-(7-t-Butyl-6-hydroxy-2-methylchroman-2-ylmethoxy)benzyl]thiazolidine-2,4-dione (Step A5)

Following the procedure described in Example 28, a mixture of 1.43 g of ethyl 3-[4-(6-acetoxy-8-t-butyl-2-methylchroman-2-ylmethoxy)phenyl]-2-chloropropionate (prepared as described in Preparation 59), 430 mg of thiourea and 5 ml of sulfolane was heated for 3.5 hours at 120° C. 15 ml of ethylene glycol monomethyl ether and 10 ml of 10% w/v aqueous hydrochloric acid were then added to the reaction mixture, after which it was heated under reflux for 13 hours. The product was then separated and purified as described in Example 27, to give the title compound as a slightly yellow powder.

Rf value on silica gel thin layer chromatography=0.31 (developing solvent, benzene:ethyl acetate=5:1 by volume).

Nuclear Magnetic Resonance Spectrum (CDCl$_3$) δ ppm:
1.37 (9H, singlet);
1.43 (3H, singlet);
1.63–2.30 (2H, multiplet);
2.67 (2H, broad triplet, J=7 Hz);
3.07 (1H, doublet of doublets, J=9 δ 15 Hz);
3.45 (1H, doublet of doublets, J=4 δ 15 Hz);
3.87 δ 3.97 (2H, AB type, J=9 Hz);
4.48 (1H, doublet of doublets, J=4 δ 9 Hz);
4.62 (1H, broad singlet, disappeared on adding heavy water);
6.41 (1H, singlet);
6.78 (1H, singlet);
6.88 (2H, doublet, J=9 Hz);
7.15 (2H, doublet, J=9 Hz);
8.40–8.93 (1H, broad, disappeared on adding heavy water).

5-[4-(4,6-Dihydroxy-2,5,7,8-tetramethylchroman-2-ylmethoxy)benzyl]thiazolidine-2,4-dione (Step H1)

450 mg of sodium borohydride were added to a mixture of 278 mg of 5-[4-(6-hydroxy-2,5,7,8-tetramethyl-4-oxochroman-2-ylmethoxy)benzyl]thiazolidine -2,4-dione (prepared as described in Example 22 of copending U.S. Ser. No. 644,996) and 9 ml of methanol, and the mixture was stirred for 2 hours at room temperature, after which a 1% w/v aqueous solution of acetic acid was added and the mixture was neutralized with an aqueous solution of potassium carbonate. It was then extracted with ethyl acetate. The ethyl acetate extract was washed with water and dried over anhydrous sodium sulfate. The ethyl acetate was distilled from the extract under reduced pressure and the resulting residue was purified by silica gel column chromatography, using a 5:3 by volume mixture of hexane and ethyl acetate as eluent, to give the title compound, melting at 102°–118° C.

Nuclear Magnetic Resonance Spectrum [(CD$_3$)$_2$CO+D$_2$O] δ ppm:
1.52 (3H, singlet);
2.01 (3H, singlet);
2.13 (3H, singlet: 2.29 (3H, singlet);
1.9–2.5 (1H, nd);
2.9–3.6 (2H, multiplet);
4.03 (2H, singlet);
3.9–4.5 (1H, nd);
4.6–5.1 (2H, multiplet);
6.7–7.4 (4H, nd).

EXAMPLE 31

(a)

2-[4-(2,4-Dioxothiazolidin-5-ylmethyl)phenoxymethyl]-2,5,7,8-tetramethylchroman-6-yl hydrogen succinate A mixture of 1.0 g of 5-[4-(6-hydroxy-2,5,7,8-tetramethylchroman-2-ylmethoxy)benzyl]thiazolidine -2,4-dione (prepared as described in Example 28), 0.31 g of succinic anhydride and 1 ml of pyridine was allowed to stand overnight at room temperature. The reaction mixture was then washed 3 times, each time with 10 ml of cyclohexane, and the insoluble residue obtained was purified by silica gel column chromatography (eluted by mixtures of benzene and ethyl acetate ranging from 5:1 to 1:1) to give the title compound melting at 197°-202° C.

Nuclear Magnetic Resonance Spectrum (pentadeuterated pyridine) δ ppm:
1.36 (3H, singlet);
1.5-2.3 (2H, multiplet);
2.10 (6H, singlet);
2.14 (3H, singlet);
2.5 (2H, broad triplet, J=6 Hz);
2.7-3.35 (5H, multiplet;
3.60 (1H, doublet of doublets, J=4 δ 15 Hz);
3.95 δ 4.05 (2H, AB-type, J=9 Hz);
4.90 (1H, doublet of doublets, J=4 δ 9 Hz);
6.98 (2H, doublet, J=9 Hz);
7.30 (2H, doublet, J=9 Hz).

(b)
2-[4-(2,4-dioxothiazolidin-5-ylmethyl)phenoxymethyl]-2,5,7,8-tetramethylchroman-6-yl hydrogen succinate sodium salt 1 ml of a 2.5% w/v methanolic solution of sodium methoxide was added to a suspension of 246 mg of the compound obtained as described in (a) above in 100 ml of methanol at room temperature. Insoluble matter was filtered off, and then the methanol was distilled off under reduced pressure and the residue was washed with diethyl ether to give the title compound, melting at 178°-180° C.

EXAMPLE 32

5-[4-(6-Hydroxy-2,5,7,8-tetramethyl-2H-chromen-2-ylmethoxy)benzyl]thiazolidine-2,4-dione A mixture of 140 mg of 5-[4-(4,6-dihydroxy-2,5,7,8-tetramethylchroman-2-ylmethoxy)benzyl]thiazolidine-2,4-dione (prepared as described in Example 30), 10 mg of p-toluenesulfonic acid, 10 ml of benzene and 0.5 ml of dimethylformamide was heated under reflux for 1 hour. The reaction solution was cooled, washed with a saturated aqueous solution of sodium bicarbonate and then with water and dried over anhydrous sodium sulfate. The solvent was distilled off under reduced pressure and the residue was purified by silica gel column chromatography eluted with a 4:1 by volume mixture of benzene and ethyl acetate, to give the title compound, softening at 173°-176° C.

Nuclear Magnetic Resonance Spectrum [(CD$_3$)$_2$CO] δppm:
1.50 (3H, singlet);
2.02 (3H, singlet);
2.12 (3H, singlet);
2.18 (3H, singlet);
3.06 (1H, doublet of doublets, J=9 δ 14 Hz);
3.40 (1H, doublet of doublets, J=4 δ 14 Hz);
3.94 (1H, doublet, J=10 Hz);
4.05 (1H, doublet, J=10 Hz);
4.70 (1H, doublet of doublets, J=4 δ 9 Hz);
5.75 (1H, doublet, J=10 Hz);
6.72 (1H, doublet, J=10 Hz);
6.85 (2H, doublet, J=9 Hz);
7.19 (2H, doublet, J=9 Hz).

EXAMPLE 33

5-[4-(6-Hydroxy-2,5,7,8-tetramethylchroman-2-ylmethoxy)benzyl]thiazolidine-2,4-dione (Step H3)

Following the procedure described in Preparation 58, 120 mg of 5-[4-(6-hydroxy-2,5,7,8-tetramethyl-2H-chromen-2-ylmethoxy)benzyl]thiazolidine -2,4-dione (prepared as described in Example 32) were dissolved in 4 ml of methanol and, in the presence of 40 mg of 10% w/w palladium-on-carbon, it was reduced under 3-5 atmospheres (about 3-5 bars) pressure of hydrogen, to give the title compound. The melting point and nuclear magnetic resonance spectrum of this compound accorded with those of the compound obtained in Example 27(b).

EXAMPLE 34

5-[4-(4-Carboxymethoxyimino-6-hydroxy-2,5,7,8-tetramethylchroman-2-ylmethoxy)benzyl]thiazolidine -2,4-dione A mixture of 0.7 g of 5-[4-(4-t-butoxycarbonylmethoxyimino-6-hydroxy-2,5,7,8-tetramethylchroman -2ylmethoxy)benzyl]thiazolidine-2,4-dione (prepared as described in Example 26) and 7 ml of a 4N dioxane solution of hydrogen chloride was allowed to stand at room temperature for 15 hours. At the end of this time, the solvent was distilled off and the residue was washed with warm water to give the title compound, softening at 75°-85° C.

Nuclear Magnetic Resonance Spectrum ](CD$_3$)$_2$SO]δ ppm:
1.33 (3H, singlet);
1.98 (3H, singlet);
2.09 (3H, singlet);
2.14 (3H, singlet);
2.9-3.5 (2H, multiplet);
3.0 (2H, singlet);
4.02 (2H, singlet);
4.65 (2H, singlet);
4.84 (1H, doublet of doublets, J=4 δ9 Hz);
6.90 (2H, doublet, J=9 Hz);
7.17 (2H, doublet, J=9 Hz);
7.55-7.95 (1H, broad, disappeared on adding heavy water).

EXAMPLE 35

2-Methoxyethyl α-{2-[4-(2,4-dioxothiazolidin-5-ylmethyl)phenoxymethyl]-2,5,7,8-tetramethyl -4-oxochroman-6-yloxy}acetate A mixture of 13 g of ethyl 3-[4-(6-t-butoxycarbonylmethoxy-2,5,7,8-tetramethyl-4-oxochroman-2-ylmethoxy)phenyl]-2-chloropropionate (prepared as described in Preparation 64), 2.6 g of thiourea and 15 ml of sulfolane was heated under a nitrogen stream at 120°-130° C. for 5 hours. 30 ml of 2N aqueous hydrochloric acid and 60 ml of 2-methoxyethanol were added to the resulting mixture, which was then heated at 110° C. for 3 hours. The reaction mixture was then poured into water and extracted with ethyl acetate. The extract was washed with water and dried over anhydrous sodium sulfate. The solvent was distilled from the dried extract, and the residue was purified by silica gel column chromatography (eluted with a 4:1 by volume mixture of benzene and ethyl acetate) to give the title compound.

Rf value on silica gel thin layer chromatography=0.14 (developing solvent, benzene:ethyl acetate=4:1 by volume).

Nuclear magnetic Resonance Spectrum (CDCl$_3$) δ ppm:
  1.50 (3H, singlet);
  2.10 (3H, singlet);
  2.26 (3H, singlet);
  2.45–2.8 (1H, nd);
  2.56 (3H, singlet);
  2.9–3.25 (1H, nd);
  3.07 (1H, doublet, J=16 Hz);
  3.40 (3H, singlet);
  3.4–3.6 (1H, nd);
  3.6–3.75 (2H, multiplet);
  3.98 δ 4.11 (2H, AB type, J=10 Hz);
  4.3–4.45 (2H, multiplet);
  4.34 (2H, singlet);
  4.45–4.6 (1H, nd);
  6.85 (2H, doublet, J=9 Hz);
  7.16 (2H, doublet, J=9 Hz);
  8.7–9.3 (1H, broad).

EXAMPLE 36

5-[4-(6-Ethoxy-2,5,7,8-tetramethylchroman-2-ylmethoxy)benzyl]thiazolidine-2,4-dione The title compound, melting at 56°–60° C., was obtained from 5.1 g of ethyl 2-chloro-3-[4-(6-ethoxy-2,5,7,8-tetramethylchroman-2-ylmethoxy)phenyl]propionate (prepared as described in Preparation 65), 1 g of thiourea, 6 ml of sulfolane, 16 ml of 2N aqueous hydrochloric acid and 5 ml of 2-methoxyethanol, according to the same procedure as described in Example 35.

Mass spectrum (m/e): 469 (M+).

Nuclear Magnetic Resonance Spectrum (CDCl$_3$) δ ppm:
  1.39 (3H, triplet, J=7 Hz);
  1.41 (3H, singlet);
  1.7–2.1 (2H, nd);
  2.07 (3H, singlet);
  2.14 (3H, singlet);
  2.17 (3H, singlet);
  2.61 (2H, broad triplet, J=7 Hz);
  3.05 (1H, doublet of doublets, J=10 δ 14 Hz);
  3.45 (1H, doublet of doublets, J=4 δ 14 Hz);
  3.72 (2H, quartet, J=7 Hz);
  3.87 δ 3.97 (2H, AB type, J=9 Hz);
  4.47 (1H, doublet of doublets, J=4 δ 10 Hz);
  6.87 (2H, doublet, J=9 Hz);
  7.14 (2H, doublet, J=9 Hz);
  8.6–8.8 (1H, broad, disappeared on adding heavy water).

EXAMPLE 37

2-Methoxyethyl α-{2-[4-(2,4-dioxothiazolidin-5-ylmethyl)phenoxymethyl]-4-hydroxy-2,5,7,8-tetramethylchroman-6-yloxy}acetate 1.5 g of sodium borohydride were added, whilst ice-cooling, to a mixture of 1.2 g of 2-methoxyethyl α-{2-[4-(2,4-dioxothiazolidin-5-ylmethyl)-phenoxymethyl]-2,5,7,8-tetramethyl-4-oxochroman-6-yloxy}acetate (prepared as described in Example 35) and 20 ml of methanol, and the mixture was stirred for 60 minutes. The reaction mixture was then poured into ice-water, neutralized with 10% w/v aqueous hydrochloric acid, and then extracted with ethyl acetate. The extract was washed with water and dried over anhydrous sodium sulfate. The solvent was distilled off under reduced pressure to give the title compound as a pale yellow powder.

Rf value on silica gel thin layer chromatography=0.20 (developing solvent, benzene:ethyl acetate=1:1 by volume).

Mass spectrum (m/e) : 573 (M+).

EXAMPLE 38

Methyl α-{2-[4-(2,4-dioxothiazolidin-5-ylmethyl)phenoxymethyl]-2,5,7,8-tetramethyl-2H-chromen -6-yloxy}acetate A mixture of 970 mg of 2-methoxyethyl α-{2-[4-(2,4-dioxothiazolidin-5-ylmethyl)phenoxymethyl]4-hydroxy-2,5,7,8-tetramethylchroman-6-yloxy}acetate (prepared as described in Example 37), 50 mg of p-toluenesulfonic acid, 10 ml of benzene and 1 ml of dioxane was heated under reflux in a nitrogen stream for 60 minutes. The reaction mixture was then washed with a 5% w/v aqueous solution of sodium bicarbonate and then with water, and dried over anhydrous sodium sulfate. The solvent was distilled off under reduced pressure. The residue was purified by silica gel column chromatography (eluted with a 7:3 by volume mixture of benzene and ethyl acetate), to give the title compound.

Rf value on silica gel thin layer chromatography=0.74 (developing solvent, benzene:ethyl acetate=1:1 by volume).

Nuclear Magnetic Resonance Spectrum [(CD$_3$)$_2$CO]δ ppm:
  1.51 (3H, singlet);
  2.01 (3H, singlet);
  2.14 (3H, singlet);
  2.22 (3H, singlet);
  3.07 (1H, doublet of doublets, J=9 δ 14 Hz);
  3.42 (1H, doublet of doublets, J=4 δ 14 Hz);
  3.74 (3H, singlet);
  4.03 (2H, singlet);
  4.32 (2H, singlet);
  4.73 (1H, doublet of doublets, J=4 δ 9 Hz);
  5.80 (1H, doublet, J=10 Hz);
  6.70 (1H, doublet, J=10 Hz);
  6.86 (2H, doublet, J=9 Hz);
  7.20 (2H, doublet, J=9 Hz).

EXAMPLE 39

2-Methoxyethyl α-{2-[4-(2,4-dioxothiazolidin-5-ylmethyl)phenoxymethyl]-2,5,7,8-tetramethyl -2H-chromen-6-yloxy}acetate The title compound was obtained from the fraction eluted after the one giving the methyl ester in the column chromatography described in Example 38, using the same eluent.

Rf value on silica gel thin layer chromatography=0.59 (developing solvent, benzene;ethyl acetate=1:1 by volume).

Nuclear Magnetic Resonance Spectrum [(CD$_3$)$_2$CO]δ ppm:
  1.52 (3H, singlet);
  2.02 (3H, singlet);
  2.16 (3H, singlet);
  2.23 (3H, singlet);
  3.09 (1H, doublet of doublets, J=9 δ 15 Hz);
  3.30–3.60 (1H, nd);
  3.32 (3H, singlet);

3.5–3.7 (2H, multiplet);
4.04 (2H, singlet);
4.25–4.45 (2H, multiplet);
4.35 (2H, singlet);
4.75 (1H, doublet of doublets, J=4 δ 9 Hz);
5.82 (1H, doublet, J=10 Hz);
6.72 (1H, doublet, J=10 Hz);
6.88 (2H, doublet, J=9 Hz);
7.21 (2H, doublet, J=9 Hz).

EXAMPLE 40

5-{4-[6-(2-Hydroxyethoxy)-2,5,7,8-tetramethyl-2H-chromen-2-ylmethoxy]benzyl}thiazolidine-2,4-dione The title compound was obtained from the fraction eluted after the one giving the 2-methoxyethyl ester in the silica gel column chromatography described in Example 39, using the same eluent.

Rf value on silica gel thin layer chromatography=0.44 (developing solvent, benzene:ethyl acetate=1:1 by volume).

Nuclear magnetic Resonance Spectrum [(CD$_3$)$_2$CO]δ ppm:
1.51 (3H, singlet);
2.01 (3H, singlet);
2.15 (3H, singlet);
2.21 (3H, singlet);
3.08 (1H, doublet of doublets, J=9 δ 14 Hz);
3.42 (1H, doublet of doublets, J=4 δ 14 Hz);
3.6–3.95 (4H, multiplet);
4.03 (2H, singlet);
4.74 (1H, doublet of doublets, J=4 δ 9 Hz);
5.78 (1H, doublet, J=10 Hz);
6.71 (1H, doublet, J=10 Hz);
6.88 (2H, doublet, J=9 Hz);
7.21 (2H, doublet, J=9 Hz).

EXAMPLE 41

2-Methoxyethyl α-{2-[4-(2,4-dioxothiazolidin-5-ylmethyl)phenoxymethyl]-2,5,7,8-tetramethylchroman-6-yloxy}acetate Using Paar's hydrogenation apparatus, a mixture of 260 mg of 2-methoxyethyl α-{2-[4-(2,4-dioxothiazolidin-5-ylmethyl)phenoxymethyl]-2,5,7,8-tetramethyl-2H-chromen-6-yloxy}acetate (prepared as described in Example 39), 300 mg of 10% w/v palladium-on-carbon and 50 ml of ethanol was stirred for 10 hours under a hydrogen pressure of 3–5 atmospheres. The palladium-on-carbon was then filtered off, and the filtrate was condensed by evaporation under reduced pressure, to give the title compound as a colorless oily substance.

Rf value on silica gel thin layer chromatography=0.34 (developing solvent, benzene:ethyl acetate=2:1 by volume).

Nuclear magnetic Resonance Spectrum (CDCl$_3$) δ ppm:
1.40 (3H, singlet);
1.75–2.15 (2H, nd);
2.06 (3H, singlet);
2.14 (3H, singlet);
2.18 (3H, singlet);
2.61 (2H, broad triplet, J=7 Hz);
3.05 (1H, doublet of doublets, J=9 δ 14 Hz);
3.35–3.8 (3H, nd);
3.39 (3H, singlet);
3.86 δ 3.96 (2H, AB type, J=10 Hz);
4.25–4.6 (3H, nd);
4.34 (2H, singlet);
6.87 (2H, doublet, J=9 Hz);
7.15 (2H, doublet, J=9 Hz);
8.35–8.8 (1H, broad, disappeared on adding heavy water).

EXAMPLE 42

5-{4-[6-(2-Hydroxyethoxy)-2,5,7,8-tetramethylchroman-2-ylmethoxy]benzyl}thiazolidine-2,4-dione Following the same procedure as described in Example 41, 0.35 g of 5-{4-[6-(2-hydroxyethoxy)-2,5,7,8-tetramethyl-2H-chromen-2-ylmethoxy]benzyl}-thiazolidine-2,4-dione (prepared as described in Example 40), 0.3 g of 10% w/w palladium on activated carbon and 10 ml of ethanol gave the title compound.

Rf value on silica gel thin layer chromatography=0.45 (developing solvent, benzene:ethyl acetate=1:1 by volume).

Nuclear magnetic Resonance Spectrum (CDCl$_3$) δ ppm:
1.41 (3H, singlet);
1.7–2.2 (2H, nd);
2.07 (3H, singlet);
2.13 (3H, singlet);
2.18 (3H, singlet);
2.61 (2H, broad triplet, J=7 Hz);
3.05 (1H, doublet of doublets, J=9 δ 14 Hz);
3.44 (1H, doublet of doublets, J=5 δ 14 Hz);
3.7–4.1 (6H, multiplet);
4.47 (1H, doublet of doublets, J=4 δ 9 Hz);
4.8–5.2 (2H, broad);
6.87 (2H, doublet, J=9 Hz);
7.14 (2H, doublet, J=9 Hz).

EXAMPLE 43

Ethyl α-{2-[4-(2,4-dioxothiazolidin-5-ylmethyl)phenoxymethyl]-2,5,7,8-tetramethyl-4-oxochroman-6-yloxy}acetate A mixture of 0.5 g of α-{2-[4-(2,4-dioxothiazolidin-5-ylmethyl)phenoxymethyl]-2,5,7,8-tetramethyl-4-oxochroman-6-yloxy}acetic acid (obtained as described in Example 59), 0.5 ml of a 4N dioxane solution of hydrogen chloride and 5 ml of ethanol was allowed to stand overnight at room temperature. The reaction mixture was then poured into water and the solution was neutralized with sodium bicarbonate and extracted with ethyl acetate. The extract was washed with water and dried over anhydrous sodium sulfate. The solvent was distilled off, and the residue was subjected to preparative silica gel thin layer chromatography (developing solvent, benzene:ethyl acetate=7:3 by volume) to obtain the title compound.

Rf value on silica gel thin layer chromatography=0.70 (developing solvent, benzene:ethyl acetate=1:1 by volume).

Nuclear Magnetic Resonance Spectrum (CDCl$_3$) δ ppm:
1.33 (3H, triplet, J=7 Hz);
1.50 (3H, singlet);
2.10 (3H, singlet);
2.26 (3H, singlet);
2.57 (3H, singlet);
2.55–2.8 (1H, nd);
3.06 (1H, doublet, J=16 Hz);
3.07 (1H, doublet of doublets, J=9 δ 14 Hz);
3.45 (1H, doublet of doublets, J=4 δ 14 Hz);
4.00 δ 4.11 (2H, AB type, J=10 Hz);

4.29 (2H, singlet);
4.31 (2H, quartet, J=7 Hz);
4.48 (1H, doublet of doublets, J=4 δ 9 Hz);
6.85 (2H, doublet, J=9 Hz);
7.16 (2H, doublet, J=9 Hz);
8.3-8.9 (1H, broad).

EXAMPLE 44 t-Butyl
α-{5-[4-(6-acetoxy-2,5,7,8-tetramethylchroman-2-ylmethoxy)benzyl]-2,4-dioxothiazolidin-3yl}acetate 0.87 g of t-butyl bromoacetate was added dropwise, whilst ice-cooling, to a mixture of 1 g of 5-[4-(6-acetoxy-2,5,7,8-tetramethylchroman-2-ylmethoxy)benzyl ]thiazolidine-2,4-dione [prepared as described in Example 3(b) of copending U.S. Ser. No. 644,996], 0.43 g of anhydrous potassium carbonate, and 8 ml of acetone. The resulting mixture was stirred for 2 hours at room temperature and then allowed to stand for 2 days, also at room temperature. The reaction mixture was then poured into ice-water and extracted with ethyl acetate. The extract was washed with a saturated aqueous solution of sodium chloride and dried over anhydrous sodium sulfate. The solvent was distilled off and the residue was subjected to silica gel column chromatography (eluent:benzene) to give the title compound.

Rf value on silica gel thin layer chromatography=0.6 (developing solvent, benzene:ethyl acetate=10:1 by volume).

Nuclear Magnetic Resonance Spectrum (CDCl$_3$) δ ppm:
1.41 (3H, singlet);
1.47 (9H, singlet);
1.7-2.1 (2H, nd);
1.98 (3H, singlet);
2.02 (3H, singlet);
2.07 (3H, singlet);
2.30 (3H, singlet);
2.62 (2H, broad triplet, J=7 Hz);
2.98 (1H, doublet of doublets, J=10 δ 14 Hz);
3.55 (1H, doublet of doublets, J=4 δ 14 Hz);
3.86 δ 3.97 (2H, AB type, J=9 Hz);
4.19 (2H, singlet);
4.45 (1H, doublet of doublets, J=4 δ 10 Hz);
6.86 (2H, doublet J=9 Hz);
7.15 (2H, doublet, J=9 Hz).

EXAMPLE 45

Methyl
α-{5-[4-(6-acetoxy-2,5,7,8-tetramethylchroman-2-ylmethoxy)benzyl]-2,4-dioxothiazolidin -3-yl}acetate Following the procedure described in Example 44, 2.4 g of 5-[4-(6-acetoxy-2,5,7,8-tetramethylchroman-2-ylmethoxy)benzyl]thiazolidine-2,4-dione [prepared as described in Example 3(b) of copending U.S. Ser. No. 644,996], 1.5 g of methyl bromoacetate, 1.5 g of potassium carbonate and 25 ml of acetone gave the title compound as a colourless oil.

Rf value on silica gel thin layer chromatography=0.26 (developing solvent, benzene:ethyl acetate=20:1 by volume).

Nuclear Magnetic Resonance Spectrum (CDCl$_3$) δ ppm:
1.42 (3H, singlet);
1.8-2.25 (2H, nd);
1.98 (3H, singlet);
2.02 (3H, singlet);
2.08 (3H, singlet);
2.30 (3H, singlet);
2.64 (2H, broad triplet, J=7 Hz);
3.01 (1H, doublet of doublets, J=10 δ 14 Hz);
3.54 (1H, doublet of doublets, J=4.5 δ 14 Hz);
3.75 (3H, singlet);
3.87 δ 4.00 (2H, AB type, J=9 Hz);
4.31 (2H, singlet);
4.50 (1H, doublet of doublets, J=4.5 δ 10 Hz);
6.89 (2H, doublet, J=9 Hz);
7.17 (2H, doublet, J=9 Hz).

EXAMPLE 46 t-butyl
α-{5-[4-(6hydroxy-2,5,7,8-tetramethylchroman-2-ylmethoxy)benzyl]-2,4-dioxothiazolidin -3-yl}acetate Following the procedure described in Example 44, 1 g of 5-[4-(6-hydroxy-2,5,7,8-tetramethylchroman-2-ylmethoxy)benzyl]thiazolidine-2,4-dione [prepared as described in Example 27(b)], 0.47 g of anhydrous potassium carbonate, 0.93 g of t-butyl bromoacetate and 8 ml of acetone gave the title compound.

Rf value on silica gel thin layer chromatography=0.52 (developing solvent, benzene:ethyl acetate=10:1 by volume).

Nuclear Magnetic Resonance Spectrum (CDCl$_3$) δ ppm:
1.42 (3H, singlet);
1.48 (9H, singlet);
1.7-2.15 (2H, nd);
2.11 (6H, singlet);
2.16 (3H, singlet);
2.64 (2H, broad triplet, J=7 Hz);
2.99 (1H, doublet of doublets, J=10 δ 14 Hz);
3.56 (1H, doublet of doublets, J=4 δ 14 Hz);
3.85 δ 3.98 (2H, AB type, J=9 Hz);
4.21 (2H, singlet);
4.24 (1H, singlet);
4.46 (1H, doublet of doublets, J=4 δ 10 Hz);
6.88 (2H, doublet, J=9 Hz);
7.15 (2H, doublet, J=9 Hz).

EXAMPLE 47

Di-t-butyl
α,α'-{5-[4-(6-t-butoxycarbonylmethoxy-2,5,7,8-tetramethylchroman-2-ylmethoxy)benzyl ]-2,4-dioxothiazolidine-3,5-diyl}diacetate 1.9 g of t-butyl bromoacetate was added dropwise, whilst ice-cooling, to a mixture of 1 g of 5-[4-(6-hydroxy-2,5,7,8-tetramethylchroman-2-ylmethoxy)benzyl]thiazolidine-2,4-dione [prepared as described in Example 27(b)], 0.94 g of anhydrous potassium carbonate and 10 ml of acetone. The resulting mixture was stirred for 2 days at room temperature. The reaction mixture was then poured into ice-water and extracted with benzene. The extract was washed with water and dried over anhydrous sodium sulfate. The solvent was distilled off and the residue was subjected to silica gel column chromatography (eluent, benzene:ethyl acetate =20:1 by volume) to give the title compound.

Rf value on silica gel thin layer chromatography=0.54 (developing solvent, cyclohexane:ethyl acetate=4:1 by volume).

Nuclear magnetic Resonance Spectrum (CDCl$_3$ δ ppm:
1.44 (9H, singlet);
1.48 (12H, singlet);

1.54 (9H, singlet);
1.8–2.1 (2H, nd);
2.07 (3H, singlet);
2.16 (3H, singlet);
2.20 (3H, singlet);
2.5–2.7 (2H, multiplet);
2.9–3.15 (2H, multiplet);
3.24 (2H, singlet);
3.93 (2H, broad singlet);
4.13 (2H, singlet);
4.17 (2H, singlet);
6.85 (2H, broad doublet, J=9 Hz);
7.15 (2H, broad doublet, J=9 Hz).
Mass Spectrum (m/e) : 783 (M+).

EXAMPLE 48 t-Butyl-α-{55-[4-(6-t-butoxycarbonylmethoxy-2,5,7,8-tetramethylchroman-2-ylmethoxy)benzyl]-2,4-dioxothiazolidin-3-yl}acetate In the column chromatography separation process described in Example 47, the title compound was obtained from the fractions eluted after those giving the t-butyl ester of Example 47, using the same eluent.

Rf value on silica gel thin layer chromatography=0.42 (developing solvent, cyclohexane:ethyl acetate=4:1 by volume).

Nuclear Magnetic Resonance Spectrum (CDCl$_3$) δ ppm:
1.42 (3H, singlet);
1.48 (9H, singlet);
1.54 (9H, singlet);
1.7–2.1 (2H, nd);
2.06 (3H, singlet);
2.15 (3H, singlet);
2.19 (3H, singlet);
2.61 (2H, broad triplet, J=7 Hz);
2.99 (1H, doublet of doublets, J=10 δ 14 Hz);
3.56 (1H, doublet of doublets, J=4 δ 14 Hz);
3.87 δ 3.96 (2H, AB type, J=9 Hz);
4.17 (2H, singlet);
4.20 (2H, singlet);
4.46 (1H, doublet of doublets, J=4 δ 10 Hz);
6.87 (2H, doublet, J=9 Hz);
7.15 (2H, doublet, J=9 Hz).
Mass Spectrum (m/e) : 669 (M+).

EXAMPLE 49 t-Butyl
α-{5-[4-(6-hydroxy-2,5,7,8-tetramethyl-4-oxochroman-2-ylmethoxy)benzyl]-2,4-dioxothiazolidin-3-yl}acetate Following the procedure described in Example 44, 1 g of 5-[4-(6-hydroxy-2,5,7,8-tetramethyl-4-oxochroman-2-ylmethoxy)benzyl]thiazolidine-2,4-dione (prepared as described in Example 22 of copending U.S. Ser. No. 644,996), 0.45 g of anhydrous potassium carbonate, 0.9 g of t-butyl bromoacetate and 8 ml of acetone gave the title compound, softening at 170°–180° C.

Nuclear Magnetic Resonance Spectrum [(CD$_3$)$_2$CO]δ ppm:
1.46 (9H, singlet);
1.50 (3H, singlet);
2.10 (3H, singlet);
2.22 (3H, singlet);
2.5–2.8 (1H, nd);
2.54 (3H, singlet);
3.03 (1H, doublet of doublets, J=10 δ 14 Hz);
3.04 (1H, doublet, J=16 Hz);
3.53 (1H, doublet of doublets, J=4 δ 14 Hz);
4.16 (2H, singlet);
4.22 (2H, singlet);
4.82 (1H, doublet of doublets, J=4 δ 10 Hz);
6.96 (2H, doublet, J=9 Hz);
7.25 (2H, doublet, J=9 Hz).

EXAMPLE 50

Di-t-butyl
α,α'{5-[4-(6-t-butoxycarbonylmethoxy-2,5,7,8-tetramethyl-4-oxochroman-2-ylmethoxy)benzyl]-2,4-dioxothiazolidine-3,5-diyl}diacetate Following the procedure described in Example 47, 1.5 g of 5-[4-(6-hydroxy-2,5,7,8-tetramethyl-4-oxochroman-2-ylmethoxy)benzyl]thiazolidine-2,4-dione (prepared as described in Example 22 of copending U.S. Ser. No. 644,996), 1.3 g of anhydrous potassium carbonate, 5.4 g of t-butyl bromoacetate and 10 ml of acetone gave the title compound.

Rf value on silica gel thin layer chromatography=0.57 (developing solvent, cyclohexane:ethyl acetate=7:3 by volume).

Nuclear Magnetic Resonance Spectrum (CDCl$_3$) δ ppm:
1.42 (9H, singlet);
1.46 (9H, singlet);
1.48 (3H, singlet);
1.52 (9H, singlet);
2.10 (3H, singlet);
2.26 (3H, singlet);
2.55–3.20 (4H, nd);
2.56 (3H, singlet);
3.23 (2H, singlet);
3.97 δ 4.08 (2H, AB type, J=10 Hz);
4.12 (2H, singlet);
4.16 (2H, singlet);
6.82 (2H, doublet, J=9 Hz);
7.15 (2H, doublet, J=9 Hz).
Mass spectrum (m/e): 797 (M+).

EXAMPLE 51 t-Butyl
α-{5-[4-(6-t-butoxycarbonylmethoxy-2,5,7,8-tetramethyl-4-oxochroman-2-ylmethoxy)benzyl]-2,4-dioxothiazolidin-3-yl}acetate From the fraction eluted following the one giving di-t-butyl α,α'-{5-[4-(6-t-butyloxycarbonylmethoxy-2,5,7,8-tetramethyl-4-oxochroman-2-ylmethoxy)benzyl]-2,4-dioxothiazolidine-3,5-diyl}diacetate as described in Example 50, the title compound was obtained, using the same eluent.

Rf value on silica gel thin layer chromatography=0.46 (developing solvent, cyclohexane:ethyl acetate=7:3 by volume).

Nuclear magnetic Resonance Spectrum (CDCl$_3$) δ ppm:
1.47 (9H, singlet);
1.50 (3H, singlet);
1.53 (9H, singlet);
2.10 (3H, singlet);
2.26 (3H, singlet);
2.56 (3H, singlet);
2.6–3.2 (3H, nd);
3.57 (1H, doublet of doublets, J=4 δ 14 Hz);
3.98 δ 4.11 (2H, AB type, J=10 Hz);
4.17 (2H, singlet);
4.20 (2H, singlet);

4.47 (1H, doublet of doublets, J=4 δ 10 Hz);
6.86 (2H, doublet, J=9 Hz);
7.16 (2H, doublet, J=9 Hz).
Mass spectrum (m/e): 683 (M+).

EXAMPLE 52

3-Ethyl-5-[4-(6-hydroxy-2,5,7,8-tetramethylchroman-2-ylmethoxy)benzyl]thiazolidine-2,4dione Following the procedure described in Example 44, 0.58 g of 5-[4-(6-hydroxy-2,5,7,8-tetramethylchroman-2-ylmethoxy)benzyl]thiazolidine-2,4-dione [prepared as described in Example 27(b)], 0.27 g of anhydrous potassium carbonate, 0.6 g of ethyl iodide and 5 ml of acetone gave the title compound.

Rf value on silica gel thin layer chromatography=0.30 (developing solvent, benzene:ethyl acetate=20:1 by volume).

Nuclear magnetic Resonance Spectrum (CDCl$_3$) δ ppm:
1.09 (3H, triplet, J=7 Hz);
1.40 (3H, singlet);
1.7-2.2 (2H, nd);
2.09 (6H, singlet);
2.14 (3,singlet);
2.62 (2H, broad triplet, J=7 Hz);
3.02 (1h, doublet of doublets, J=9 δ 14 Hz);
3.25-3.5 (1H, nd);
3.59 (2H, quartet, J=7 Hz);
3.83 δ 3.96 (2H, AB type, J=10 Hz);
4.23 (1H, singlet, disappeared on adding heavy water);
4.36 (1H, doublet of doublets, J=4 δ 9 Hz);
6.84 (2H, doublet, J=9 Hz);
7.11 (2H, doublet, J=9 Hz).

EXAMPLE 53 t-Butyl α-{5-[4-(6-hydroxy-4-hydroxyimino-2,5,7,8-tetramethylchroman-2-ylmethoxy)benzyl]-2,4-dioxothiazolidin-3-yl}acetate A mixture of 0.5 g of t-butyl α-{5-[4-(6-hydroxy-2,5,7,8-tetramethyl-4-oxochroman-2-ylmethoxy)benzyl]-2,4-dioxothiazolidin-3yl}acetate (prepared as described in Example 49), 0.25 g of hydroxylamine hydrochloride, 0.25 g of pyridine and 5 ml of methanol was allowed to stand t 25°-30° C. for 2 days. Ethyl acetate and an aqueous solution of potassium carbonate were added to the mixture, and the organic layer was separated. The organic layer was dried over anhydrous sodium sulfate. The solvent was distilled off and the residue was subjected to silica gel column chromatography (eluted with a 9:1 by volume mixture of benzene and ethyl acetate) to obtain the title compound.

Rf value on silica gel thin layer chromatography=0.55 (developing solvent, benzene:ethyl acetate=4:1 by volume).

Nuclear Magnetic Resonance Spectrum [(CD$_3$)$_2$CO]δ ppm:
1.42 (3H, singlet);
1.45 (9H, singlet);
2.07 (3H, singlet);
2.17 (3H, singlet);
2.46 (3H, singlet);
3.03 (1H, doublet of doublets, J=δ 13.5 Hz);
3.07 (2H, singlet);
3.55 (1H, doublet of doublets, J=4 δ 13.5 Hz);
4.06 (2H, singlet);
4.18 (2H, singlet);
4.83 (1H, doublet of doublets, J=4 δ 10 Hz);
6.94 (2H, doublet, J=9 Hz);
7.25 (2H, doublet, J=9 Hz);
10.2 (1H, broad singlet, disappeared adding heavy water).

EXAMPLE 54

2-Methoxyethyl α-{2-[4-(2,4-dioxothiazolidin-5-ylmethyl)phenoxymethyl-4-hydroxyimino-2,5,7,8-tetramethylchroman-6-yloxy}acetate A mixture of 0.6 g of 2-methoxyethyl α-{2-[49(2,4-dioxothiazolidin-5-oxochroman-6-yloxy {acetate (prepared as described in Example 35), 0.3 g of hydroxylamine hydrochloride, 0.3 g of pyridine and 6 ml of methanol was allowed to stand at 25°-30 ° C. for 2 days. Ethyl acetate and an aqueous solution of potassium carbonate were added to the mixture, and the organic layer was separated. The organic layer was dried over anhydrous sodium sulfate. The solvent was distilled off and the residue was subjected to silica gel column chromatography (eluted with a 7:3 by volume mixture of benzene and ethyl acetate) to obtain the title compound.

Rf value on silica gel thin layer chromatography=0.32 (tailing) (developing solvent, benzene:ethyl acetate=3:2 by volume).

Nuclear Magnetic Resonance Spectrum [(CD$_3$)$_2$CO]δ ppm:
1.43 (3H, singlet);
2.06 (3H, singlet);
2.20 (3H, singlet);
2.46 (3H, singlet);
2.8-3.55 (2H, nd);
3.10 (2H, AB type, J=13.5 Hz);
3.32 (3H, singlet);
3.55-3.7 (2H, multiplet);
4.08 (2H, AB type, J=6 Hz);
4.25-4.4 (2H, multiplet);
4.34 (2H, singlet);
4.76 (1H, doublet of doublets, J=4 δ 9 Hz);
6.93 (2H, doublet, J=9 Hz);
7.24 (2H, doublet, J=9 Hz);
10.0-10.6 (1H, broad, disappeared on adding heavy water).

EXAMPLE 55 t-Butyl α-{5-[4-(6-t-butoxycarbonylmethoxy-4-hydroxyimino-2,5,7,8-tetramethylchroman-2-ylmethoxy)benzyl]-2,4-dioxothiazolidin-3-yl}acetate A mixture of 0.5 g of t-butyl α-{5-[4-(6-t-butoxycarbonylmethoxy-2,5,7,8-tetramethyl-4-oxochroman-2-ylmethoxy)benzyl]-2,4-dioxothiazolidin-3-yl}acetate (prepared as described in Example 51), 0.2 g of hydroxylamine hydrochloride, 0.2 g of pyridine and 5 ml of methanol was allowed to stand at 25°-30° C. for 5 days. Ethyl acetate and an aqueous solution of potassium carbonate were added to the mixture, and the organic layer was separated. The organic layer was dried over anhydrous sodium sulfate. The solvent was distilled off and the residue was subjected to silica gel column chromatography (eluted with a 20:1 by volume mixture of benzene and ethyl acetate) to obtain the title compound.

Rf value on silica gel thin layer chromatography=0.43 (developing solvent, benzene:ethyl acetate=10:1 by volume).

Nuclear Magnetic Resonance Spectrum (CDCl$_3$) δ ppm:
1.45 (3H, singlet);
1.47 (9H, singlet);
1.54 (9H, singlet);
2.07 (3H, singlet);
2.23 (3H, singlet);
2.47 (3H, singlet);
2.85-3.15 (1H, nd);
3.08 (2H, singlet);
3.57 (1H, doublet of doublets, J=4 δ 13.5 Hz);
3.97 (2H, singlet);
4.20 (4H, singlet);
4.46 (1H, doublet of doublets, J=4 δ 9 Hz);
6.87 (2H, doublet, J=9 Hz);
7.15 (2H, doublet, J=9 Hz);
7.5-8.05 (1H, broad).

EXAMPLE 56

Di-t-butyl α,α'-{5-[4-(6-t-butoxycarbonylmethoxy-4-hydroxyimino-2,5,7,8-tetramethylchroman-2-ylmethoxy)benzyl]-2,4-dioxothiazolidine-3,5-diyl}diacetate A mixture of 350 mg of di-t-butyl α,α'-{5-[4-(6-t-butoxycarbonylmethoxy-2,5,7,8-tetramethyl-4-oxochroman-2-ylmethoxy)benzyl]-2,4-dioxothiazolidine-3,5-diyl}diacetate (prepared as described in Example 50), 122 mg of hydroxylamine hydrochloride, 122 mg of pyridine and 4 ml of methanol was allowed to stand at 25°-+° C. for 5 days. Ethyl acetate and an aqueous solution of potassium carbonate were added to the mixture, and the organic layer was separated. The organic layer was dried over anhydrous sodium sulfate. The solvent was distilled off and the residue was subjected to silica gel column chromatography (eluted with a 20:1 by volume mixture of benzene and ethyl acetate) to obtain the title compound.

Rf value on silica gel thin layer chromatography=0.48 (developing solvent, benzene:ethyl acetate=10:1 by volume).

Nuclear Magnetic Resonance Spectrum (CDCl$_3$) δ ppm:
1.45 (21H, singlet);
1.53 (9H, singlet);
2.08 (3H, singlet);
2.23 (3H, singlet);
2.47 (3H, singlet);
2.9-3.2 (1H, nd);
3.07 (2H, broad singlet);
3.22 (2H, singlet);
3.95 (2H, broad singlet);
4.11 (2H, singlet);
4.18 (2H, singlet);
6.83 (2H, doublet, J=9 Hz);
7.13 (2H, doublet, J=9 Hz);
7.68 (1H, broad singlet).

EXAMPLE 57

Ethyl α-{2-[4-(2,4-dioxothiazolidin-5-ylmethyl)phenoxymethyl]-4-hydroxyimino-2,5,7,8-tetramethylchroman-6-yloxy}acetate Following the procedure described in Example 54, the title compound was obtained as a pale yellow powder by using 330 mg of ethyl α-{2-[4-(2,4-dioxothiazolidin-5-ylmethyl)phenoxymethyl]-2,5,7,8tetramethyl-4-oxochroman-6-yloxy}acetate (prepared as described in Example 43), 170 mg of hydroxylamine hydrochloride, 170 mg of pyridine and 3 ml of methanol.

Rf value on silica gel thin layer chromatography=0.67 (developing solvent, benzene:ethyl acetate=1:1 by volume).

Mass spectrum (m/e): 556 (M+).

Nuclear Magnetic Resonance Spectrum [(CD$_3$)$_2$CO]δ ppm:
1.27 (3H, triplet, J=7 Hz);
1.43 (3H, singlet);
2.06 (3H, singlet);
2.20 (3H, singlet);
2.46 (3H, singlet);
2.95-3.25 (1H, nd);
3.08 (2H, singlet);
3.43 (1H, doublet of doublets, J=4 δ 14 Hz);
4.08 (2H, singlet);
4.1-4.4 (2H, nd);
4.30 (2H, singlet);
4.74 (1H, doublet of doublets, J=4 δ 9 Hz);
6.93 (2H, doublet, J=9 Hz);
7.23 (2H, doublet, J=9 Hz);
10.30 (1H, broad singlet, disappeared on adding heavy water).

EXAMPLE 58

α-{2-[4-(2,4-Dioxothiazolidin-5-ylmethyl)phenoxymethyl]-2,5,7,8-tetramethylchroman-6yloxy}acetic acid A mixture of 220 mg of 2-methoxyethyl α-{2-[4-(2,4-dioxothiazolidin-5-ylmethyl)phenoxymethyl)9 2,5,7,8-tetramethylchroman-6-yloxy}acetate (prepared as described in Example 41), 3 ml of a 4N dioxane solution of hydrogen chloride and 0.3 ml of water was heated under reflux for 5 hours. At the end of this time, the solvent was distilled off and the residue was washed with water to give the title compound as a pale yellow powder.

Nuclear Magnetic Resonance Spectrum [(CD$_3$)$_2$CO]δ ppm:
1.38 (3H, singlet);
1.8-2.2 (2H, nd);
2.02 (3H, singlet);
2.15 (6H, singlet);
2.65 (2H, broad triplet, J=7 Hz);
3.08 (1H, doublet of doublets, J=9 δ 14 Hz);
3.41 (1H, doublet of doublets, J=4 δ 14 Hz);
4.00 (2H, singlet);
4.27 (2H, singlet);
4.73 (1H, doublet of doublets, J=4 δ 9 Hz);
6.92 (2H, doublet, J=9 Hz);
7.23 (2H, doublet, J=9 Hz);
9.9-11.3 (1H, broad, disappeared on adding heavy water).

Mass spectrum (m/e): 499 (M+).

EXAMPLE V

α-{2-[4-(2,4-Dioxothiazolidin-5-ylmethyl)-phenoxymethyl]-2,5,7,8-tetramethyl-4-oxochroman-6-yloxy}acetic acid After eluting the 2-methoxyethyl ester which was obtained from the silica gel column chromatography described in Example 35, the title compound was obtained as pale yellow powder by continuing the elution with a 2:2:1 by volume mixture of ethyl acetate, tetrahydrofuran and methanol.

Nuclear Magnetic Resonance Spectrum [(CD$_3$)$_2$SO]δ ppm:
  1.41 (3H, singlet);
  2.02 (3H, singlet);
  2.18 (3H, singlet);
  2.46 (3H, singlet);
  2.68 (1H, doublet, J=16 Hz);
  2.85-3.20 (2H, nd);
  3.22 (1H, doublet of doublets, J=4 δ 14 Hz);
  4.01 (2H, singlet);
  4.12 (2H, singlet);
  4.61 (1H, doublet of doublets, J=4 δ 9 Hz);
  6.87 (2H, doublet, J=9 Hz);
  7.15 (2H, doublet, J=9 Hz).
  Mass spectrum (m/e): 513 (M+).

EXAMPLE 60

α-{2-[4-(2,4-Dioxothiazolidin-5-ylmethyl)phenoxymethyl]-4-hydroxyimino-2,5,7,8-tetramethylchroman-6-yloxy}acetic acid A mixture of 8.9 mg of ethyl α-{2-[4-(2,4-dioxothiazolidin-5-ylmethyl)phenoxymethyl]-4-hydroxyimino-2,5,7,8-tetramethylchroman-6-yloxy}acetate [prepared as described in Example 57], 1 ml of ethanol and 0.2 ml of a 0.312M aqueous solution of sodium hydroxide was allowed to stand for 19 hours at 0°-5° C.

After the absence of the starting material had been confirmed by high pressure liquid chromatography, 0.56 ml of 0.35% w/v aqueous hydrochloric acid was then added to the reaction mixture. The solvent was distilled off under reduced pressure, and chloroform and water were added to the residue.

The pale yellow precipitate was filtered and then washed with water, to give the title compound.

Fast Atom Bombardment Mass Spectrum (m/e measured with glycerol as a matrix)

[M+H]+ =529.
[M−H]− =527.
From the above data, the molecular weight was deduced to be 528.

EXAMPLE 61

α-{5-[4-(6-Hydroxy-2,5,7,8-tetramethylchroman-2-ylmethoxy)benzyl]-2,4-dioxothiazolidin -3yl}acetic acid A mixture of 1.0 g of t-butyl α-{5-[4-(6-hydroxy-2,5,7,8-tetramethylchroman-2-ylmethoxy)benzyl ]-2,4-dioxothiazolidin-3-yl}acetate (prepared as described in Example 46) and 10 ml of a 4N dioxane solution of hydrogen chloride was allowed to stand at room temperature overnight. At the end of this time, the solvent was distilled off and the residue was washed with water to give the title compound as a pale yellow powder, softening at 85°-90° C.

Nuclear magnetic Resonance Spectrum: the signal assigned to the t-butyl group had disappeared, as compared with the spectrum of the starting material.
Mass spectrum (m/e): 499 (M+).

EXAMPLE 62

α-{5-[4-(6-Hydroxy-2,5,7,8-tetramethyl-4-oxochroman-2-ylmethoxy)benzyl]-2,4-dioxothiazolidin-3-yl}acetic acid A mixture of 350 mg of t-butyl α-{5-[4-(6-hydroxy-2,5,7,8-tetramethyl-4-oxochroman-2-ylmethoxy)benzyl]-2,4-dioxothiazolidin-3yl}acetate (prepared as described in Example 49) and 4 ml of a 4N dioxane solution of hydrogen chloride was treated in the same manner described in Example 61, to give the title compound as a pale yellow powder, softening at 60°-70° C.

Nuclear Magnetic Resonance Spectrum: the signal assigned to the t-butyl group had disappeared, as compared with the spectrum of the starting material.
Mass spectrum (m/e): 513 (M+).

EXAMPLE 63

α-{5-[4-(6-Hydroxy-4-hydroxyimino-2,5,7,8-tetramethylchroman-2-ylmethoxy)benzyl]-2,4-dioxothiazolidin-3-yl}acetic acid A mixture of 400 mg of t-butyl α-{5-[4-)6-hydroxy-4-hydroxyimino-2,5,7,8-tetramethylchroman -2-ylmethoxy)benzyl]-2,4-dioxothiazolidin-3-yl}acetate (prepared as described in Example 53) and 5 ml of a 4N dioxane solution of hydrogen chloride was treated in the same manner described in Example 61, to give the title compound as a pale brown powder, softening at 90°-95° C.

Nuclear Magnetic Resonance Spectrum: the signal assigned to the t-butyl group had disappeared, as compared with the spectrum of the starting material.

EXAMPLE 64

α-{5-[4-(6-Carboxymethoxy-2,5,7,8-tetramethylchroman-2-ylmethoxy)benzyl]-2,4-dioxothiazolidin -3-yl}acetic acid A mixture of 0.63 g of t-butyl α-{5-[4-(6-t-butoxycarbonylmethoxy-2,5,7,8-tetramethylchroman-2-ylmethoxy)benzyl]-2,4-dioxothiazolidin-3-yl}acetate (prepared as described in Example 48) and 6 ml of a 4N dioxane solution of hydrogen chloride was allowed to stand at room temperature overnight. At the end of this time, the reaction mixture was treated as the same manner described in Example 61, to give the title compound as a pale yellow powder, softening at 95°-100° C.

Nuclear Magnetic Resonance Spectrum: the signal assigned to the t-butyl group had disappeared, as compared with the spectrum of the starting material.
Mass spectrum (m/e): 557 (M+).

EXAMPLE 65

α-{5-[4-(6-Carboxymethoxy-2,5,7,8-tetramethyl-4-oxochroman-2-ylmethoxy)benzyl]-2,4-dioxothiazolidin-3-yl}acetic acid A mixture of 570 mg of t-butyl α-{5-[4-(6-t-butoxycarbonylmethoxy-2,5,7,8-tetramethyl-4-oxochroman-2-ylmethoxy)benzyl]-2,4-dioxothiazolidin3-yl}acetate (prepared as described in Example 51) and 6 ml of a 4N dioxane solution of hydrogen chloride was treated in the same manner described in Example 61, to give the title compound as a pale yellow powder, softening at 80°-85° C.

Nuclear Magnetic Resonance Spectrum: the signal assigned to the t-butyl group had disappeared, as compared with the spectrum of the starting material.
Mass spectrum (m/e): 571 (M+).

EXAMPLE 66

α-{5-[4-(6-Carboxymethoxy-4-hydroxyimino-2,5,7,8-tetramethylchroman-2-ylmethoxy)benzyl]-2,4-dioxothiazolidin-3-yl}acetic acid A mixture of 370 mg of t-butyl α-{5-[4-(6-t-butoxycarbonylmethoxy-4-hydroxyimino-2,5,7,8-tetramethylchroman-2-ylmethoxy)benzyl]-2,4-dioxothiazolidin-3-yl}acetate (prepared as described in Example 55) and 4 ml of a 4N dioxane solution of hydrogen chloride was treated in the same manner described in Example 61, to give the title compound as a pale yellow powder, softening at 90°-100° C.

Nuclear Magnetic Resonance Spectrum: the signal assigned to the t-butyl group had disappeared, as compared with the spectrum of the starting material.

EXAMPLE 67

α,α'-{5-[4-(6-Carboxymethoxy-2,5,7,8-tetramethylchroman-2-ylmethoxy)benzyl]-2,4-dioxothiazolidine-3,5-diyl}diacetic acid A mixture of 0.41 g of di-t-butyl α,α'-{5-[4-(6-t-butoxycarbonylmethoxy-2,5,7,8-tetramethylchroman-2-ylmethoxy)benzyl]-2,4-dioxothiazolidine-3,5-diyl}diacetate (prepared as described in Example 47) and 4 ml of a 4N dioxane solution of hydrogen chloride was allowed to stand at room temperature overnight. At the end of this time, the reaction mixture was treated in the same manner described in Example 61, to give the title compound as a pale yellow powder, softening at 105°-110° C.

Nuclear Magnetic Resonance Spectrum: the signal assigned to the t-butyl group had disappeared, as compared with the spectrum of the starting material.

Mass spectrum (m/e): 615 (M+).

EXAMPLE 68

α,α'-{5-[4-(6-Carboxymethoxy-2,5,7,8-tetramethyl-4-oxochroman-2-ylmethoxy)benzyl]-2,4-dioxothiazolidine-3,5-diyl}diacetic acid A mixture of 340 mg of di-t-butyl α,α'-{5-[4-(6-t-butoxycarbonylmethoxy-2,5,7,8-tetramethyl-4-oxochroman-2-ylmethoxy)benzyl]-2,4-dioxothiazolidine-3,5-diyl}diacetate (prepared as described in Example 50) and 4 ml of a 4N dioxane solution of hydrogen chloride was treated in the same manner described in Example 61, to give the title compound as a pale yellow powder, softening at 105°-110° C.

Nuclear Magnetic Resonance Spectrum: the signal assigned to the t-butyl group had disappeared, as compared with the spectrum of the starting material.

Mass Spectrum (m/e): 629 (M+).

EXAMPLE 69

α,α'-{5-[4-(6-Carboxymethoxy-4-hydroxyimino-2,5,7,8-tetramethylchroman-2-ylmethoxy)benzyl]-2,4-dioxothiazolidine-3,5-diyl}diacetic acid A mixture of 270 mg of di-t-butyl α,α'-{5-[4-(6-t-butoxycarbonylmethoxy-4-hydroxyimino-2,5,7,8-tetramethylchroman-2-ylmethoxy)benzyl]-2,4-dioxothiazolidine-3,5-diyl}diacetate (prepared as described in Example 56) and 3 ml of a 4N dioxane solution of hydrogen chloride was treated in the same manner described in Example 61, to give the title compound as a pale yellow powder, softening at 90°-100° C.

Nuclear Magnetic Resonance Spectrum: the signal assigned to the t-butyl group had disappeared, as compared with the spectrum of the starting material.

EXAMPLE 70

5-[4-(6-Hydroxy-2,5,7,8-tetramethylchroman-2-ylmethoxy)benzyl]thiazolidine-2,4-dione sulfuric acid ester A solution of 5 g of 5-[4-(6-hydroxy-2,5,7,8-tetramethylchroman-2-ylmethoxy)benzyl]thiazolidine-2,4-dione (synthesized as described in copending U.S. Ser. No. 644,996) in 10 ml of pyridine was added to a solution of 7.3 g (62.64 mmole) of chlorosulfonic acid in 20 ml of pyridine, and the reaction mixture was heated at 70°-80° C. for 1 hour. At the end of this time, petroleum ether was added to the reaction mixture, the supernatant liquid was removed by decantation, and then these procedures were repeated a further 2 times. 10 ml of water were added to the resulting residue. The reaction mixture was adjusted to a pH value of 6.5 with a 2N aqueous solution of sodium hydroxide and extracted with ethyl acetate. The ethyl acetate was distilled from the extract under reduced pressure, to give 5.72 g of the title compound as a white powder, melting at 140.5°142.5° C.

Infrared Absorption Spectrum (Nujol-trade markmull): $\nu_{max}$cm$^{-1}$:
3600, 3330, 1270, 1050.

Nuclear Magnetic Resonance Spectrum:(CD$_3$CN) δ ppm:
7.2 (2H, doublet);
6.9 (2H, doublet);
4.6 (1H, doublet of doublets);
4.0 (1H, doublet);
3.9 (1H, doublet);
3.3 (1H, doublet of doublets);
3.1 (1H, doublet of doublets);
2.6 (2H, triplet);
2.19 (3H, singlet);
2.18 (3H, singlet);
2.1 (1H, multiplet);
2.0 (3H, singlet);
1.9 (1H, multiplet);
1.4 (3H, singlet).

Fast Atom Bombardment Mass Spectrum (m/e measured with glycerol as a matrix)

(M+H)+ =522;
(M−H)− =520.

From this, we concluded that molecular weight is 521.

PREPARATION 1

Ethyl 6-hydroxy-5,7,8-trimethyl-4-oxochroman-2-carboxylate (Step E1)

12 g of ethyl 6-hydroxy-5,7,8-trimethyl-4-oxo-2H-chromene-2-carboxylate [prepared as described in J. Med Chem., 18, 934 (1975)] were dissolved in 250 ml of dimethylformamide and reduced catalytically in the presence of 16 g of 10% w/w palladium-on-carbon, under a hydrogen pressure of 5 atmospheres at 50° to 60° C. for 7 hours. The catalyst was then filtered off, and the filtrate was mixed with a large amount of water. The crystals which separated were collected by filtration and then recrystallized from ethyl acetate, to give the title compound, melting at 120°-121° C.

Nuclear Magnetic Resonance Spectrum (CDCl$_3$) δ ppm:
1.26 (3H, triplet, J=7 Hz);
2.23 (6H, singlet);
2.52 (3H, singlet);
2.98 (2H, doublet, J=7 Hz);
4.24 (2H, quartet, J=7 Hz);
4.83 (1H, singlet);
4.94 (1H, triplet, J=7 Hz).

The filtrate from which the title compound had been filtered off was extracted with ethyl acetate. The solution was dried over anhydrous sodium sulfate, and the solvent was distilled off. The residue was purified by silica gel column chromatography, eluted with a 1:1 by volume mixture of hexane and ethyl acetate. The first fraction gave the title compound, while the second fraction gave ethyl 4,6-dihydroxy-5,7,8-trimethylchroman-2-carboxylate, melting at 138°–144 ° C.

PREPARATION 2

Ethyl 6-hydroxy-5,7,8trimethylchromanspiro-4,2'-(1',3'-dithiane)-2-carboxylate (Step E2)

20 ml of a boron trifluoride-acetic acid complex salt (boron trifluoride content 40% w/w) were added dropwise to 500 ml of a chloroform solution containing 16.6 g of ethyl 6-hydroxy-5,7,8-trimethyl-4-oxochroman-2-carboxylate (prepared as described in Preparation 1) and 9.7 g of 1,3-propanedithiol in an ice bath, and the reaction mixture was allowed to stand for 24 hours at room temperature. The reaction mixture was then poured into ice-water, neutralized with potassium carbonate and extracted with ethyl acetate. The ethyl acetate extract was dried over anhydrous sodium sulfate and the solvent was distilled off. Recrystallization of the residue from ethyl acetate afforded the title compound, melting at 186°–188° C.

Nuclear Magnetic Resonance Spectrum (CDCl$_3$) δ ppm:
 1.35 (3H, triplet, J=7 Hz);
 1.8–2.4 (2H, nd);
 2.18 (6H, singlet);
 2.5–2.9 (3H, nd);
 2.80 (3H, singlet);
 3.0–3.5 (3H, multiplet);
 4.31 (2H, quartet, J=7 Hz);
 4.50 (1H, singlet);
 4.79 (1H, doublet of doublets, J=2 & 10 Hz).

PREPARATION 3

Ethyl 6 methoxymethoxy-5,7,8-trimethylchromanspiro-4,2'-(1',3'-dithiane)-2-carboxylate (Step E3)

A mixture of 6.6 g of ethyl 6-hydroxy-5,7,8-trimethylchromanspiro-4,2'-(1',3'-dithiane)-2-carboxylate (prepared as described in Preparation 2), 100 ml of dimethylformamide and 1 g of a 55% w/w suspension of sodium hydride in mineral oil was subjected to ultrasonic treatment for mixing at room temperature for 1 hour, and then, whilst ice-cooling, 3 g of chloromethyl methyl ether were added, and the mixture was allowed to stand at room temperature overnight. Water was added to the reaction mixture, which was then extracted with ethyl acetate. The water layer was extracted additionally with benzene. Both the ethyl acetate and benzene extracts were washed with water three times, after which the extracts were combined and dried over anhydrous sodium sulfate. The solvent was distilled off and the residue was purified by silica gel column chromatography, eluted with a 5:1 by volume mixture of hexane and ethyl acetate, to give the title compound.

Rf value on silica gel thin layer chromatography=0.21 (developing solvent, hexane:ethyl acetate=5:1 by volume).

Nuclear Magnetic Resonance Spectrum (CDCl$_3$) δ ppm:
 1.34 (3H, triplet, J=7 Hz);
 1.7–2.4 (2H, nd);
 2.16 (3H, singlet);
 2.21 (3H, singlet);
 2.5–3.0 (3H, nd);
 2.87 (3H, singlet);
 3.0–3.5 (3H, nd);
 3.60 (3H, singlet);
 4.30 (2H, quartet, J=7 Hz);
 4.7–5.0 (1H, nd);
 4.89 (2H, singlet).

PREPARATION 4

2-Hydroxymethyl-2-isobutyl-6-methoxymethoxy-5,7,8-trimethylchromanspiro-4,2'-(1',3'-dithiane) (Steps E4 & E5)

15 ml of a hexane solution of butyllithium (butyllithium content 1.62 mmole/ml) were added dropwise at a temperature of −60° C. to −50° C. to 90 ml of a tetrahydrofuran solution containing 3 g of diisopropylamine, and the mixture was allowed to stand for 20 minutes at room temperature. 4.8 g of ethyl 6-methoxymethoxy-5,7,8-trimethylchromanspiro-4,2'-(1',3'-dithiane)-2-carboxylate (prepared as described in Preparation 3) were added at −60° C. to the mixture, which was then stirred for 10 minutes at the same temperature. 4.1 g of isobutyl bromide were added, and the mixture was stirred for 30 minutes at the same temperature, and then stirred at room temperature for 1.5 hours. Another 3 g of isobutyl bromide were added, and the mixture was heated at 40° C. for 5 hours. The reaction mixture was then cooled to −50° C., 0.6 g of lithium aluminum hydride were added, and the mixture was stirred for 1 hour at room temperature. Benzene, ethyl acetate and water were added to this reaction mixture. The organic layer was separated, washed with water and dried over anhydrous sodium sulfate. The solvent was distilled off under reduced pressure. The residue was purified by silica gel column chromatography, eluted with a 5:1 by volume mixture of hexane and ethyl acetate, to give the title compound.

Rf value on silica gel thin layer chromatography=0.16 (developing solvent, hexane:ethyl acetate=5:1 by volume).

Nuclear Magnetic Resonance Spectrum (CDCl$_3$) δ ppm:
 1.03 (3H, doublet, J=6 Hz);
 1.04 (3H, doublet, J=6 Hz);
 1.70 (2H, doublet, J=6 Hz);
 1.8–2.3 (3H, nd);
 2.08 (3H, singlet);
 2.20 (3H, singlet);
 2.3–3.0 (4H, nd);
 2.91 (3H, singlet);
 3.05–3.95 (5H, nd);
 3.62 (3H, singlet);
 4.88 (2H, singlet).

PREPARATION 5

2-Isobutyl-6-methoxymethoxy-5,7,8-trimethyl-2-(4-nitrophenoxymethyl)chromanspiro-4,2'-(1',3'-dithiane) (Step E6)

4 ml of ethanol were added to a mixture of 0.6 g of a 55% w/w suspension of sodium hydride in mineral oil and 20 ml of tetrahydrofuran, followed by 20 ml of a tetrahydrofuran solution containing 3.2 g of 2-hydroxymethyl-2-isobutyl-6-methoxymethoxy-5,7,8-trimethylchromanspiro-4,2'-(1',3'-dithiane) (prepared as described in Preparation 4). The solvent was then distilled off under reduced pressure to dryness. The residue was mixed with 30 ml of dimethylformamide and heated at 40° C. for 1 hour under reduced pressure. 10 g of p-nitrochlorobenzene were then added to the reaction mixture, and the mixture was heated at 50° C. for 2 hours, mixed with water and extracted with benzene. The benzene extract was washed twice with water and dried over anhydrous sodium sulfate. The solvent was distilled off under reduced pressure. The residue was purified by silica gel column chromatography eluted with a 6:1 by volume mixture of hexane and ethyl acetate, to give the title compound.

Rf value on silica gel thin layer chromatography=0.54 (developing solvent, hexane:ethyl acetate=2:1 by volume).

Nuclear Magnetic Resonance Spectrum (CDCl$_3$) δ ppm:
1.02 (3H, doublet, J=6 Hz);
1.09 (3H, doublet, J=6 Hz);
1.83 (2H, doublet, J=6 Hz);
1.8–2.3 (3H, nd);
2.11 (3H, singlet);
2.22 (3H, singlet);
2.3–2.9 (3H, nd);
2.89 (3H, singlet);
3.0–3.7 (3H, nd);
3.62 (3H, singlet);
3.92 (1H, doublet, J=4.5 Hz);
4.50 (1H, doublet, J=4.5 Hz);
4.90 (2H, singlet);
6.90 (2H, doublet, J=4.5 Hz);
8.17 (2H, doublet, J=4.5 Hz).

PREPARATION 6

(a) 2-Isobutyl-6-methoxymethoxy-5,7,8-trimethyl-2-(4-nitrophenoxymethyl)chroman-4-one and (b) 6-hydroxy-2-isobutyl-5,7,8-trimethyl-2-(4-nitrophenoxymethyl)chroman-4-one (Step E7)

A mixture of 3.3 g of 2-isobutyl-6-methoxymethoxy-5,7,8-trimethyl-2-(4-nitrophenoxymethyl)chromanspiro-4,2'-(1',3'-dithiane) (prepared as described in Preparation 5), 4 g of mercuric chloride, 1.4 g of mercuric oxide and 30 ml of 10% v/v aqueous methanol was heated under reflux for 2 hours. The reaction mixture was then mixed with diethyl ether, and the insoluble residue was filtered off. The filtrate was washed with an aqueous solution of sodium chloride and then with an aqueous solution of ammonium sulfate, and dried over anhydrous sodium sulfate. The solvent was distilled off and the residue was purified by silica gel column chromatography eluted with a 4:1 by volume mixture of hexane and ethyl acetate, to give the title compounds (a) and (b) separately.

Silica gel thin layer chromatography (developing solvent, hexane:ethyl acetate=2:1 by volume),
(a) Rf value=0.48
(b) Rf value=0.40.

Nuclear Magnetic Resonance Spectrum (CDCl$_3$) δ ppm:
(a) 1.01 (6H, doublet, J=6 Hz);
1.84 (2H, singlet);
1.6–2.1 (1H, singlet);
2.12 (3H, singlet);
2.27 (3H, singlet);
2.58 (3H, singlet);
2.81 (1H, doublet, J=19 Hz);
3.00 (1H, doublet, J=19 Hz);
3.62 (3H, singlet);
4.14 (1H, doublet, J=11 Hz);
4.25 (1H, doublet, J=11 Hz);
4.89 (2H, singlet);
6.95 (2H, doublet, J=4.5 Hz);
8.20 (2H, doublet, J=4.5 Hz).
(b) 0.98 (3H, doublet, J=6 Hz);
1.00 (3H, doublet, J=6 Hz);
1.80 (2H, doublet, J=6 Hz);
1.65–2.1 (1H, nd);
2.13 (3H, singlet);
2.23 (3H, singlet);
2.57 (3H, singlet);
2.82 (1H, doublet, J=14 Hz);
3.00 (1H, doublet, J=14 Hz);
4.13 (1H, doublet, J=12 Hz);
4.27 (1H, doublet, J=12 Hz);
4.66 (1H, singlet);
6.95 (2H, doublet, J=9 Hz);
8.19 (2H, doublet, J=9 Hz).

PREPARATION 7

6-Acetoxy-2-isobutyl-5,7,8-trimethyl-2-(4-nitrophenoxymethyl)chroman-4-one

A mixture of 1.5 g of 6-hydroxy-2-isobutyl-5,7,8-trimethyl-2-(4-nitrophenoxymethyl)chroman-4-one (prepared as described in Preparation 6) and 30 ml of pyridine was mixed with 3 g of acetic anhydride and stirred for 35 hours at room temperature. The reaction mixture was then condensed by evaporation under reduced pressure, mixed with water and extracted with ethyl acetate and benzene. The extract was dried over anhydrous sodium sulfate, and the solvent was distilled off under reduced pressure. The residue was purified by silica gel column chromatography, using a 5:1 by volume mixture of hexane and ethyl acetate, to give the title compound.

Rf value on silica gel thin layer chromatography=0.42 (developing solvent, hexane:ethyl acetate=2:1 by volume).

Nuclear Magnetic Resonance Spectrum (CDCl$_3$) δ ppm:
1.01 (6H, doublet, J=6 Hz);
1.7–2.2 (3H, nd);
2.09 (3H, singlet);
2.12 (3H, singlet);
2.33 (3H, singlet);
2.42 (3H, singlet);
2.91 (2H, AB type, J=18 Hz);
4.13 δ 4.25 (2H, AB type, J=9 Hz);
6.95 (2H, doublet, J=9 Hz);
8.20 (2H, doublet, J=9 Hz).

PREPARATION 8

6-Acetoxy-2-(4-aminophenoxymethyl)-2-isobutyl-5,7,8-trimethylchroman-4-one 1.4 g of 6-acetoxy-2-isobutyl-5,7,8-trimethyl-2-(4-nitrophenoxymethyl)chroman-4-one (prepared as described in Preparation 7) was dissolved in 35 ml of methanol, and, in the presence of 1 g of 10% w/w palladium-on-carbon, it was reduced for 3 hours under about 1 atmosphere (about 1 bar) pressure of hydrogen. The catalyst was filtered off, and the solvent was then distilled off under reduced pressure to give the title compound.

Rf value on silica gel thin layer chromatography=0.54 (developing solvent, ethyl acetate).

Nuclear magnetic Resonance Spectrum (CDCl$_3$) δ ppm:
- 0.97 (6H, doublet, J=6 Hz);
- 1.6-2.2 (3H, nd);
- 2.08 (3H, singlet);
- 2.14 (3H, singlet);
- 2.32 (3H, singlet);
- 2.42 (3H, singlet);
- 2.74 δ 3.02 (2H, AB type, J=16 Hz);
- 3.2 -3.7 (2H, broad singlet);
- 3.94 δ 4.06 (2H, AB type, J=9 Hz);
- 6.58 (2H, doublet, J=9 Hz);
- 6.73 (2H, doublet, J=9 Hz).

PREPARATION 9

Ethyl 3-[4-(6-acetoxy-2-isobutyl-5,7,8-trimethyl-4-oxochroman-2-ylmethoxy)phenyl]-2-chloropropionate (Step D3)

1.5 ml of concentrated hydrochloric acid was added to mixture of 1.1 g of 6-acetoxy-2-(4-aminophenoxymethyl)-2-isobutyl-5,7,8-trimethylchroman-4-one (prepared as described in Preparation 8) and 20 ml of acetone under a nitrogen stream and at room temperature. This was followed by 0.8 g of sodium nitrite and 0.3 ml of water, and then by 4 g of ethyl acrylate. 0.1 g of cuprous oxide was added at room temperature to the reaction mixture, which was then stirred for 1 hour. Water was then added, and the mixture was extracted with benzene. The benzene extract was washed with water and dried over anhdyrous sodium sulfate, and the solvent was distilled off under reduced pressure. The residue was purified by silica gel column chromatography using a 5.1 by volume mixture of hexane and ethyl acetate as eluent, to give the title compound.

Rf value on silica gel thin layer chromatography=0.74 (developing solvent, hexane:ethyl acetate=1:2 by volume).

Nuclear magnetic Resonance Spectrum (CDCl$_3$) δ ppm:
- 0.98 (6H, doublet, J=6 Hz);
- 1.25 (3H, triplet, J=7 Hz);
- 1.5-2.2 (3H, nd);
- 2.08 (3H, singlet);
- 2.13 (3H, singlet);
- 2.32 (3H, singlet);
- 2.42 (3H, singlet);
- 2.78 δ 3.01 (2H, AB type, J=17 Hz);
- 2.8-3.5 (2H, nd);
- 3.8-4.5 (5H, nd);
- 6.82 (2H, doublet, J=9 Hz);
- 7.11 (2H, doublet, J=9 Hz).

PREPARATION 10

Ethyl 6-hydroxy-5,7,8-trimethylchroman-2-carboxylate (Step C4)

14 g of ethyl 6-hydroxy-5,7,8-trimethyl-4-oxo-2H-chromene-2-carboxylate [prepared as described in J. Med. Chem., 18, 934 (1975)] were dissolved in 320 ml of acetic acid, and the resulting solution was catalytically reduced for 1 hour at 60°-65° C., under a hydrogen pressure of 3 atmospheres and in the presence of 3.5 g of 10% w/w palladium-on-carbon. The catalyst was filtered off, and the filtrate was poured into water. The white crystals which separated were collected by filtration, to give the title compound, melting at 108°-109° C.

Nuclear Magnetic Resonance Spectrum (CDCl$_3$) δ ppm:
- 1.28 (3H, triplet, J=7 Hz);
- 2.07 (3H, singlet);
- 2.17 (6H, singlet);
- 1.9-2.3 (2H, nd);
- 2.65 (2H, broad triplet, J=7 Hz);
- 4.22 (2h, broad triplet, J=7 hz);
- 4.1-4.3 (1H, nd);
- 4.60 (1H, doublet of doublets, J=7 δ 4 Hz).

PREPARATION 11

Ethyl 6-methoxymethoxy-5,7,8-trimethylchroman-2-carboxylate (Step C5)

3 g of a 55% w/w suspension of sodium hydride in mineral oil were washed twice with cyclohexane. A mixture of 14.3 g of ethyl 6-hydroxy-5,7,8-trimethylchroman-2-carboxylate (prepared as described in Preparation 10) and 130 ml of dimethylformamide was added slowly to this suspension under a nitrogen stream at 5°-10° C. The reaction mixture was stirred for 1 hour, and then cooled in ice to 3°-5° C., after which 5.6 g of chloromethyl methyl ether were added dropwise. After this addition, the reaction mixture was stirred for 1 hour at room temperature, poured into ice-water, and then extracted with cyclohexane. The cyclohexane extract was washed with water and dried over anhydrous sodium sulfate. The solvent was then distilled off under reduced pressure. The residue was purified by silica gel column chromatography using a 25:1 by volume mixture of benzene and ethyl acetate as eluent, to give the title compound.

Rf value on silica gel thin layer chromatography=0.41 (developing solvent, benzene:ethyl acetate=20:1 by volume).

Nuclear Magnetic Resonance Spectrum (CDCl$_3$) δ ppm:
- 1.27 (3H, triplet, J=7 Hz);
- 2.0-2.4 (2H, nd);
- 2.15 (3H, singlet);
- 2.16 (3H, singlet);
- 2.2 (3H, singlet);
- 2.64 (2H, broad triplet, J=7 Hz);
- 3.61 (3H, singlet);
- 4.24 (2H, quartet, J=7 Hz);
- b 4.64 (1H, doublet of doublets, J=4 δ 7 Hz);
- 4.87 (2H, singlet).

PREPARATION 12

Ethyl 6-methoxymethoxy-5,7,8-trimethyl-2-octylchroman-2-carboxylate (Step C6)

7.8 ml of a hexane solution containing 1.62 mmole/ml of butyllithium were added dropwise to a mixture of 2 g of diisopropylamine and 80 ml of tetrahydrofuran under a nitrogen stream at a temperature from −60° to −50° C. The resulting mixture was then allowed to stand for 10 minutes at room temperature, after which about 10 ml of tetrahydrofuran containing 4 g of ethyl 6-methoxymethoxy-5,7,8-trimethylchroman-2-carboxylate (prepared as described in Preparation 11) were added and the mixture was stirred for 1 hour at −60° C. About 20 ml of tetrahydrofuran containing 5 g of octyl bromide were added, and the mixture was stirred for 1 hour at −60° C. and then for 1 hour at room temperature, after which it was heated for 1 hour at 50° C. The reaction mixture was then poured into ice-water and extracted with ethyl acetate. The extract was washed with water and dried over anhydrous sodium sulfate. The solvent was removed by distillation under reduced pressure, and the residue was subjected to silica gel column chromatography eluted with benzene, to give the title compound.

Rf value on silica gel thin layer chromatography=0.58 (developing solvent, benzene:ethyl acetate=20:1 by volume).

Nuclear Magnetic Resonance Spectrum (CDCl$_3$) δ ppm:
0.89 (3H, broad triplet, J=6 Hz);
1.15 (3H, triplet, J=7 Hz);
1.2–1.6 (12H, multiplet);
1.6–2.4 (4H, multiplet);
2.1 (3H, singlet);
2.18 (3H, singlet);
2.2 (3H, singlet);
2.4–2.7 (2H, multiplet);
3.59 (3H, singlet);
4.11 (2H, quartet, J=7 Hz);
4.85 (2H, singlet).

PREPARATION 13

6-Methoxymethoxy-5,7,8-trimethyl-2-octylchroman-2-yl-methanol (Step A1')

10 ml of tetrahydrofuran containing 3.3 g of ethyl 6-methoxymethoxy-5,7,8-trimethyl-2-octylchroman-2-carboxylate (prepared as described in Preparation 12) were added dropwise to a mixture of 0.45 g of lithium aluminum hydride and 30 ml of tetrahydrofuran under a nitrogen stream, and whilst ice-cooling. The resulting mixture was stirred for 3 hours at room temperature. Ethyl acetate and 5% w/v aqueous hydrochloric acid were then added to the reaction mixture, whilst ice-cooling, and the organic layer was separated. Then the aqueous layer was extracted with ethyl acetate. The organic layer and the extract were combined, washed with a saturated aqueous solution of sodium chloride and dried over anhydrous sodium sulfate. The solvent was removed by distillation under reduced pressure, to give the title compound.

Rf value on silica gel thin layer chromatography=0.45 (developing solvent, benzene:ethyl acetate=10.1 by volume).

Nuclear magnetic Resonance Spectrum (CDCl$_3$) δ ppm:
0.7–1.0 (3H, multiplet);
1.0–2.3 (16H, multiplet);
2.10 (3H, singlet);
2.15 (3H, singlet);
2.20 (3H, singlet);
2.59 (2H, broad triplet, J=7 Hz);
3.6 (5H, singlet);
4.87 (2H, singlet).

PREPARATION 14

6-Methoxymethoxy-5,7,8-trimethyl-2-(4-nitrophenoxymethyl)-2-octylchroman (Step A2)

0.38 g of a 55% w/w suspension of sodium hydride in mineral oil was added to a mixture of 3 g of 6-methoxymethoxy-5,7,8-trimethyl-2-octylchroman-2-ylmethanol (prepared as described in Preparation 13) and 25 ml of dimethylformamide under a nitrogen stream at room temperature, and the resulting mixture was heated for 2 hours at 50° C. A mixture of 1.4 g of p-chloronitrobenzene and 2 ml of benzene was then added dropwise, whilst ice-cooling, and the resulting mixture was heated for 2 hours at 50° C. The reaction mixture was then poured into ice-water and extracted with benzene. The extract was washed with water and dried over anhydrous sodium sulfate. The solvent was removed by distillation under reduced pressure, and the residue was purified by silica gel column chromatography eluted with benzene, to give the title compound.

Rf value on silica gel thin layer chromatography=0.46 (developing solvent, benzene).

Nuclear Magnetic Resonance Spectrum (CDCl$_3$) δ ppm:
0.7–1.0 (3H, multiplet);
1.0–1.9 (14H, multiplet);
1.9–2.3 (2H, nd);
2.06 (3H, singlet);
2.15 (3H, singlet);
2.19 (3H, singlet);
2.6 (2H, broad triplet, J=7 Hz);
3.60 (3H, singlet);
4.05 (2H, singlet);
4.87 (2H, singlet);
6.97 (2H, doublet, J=9 Hz);
8.18 (2H, doublet, J=9 Hz).

PREPARATION 15

6-Hydroxy-5,7,8-trimethyl-2-(4-nitrophenoxymethyl)-2-octylchroman (Step A3, Deprotection)

A mixture of 3.7 g of 6-methoxymethoxy-5,7,8-trimethyl-2-(4-nitrophenoxymethyl)-2-octylchroman (prepared as described in Preparation 14), 10 ml of acetic acid, 30 ml of benzene and 0.75 ml of 10% w/v aqueous sulfuric acid was heated under reflux for 30 minutes. The reaction mixture was then poured into water and extracted with benzene. The extract was washed with water and dried over anhydrous sodium sulfate. The solvent was removed by distillation under reduced pressure, to give the title compound.

Rf value on silica gel thin layer chromatography=0.34 (developing solvent, benzene).

Nuclear magnetic Resonance Spectrum (CDCl$_3$) δ ppm:
0.7–1.0 (3H, multiplet);
1.0–1.85 (14H, multiplet);
1.85–2.2 (2H, nd);
2.10 (6H, singlet);
2.16 (3H, singlet);
2.63 (2H, broad triplet, J=7 Hz);
4.06 (2H, singlet);
4.19 (1H, singlet, disappeared on adding heavy water);
6.97 (2H, doublet, J=9 Hz);
8.19 (2H, doublet, J=9 Hz).

PREPARATION 16

6-Acetoxy-5,7,8-trimethyl-2-(4-nitrophenoxymethyl)-2-octylchroman (Step A3, Acylation)

1.2 g of acetic anhydride was added to a mixture of 3.5 g of 6-hydroxy-5,7,8-trimethyl-2-(4-nitrophenoxymethyl)-2-octylchroman (prepared as described in Preparation 15), 10 ml of pyridine and 10 ml of benzene, and the mixture was stirred for 2hours at room temperature. The reaction mixture was then poured into water and extracted with benzene. The extract was washed with 5% w/v aqueous hydrochloric acid and water, successively in that order, and dried over anhydrous sodium sulfate. The solvent was removed by distillation under reduced pressure, to give the title compound.

Rf value on silica gel thin layer chromatography=0.4 (developing solvent, benzene).

Nuclear Magnetic Resonance Spectrum (CDCl₃) δ ppm:
0.75-1.0 (3H, multiplet);
1.1-1.65 (12H, multiplet);
1.65-2.15 (4H, nd);
1.99 (3H, singlet);
2.04 (3H, singlet);
2.08 (3H, singlet);
2.32 (3H, singlet);
2.63 (2H, broad triplet, J=7 Hz);
4.07 (2H, singlet);
6.98 (2H, doublet, J=9 Hz);
8.20 (2H, doublet, J=9 Hz).

PREPARATION 17

6-Acetoxy-2-(4-aminophenoxymethyl)-5,7,8-trimethyl-2-octylchroman (Step A3, Hydrogenation)

Using Paar's hydrogenation apparatus, a mixture of 4 g of 6-acetoxy-5,7,8-trimethyl-2-(4-nitrophenoxymethyl)-2-octylchroman (prepared as described in Preparation 16), 0.8 g of 10% w/w palladium-on-carbon, 30 ml of methanol and 10 ml of benzene was stirred for 5 hours under 3-5 atmospheres (about 3-5 bars) pressure or hydrogen. The catalyst was filtered off, and the filtrate was condensed by evaporation under reduced pressure. The crystals thus obtained were washed with hexane to give the title compound, melting at 112°-114° C.

Nuclear Magnetic Resonance Spectrum (CDCl₃) δ ppm:
0.7-1.05 (3H, multiplet);
1.05-1.65 (12H, multiplet);
1.65-2.2 (4H, nd);
1.97 (3H, singlet);
2.02 (3H, singlet);
2.10 (3H, singlet);
2.31 (3H, singlet);
2.59 (2H, broad triplet, J=7 Hz);
3.0-3.7 (2H, broad singlet, disappeared on adding heavy water);
3.86 (2H, singlet);
6.62 (2H, doublet, J=10 Hz);
6.75 (2H, doublet, J=10 Hz).

PREPARATION 18

Ethyl 3[4-(6-acetoxy-5,7,8-trimethyl-2-octylchroman-2-ylmethoxy)phenyl]-2-chloropropionate (Step A4)

3.5 ml of concentrated hydrochloric acid, 1.7 ml of water containing 0.61 g of sodium nitrite and 7.2 ml of ethyl acrylate were added dropwise successively, in that order, under a nitrogen stream and at 5°-10° C., to a mixture of 3.2 g of 6-acetoxy-2-(4-aminophenoxymethyl)-5,7,8-trimethyl-2-octylchroman (prepared as described in Preparation 17) and 35 ml of acetone. The reaction mixture was then heated to 40°-43° C. (inner temperature), and 0.1 g of cuprous oxide was slowly added. After about 30 minutes, nitrogen generation ceased. The reaction mixture was then poured into water and extracted with benzene. The extract was washed with water and dried over anhydrous sodium sulfate. The solvent was removed by distillation under reduced pressure. The residue was purified by silica gel column chromatography using a 10:1 by volume mixture of cyclohexane and ethyl acetate as eluent, to give the title compound.

Rf value on silica gel thin layer chromatography=0.27 (developing solvent, cyclohexane:ethyl acetate=9:1 by volume).

Nuclear Magnetic Resonance Spectrum (CDCl₃) δ ppm:
0.8-1.05 (3H, multiplet);
1.05-1.65 (15H, multiplet);
1.65-2.2 (4H, nd);
1.97 (3H, singlet);
2.03 (3H, singlet);
2.09 (3H, singlet);
2.30 (3H, singlet);
2.6 (2H, broad triplet, J=7 Hz);
3.07 (1H, doublet of doublets, J=7 δ 14 Hz);
3.30 (1H, doublet of doublets, J=7 δ 14 Hz);
3.92 (2H, singlet);
4.18 (2H, quartet, J=7 Hz);
4.36 (1H, triplet, J=7 Hz);
6.85 (2H, doublet, J=9 Hz);
7.13 (2H, doublet, J=9 Hz).

PREPARATION 19

6-Acetoxy-2-methyl-2-(4-nitrophenoxymethyl)-7-(1,1,3,3-tetramethylbutyl)chroman-4-one (Step D1)

A mixture of 23 g of 5-acetoxy-2-hydroxy-4-(1,1,3,3-tetramethylbutyl)acetophenone, 14.7 g of 1-(4-nitrophenoxy)-2-propanone, 8 g of pyrrolidine and 300 ml of benzene was stirred for 3 hours at room temperature, and then heated under reflux for 10 hours. The reaction mixture was then poured into ice-water and extracted with benzene. The extract was washed with 5% w/v aqueous hydrochloric acid and water successively in that order, and then dried over anhydrous sodium sulfate. The solvent was removed by distillation under reduced pressure. The residue was mixed with 15 g of acetic anhydride and 400 ml of pyridine, and the mixture was allowed to stand for 1 day at room temperature. The reaction mixture was then poured into ice-water and extracted with benzene. The extract was washed with 5% w/v aqueous hydrochloric acid and water in that order, and then dried over anhydrous sodium sulfate. The solvent was removed by distillation under reduced pressure. The residue was purified by silica gel column chromatography, eluted with a 20:1 by volume mixture of benzene and ethyl acetate, and recrystallized from methanol, to give the title compound, melting at 165.5°-167° C.

Nuclear Magnetic Resonance Spectrum (CDCl₃) δ ppm:
0.76 (9H, singlet);
1.36 (6H, singlet);
1.57 (3H, singlet);
1.83 (2H, singlet);
2.32 (3H, singlet);
2.74 (1H, doublet, J=17 Hz);
3.10 (1H, doublet, J=17 Hz);
4.11 δ 4.24 (2H, AB type, J=9 Hz);
6.95 (2H, doublet J=9 Hz);
6.98 (1H, singlet);
7.50 (1H, singlet);
8.20 (2H, doublet, J=9 Hz).

PREPARATION 20

6-Acetoxy-4-hydroxy-2-methyl-2-(4-nitrophenoxymethyl)-7-(1,1,3,3-tetramethylbutyl)chroman (Step F1)

1 g of sodium borohydride was added, whilst ice-cooling, to a mixture of 100 ml of methanol and 10 ml of benzene containing 13 g of 6-acetoxy-2-methyl-2-(4-nitrophenoxymethyl)-7-(1,1,3,3-tetramethylbutyl)chroman-4-one (prepared as described in Preparation 19), and the mixture was stirred for 30 minutes whilst ice-cooling. The reaction mixture was then poured into ice-water, neutralized with 10% w/v aqueous hydrochloric acid and extracted with benzene. The extract was washed with water and dried over anhydrous sodium sulfate. The solvent was removed by distillation under reduced pressure. The residue was purified by silica gel column chromatography, eluted with a 4:1 by volume mixture of benzene and ethyl acetate, to give the title compound.

Rf value on silica gel thin layer chromatography=0.32 (developing solvent, benzene:ethyl acetate=4:1 by volume).

Nuclear Magnetic Resonance Spectrum (CDCl$_3$) $\delta$ ppm:
0.77 (9H, singlet);
1.34 (6H, singlet);
1.54 (3H, singlet);
1.80 (2H, singlet);
1.85-2.25 (1H, nd);
2.29 (3H, singlet);
2.48 (1H, doublet of doublets, J=7 & 14 Hz);
4.02 (2H, AB type, J=12 Hz);
4.7-5.0 (1H, multiplet);
6.85 (1H, singlet);
6.95 (2H, doublet, J=9 Hz);
7.08 (1H, singlet);
8.18 (2H, doublet, J=9 Hz).

PREPARATION 21

(a) 6-Hydroxy-2-methyl-2-(4-nitrophenoxymethyl)-7-(1,1,3,3-tetramethylbutyl)-2H-chromene and (b) 6-Acetoxy-2-methyl-2-(4-nitrophenoxymethyl)-7-(1,1,3,3-tetramethylbutyl)-2H-chromene (Step F3)

A solution of 10.2 g of 6-acetoxy-4-hydroxy-2-methyl-2-(4-nitrophenoxymethyl)-7-(1,1,3,3-tetramethylbutyl)chroman (prepared as described in Preparation 20) and 0.4 g of p-toluenesulfonic acid in 200 ml of benzene was heated under reflux for 30 minutes under a nitrogen stream. The reaction mixture was then poured into ice-water and extracted with benzene. The extract was washed with water and dried over anhydrous sodium sulfate. The solvent was removed by distillation under reduced pressure. The residue was purified by silica gel column chromatography, eluted with benzene, to give the title compounds (a) and (b).

Rf value on silica gel thin layer chromatography (developing solvent, benzene:ethyl acetate=20:1 by volume)=0.53 and 0.50, respectively.

Nuclear Magnetic Resonance Spectrum (a) (CDCl$_3$) $\delta$ ppm:
0.75 (9H, singlet);
1.38 (6H, singlet);
1.56 (3H, singlet);
1.89 (2H, singlet);
4.09 (2H, singlet);
4.43 (1H, singlet, disappeared on adding heavy water);
5.63 (1H, doublet, J=10 Hz);
6.32 (1H, singlet);
6.41 (1H, doublet, J=10 Hz);
6.73 (1H, singlet);
6.96 (2H, doublet, J=9 Hz);
8.20 (2H, doublet, J=9 Hz).

Nuclear Magnetic Resonance Spectrum (b) (CDCl$_3$) $\delta$ ppm:
0.76 (9H, singlet);
1.32 (6H, singlet);
1.58 (3H, singlet);
1.79 (2H, singlet);
2.29 (3H, singlet);
4.10 (2H, singlet);
5.62 (1H, doublet, J=10 Hz);
6.43 (1H, doublet, J=10 Hz);
6.69 (1H, singlet);
6.79 (1H, singlet);
6.93 (2H, doublet, J=9 Hz);
8.18 (2h, doublet, J=9 Hz).

PREPARATION 22

6-Acetoxy-2-(4-aminophenoxymethyl)-2-methyl-7-(1,1,3,3-tetramethylbutyl)chroman (Step F5)

Using Paar's hydrogenation apparatus, a mixture of 9.1 g of 6-acetoxy-2-methyl-2-(4-nitrophenoxymethyl)-7-(1,1,3,3-tetramethylbutyl)-2H-chromene (prepared as described in Preparation 21), 2g of 10% w/w palladium-on-carbon and 150 ml of methanol was stirred for 10 hours under 3-5 atmospheres (about 3-5-bars) pressure of hydrogen. The catalyst was filtered off, and the filtrate was condensed by evaporation under reduced pressure. The residue was purified by silica gel column chromatography, eluted with a 10:1 by volume mixture of benzene and ethyl acetate, to give the title compound.

Rf value on silica gel thin layer chromatography=0.27 (developing solvent, benzene:ethyl acetate=9:1 by volume).

Nuclear Magnetic Resonance Spectrum (CDCl$_3$) $\delta$ ppm:
0.77 (9H, singlet);
1.34 (6H, singlet);
1.42 (3H, singlet);
1.7-2.2 (2H, nd);
1.78 (2H, singlet);
2.27 (3H, singlet);
2.65 (2H, broad quartet, J=7 Hz);
3.36 (2H, broad singlet, disappeared on adding heavy water);
3.85 (2H, AB type J9 Hz);
6.54-6.88 (6H, multiplet).

PREPARATION 23

Ethyl 3-{4-[6-acetoxy-2-methyl-7-(1,1,3,3-tetramethylbutyl)-chroman-2-ylmethoxy]phenyl{-2-chloropropionate (Step A4)

Following the same procedure as described in Preparation 18, 7.9 g of 6-acetoxy-2-(4-aminophenoxymethyl)-2-methyl-7-(1,1,3,3-tetramethylbutyl) chroman (prepared as described in Preparation 22), 1.6 g of sodium nitrite, 9 ml of concentrated hydrochloric acid, 18 g of ethyl acrylate, 260 mg of cuprous oxide, 90 ml of acetone and about 5 ml of water were reacted, to give the title compound.

Rf value on silica gel thin layer chromatography=0.55 (developing solvent, benzene:ethyl acetate=20:1 by volume).

Nuclear Magnetic Resonance Spectrum (CDCl$_3$) δ ppm:
0.78 (9H, singlet);
1.22 (3H, triplet, J=7 Hz);
1.35 (6H, singlet);
1.43 (3H, singlet);
1.7-2.3 (2H, nd);
1.79 (2H, singlet);
2.27 (3H, singlet);
2.70 (2H, broad triplet, J=6 Hz);
3.07 (1H, doublet of doublets, J=7.5 δ 15 Hz);
3.32 (1H, doublet of doublets, J=7.5 δ 15 Hz);
3.91 (2H, AB type, J=9 Hz);
4.18 (2H, quartet, J=7 Hz);
4.37 (1H, triplet, J=7 Hz);
6.72 (1H, singlet);
6.85 (1H, singlet);
6.86 (2H, doublet, J=9 Hz);
7.16 (2H, doublet, J=9 Hz).

PREPARATION 24

6-Acetoxy-2-(4-aminophenoxymethyl)-2-methyl-4-oxo-7-(1,1,3,3-tetramethylbutyl)chroman (Step D2)

12.3 g of 6-acetoxy-2-methyl-2-(4-nitrophenoxymethyl)-7-(1,1,3,3-tetramethylbutyl)chroman-4-one (prepared as described in Preparation 19) were dissolved in a mixture of 200 ml of methanol and 20 ml of benzene, and then catalytically reduced for 6 hours at room temperature, in the presence of 2.4 g of 10% w/w palladium-on-carbon, under 1 atmosphere (about 1 bar) pressure of hydrogen. The catalyst was filtered off, and the filtrate was condensed by evaporation under reduced pressure. The residue was purified by silica gel column chromatography, eluted with a 4:1 by volume mixture of benzene and ethyl acetate, to give the title compound.

Rf value on silica gel thin layer chromatography =0.29 (developing solvent, benzene:ethyl=4:1 by volume).

Nuclear Magnetic Resonance Spectrum (CDCl$_3$) δ ppm:
0.78 (9H, singlet);
1.37 (6H, singlet);
1.52 (3H, singlet);
1.83 (2H, singlet);
2.30 (3H, singlet);
2.66 (1H, doublet, J=17 Hz);
3.10 (1H, doublet, J=17 Hz);
3.4 (2H, broad singlet, disappeared on adding heavy water);
3.92 δ 4.06 (2H, AB type, J=9 Hz);
6.58 (2H, doublet, J=9 Hz);
6.76 (2H, doublet, J=9 Hz);
7.00 (1H, singlet);
7.50 (1H, singlet).

PREPARATION 25

Ethyl 3-{4-[6-acetoxy-2-methyl-4-oxo-7-(1,1,3,3-tetramethylbutyl)chroman-2-ylmethoxy]phenyl}-2-chloropropionate (Step D3)

Following the same procedure as described in Preparation 18, 9 g of 6-acetoxy-2-(4-aminophenoxymethyl)-2-methyl-7-(1,1,3,3-tetramethylbutyl) chroman-4-one (prepared as described in Preparation 24), 1.8 g of sodium nitrite, 10 ml of concentrated hydrochloric acid, 20 g of ethyl acrylate, 0.3 g of cuprous oxide, 100 ml of acetone and about 8 ml of water were reacted, to give the title compound.

Rf value on silica gel thin layer chromatography=0.32 (developing solvent, benzene:ethyl acetate=20:1 by volume).

Nuclear Magnetic Resonance Spectrum (CDCl$_3$) δ ppm:
0.78 (9H, singlet);
1.23 (3H, triplet, J=7 Hz);
1.38 (6H, singlet);
1.53 (3H, singlet);
1.85 (2H, singlet);
2.30 (3H, singlet);
2.69 (1H, doublet, J=17 Hz);
3.08 (1H, doublet of doublets, J=7.5 δ 15 Hz);
3.10 (1H, doublet, J=17 Hz);
3.32 (1H, doublet of doublets, J=7.5 δ 15 Hz);
3.99 δ 4.12 (2H, AB type, J=10.5 Hz);
4.18 (2H, quartet, J=7 Hz);
4.36 (1H, triplet, J>7 Hz);
6.82 (2H, doublet, J=9 Hz);
7.01 (1H, singlet);
7.16 (2H, doublet, J=9 Hz);
7.52 (1H, singlet).

PREPARATION 26

5-{4-[6-Acetoxy-2-methyl-4-oxo-7-(1,1,3,3-tetramethylbutyl)chroman-2-ylmethoxy]benzyl}-2-iminothiazolidin-4-one After completing the silica gel column chromatography described in Example 6, the column was further eluted with a 4:1 by volume mixture of benzene and tetrahydrofuran, to give the title compound melting at 125°-130° C.

Nuclear magnetic Resonance Spectrum [(CD$_3$)$_2$CO] δppm:
0.77 (9H, singlet);
1.39 (6H, singlet);
1.53 (3H, singlet);
1.89 (2H, singlet);
2.34 (3H, singlet);
2.6-3.0 (1H, nd);
2.75 (1H, doublet, J=16 Hz);
3.13 (1H, doublet, J=16 Hz);
3.40 (1H, doublet of doublets, J=4 δ 14 Hz);
4.17 (2H, singlet);
4.48 (1H, doublet of doublets, J=4 δ 10 Hz);
6.87 (2H, doublet, J=9 Hz);
7.01 (1H, singlet);
7.20 (2H, doublet, J=9 Hz);
7.46 (1H, singlet);
7.8-8.7 (2H, broad, disappeared on adding heavy water.

PREPARATION 27

Ethyl 2-(3,7-dimethyloctyl)-6-methoxymethoxy-5,7,8-trimethylchromanspiro-4,2'-(1',3 -dithiane) -2-carboxylate (Step E4)

17.7 ml of a hexane solution containing 1.62 mmole/ml of butyllithium were added dropwise under a nitrogen stream at a temperature between −60° C. and −50° C. to a solution of 2.9 g of diisopropylamine in 30 ml of tetrahydrofuran, and the mixture was allowed to stand for 10 minutes at room temperature. 10 ml of tetrahydrofuran containing 6 g of ethyl 6-methoxymethoxy-5,7,8-trimethylchromanspiro-4,2'-(1',3'-dithiane)-2-carboxylate (prepared as described in Preparation 3) were added dropwise to the reaction mixture at −60° C. The reaction mixture was stirred for 1 hour, and then 5 ml of tetrahydrofuran containing 6.4 g of 3,7-dimethyloctyl bromide were added dropwise, and the mixture was stirred for a further 1 hour at the same temperature. After the mixture had been stirred for a further 1 hour at room temperature and then stirred for 1.5 hours at 45°–50° C., the resulting mixture was allowed to stand overnight at room temperature. The reaction mixture was then poured into ice-water and extracted with ethyl acetate. The extract was washed with a saturated aqueous solution of sodium chloride and dried over anhydrous sodium sulfate. The solvent was removed by distillation under reduced pressure. The residue was purified by silica gel column chromatography, eluted with a 10:1 by volume mixture of hexane and ethyl acetate, to give the title compound as a pale yellow oily substance.

Rf value on silica gel thin layer chromatography=0.57 (developing solvent, benzene:ethyl acetate=20:1 by volume).

Nuclear magnetic Resonance Spectrum (CDCl$_3$) δ ppm:

0.87 (9H, doublet, J=7 Hz);
1.0–2.3 (14H, multiplet);
1.17 (3H, triplet, J=7 Hz);
2.17 (3H, singlet);
2.21 (3H, singlet);
2.3–2.9 (2H, nd);
2.62 (1H, doublet, J=14 Hz);
2.83 (3H, singlet);
2.97–3.5 (2H, multiplet);
3.59 (3H, singlet);
3.73 (1H, doublet, J=14 Hz);
4.03 (1H, quarter, J=7 Hz);
4.07 (1H, quartet, J=7 Hz);
4.88 (2H, singlet).

PREPARATION 28

2-(3,7-Dimethyloctyl)-2-hydroxymethyl-6-methoxymethoxy-5,7,8-trimethylchromanspiro-4,2'-(1',3'-dithiane) (Step E5)

20 ml of tetrahydrofuran containing 4 g of ethyl 2-(3,7-dimethyloctyl)-6-methoxymethoxy-5,7,8-trimethylchromanspiro-4,2'-(1'3'-dithiane)-2-carboxylate (prepared as described in Preparation 27) were added dropwise under a nitrogen stream and whilst ice-cooling to a mixture of 0.41 g of lithium aluminum hydride and 30 ml of tetrahydrofuran, and the mixture was then stirred for 3 hours at room temperature. About 10 ml of ethyl acetate and about 30 ml of 5% w/v aqueous hydrochloric acid were then added, and the organic layer was separated. The aqueous layer was further extracted with ethyl acetate. The organic layer and the ethyl acetate extract were combined and washed with a saturated aqueous solution of sodium chloride and then dried over anhydrous sodium sulfate. The solvent was removed by distillation under reduced pressure to give the title compound as a pale yellow oil.

Rf value on silica gel thin layer chromatography=0.36 (developing solvent, benzene:ethyl acetate=20.1 by volume).

Nuclear magnetic Resonance Spectrum (CDCl$_3$) δ ppm:

0.87 (9H, doublet, J=7 Hz);
1.0–2.0 (12H, multiplet);
3.0–2.5 (2H, nd);
2.08 (3H, singlet);
2.20 (3, singlet);
2.34 (1H, broad singlet, disappeared on adding heavy water);
2.5–3.0 (3H, multiplet);
2.92 (3H, singlet);
3.0–3.6 (4H, multiplet);
3.61 (3H, singlet); 3.76 (1H, doublet of doublets, J=6 & 12 Hz); 4.89 (2H, singlet).

PREPARATION 29

2-(3,7-Dimethyloctyl)-6-methoxymethoxy-5,7,8-trimethyl-2-(4-nitrophenoxymethyl)chromanspiro-4,2'-(1',3'-dithiane) (Step E6)

0.46 g of a 55% w/w suspension of sodium hydride in mineral oil were added to a mixture of 3.6 g of 2-(3,7-dimethyloctyl)-2-hydroxymethyl-6-methoxymethoxy-5,7,8-trimethylchromanspiro-4,2'-(1',3'-dithiane) (prepared as described in Preparation 28) and 30 ml of dimethylformamide under a nitrogen stream at room temperature, and the resulting mixture was heated at 50° C. for 2 hours. A mixture of 1.66 g of p-chloronitrobenzene and 3 ml of benzene was added dropwise, and then the mixture was heated at 50° C. for 2 hours. The reaction mixture was then poured into water and extracted with benzene. The extract was washed with water and dried over anhydrous sodium sulfate. The solvent was distilled off under reduced pressure. The residue was purified by silica gel column chromatography, eluted with a 50:1 by volume mixture of benzene and ethyl acetate, to give the title compound.

Rf value on silica gel thin layer chromatography=0.55 (developing solvent, benzene:ethyl acetate=20:1 by volume).

Nuclear Magnetic Resonance Spectrum (CDCl$_3$) δ ppm: 0.87 (9H doublet, J=7 Hz); 1.0–2.3 (14H, multiplet); 2.08 (3H, singlet); 2.21 (3H, singlet); 2.3–3.0 (3H, multiplet); 2.89 (3H, singlet); 3.0–3.6 (3H, multiplet); 3.61 (3H, singlet); 3.99 (1H, doublet, J=9 Hz); 4.45 (1H, doublet, J=9 Hz); 4.89 (2H, singlet); 6.92 (2H, doublet, J=9 Hz); 8.17 (2H, doublet, J=9 Hz).

PREPARATION 30

2-(3,7-Dimethyloctyl)-6-hydroxy-5,7,8-trimethyl-2-(4-nitrophenoxymethyl)chroman-4-one (Steps E7 and A3, Deprotection)

A mixture of 3.4 g of 2-(3,7-dimethyloctyl)-6-methoxymethoxy-5,7,8-trimethyl-2-(4-nitrophenoxymethyl)-chromanspiro-4,2'-(1',3'-dithiane) (prepared as described in Preparation 29), 2.2 g of mercuric chloride, 1.7 g of mercuric oxide, 10 ml of tetrahydrofuran, 27 ml of methanol and 3 ml of water was heated under reflux for 2 hours. Benzene was then added to the reaction mixture, and the insoluble residue was filtered off. The filtrate was washed with an aqueous ammonium sulfate solution, and then with water, and dried over anhydrous sodium sulfate. The solvent was distilled off under reduced pressure. 30 ml of benzene, 10 ml of acetic acid and 0.5 ml of 10% w/v aqueous sulfuric acid was added to the residue, and the mixture was heated under reflux for 30 minutes. The reaction mixture was then poured into water and extracted with benzene. The extract was washed with water and dried over anhydrous sodium sulfate. The solvent was distilled off under reduced pressure. The residue was subjected to silica gel column chromatography, eluted with a 100:3 by volume mixture of benzene and ethyl acetate, and the resulting crystals were recrystallized from a mixture of benzene and hexane to give the title compound, melting at 121°–123° C.

Nuclear Magnetic Resonance Spectrum (CDCl$_3$) δ ppm: 0.85 (9H, doublet, J=7 Hz); 1.0–1.7 (10H, multiplet); 1.7–2.1 (2H, multiplet); 2.11 (3H, singlet); 2.21 (3H, singlet); 2.55 (3H, singlet); 2.76 & 2.98 (2H, AB type, J=16 Hz); 4.16 (2H, singlet); 4.57 (1H, singlet, disappeared on adding heavy water); 7.96 (2H, doublet, J=9 Hz); 8.20 (2H, doublet, J=9 Hz);

PREPARATION 31

6 Acetoxy-2-(3,7-dimethyloctyl)-5,7,8-trimethyl-2-(4-nitrophenoxymethyl)chroman-4-one (Step A3, Acylation)

Following the same procedure as described in Preparation 16, 1.8 g of 2-(3,7-dimethyloctyl)-6-hydroxy-5,7,8-trimethyl-2-(4-nitrophenoxymethyl)chroman-4-one (prepared as described in Preparation 30), 0.5 g of acetic anhydride, 5 ml of pyridine and 10 ml of benzene were reacted, to give the title compound.

Rf value on silica gel thin layer chromatography=0.41 (developing solvent, benzene:ethyl acetate=20:1 by volume).

Nuclear Magnetic Resonance Spectrum (CDCl$_3$) δ ppm: 0.85 (9H, doublet, J=7 Hz); 1.0–2.0 (12H, multiplet); 2.08 (3H, singlet); 2.11 (3H, singlet); 2.33 (3H, singlet); 2.41 (3H, singlet); 2.80 & 3.00 (2H, AB type, J=16 Hz); 4.17 (2H, singlet); 6.95 (2H, doublet, J=9 Hz); 8.20 (2H, doublet, J=9 Hz).

PREPARATION 32

6-Acetoxy-2-(4-aminophenoxymethyl)-2-(3,7-dimethyloctyl-5,7,8-trimethylchroman-4-one (Step D2)

Following the same procedure as described in Preparation 24, 1.95 g of 6-acetoxy-2-(3,7-dimethyloctyl)-5,7,8-trimethyl-2-(4-nitrophenoxymethyl)chroman-4-one (prepared as described in Preparation 31) were treated with 0.4 g of 10% w/w palladium-on-carbon, to give the title compound.

Rf value on silica gel thin layer chromatography=0.31 (developing solvent, benzene:ethyl acetate=4:1 by volume).

Nuclear Magnetic Resonance Spectrum (CDCl$_3$) δ ppm: 0.85 (9H, doublet, J=7 Hz); 1.0–2.0 (12H, multiplet); 2.09 (3H, singlet); 2.13 (3H, singlet); 2.32 (3H, singlet); 2.41 (3H, singlet); 2.77 & 3.00 (2H, AB type, J=16 Hz); 3.4 (2H, broad singlet, disappeared on adding heavy water); 3.99 (2H, singlet); 6.60 (2H, doublet, J=9 Hz); 6.70 (2H, doublet, J=9 Hz).

PREPARATION 33

Ethyl 3-{4-[6-acetoxy-2-(3,7-dimethyloctyl)-5,7,8-trimethyl-4-oxochroman-2-ylmethoxy]phenyl}-2-chloropropionate (Step D3)

Following the same procedure as described in Preparation 18, 1.6 g of 6-acetoxy-2-(4-aminophenoxymethyl)-2-(3,7-dimethyloctyl)-5,7,8-trimethylchroman-4-one (prepared as described in Preparation 32), 0.28 g of sodium nitrite, 1.7 ml of concentrated hydrochloric acid, 3.3 ml of ethyl acrylate and 0.1 g of cuprous oxide were reacted, to give the title compound.

Rf value on silica gel thin layer chromatography=0.45 (developing solvent, benzene:ethyl acetate=20:1 by volume).

Nuclear Magnetic Resonance Spectrum (CDCl$_3$) δ ppm: 0.86 (9H, doublet, J=7 Hz); 1.0–2.0 (12H, multiplet); 1.24 (3H, triplet, J=7 Hz); 2.09 (3H, singlet); 2.13 (3H, singlet); 2.33 (3H, singlet); 2.42 (3H, singlet); 2.80 & 2.98 (2H, AB type, J=16 Hz); 3.07 (1H, doublet of doublets, J=7 & 14 Hz); 3.31 (1H, doublet of doublets, J=7 & 14 Hz); 4.06 (2H, singlet); 4.18 (2H, quartet, J=7 Hz); 4.37 (1H, triplet, J=7 Hz); 6.83 (2H, doublet, J=9 Hz); 7.15 (2H, doublet, J=9 Hz).

PREPARATION 34

6-Methoxymethoxy-2,5,7,8-tetramethyl-2-(5-nitropyridin-2-yloxymethyl)chroman (Step A2, Introduction of Aromatic group)

0.96 g of a 55% w/w suspension of sodium hydride in mineral oil was washed 4 times with cyclohexane and then slowly added to a mixture of 5.0 g of 2-hydroxymethyl-6-methoxymethoxy-2,5,7,8-tetramethylchroman (prepared as described in Preparation 1 of copending U.S. Ser. No. 644,996) and 20 ml of dimethylformamide, under a nitrogen stream at room temperature. The reaction mixture was heated at 50° C. for 10 minutes and then cooled to 10° C. 4.2 g of 2-chloro-5-nitropyridine were then added in limited amounts. The reaction mixture was allowed to stand overnight at room temperature and poured into water. The resulting mixture was extracted with benzene. The extract was washed with water and dried over sodium sulfate. The solvent was distilled off under reduced pressure, and the residue was purified by silica gel column chromatography, eluted with a 25:1 by volume mixture of benzene and ethyl acetate, to give the title compound.

Rf value on silica gel thin layer chromatography=0.56 (developing solvent, benzene:ethyl acetate=10:1 by volume).

Nuclear Magnetic Resonance Spectrum (CDCl$_3$) δ ppm: 1.40 (3H, singlet); 1.7–2.3 (2H, multiplet); 2.02 (3H, singlet); 2.17 (6H, singlet); 2.65 (2H, broad triplet, J=6 Hz); 3.61 (3H, singlet); 4.51 (2H, singlet); 4.88 (2H, singlet); 6.87 (1H, doublet, J=9 Hz); 8.37 (1H, doublet of doublets, J=9 & 3 Hz); 9.06 (1H, doublet, J=3 Hz).

PREPARATION 35

6-Hydroxy-2,5,7,8-tetramethyl-2-(5-nitropyridin-2-yloxymethyl)chroman (Step A3, Deprotection)

1 g of 10% w/v aqueous sulfuric acid was added to 45 ml of acetic acid containing 5.2 g of 6-methoxymethoxy-2,5,7,8-tetramethyl-2-(5-nitropyridin-2-yloxymethyl)chroman prepared as described in Preparation 34), and the resulting mixture was heated at 55°–58° C. for 15 minutes. The reaction mixture was cooled, poured into a mixture of 75 g of sodium bicarbonate and 75 g of ice, and then extracted with ethyl acetate. The extract was washed with water and dried over anhydrous sodium sulfate. The solvent was distilled off under reduced pressure. The residue gave the title compound as a light-brown oil.

Rf value on silica gel thin layer chromatography=0.46 developing solvent, benzene:ethyl acetate=10:1 by volume).

Nuclear Magnetic Resonance Spectrum (CDCl₃) δ ppm: 1.39 (3H, singlet); 1.7–2.3 (2H, multiplet); 2.05 (3H, singlet); 2.11 (3H, singlet); 2.15 (3H, singlet); 2.67 (2H, broad triplet, J=6 Hz); 4.19 (1H, singlet, disappeared on adding heavy water); 4.50 (2H, singlet), 6.85 (1H, doublet, J=9 Hz); 8.36 (1H, doublet of doublets, J=9 & 3 Hz); 9.06 (1H, doublet, J=3 Hz).

PREPARATION 36

6-Acetoxy-2,5,7,8-tetramethyl-2-(5-nitropyridin-2-yloxymethyl)chroman (Step A3, Acylation)

Following the same procedure as described in Preparation 16, 5.2 g of 6-hydroxy-2,5,7,8-tetramethyl-2-(5-nitropyridin-2-yloxymethyl)chroman (prepared as described in Preparation 35), 3 ml of acetic anhydride, 3 ml of pyridine and about 20 ml of benzene were reacted to give the title compound.

Rf value on silica gel thin layer chromatography=0.52 (developing solvent, benzene:ethyl acetate=10:1 by volume).

Nuclear Magnetic Resonance Spectrum (CDCl₃) δ ppm: 1.40 (3H, singlet); 1.7–2.3 (2H, multiplet); 2.02 (9H, singlet); 2.32 (3H, singlet); 2.69 (2H, broad triplet, J=6 Hz); 4.52 (2H, AB type, J=12 Hz); 6.86 (1H, doublet, J=9 Hz); 8.36 (1H, doublet of doublets, J=9 & 3 Hz); 9.07 (1H, doublet, J=3 Hz).

PREPARATION 37

6-Acetoxy-2-(5-aminopyridin-2-yloxymethyl)-2,5,7,8-tetramethylchroman (Step A3, Hydrogenation)

6 g of 6-acetoxy-2,5,7,8-tetramethyl-2-(5-nitropyridin-2-yloxymethyl)chroman (prepared as described in Preparation 36) were dissolved in a mixture of 80 ml of methanol and 15 ml of benzene, and, in the presence of 1.5 g of 10% w/w palladium-on-carbon, were catalytically reduced at room temperature for about 20 hours under about 1 atmosphere (about 1 bar) pressure of hydrogen. The catalyst was filtered off, and the filtrate was condensed by evaporation under reduced pressure, to give the title compound.

Rf value on silica gel thin layer chromatography=0.04 (developing solvent, benzene:ethyl acetate=10:1 by volume).

Nuclear Magnetic Resonance Spectrum (CDCl₃) δ ppm: 1.39 (3H, singlet); 1.6–2.4 (2H, multiplet); 1.97 (3H, singlet); 2.01 (3H, singlet); 2.07 (3H, singlet); 2.30 (3H, singlet); 2.64 (2H, broad triplet, J=6 Hz); 3.9 (2H, broad singlet, disappeared on adding heavy water); 4.25 (2H, AB type, J=12 Hz); 6.61 (1H, doublet, J=9 Hz); 7.02 (1H, doublet of doublets, J=9 & 3 Hz); 7.64 (1H, doublet, J=3 Hz).

PREPARATION 38

Ethyl 3-[2-(6-acetoxy-2,5,7,8-tetramethylchroman-2-ylmethoxy)pyridin-5-yl]-2-chloropropionate (Step A4)

Following the same procedure as described in Preparation 18, 4.5 g of 6-acetoxy-2-(5-aminopyridin-2-yloxymethyl)-2,5,7,8-tetramethylchroman (prepared as described in Preparation 37), 1.1 g of sodium nitrite, 5 ml of concentrated hydrochloric acid, 10 g of ethyl acrylate, 175 mg of cuprous oxide, 40 ml of acetone and about 2.5 g of water were reacted, to give the title compound.

Rf value on silica gel thin layer chromatography=0.45 (developing solvent, benzene:ethyl acetate=10:1 by volume).

Nuclear Magnetic Resonance Spectrum (CDCl₃) δ ppm: 1.26 (3H, triplet, J=7.5 Hz); 1.40 (3H, singlet); 1.7–2.3 (2H, multiplet); 1.99 (3H, singlet); 2.02 (3H, singlet); 2.07 (3H, singlet); 2.31 (3H, singlet); 2.65 (2H, broad triplet, J=6 Hz); 3.07 (1H, doublet of doublets, J=13.5 & 7.5 Hz); 3.30 (1H, doublet of doublets, J=13.5 & 7.5 Hz); 4.0–4.5 (5H, multiplet); 6.72 (1H, doublet, J=9 Hz); 7.48 (1H, doublet of doublets, J=9 & 3 Hz); 8.02 (1H, doublet, J=3 Hz).

PREPARATION 39

5-Acetoxy-4-t-butyl-2-hydroxyacetophenone

A mixture of 100 g of t-butylhydroquinone, 130 ml of acetic anhydride and 1 kg of a boron trifluoride-acetic acid complex salt (boron trifluoride content 40%) was heated for 2 hours at 60° C. whilst stirring, and was then heated for a further 2 hours at 90° C. The reaction mixture was cooled, and then it was poured into 3 liters of ice-water and extracted with benzene. The benzene extract was washed with a saturated aqueous solution of sodium bicarbonate and then with water and dried over anhydrous sodium sulfate. The solvent was distilled off and the resulting oily residue was purified by silica gel column chromatography eluted with benzene, to give the title compound, melting at 86.5°–87.5° C.

PREPARATION 40

6-Acetoxy-7-t-butyl-2-methyl-2-(2-methyl-5-nitrophenoxymethyl)chroman-4-one (Step D1)

Following the same procedure as described in Preparation 19, 4.78 g of 5-acetoxy-4-t-butyl-2-hydroxyacetophenone (prepared as described in Preparation 39), 4.0 g of 1-(2-methyl-5-nitrophenoxy)propan-2-one, 2.0 g of pyrrolidine, 50 ml of benzene, 4 ml of acetic anhydride and 50 ml of pyridine were reacted, to give the title compound, as a slightly red, foamy substance.

Rf value on silica gel thin layer chromatography=0.24 (developing solvent, benzene:ethyl acetate=20:1 by volume).

Nuclear Magnetic Resonance Spectrum [(CD₃)₂CO] δ ppm: 1.32 (9H, singlet); 1.63 (3H, singlet); 2.17 (3H, singlet); 2.32 (3H, singlet); 2.90 (1H, doublet, J=16.5 Hz); 3.15 (1H, doublet, J=16.5 Hz); 4.43 (2H, AB type, J=12 Hz); 6.97 (1H, singlet); 7.38 (1H, doublet, J=8 Hz); 7.45 (1H, singlet); 7.70–7.90 (2H, multiplet).

PREPARATION 41

6-Acetoxy-2-(5-amino-2-methylphenoxymethyl)-7-t-butyl-2-methylchroman-4-one (Step D2)

Following the same procedure as described in Preparation 24, hydrogenation of 7.3 g of 6-acetoxy-7-t-butyl-2-methyl-2-(2-methyl-5-nitrophenoxymethyl)chroman-4-one (prepared as described in Preparation 40) in the presence of 1 g of 10% w/w palladium-on-carbon and 100 ml of ethanol gave the title compound as a slightly red, foamy substance.

Rf value on silica gel thin layer chromatography=0.13 (developing solvent, benzene:ethyl acetate=5:1 by volume).

Nuclear Magnetic Resonance Spectrum [(CD₃)₂CO] δ ppm: 1.33 (9H, singlet); 1.56 (3H, singlet); 1.95 (3H, singlet); 2.31 (3H, singlet); 2.80 (1H, doublet, J=16.5 Hz); 3.10 (1H, doublet, J=16.5 Hz); 4.06 (2H, singlet); 3.90–4.70 (2H, broad, disappeared on adding heavy water); 6.18 (1H, doublet of doublets, J=8 & 1.5 Hz); 6.28 (1H, doublet, J=1.5 Hz); 6.78 (1H, doublet, J=8 Hz); 7.00 (1H, singlet); 7.47 (1H, singlet).

PREPARATION 42

Ethyl 3-[3-(6-acetoxy-7-t-butyl-2-methyl-4-oxochroman-2-ylmethoxy)-4-methylphenyl]-2-chloropropionate (Step D3)

Following the same procedure as described in Preparation 25, 5.53 g of 6-acetoxy-2-(5-amino-2-methylphenoxymethyl)-7-t-butyl-2-methylchroman-4-one (prepared as described in Preparation 41), 1.2 g of sodium nitrite, 2.4 ml of concentrated hydrochloric acid, 14 ml of ethyl acrylate, 190 ml of cuprous oxide and 50 ml of acetone were reacted, to give the title compound as a pale yellow oil.

Rf value on silica gel thin layer chromatography=0.41 (developing solvent, benzene:ethyl acetate=10:1 by volume).

Nuclear Magnetic Resonance Spectrum (CDCl$_3$) δ ppm: 1.22 (3H, triplet, J=7.5 Hz); 1.32 (9H, singlet); 1.57 (3H, singlet); 2.10 (3H, singlet); 2.30 (3H, singlet); 2.74 (1H, doublet, J=17 Hz); 2.94–3.25 (1H, nd); 3.08 (1H, doublet, J=17 Hz); 3.33 (1H, doublet of doublets, J=7 & 14 Hz); 3.99 & 4.11 (2H, AB type, J=10 Hz); 4.18 (2H, quartet, J=7.5 Hz); 4.40 (1H, triplet, J=7 Hz); 6.65–6.85 (2H, nd); 6.99 (1H, singlet); 7.07 (1H, doublet, J=7.5 Hz); 7.50 (1H, singlet).

PREPARATION 43

6-Acetoxy-2-hydroxy-5,7,8-trimethyl-2-(4-nitrophenoxymethyl)chroman-4-one (Step H1)

A solution of 3 g of potassium t-butoxide in 100 ml of tetrahydrofuran was added dropwise to a solution of 15 g of 3-acetoxy-2,4,5-trimethyl-6-(4-nitrophenoxyacetoxy)acetophenone in 1 liter of tetrahydrofuran, whilst ice-cooling, and the resulting mixture was stirred at the same temperature for 2.5 hours. The reaction mixture was then poured into a mixture of ethyl acetate and an aqueous solution of sodium chloride, and the organic layer was separated and dried over anhydrous sodium sulfate. The solvent was distilled off. The residue was purified by silica gel column chromatography, eluted with a 1:1 by volume mixture of hexane and ethyl acetate, to give the title compound, melting at 204°–207° C.

Nuclear Magnetic Resonance Spectrum [(CD$_3$)$_2$SO] δ ppm: 2.05 (3H, singlet); 2.11 (3H, singlet); 2.34 (6H, singlet); 2.76 (1H, doublet, J=17 Hz); 3.24 (1H, doublet, J=17 Hz); 4.28 & 4.50 (2H, AB type, J=10 Hz); 7.24 (2H, doublet, J=9 Hz); 7.30 (1H, singlet, disappeared on adding heavy water); 8.24 (2H, J=9 Hz).

PREPARATION 44

6-Acetoxy-2-(4-aminophenoxymethyl)-2-hydroxy-5,7,8-trimethylchroman-4-one (Step H2)

Following the same procedure as described in Preparation 24, 7 g of 6-acetoxy-2-hydroxy-5,7,8-trimethyl-2-(4-nitrophenoxymethyl)chroman-4-one (prepared as described in Preparation 43) were treated with 5 g of 10% w/w palladium-on-carbon, 100 ml of tetrahydrofuran and 100 ml of ethanol, to give the title compound.

Rf value on silica gel thin layer chromatography=0.48 (developing solvent, ethyl acetate).

Nuclear Magnetic Resonance Spectrum (CDCl$_3$) δ ppm: 2.08 (3H, singlet); 2.10 (3H, singlet); 2.32 (3H, singlet); 2.41 (3H, singlet); 2.78 & 3.03 (2H, AB type, J=16 Hz); 3.4–4.3 (3H, broad singlet, disappeared on adding heavy water); 3.98 & 4.12 (2H, AB type, J=10 Hz); 6.62 (2H, doublet, J=9 Hz); 6.80 (2H, doublet, J=9 Hz).

PREPARATION 45

Ethyl 3-[4-(6-acetoxy-2-hydroxy-5,7,8-trimethyl-4-oxochroman-2-ylmethoxy)phenyl]-2-chloropropionate (Step H3)

Following the same procedure as described in Preparation 18, 3.4 g of 6-acetoxy-2-(4-aminophenoxymethyl)-2-hydroxy-5,7,8-trimethylchroman-4-one (prepared as described in Preparation 44), 40 ml of acetone, 5 ml of 35% w/v aqueous hydrochloric acid, 1.2 g of sodium nitrite, 1.6 ml of water, 13 g of ethyl acrylate and 0.32 g of cuprous oxide were reacted, to give the title compound.

Rf value on silica gel thin layer chromatography=0.20 (developing solvent, hexane:ethyl acetate=2:1 by volume).

Nuclear Magnetic Resonance Spectrum (CDCl$_3$) δ ppm: 1.24 (3H, triplet, J=7 Hz); 2.09 (6H, singlet); 2.33 (3H, singlet); 2.42 (3H, singlet); 2.5–3.6 (4H, nd); 3.9–4.6 (5H, nd); 6.93 (2H, doublet, J=9 Hz); 7.20 (2H, doublet, J=9 Hz).

PREPARATION 46

Ethyl 3-[4-(6-acetoxy-2,5,7,8-tetramethylchroman-2-ylmethoxy)phenyl]-2-chloro-2-methylpropionate (Step A4)

Following the same procedure as described in Preparation 18, 2 g of 6-acetoxy-2-(4-aminophenoxymethyl)-2,5,7,8-tetramethylchroman (prepared as described in Preparation 50), 25 ml of acetone, 3 ml of 35% w/v aqueous hydrochloric acid, 0.7 g of sodium nitrite, 1 ml of water, 8 g of ethyl methacrylate and 0.2 g of cuprous oxide were reacted, to give the title compound.

Rf value on silica gel thin layer chromatography=0.54 (developing solvent, hexane:ethyl acetate=2:1 by volume).

Nuclear Magnetic Resonance Spectrum (CDCl$_3$) δ ppm: 1.29 (3H, triplet, J=7 Hz); 1.43 (3H, singlet); 1.68 (3H, singlet); 1.98 (3H, singlet); 2.03 (3H, singlet); 2.09 (3H, singlet); 2.32 (3H, singlet); 1.5–2.5 (2H, nd); 2.62 (2H, broad triplet, J=7 Hz); 3.18 & 3.36 (2H, AB type, J=17 Hz); 3.84 & 3.98 (2H, AB type, J=9 Hz); 4.21 (2H, quartet, J=7 Hz); 6.84 (2H, doublet, J=9 Hz); 7.14 (2H, doublet, J=9 Hz).

PREPARATION 47

6-Acetoxy-2,5,7,8-tetramethyl-2-(4-nitrophenoxymethyl)chroman-4-one (Step D1)

(a) A mixture of 17.7 g of 5-acetoxy-2-hydroxy-3,4,6-trimethylacetophenone, 14.6 g of 4-nitrophenoxyacetone, 7.5 g of pyrrolidine and 60 ml of benzene was allowed to stand for 1 day at room temperature, and then heated under reflux for 7 hours using a water separator. Water and ethyl acetate were added to the reaction mixture. The organic layer was separated and dried over anhydrous sodium sulfate. The solvent was distilled off and the resulting residue was purified by silica gel column chromatography using a 2:1 by volume mixture of hexane and ethyl acetate as eluent, to give the title compound.

Rf value on silica gel thin layer chromatography=0.17 (developing solvent, hexane:ethyl acetate=3:1 by volume).

Nuclear Magnetic Resonance Spectrum (CDCl$_3$) δ ppm: 1.56 (3H, singlet); 2.10 (6H, singlet); 2.36 (3H, singlet); 2.43 (3H, singlet); 2.70 (1H, doublet, J=15 Hz); 3.06 (1H, doublet, J=15 Hz); 4.11 (1H, doublet, J=10 Hz); 4.24 (1H, doublet, J=10 Hz); 6.98 (2H, doublet, J=9 Hz); 8.20 (2H, doublet, J=9 Hz).

(b) A mixture of the same components as mentioned in (a), but containing piperidine instead of pyrrolidine, was heated under reflux for 3 hours using a water separator. 5% w/v aqueous hydrochloric acid was added, and the reaction mixture was extracted with benzene. The benzene extract was washed with water and dried over anhydrous sodium sulfate. The solvent was distilled off to give the title compound. The Rf value and nuclear magnetic resonance spectrum of this compound accorded with those of the compound obtained in (a).

(c) In a similar manner to (b), the use of morpholine instead of piperidine afforded the title compound. The Rf value and nuclear magnetic resonance spectrum of this compound accorded with those of the compound obtained in (a).

(d) A mixture of the same components as mentioned in (a), but containing morpholine instead of pyrrolidine, and toluene instead of benzene, was heated under reflux for 1 hour. Then, in a similar manner to (b), the title compound was obtained. The Rf value and nuclear magnetic resonance spectrum of this compound accorded with those of the compound obtained in (a).

PREPARATION 48

6-Acetoxy-4-hydroxy-2,5,7,8-tetramethyl-2-(4-nitrophenoxymethyl)chroman (Step F1)

160 mg of sodium borohydride were added to a mixture of 1.8 g of 6-acetoxy-2,5,7,8-tetramethyl-2-(4-nitrophenoxymethyl)chroman-4-one (prepared as described in Preparation 47), 15 ml of methanol and 1 ml of benzene in an ice bath, and the mixture was stirred for 30 minutes. The reaction mixture was then poured into ice-water, neutralized with 10% w/v aqueous hydrochloric acid and extracted with benzene. The benzene extract was washed with water and dried over anhydrous sodium sulfate. The solvent was distilled off under reduced pressure. The residue was purified by silica gel column chromatography eluted with a 9:1 by volume mixture of benzene and ethyl acetate, to give crystals. These crystals were recrystallized from a mixture of benzene and hexane to give the title compound, melting at 139°–141° C.

Nuclear Magnetic Resonance Spectrum (CDCl$_3$) δ ppm: 1.56 (3H, singlet); 2.05 (6H, singlet); 2.0–2.4 (2H, nd); 2.19 (3H, singlet); 2.33 (3H, singlet); 4.10 (2H, AB type, J=9 Hz); 5.0 (1H, doublet of doublets, J=3 & 9 Hz); 7.03 (2H, doublet, J=9 Hz); 8.23 (2H, doublet, J=9 Hz).

PREPARATION 49

6-Acetoxy-2,5,7,8-tetramethyl-2-(4-nitrophenoxymethyl)-2H-chromene (Step F3)

Following the procedure described in Preparation 57, 160 mg of 6-acetoxy-4-hydroxy-2,5,7,8-tetramethyl-2-(4-nitrophenoxymethyl)chroman (prepared as described in Preparation 48), 10 mg of p-toluenesulfonic acid and 2 ml of benzene gave the title compound.

Rf value on silica gel thin layer chromatography=0.49 (developing solvent, benzene:ethyl acetate=20:1 by volume).

Nuclear Magnetic Resonance Spectrum (CDCl$_3$) δ ppm: 1.59 (3H, singlet); 2.03 (3H, singlet); 2.05 (3H, singlet); 2.09 (3H, singlet); 2.33 (3H, singlet); 4.10 (2H, AB type, J=9 Hz); 5.73 (1H, doublet, J=10 Hz); 6.73 (1H, doublet, J=10 Hz); 6.96 (2H, doublet, J=9 Hz); 8.22 (2H, doublet, J=9 Hz).

PREPARATION 50

6-Acetoxy-2-(4-aminophenoxymethyl)-2,5,7,8-tetramethylchroman (Step F5)

Following the procedure described in Preparation 58, 100 mg of 6-acetoxy-2,5,7,8-tetramethyl-2-(4-nitrophenoxymethyl)-2H-chromene (prepared as described in Preparation 49) were dissolved in 2 ml of methanol and, in the presence of 20 mg of 10% w/w palladium-on-carbon, the compound was reduced under 1 atmosphere (about 1 bar) pressure of hydrogen, to give the title compound melting at 138°–140° C.

Nuclear Magnetic Resonance Spectrum (CDCl$_3$) δ ppm: 1.42 (3H, singlet); 2.00 (3H, singlet); about 2 (2H, multiplet); 2.04 (3H, singlet); 2.10 (3H, singlet); 2.31 (3H, singlet); 2.6 (2H, broad triplet, J=6 Hz); 3.37 (2H, broad, disappeared on adding heavy water); 3.80 & 3.95 (2H, AB type, J=9 Hz); 6.62 (2H, doublet, J=7.5 Hz); 6.78 (2H, doublet, J=7.5 Hz).

PREPARATION 51

Ethyl 3-[4-(6-acetoxy-2,5,7,8-tetramethylchroman-2-ylmethoxy)phenyl]-2-chloropropionate (Step A4)

17.5 g of 6-acetoxy-2-(4-aminophenoxymethyl)-2,5,7,8-tetramethylchroman (prepared as described in Preparation 50) were dissolved in a mixture of 130 ml of acetone and 30 ml of water. 13 ml of concentrated hydrochloric acid, and then 8.5 ml of water containing 4.3 g of sodium nitrite, was added dropwise to this solution in an ice bath. A further 37.3 ml of ethyl acrylate were then added dropwise, and then the reaction mixture was heated to 40°–43° C.; at this temperature, 680 mg of cuprous oxide were added slowly. After about 30 minutes, nitrogen generation finished. The reaction mixture, which had separated into two layers, was mixed with benzene to extract the organic layer. The benzene extract was washed with a saturated aqueous solution of sodium chloride and then dried over anhydrous sodium sulfate. The solvent was distilled off and the resulting dark brown oil was subjected to silica gel column chromatography. After the first elution with a 1:1 by volume mixture of benzene and cyclohexane, the title compound was obtained from the next elution with a 2:1 by volume mixture of benzene and cyclohexane and from the subsequent elution with benzene alone.

Rf value on silica gel thin layer chromatography=0.39 (developing solvent, benzene:ethyl acetate=20:1 by volume).

Nuclear Magnetic Resonance Spectrum (CDCl$_3$) δ ppm: 1.23 (3H, triplet, J=7.5 Hz); 1.42 (3H, singlet); about 2 (2H, multiplet); 1.98 (3H, singlet); 2.04 (3H, singlet); 2.09 (3H, singlet); 2.31 (3H, singlet); 2.6 (2H, broad triplet, J=6 Hz); 3.05 (1H, doublet of doublets, J=15 & 7.5 Hz); 3.31 (1H, doublet of doublets, J=15 & 7.5 Hz); 3.83 & 3.99 (2H, AB type, J=9 Hz); 4.18 (2H, quartet, J=7.5 Hz); 4.38 (1H, triplet, J=7.5 Hz); 6.85 (2H, doublet, J=9 Hz); 7.14 (2H, doublet, J=9 Hz).

PREPARATION 52

6-Hydroxy-2,5,7,8-tetramethyl-2-(4-nitrophenoxymethyl)chroman-4-one (Step D1)

A mixture of 3.9 g of 2,5 -dihydroxy-3,4,6-trimethylacetophenone, 3.9 g of 4-nitrophenoxyacetone, 2.0 g of pyrrolidine and 15 g of toluene was allowed to stand for 2 days at room temperature. Dilute hydrochloric acid was then added to the reaction mixture and the mixture was extracted with diethyl ether. The aqueous layer was further extracted with ethyl acetate. The ethyl acetate extract and the ethereal extract were combined and dried over anhydrous sodium sulfate. The solvent was distilled off and hexane was added to the resulting residue. The crystals which separated were collected by filtration and purified by silica gel column chromatography using a 5:1 by volume mixture of hexane and ethyl acetate as eluent. Recrystallization of the product from ethyl acetate gave the title compound, melting at 199°-204° C.

Nuclear Magnetic Resonance Spectrum [(CD$_3$)$_2$SO] δ ppm: 1.43 (3H, singlet); 2.01 (3H, singlet); 2.14 (3H, singlet); 2.46 (3H, singlet); 2.67 (1H, doublet, J=16 Hz); 3.03 (1H, doublet, J=16 Hz); 4.31 (2H, singlet); 7.19 (2H, doublet, J=9 Hz); 7.92 (1H, singlet); 8.21 (2H, doublet, J=9 Hz).

PREPARATION 53

7-t-Butyl-6-hydroxy-2-methyl-2-(4-nitrophenoxymethyl)chroman-4-one (Step D1)

Following the procedure described in Preparation 52, the title compound was prepared from 2.0 g of 4-t-butyl-2,5-dihydroxyacetophenone, 1.9 g of 4-nitrophenoxyacetone, 1.0 g of pyrrolidine and 10 ml of benzene. The compound obtained melted at 205°-209° C.

Nuclear Magnetic Resonance Spectrum [(CD$_3$)$_2$CO] δ ppm: 1.39 (3H, singlet); 1.53 (9H, singlet); 2.70 (1H, doublet, J=16.5 Hz); 3.05 (1H, doublet, J=16.5 Hz); 4.37 (2H, singlet); 6.80 (1H, singlet); 7.18 (2H, doublet, J=10 Hz); 7.22 (1H, singlet); 8.22 (2H, doublet, J=10 Hz); 8.31 (1H, singlet, disappeared on adding heavy water).

PREPARATION 54

6-Acetoxy-7-t-butyl-2-methyl-2-(4-nitrophenoxymethyl)chroman-4-one

A mixture of 1.7 g of 7-t-butyl-6-hydroxy-2-methyl-2-(4-nitrophenoxymethyl)chroman-4-one (prepared as described in Preparation 53), 1 ml of acetic anhydride and 10 ml of pyridine was allowed to stand for 1 day at room temperature. The reaction mixture was then poured into ice-water, stirred for 2 hours and extracted with benzene. The benzene extract was washed with 3N aqueous hydrochloric acid, water, a saturated aqueous solution of sodium bicarbonate and water in that order, and then dried over anhydrous sodium sulfate. The solvent was distilled off under reduced pressure and the resulting residue was recrystallized from a mixture of benzene and ethyl acetate (about 10:1 by volume) to give the title compound, melting at 82°-84° C.

Nuclear Magnetic Resonance Spectrum [(CD$_3$)$_2$CO] δ ppm: 1.33 (9H, singlet); 1.57 (3H, singlet); 2.33 (3H, singlet); 2.82 (1H, doublet, J=16.5 Hz); 3.13 (1H, doublet, J=16.5 Hz); 4.42 (2H, singlet); 6.93 (1H, singlet); 7.25 (2H, doublet, J=9 Hz); 7.44 (1H, singlet); 8.22 (2H, doublet, J=9 Hz).

PREPARATION 55

7-t-Butyl-4,6-dihydroxy-2-methyl-2-(4-nitrophenoxymethyl)chroman (Step F1)

A solution of 3.0 g of 6-acetoxy-7-t-butyl-2-methyl-2-(4-nitrophenoxymethyl)chroman-4-one (prepared as described in Preparation 54) in 20 ml of tetrahydrofuran was dropped into a suspension containing 0.3 g of sodium borohydride in 10 ml of methanol whilst stirring over an ice bath. After the whole of the solution had been added, the reaction mixture was stirred for 2 hours at room temperature. The reaction mixture was then ice-cooled again, acidified weakly with 10% w/v aqueous hydrochloric acid and extracted with ethyl acetate. The ethyl acetate extract was washed with water and dried over anhydrous sodium sulfate. The solvent was removed by evaporation under reduced pressure to give crystals. Recrystallization of these crystals from a mixture of benzene and petroleum ether gave the title compound, melting at 194°-201° C.

Nuclear Magnetic Resonance Spectrum [(CD$_3$)$_2$CO] δ ppm: 1.34 (9H, singlet); 1.50 (3H, singlet); 1.88 (1H, doublet of doublets, J=13.5 & 9 Hz); 2.45 (1H, doublet of doublets, J=13.5 & 6 Hz); 2.78 (1H, singlet, disappeared on adding heavy water); 4.15 (2H, singlet); 4.75 (1H, multiplet); 6.62 (1H, singlet); 6.91 (1H, singlet); 7.15 (2H, doublet, J=9 Hz); 8.20 (2H, doublet, J=9 Hz).

PREPARATION 56

4,6-Diacetoxy-7-t-butyl-2-methyl-2-(4-nitrophenoxymethyl)chroman (Step F2)

3 ml of acetic anhydride were added to a mixture of 2.0 g of 7-t-butyl-4,6-dihydroxy-2-methyl-2-(4-nitrophenoxymethyl)chroman (prepared as described in Preparation 55) and 20 ml of pyridine, and the mixture was heated for 3 hours at 50° C. The reaction mixture was then dissolved in benzene and washed with 3N aqueous hydrochloric acid, water, a saturated aqueous solution of sodium bicarbonate and water in that order, and then dried over anhydrous sodium sulfate. The solvent was distilled off to give the title compound as a slightly yellow oil.

Rf value on silica gel thin layer chromatography=0.62 (developing solvent, benzene:ethyl acetate=5:1 by volume).

Nuclear Magnetic Resonance Spectrum [(CD$_3$)$_2$CO] δ ppm: 1.31 (9H, singlet); 1.55 (3H, singlet); 1.77 (3H, singlet); 2.0-2.3 (1H, nd); 2.27 (3H, singlet); 2.45-2.7 (1H, nd); 4.20 & 4.38 (2H, AB type, J=10 Hz); 5.85-6.10 (1H, multiplet); 6.87 (1H, singlet); 6.98 (1H, singlet); 7.20 (2H, doublet, J=9 Hz); 8.30 (2H, doublet, J=9 Hz).

PREPARATION 57

6-Acetoxy-7-t-butyl-2-methyl-2-(4-nitrophenoxymethyl)-2H-chromene (Step F4)

A mixture of 2.4 g of 4,6-diacetoxy-7-t-butyl-2-methyl-2-(4-nitrophenoxymethyl)chroman (prepared as described in Preparation 56), 0.1 g of p-toluenesulfonic acid monohydrate and 50 ml of benzene was heated under reflux for 1 hour. The reaction solution was cooled, washed with a saturated aqueous solution of sodium bicarbonate, and then with water, and dried over anhydrous sodium sulfate. The solvent was distilled off under reduced pressure, to give the title compound as a yellow oil.

Rf value on silica gel thin layer chromatography=0.58 (developing solvent, benzene:ethyl acetate=10:1 by volume).

Nuclear Magnetic Resonance Spectrum [(CD$_3$)$_2$CO] δ ppm: 1.27 (9H, singlet); 1.54 (3H, singlet); 2.27 (3H, singlet); 4.28 (2H, singlet); 5.79 (1H, doublet, J=10 Hz); 6.52 (1H, doublet, J=10 Hz); 6.67 (1H, singlet); 6.76 (1H, singlet); 7.13 (2H, doublet, J=9 Hz); 8.20 (2H, doublet, J=9 Hz).

PREPARATION 58

6-Acetoxy-2-(4-aminophenoxymethyl)-7-t-butyl-2-methylchroman (Step F5)

2.1 g of 6-acetoxy-7-t-butyl-2-methyl-2-(4-nitrophenoxymethyl)-2H-chromene (prepared as described in Preparation 57) were dissolved in a mixture of 20 ml of benzene and 2 ml of acetic acid, and the compound was reduced for 10 hours at room temperature, in the presence of 0.1 g of 10% w/w palladium-on-carbon, and under about 1 atmosphere (about 1 bar) pressure of hydrogen. The catalyst was filtered off, and the reaction mixture was washed with a saturated aqueous solution of sodium bicarbonate and then with water, after which it was dried over anhydrous sodium sulfate. The solvent was distilled off under reduced pressure, and the resulting residue was purified by silica gel column chromatography, eluted with benzene, to give the title compound as a slightly brown oil.

Rf value on silica gel thin layer chromatography=0.13 (developing solvent, benzene:ethyl acetate=10:1 by volume).

Nuclear Magnetic Resonance Spectrum [(CD$_3$)$_2$CO] δ ppm: 1.30 (9H, singlet); 1.40 (3H, singlet); 1.7-2.2 (2H, nd); 2.27 (3H, singlet); 2.73 (2H, broad triplet, J=7 Hz); 3.89 (2H, singlet); 3.7-4.5 (2H, broad, disappeared on adding heavy water); 6.50-7.05 (6H, multiplet).

PREPARATION 59

Ethyl 3-[4-(6-acetoxy-7-t-butyl-2-methylchroman-2-ylmethoxy)phenyl]-2-chloropropionate (Step A4)

Following the procedure described in Preparation 51, 1.74 g of 6-acetoxy-2-(4-aminophenoxymethyl)-7-t-butyl-2-methylchroman (prepared as described in Preparation 58), 380 mg of sodium nitrite, 0.8 ml of concentrated hydrochloric acid, 4.5 g of ethyl acrylate, 65 mg of cuprous oxide and 17 ml of acetone were reacted, to give the title compound as a slightly yellow oil.

Rf value on silica gel thin layer chromatography=0.55 (developing solvent, benzene:ethyl acetate=5:1 by volume).

Nuclear Magnetic Resonance Spectrum (CDCl$_3$) δ ppm: 1.23 (3H, triplet, J=7.5 Hz); 1.31 (9H, singlet); 1.45 (3H, singlet); 1.63-2.20 (2H, multiplet); 2.28 (3H, singlet); 2.72 (2H, broad triplet, J=7 Hz); 3.08 (1H, doublet of doublets, J=7.5 & 15 Hz); 3.30 (1H, doublet of doublets, J=7.5 & 15 Hz); 3.88 & 3.98 (2H, AB type, J=9 Hz); 4.18 (2H, quartet, J=7.5 Hz); 4.37 (1H, triplet, J=7.5 Hz); 6.73 (1H, singlet); 6.85 (1H, singlet); 6.88 (2H, doublet, J=9 Hz); 7.15 (2H, doublet, J=9 Hz).

PREPARATION 60

6-t-Butoxycarbonylmethoxy-2,5,7,8-tetramethyl-2-(4-nitrophenoxymethyl)chroman-4-one A mixture of 5.6 g of sodium hydroxide, 150 ml of ethanol and 20 ml of water was added dropwise to a mixture of 25 g of 6-acetoxy-2,5,7,8-tetramethyl-2-(4-nitrophenoxymethyl)chroman-4-one (prepared as described in Preparation 47), 30 ml of dimethylformamide and 150 ml of ethanol, whilst ice-cooling, and the reaction mixture was stirred for 3 hours. 18.3 g of t-butyl bromoacetate were then added. The reaction mixture was stirred for 1 hour at room temperature and then allowed to stand overnight. After this, the reaction mixture was poured into water, neutralized with a 10% w/v aqueous hydrogen chloride solution and extracted with benzene. This extract was washed with water and dried over anhydrous sodium sulfate. The solvent was distilled off under reduced pressure, and the residue was purified by silica gel column chromatography eluted with a 20:1 by volume mixture of benzene and ethyl acetate, to give the title compound.

Rf value on silica gel thin layer chromatography=0.49 (developing solvent, benzene:ethyl acetate=10:1 by volume)

Nuclear Magnetic Resonance Spectrum (CDCl$_3$) δ ppm: 1.53 (12H, singlet); 2.07 (3H, singlet); 2.27 (3H, singlet); 2.57 (3H, singlet); 2.68 (1H, doublet, J=16.5 Hz); 3.05 (1H, doublet, J=16.5 Hz); 4.17 (2H, singlet, and 2H, AB-type, J=10 Hz); 6.97 (2H, doublet, J=9 Hz); 8.19 (2H, doublet, J=9 Hz).

PREPARATION 61

6-Ethoxy-2,5,7,8-tetramethyl-2-(4-nitrophenoxymethyl)chroman 1.6 g of a 55% w/w suspension of sodium hydride in mineral oil was added to a mixture of 11 g of 6-hydroxy-2,5,7,8-tetramethyl-2-(4-nitrophenoxymethyl)chroman and 100 ml of dimethylformamide, and the reaction mixture was stirred for 1 hour at room temperature. Then a mixture of 5.7 g of ethyl iodide and 5 ml of benzene was added dropwise, whilst ice-cooling, and the reaction mixture was stirred for 2 hours at room temperature. The reaction mixture was then poured into water and extracted with benzene. This extract was washed with water and dried over anhydrous sodium sulfate. The solvent was distilled from the extract under reduced pressure, and the residue was purified by silica gel column chromatography eluted with a 3:7 by volume mixture of cyclohexane and benzene, to give the title compound.

Rf value on silica gel thin layer chromatography=0.48 (developing solvent, benzene).

Nuclear Magnetic Resonance Spectrum (CDCl$_3$) δ ppm: 1.39 (3H, triplet, J=7 Hz); 1.43 (3H, singlet); 1.7-2.1 (2H, nd); 2.06 (3H, singlet); 2.14 (3H, singlet); 2.17 (3H, singlet); 2.63 (2H, broad triplet, J=7 Hz); 3.72 (2H, quartet, J=7 Hz); 4.00 & 4.08 (2H, AB-type, J=10 Hz); 6.98 (2H, doublet, J=9 Hz); 8.17 (2H, doublet, J=9 Hz).

PREPARATION 62

2-(4-Aminophenoxymethyl)-6-t-butoxycarboxymethoxy-2,5,7,8-tetramethylchroman-4-one A mixture of 17 g of 6-t-butoxycarbonylmethoxy-2,5,7,8-tetramethyl-2-(4-nitrophenoxymethyl)chroman- 4-one (prepared as described in Preparation 60), 3.5 g of 10% w/w palladium-on-carbon, 150 ml of methanol and 50 ml of dimethylformamide was subjected to reduction with Paar's hydrogenation apparatus under a hydrogen pressure of 3-5 atmospheres (about 3-5 bars) for 7 hours. The palladium-on-carbon was then filtered off, and the solvent was distilled from the filtrate under reduced pressure. The residue was dissolved in benzene, washed with water and dried over anhydrous sodium sulfate. This solvent was then distilled off under reduced pressure to give the title compound.

Rf value on silica gel thin layer chromatography=0.29 (developing solvent, benzene:ethyl acetate=4:1 by volume).

Nuclear Magnetic Resonance Spectrum (CDCl$_3$) δ ppm: 1.47 (3H, singlet); 1.54 (9H, singlet); 2.11 (3H, singlet); 2.26 (3H, singlet); 2.55-2.75 (1H, nd); 2.57 (3H, singlet); 3.05 (1H, doublet, J=16 Hz); 3.15-3.65 (2H, broad singlet); 3.90 & 4.03 (2H, AB-type, J=10 Hz); 4.17 (2H, singlet); 6.60 (2H, doublet, J=9 Hz); 6.76 (2H, doublet J=9 Hz).

PREPARATION 63

2-(4-Aminophenoxymethyl)-6-ethoxy-2,5,7,8-tetramethylchroman

The procedure described in Preparation 62 was repeated, except that 11 g of 6-ethoxy-2,5,7,8-tetramethyl-2-(4-nitrophenoxymethyl)chroman (prepared as described in Preparation 61), 2.2 g of 10% w/w palladium-on-carbon, 100 ml of methanol and 30 ml of benzene were used as the starting materials to give the title compound, melting at 121°-123° C.

Nuclear Magnetic Resonance Spectrum (CDCl$_3$) δ ppm: 1.38 (3H, triplet, J=7 Hz); 1.40 (3H, singlet); 1.7-2.1 (2H, nd); 2.08 (3H, singlet); 2.12 (3H, singlet); 2.17 (3H, singlet); 2.60 (2H, broad triplet, J=7 Hz); 3.1-3.6 (2H, broad, disappeared on adding heavy water); 3.71 (2H, quartet, J=7 Hz); 3.80 & 3.91 (2H, AB-type J=10 Hz); 6.60 (2H, doublet, J=9 Hz); 6.78 (2H, doublet, J=9 Hz).

PREPARATION 64

Ethyl 3-[4-(6-t-Butoxycarbonylmethoxy-2,5,7,8-tetramethyl-4-oxochroman-2-ylmethoxy)phenyl]-2-chloropropionate 16 ml of concentrated hydrochloric acid, 7 ml of an aqueous solution containing 3.1 g of sodium nitrite and 37 ml of ethyl acrylate were added, in that order, at 5°-10° C. to a mixture of 16 g of 2-(4-aminophenoxymethyl)-6-t-butoxycarbonylmethoxy-2,5,7,8-tetramethylchroman-4-one (prepared as described in Preparation 62) and 160 ml of acetone. Then 0.5 g of cuprous oxide was added gradually at an internal temperature of 40°-43° C. After about 30 minutes, the evolution of nitrogen had ceased. The reaction mixture was then poured into water and extracted with benzene. This extract was washed with water and dried over anhydrous sodium sulfate. The solvent was distilled from the extract under reduced pressure, and the residue was purified by silica gel column chromatography eluted with a 9:1 by volume mixture of cyclohexane and ethyl acetate, to give the title compound.

Rf value on silica gel thin layer chromatography=0.33 (developing solvent, cyclohexane:ethyl acetate=4:1 by volume).

Nuclear Magnetic Resonance Spectrum (CDCl$_3$) δ ppm: 1.23 (3H, triplet, J=7,.5 Hz); 1.50 (3H, singlet); 1.53 (9H, singlet); 2.09 (3H, singlet); 2.26 (3H, singlet); 2.5-2.8 (1H, nd); 2.57 (3H, singlet); 3.05 (1H, doublet, J=16 Hz); 3.07 (1H, nd); 3.32 (1H, doublet of doublets, J=7 & 14 Hz); 3.98 & 4.09 (2H, AB-type, J=10 Hz); 4.05-4.35 (2H, nd); 4.18 (2H, singlet); 4.37 (1H, triplet, J=7 Hz); 6.85 (2H, doublet, J=8 Hz); 7.14 (2H, doublet, J=8 Hz);

PREPARATION 65

Ethyl 2-chloro-3-[4-(6-ethoxy-2,5,7,8-tetramethylchroman-2-ylmethoxy)phenyl]propionate The procedure described in Preparation 64 was repeated, except that 9.5 g of 2-(4-aminophenoxymethyl)-6-ethoxy-2,5,7,8-tetramethylchroman (prepared as described in Preparation 63), 10 ml of concentrated hydrochloric acid, 2.4 g of sodium nitrite, 26.8 g of ethyl acrylate, 0.4 g of cuprous oxide and 100 ml of acetone were used as the starting materials, to give the title compound.

Rf value on silica gel thin layer chromatography=0.30 (developing solvent, cyclohexane:ethyl acetate=20:1 by volume).

Nuclear Magnetic Resonance Spectrum (CDCl$_3$) δ ppm: 1.23 (3H, triplet, J=7 Hz); 1.38 (3H, triplet, J=7 Hz); 1.41 (3H, singlet); 1.7-2.1 (2H, nd); 2.07 (3H, singlet); 2.13 (3H, singlet); 2.17 (3H, singlet); 2.60 (2H, broad triplet, J=7 Hz); 3.07 (1H, doublet of doublets, J=4 & 14 Hz); 3.31 (1H, doublet of doublets, J=4 & 14 Hz); 3.71 (2H, quartet, J=7 Hz); 3.86 & 3.96 (2H, AB-type, J=9 Hz); 4.17 (2H, quarter, J=7 Hz); 4.36 (1H, triplet, J=7.5 Hz); 6.85 (2H, doublet, J=9 Hz); 7.13 (2H, doublet, J=9 Hz).

TEST EXAMPLE 1

Toxicity

The test animals used were male mice of the ddY strain. The animals were employed in groups of 3. The animals of each group were administered orally with a single test compound in a dose of 300 mg/kg body weight. The compounds employed were those prepared as described in Examples 3, 4, 5 and 13. The animals were then observed for one week after administration, during which time they showed no abnormalities which could be attributed to the test compounds. All animals were alive at the end of the 1 week observation period.

In view of the substantial dose administered to each animal, the zero mortality indicates that the compounds of the invention have a very low toxicity.

TEST EXAMPLE 2

Effect on Hyperglycemia

The test animals employed were genetically diabetic male mice of the KK strain, aged about 6 months. The animals were employed in groups of 3 (test compounds) or 5 (control) for each test.

The test compounds were suspended in a 0.5% w/v aqueous solution of carboxymethylcellulose. Each test compound was administered at a dose of 50 mg/kg body weight.

Within a period of about 3-24 hours after administration, blood samples were taken from the tip of the tail of each mouse, and the blood glucose level was measured in this sample by the glucose oxidase method. The minimum glucose level (i.e. maximum decrease) was taken for each animal.

A control group was treated with similarly, except that the test compound was omitted.

The maximum decrease in blood glucose levels was calculated for each test compound as a percentage of the corresponding level of the control group. The results are shown in Table 29:

TABLE 29

| Cpd. of Ex. No. | Blood glucose level (%) |
|---|---|
| Control | 100 |
| 13 | 61.5 |
| 58 | 67.5 |
| 59 | 53.4 |

TEST EXAMPLE 3

Effect on Aldose Reductase

Aldose reductase was separated and partially purified from bovine lenses by the method of Hayman and Kinoshita [J. Biol. Chem., 240, 877 (1965)]. Enzyme activities were photometrically determined by the method of Varma et al. [Biochem, Pharmac., 25, 2505 (1976)].

The inhibition of aldose reductase activity was determined employing each test compound in a concentration of $1 \times 10^{-5}$M, and the results are as shown in Table 30.

As a control, the known compound, 5-[4-(1-methylcyclohexylmethoxy)benzyl]thiazolidine-2,4-dione ("Cpd. A") was tested by the same method and the result is also shown in Table 30:

TABLE 30

| Cpd. of Ex. No. | Percent Inhibition |
|---|---|
| 13 | 55.5 |
| 58 | 51.6 |
| 59 | 79.5 |
| Cpd. A | 16.2 |

We claim:

1. A compound of formula (I):

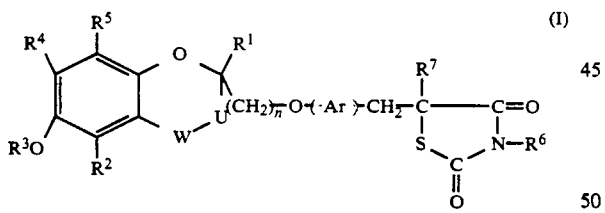

in which:
R$^1$ represents a hydrogen atom, a C$_1$–C$_{10}$ alkyl group or a C$_7$–C$_{13}$ aralkyl group;
R$^2$ represents a hydrogen atom or a C$_1$–C$_5$ alkyl group;
R$^3$ represents a hydrogen atom, a C$_1$–C$_{23}$ alkanoyl group, a C$_3$–C$_{23}$ alkenoyl group, a C$_3$–C$_{23}$ alkynoyl group, a substituted C$_1$–C$_{23}$ alkanoyl, C$_3$–C$_{23}$ alkenoyl or C$_3$–C$_{23}$ alkynoyl group having at least one substituent selected from the group consisting of substituents (a), an aromatic acyl group selected from the group consisting of benzoyl and naphthoyl, a 5 to 8-membered heterocyclic acyl group having 1 to 3 hetero atoms of N, S or O, a group of formula —SO$_3$R$^8$ where
R$^6$ represents a hydrogen atom, an aralkyl group where the alkyl part is C$_1$–C$_3$ alkyl, a C$_1$–C$_5$ alkyl group or a C$_1$–C$_5$ alkyl group having at least one substituent selected from the group consisting of hydroxy groups and C$_1$–C$_5$ alkoxy groups,
a C$_1$–C$_{10}$ alkyl group or a substituted C$_1$–C$_{10}$ alkyl group having at least one substituent selected from the group consisting of substituents (b);
R$^4$ represents a hydrogen atom, a C$_1$–C$_{10}$ alkyl group or a C$_1$–C$_5$ alkoxy group;
R$^5$ represents a hydrogen atom, a C$_1$–C$_5$ alkyl group or a C$_1$–C$_5$ alkoxy group;
R$^6$ and R$^7$ are independently selected from the group consisting of hydrogen atoms, C$_1$–C$_{10}$ alkyl groups and substituted C$_1$–C$_{10}$ alkyl groups having at least one substituent selected from the group consisting of substituents (b);
Ar is a divalent group selected from the group consisting of divalent carbocyclic aromatic groups, and divalent heterocyclic aromatic groups formed from a pyridine, furan, thiophene or pyrrole ring;
W represents a —CH$_2$— group, a >C=O group, a group of formula >CH—OR$^{11}$
wherein R$^{11}$ represents a hydrogen atom, a C$_1$–C$_{23}$ alkanoyl group, a C$_3$–C$_{23}$ alkenoyl group, a C$_3$–C$_{23}$ alkynoyl group, a substituted C$_1$–C$_{23}$ alkanoyl, C$_3$–C$_{23}$ alkenoyl or C$_3$–C$_{23}$ alkynoyl group having at least one substituent selected from the group consisting of substituents (a), an aromatic acyl group selected from the group consisting of benzoyl and napthoyl, a 5-8 membered heterocyclia acyl having 1 to 3 heteroatoms of N, S, or O, A C$_1$–C$_{10}$ alkyl group or a substituted C$_1$–C$_{10}$ alkyl group having at least one substituent selected from the group consisting of substituents (b), or a group of formula >C=N—O—R$^{12}$
in which R$^{12}$ represents a hydrogen atom, a C$_1$–C$_{10}$ alkyl group, a C$_1$–C$_{10}$ alkyl group having at least one substituent selected from the group consisting of substituents (b), a C$_1$–C$_{23}$ alkanoyl group, a C$_3$–C$_{23}$ alkenoyl group, a C$_3$–C$_{23}$ alkynoyl group, a substituted C$_1$–C$_{23}$ alkanoyl, C$_3$–C$_{23}$ alkenoyl or C$_3$–C$_{23}$ alkynoyl group having at least one substituent selected from the group consisting of substituents (a), an aromatic acyl group selected from the group consisting of benzoyl and naphthoyl or a heterocyclic acyl group having 1 to 3 heteroatoms of N, S or O;
U represents a —CH$_2$— group; or
W and U together represent a group of formula —CH=CH—; or
when W represents a carbonyl group or said group of formula >C=N—OR$^{12}$, U, R$^1$ and the carbon atom to which R$^1$ is attached together represent a group of formula —CH=C<;
n is an integer of from 1 to 3;
said aryl groups and the aryl parts of said aralkyl, aralkyloxycarbonyl, and aromatic acyloxy being C$_6$–C$_{10}$ carbocyclic aryl groups which are unsubstituted or have at least one substituent selected from the group consisting of substituents (c);
said heterocyclic groups, heterocyclic parts of said heterocyclic acyl and acyloxy groups have from 5 to 10 ring atoms, of which from 1 to 5 are heteroatoms selected from the group consisting of nitrogen, oxygen and sulfur hetero-atoms, said heterocyclic groups being unsubstituted or having at least one substituent selected from the group consisting of substituents (d); said substituents (a) being selected from the group consisting of aryl groups, carboxy groups, $C_2$–$C_6$ alkoxycarbonyl groups and aralkyloxycarbonyl groups;

said substituents (b) being selected from the group consisting of hydroxy groups, $C_1$–$C_5$ alkoxy groups, aryl groups, $C_1$–$C_{23}$ alkanoyloxy groups, $C_3$–$C_{23}$ alkenoyloxy groups, $C_3$–$C_{23}$ alkynoyloxy groups, substituted $C_1$–$C_{23}$ alkanoyloxy, $C_3$–$C_{23}$ alkenoyloxy or $C_3$–$C_{23}$ alkynoyloxy groups having at least one substituent selected from the group consisting of substituents (a), aromatic acyloxy groups, heterocyclic acyloxy groups, groups of formula —COOR$^8$ where R$^8$ is as defined above and groups of formula —CONR$^9$R$^{10}$ where R$^9$ and R$^{10}$ are independently selected from the group consisting of hydrogen atoms and $C_1$–$C_5$ alkyl groups or R$^9$ and R$^{10}$, together with the nitrogen atom to which they are attached, represent a heterocyclic group having from 5 to 7 ring atoms of which from 1 to 3 atoms, including nitrogen atom, are hetero-atoms selected from the group consisting of nitrogen, oxygen and sulfur hetero-atoms, said heterocyclic group being unsubstituted, or, where said ring atoms include an additional nitrogen hetero-atom, said additional nitrogen atom being unsubstituted or having a single substituent selected from the group consisting of substituents (e);

said substituents (c) being selected from the group consisting of $C_1$–$C_5$ alkyl groups, $C_1$–$C_5$ alkoxy groups, $C_1$–$C_5$ alkyl groups having at least one halogen substituent, halogen atoms, amino groups, $C_1$–$C_5$ alkylamino groups, dialkylamino groups in which each alkyl part is $C_1$–$C_5$, nitro groups, cyano groups, groups of formula —CONR$_2$ where R represents a $C_1$–$C_5$ alkyl group or an aryl group and hydroxy groups; and said substituents (d) being selected from the group consisting of $C_1$–$C_5$ alkyl groups, $C_1$–$C_5$ alkoxy groups and doubly bonded oxygen atoms;

said substituents (e) being selected from the group consisting of $C_1$–$C_5$ alkyl groups, $C_1$–$C_5$ alkanoyl groups, $C_3$–$C_5$ alkenoyl groups and $C_3$–$C_5$ alkynoyl groups; provided that:

($\alpha$) where: R$^3$ represents said hydrogen atom, an unsubstituted $C_1$–$C_6$ alkanoyl group, an unsubstituted $C_3$–$C_6$ alkenoyl group, an unsubstituted $C_3$–$C_6$ alkynoyl group, said aromatic acyl group, said heterocyclic acyl group, an aralkanoyl group or an aralkenoyl group; and R$^6$ and R$^7$ both represent hydrogen atoms; and Ar represents a p-phenylene group; and W represents a group of formula >CH$_2$, >C=O or >CH—OR$^{11x}$ (wherein R$^{11x}$ represents a hydrogen atom, an unsubstituted $C_1$–$C_6$ alkanoyl group, an unsubstituted $C_3$–$C_6$ alkenoyl group, an unsubstituted $C_3$–$C_6$ alkynoyl group, said aromatic acyl group, said heterocyclic acyl group, an aralkanoyl group or an aralkenoyl group); and U represents said group of formula >CH$_2$, then (i) when R$^1$ represents a hydrogen atom or a $C_1$–$C_5$ alkyl group, R$^4$ represents a $C_6$–$C_{10}$ alkyl group, and (ii) when R$^4$ represents a hydrogen atom, a $C_1$–$C_5$ alkyl group or a $C_1$–$C_5$ alkoxy group, R$^1$ represents a $C_6$–$C_{10}$ alkyl group or said $C_7$–$C_{13}$ aralkyl group;

($\beta$) where: R$^1$ and R$^2$ are independently selected from the group consisting of hydrogen atoms and $C_1$–$C_5$ alkyl groups; and R$^4$ and R$^5$ are independently selected from the group consisting of hydrogen atoms, $C_1$–$C_5$ alkyl groups and $C_1$–$C_5$ alkoxy groups; and Ar represents a p-phenylene group; and W is a group of formula >CH$_2$, >C=O or >CH—OR$^{11x}$ (where R$^{11x}$ is as defined above); and U represents said group of formula >CH$_2$; and n is an integer from 1 to 3, then at least one of R$^3$, R$^6$ and R$^7$ represents said alkyl or substituted alkyl group;

and pharmaceutically acceptable salts thereof.

2. A compound as claimed in claim 1, in which:

R$^1$ represents a hydrogen atom or a $C_1$–$C_{10}$ alkyl group;

R$^2$ represents a hydrogen atom or a $C_1$–$C_3$ alkyl group;

R$^3$ represents a hydrogen atom, a sulfo group, a $C_1$–$C_{10}$ alkanoyl group, a $C_3$–$C_{10}$ alkenoyl group, a substituted $C_1$–$C_{10}$ alkanoyl or $C_3$–$C_{10}$ alkenoyl group having at least one substituent selected from the group consisting of substituents (f), an arylcarbonyl group wherein the aryl part is a $C_6$–$C_{10}$ carbocyclic aryl group which is unsubstituted or has at least one substituent selected from the group consisting of substituents (g), a group of formula R$^{13}$—(CH$_2$)$_m$—CO—, where R$^{13}$ represents a phenyl group or a phenyl group having at least one substituent selected from the group consisting of substituents (g), and m is an integer from 1 to 5, a group of formula Het—CO—, where Het represents a heterocyclic group having 5 to 6 ring atoms, of which from 1 to 3 are heteroatoms selected from the group consisting of nitrogen oxygen and sulfur hetero-atoms, said heterocyclic group being unsubstituted or having at least one substituent selected from the group consisting of $C_1$–$C_5$ alkyl groups, a $C_1$–$C_5$ alkyl group, a $C_1$–$C_5$ alkyl group substituted by a group of formula —COOR$^{8a}$, where R$^{8a}$ represents a hydrogen atom, a $C_1$–$C_5$ alkyl group or an alkoxyalkyl group were both the alkoxy part and the alkyl part are $C_1$–$C_5$, a $C_2$–$C_5$ hydroxyalkyl group, a $C_2$–$C_5$ alkyl group substituted by a group of formula —O—CO—R$^{53}$, where R$^{53}$ represents a $C_1$–$C_{10}$ alkyl group, a phenyl group, a phenyl group having at least one substituent selected from the group consisting of substituents (g) or a heterocyclic group Het, as defined above, or a $C_1$–$C_3$ alkyl group substituted by a single substituent selected from the group consisting of substituents (h);

said substituents (f) are selected from the group consisting of phenyl groups, carboxy groups, $C_2$–$C_6$ alkoxycarbonyl groups and benzyloxycarbonyl groups;

said substituents (g) are selected from the group consisting of $C_1$–$C_5$ alkyl groups, trifluoromethyl groups, $C_1$–$C_5$ alkoxy groups, halogen atoms, nitro groups, amino groups, hydroxy groups and dialkylamino groups where each alkyl part is $C_1$–$C_5$;

said substituents (h) are selected from the group consisting of alkylcarbamoyl groups where the alkyl part is $C_1$-$C_4$, dialkylcarbamoyl groups where each alkyl part is $C_1$-$C_4$, 1-pyrrolidinylcarbonyl groups, piperidinocarbonyl groups and morpholinocarbonyl groups;

$R^4$ represents a $C_1$-$C_{10}$ alkyl group or a methoxy group;

$R^5$ represents a hydrogen atom, a $C_1$-$C_5$ alkyl group or a methoxy group;

$R^6$ and $R^7$ are independently selected from the group consisting of hydrogen atoms, $C_1$-$C_5$ alkyl groups, $C_1$-$C_5$ alkyl groups substituted by a group of formula —$COOR^{8a}$ where $R^{8a}$ is as defined above, $C_2$-$C_5$ hydroxyalkyl groups, $C_1$-$C_5$ alkyl groups substituted by a $C_1$-$C_5$ alkoxy group, $C_2$-$C_5$ alkyl groups substituted by a group of formula —O—CO—$R^{53}$ where $R^{53}$ is as defined above, and $C_1$-$C_3$ alkyl groups having a single substituent selected from the group consisting of substituents (h);

Ar represents a o-phenylene, m-phenylene or p-phenylene group or a pyridine-diyl group which is attached to the part of said compound of formula (I) of formula —$(CH_2)_n$—O— at its 2-position and is attached to the —$CH_2$-thiazolidine group at its 5- or 6-position, said phenylene and pyridine-diyl groups being unsubstituted or having a $C_1$-$C_3$ alkyl substituent;

W represents a group of formula —$CH_2$—, >C=O, >CH—$OR^{11}$ or >C=N—$OR^{12}$ where $R^{11}$ represents a hydrogen atom, a $C_1$-$C_{10}$ alkanoyl group, a $C_3$-$C_{10}$ alkenoyl group, a substituted $C_1$-$C_{10}$ alkanoyl or $C_3$-$C_{10}$ alkenoyl group having at least one substituent selected from the group consisting of substituents (f), an arylcarbonyl group wherein the aryl part is a $C_6$-$C_{10}$ carbocyclic aryl group which is unsubstituted or has at least one substituent selected from the group consisting of substituents (g), a group of formula $R^{13}$—$(CH_2)_m$—CO— where $R^{13}$ and m are as defined above or a group of formula Het—CO— where Het is as defined above, and $R^{12}$ represents a hydrogen atom, a $C_1$-$C_5$ alkyl group, a $C_1$-$C_{10}$ alkyl group having at least one substituent selected from the group consisting of substituents (j), a $C_1$-$C_{10}$ alkanoyl group, a $C_3$-$C_{10}$ alkenoyl group, a substituted $C_1$-$C_{10}$ alkanoyl or $C_3$-$C_{10}$ alkenoyl group having at least one substituent selected from the group consisting of substituents (f), an arylcarbonyl group wherein the aryl part is a $C_6$-$C_{10}$ carbocyclic aryl group which is unsubstituted or has at least one substituent selected from the group consisting of substituents (g), or said group of formula $R^{13}$—$CH_2)_m$—CO— or Het—CO—; and said substituents (j) are selected from the group consisting of hydroxy groups, phenyl groups, phenyl groups having at least one substituent selected from the group consisting of substituents (g), $C_2$-$C_{11}$ alkanoyloxy groups, $C_2$-$C_{11}$ alkanoyloxy groups substituted by a group of formula —$COOR^{8a}$ where $R^{8a}$ is as defined above, $C_3$-$C_{11}$ alkenoyloxy groups substituted by a group of formula —$COOR^{8a}$ where $R^{8a}$ is as defined above, phenylalkenoyloxy groups where the alkenyl part is $C_2$-$C_{10}$ and the phenyl part is unsubstituted or has at least one substituent selected from the group consisting of substituents (g), benzoyloxy groups, benzoyloxy groups having at least one substituent selected from the group consisting of substituents (g), groups of formula —$COOR^{8a}$ where $R^{8a}$ is as defined above, benzyloxycarbonyl groups and groups of formula —$COR^9R^{10}$ where $R^9$ and $R^{10}$ are as defined above;

U represents (i) where W represents a group of formula —$CH_2$—, >C=O, >$CH_2OR^{11}$ or >C=N—$OR^{12}$, a group of formula —$CH_2$—, (ii) with W, a group of formula —CH=CH—, or (iii) where W represents a group of formula >C=O or >C=N—$OR^{14}$, in which $R^{14}$ represents any one of the acyl groups defined for $R^{12}$, with $R^1$ and the carbon atom to which $R^1$ is attached, a group of formula —CH=C<.

3. A compound as claimed in claim 2, in which:

$R^1$, $R^2$, $R^4$, $R^5$, Ar, W and U are defined in claim 2;

$R^6$ and $R^7$ both represent hydrogen atoms;

$R^3$ and $R^{11}$ are independently selected from the group consisting of hydrogen atoms, $C_1$-$C_{10}$ alkanoyl groups, $C_3$-$C_{10}$ alkenoyl groups, $C_1$-$C_{10}$ alkanoyl or $C_3$-$C_{10}$ alkenoyl groups having at least one substituent selected from the group consisting of substituents (f) as defined in claim 2, arylcarbonyl groups as defined in claim 2, and groups of formulae $R^{13}$—$(CH_2)_m$—CO— and Het—CO— where $R^{13}$, m and Het are as defined in claim 2; and $R^{12}$ represents any one of the groups or atoms defined for $R^3$ and $R^{11}$ or a $C_1$-$C_5$ alkyl group of a $C_1$-$C_3$ alkyl group having at least one substituent selected from the group consisting of substituents (f) defined in claim 2.

4. A compound as claimed in claim 2, in which:

$R^1$, $R^2$, $R^4$, $R^5$, Ar, W and U are as defined in claim 2;

$R^3$, $R^6$, $R^7$ and $R^{12}$ are independently selected from the group consisting of hydrogen atoms, $C_1$-$C_5$ alkyl groups, $C_1$-$C_5$ alkyl groups substituted by a group of formula —$COOR^{8a}$ where $R^{8a}$ is as defined in claim 2, $C_2$-$C_5$ hydroxyalkyl groups, $C_1$-$C_5$ alkyl groups substituted by a $C_1$-$C_5$ alkoxy group, $C_2$-$C_5$ alkyl groups substituted by a group of formula —O—CO—$R^{53}$ where $R^{53}$ is as defined in claim 2 and $C_1$-$C_3$ alkyl groups substituted by a single substituent selected from the group consisting of substituents (h) as defined in claim 2; and $R^{11}$ represents a hydrogen atom, an acetyl group or a benzoyl group; or $R^{12}$ represents a hydrogen atom, a $C_1$-$C_5$ alkyl group, a $C_1$-$C_{10}$ alkyl group having at least one substituent selected from the group consisting of substituents (k), a $C_2$-$C_6$ alkanoyl group, a $C_2$-$C_{10}$ alkanoyl group having at least one substituent selected from the group consisting of substituents (l), a $C_3$-$C_5$ alkenoyl group, a $C_3$-$C_5$ alkenoyl group having at least one substituent selected from the group consisting of substituents (l), a benzoyl group, a benzoyl group having at least one substituent selected from the group consisting of substituents (m), a pyridinecarbonyl group, a furoyl group, a thenoyl group or a pyridinecarbonyl, furoyl or thenoyl group having at least one substituent selected from the group consisting of $C_1$-$C_5$ alkyl groups;

said substituents (k) are selected from the group consisting of hydroxy groups, phenyl groups, phenyl groups having at least one substituent selected from the group consisting of substituents (m), $C_2$-$C_5$ alkanoyloxy groups, $C_2$-$C_{10}$ alkanoyloxy or $C_3$-$C_{10}$ alkenoyloxy groups substituted by a group of formula —COOR$^{8a}$ where R$^{8a}$ is as defined in claim 2, $C_3$-$C_{10}$ alkenoyloxy groups substituted by a phenyl group where the phenyl group is unsubstituted or has at least one substituent selected from the group consisting of substituents (m), benzoyloxy groups, benzoyloxy groups having at least one substituent selected from the group consisting of substituents (m), groups of formula —COOR$^{8a}$ where R$^{8a}$ is as defined in claim 2 and substituents (h) as defined in claim 2;

said substituents (l) are selected from the group consisting of phenyl groups, carboxy groups, alkoxycarbonyl groups where the alkoxy part is $C_1$-$C_5$ and benzyloxycarbonyl groups; and said substituents (m) are selected from the group consisting of $C_1$-$C_5$ alkyl groups, $C_1$-$C_5$ alkoxy groups, halogen atoms and trifluoromethyl groups.

5. A compound as claimed in claim 1, in which:

R$^1$ represents an alkyl group selected from the group consisting of methyl, ethyl, isobutyl, pentyl, hexyl, 3,3-dimethylbutyl, heptyl, 4,4-dimethylpentyl, octyl, 5,5-dimethylhexyl, nonyl and 3,7-dimethyloctyl groups;

R$^2$ represents a hydrogen atom or a methyl group;

R$^3$ represents a hydrogen atom, a $C_1$-$C_{10}$ alkanoyl group, a $C_3$-$C_{10}$ alkenoyl group, a substituted $C_1$-$C_{10}$ alkanoyl or $C_3$-$C_{10}$ alkenoyl group having at least one substituent selected from the group consisting of substituents (f), a benzoyl group, a benzoyl group having at least one substituent selected from the group consisting of substituents (n), an aralkanoyl group of formula R$^{15}$—(CH$_2$)$_m$—CO— where R$^{15}$ represents a phenyl group or a phenyl group having at least one substituent selected from the group consisting of substituents (n), and m is an integer from 1 to 5, a pyridinecarbonyl group, a furoyl group, a thenoyl group, a $C_1$-$C_3$ alkyl group, a $C_1$-$C_3$ alkyl group substituted by a group of formula —COOR$^{8a}$ where R$^{8a}$ represents a hydrogen atom, a $C_1$-$C_5$ alkyl group or an alkoxyalkyl group where both the alkoxy part and the alkyl part are $C_1$-$C_5$, a $C_2$-$C_3$ hydroxyalkyl group, a $C_1$-$C_5$ alkyl group substituted by a $C_1$-$C_5$ alkoxy group, a $C_2$-$C_5$ alkyl group substituted by a $C_2$-$C_4$ alkanoyloxy or a benzoyloxy group or a methyl group having a single substituent selected from the group consisting of substituents (h);

said substituents (f) are selected from the group consisting of phenyl groups, carboxy groups, $C_2$-$C_6$ alkoxycarbonyl groups and benzyloxycarbonyl groups;

said substituents (n) are selected from the group consisting of $C_1$-$C_5$ alkyl groups, $C_1$-$C_5$ alkoxy groups and halogen atoms;

R$^4$ represents a $C_1$-$C_{10}$ alkyl group;

R$^5$ represents a hydrogen atom or a $C_1$-$C_3$ alkyl group;

R$^6$ and R$^7$ are independently selected from the group consisting of hydrogen atoms, $C_1$-$C_3$ alkyl groups, $C_1$-$C_3$ alkyl groups substituted by a group of formula —COOR$^{8a}$ where R$^{8a}$ is as defined above, $C_2$-$C_3$ hydroxyalkyl groups, $C_1$-$C_5$ alkyl groups substituted by a $C_1$-$C_5$ alkoxy group, $C_2$-$C_5$ alkyl groups substituted by a $C_2$-$C_4$ alkanoyloxy of a benzoyloxy group, and methyl groups substituted by a single substituent selected from the group consisting of substituents (h);

said substituents (h) are selected from the group consisting of alkylcarbamoyl groups where the alkyl part is $C_1$-$C_4$, dialkylcarbamoyl groups where each alkyl part is $C_1$-$C_4$, 1-pyrrolidinylcarbonyl groups, piperidinocarbonyl groups and morpholinocarbonyl groups;

Ar represents a o-phenylene, m-phenylene or p-phenylene group or a pyridine-diyl group which is attached to the part of said compound of formula (I) of formula —(CH$_2$)$_n$—O— at its 2-position and is attached to the —CH$_2$-thiazolidine group at its 5- or 6-position, said phenylene and pyridine-diyl groups being unsubstituted or having a methyl substituent;

W represents a group of formula —CH$_2$—, >C=O, >CH—OR$^{11}$ or >C=N—OR$^{12}$, where:

R$^{11}$ represents a hydrogen atom or any one of the acyl groups defined above for R$^3$; and R$^{12}$ represents a benzyl group, any one of the groups or atoms defined above for R$^3$, a pyridinecarbonyl group or a pyridinecarbonyl group having at least one substituent selected from the group consisting of $C_1$-$C_5$ alkyl groups;

and U represents (i) where W represents a group of formula —CH$_2$—, >C=O, >CH—OR$^{11}$ or >C=N—OR$^{12}$, a group of formula —CH$_2$—, (ii) with W, a group of formula —CH=CH—, or (iii) where W represents a group of formula >C=O, with R$^1$ and the carbon atom to which R$^1$ is attached, a group of formula —CH=C<.

6. A compound as claimed in claim 5, in which:

R$^1$, R$^2$, R$^4$, R$^5$, Ar, W and U are as defined in claim 5;

R$^6$ and R$^7$ are both hydrogen atoms;

R$^3$ and R$^{11}$ are independently selected from the group consisting of hydrogen atoms, $C_1$-$C_{10}$ alkanoyl groups, $C_3$-$C_{10}$ alkenoyl groups, $C_1$-$C_{10}$ alkanoyl or $C_3$-$C_{10}$ alkenoyl groups having at least one substituent selected from the group consisting of substituents (f) as defined in claim 5, benzoyl groups, benzoyl groups having at least one substituent selected from the group consisting of substituents (n) as defined in claim 5, groups of formula R$^{15}$—(CH$_2$)$_m$—CO— where R$^{15}$ and m are as defined in claim 5, pyridinecarbonyl groups, furoyl groups and thenoyl groups; and R$^{12}$ represents a hydrogen atom, a methyl group, a benzyl group, a t-butoxycarbonylmethyl group or any one of the acyl groups defined above for R$^3$ and R$^{11}$.

7. A compound as claimed in claim 5, in which:

R$^1$, R$^2$, R$^4$, R$^5$, Ar, W and U are as defined in claim 5;

R$^3$, R$^6$ R$^7$ are independently selected from the group consisting of $C_1$-$C_3$ alkyl groups, $C_1$-$C_3$ alkyl groups substituted by a group of formula —COOR$^{8a}$ where R$^{8a}$ is as defined in claim 5, $C_2$-$C_3$ hydroxyalkyl groups, $C_1$-$C_5$ alkyl groups substituted by a $C_1$-$C_5$ alkoxy group, $C_2$-$C_5$ alkyl groups substituted by a $C_2$-$C_4$ alkanoyloxy or a benzoyloxy group, and methyl groups having a single substituent selected from the group consisting of substituents (h) as defined in claim 5;

$R^{11}$ represents a hydrogen atom;

$R^{12}$ represents a hydrogen atom, a $C_1$-$C_3$ alkyl group having at least one substituent selected from the group consisting of substituents (o), a $C_2$-$C_4$ alkanoyl group, a $C_2$-$C_4$ alkanoyl group substituted by a group of formula —COOR$^{8a}$ where R$^{8a}$ is as defined in claim 5, an acryloyl group, an acryloyl group having a β-substituent selected from the group consisting of substituents (f), a benzoyl group, a benzoyl group having at least one substituent selected from the group consisting of substituents (q), a pyridinecarbonyl group, a pyridinecarbonyl group having at least one substituent selected from the group consisting of $C_1$-$C_5$ alkyl groups or any one of the groups defined above for $R^3$, $R^6$ and $R^7$;

said substituents (f) are selected from the group consisting of phenyl groups, carboxy groups, $C_2$-$C_6$ alkoxycarbonyl groups and benzyloxycarbonyl groups; and said substituents (o) are selected from the group consisting of carboxy groups and alkoxycarbonyl groups where the alkoxy part is $C_1$-$C_5$;

said substituents (q) are selected from the group consisting of methyl groups, ethyl groups, methoxy groups and ethoxy groups.

8. A compound as claimed in claim 1 in which:

$R^1$ represents an alkyl group selected from the group consisting of methyl, isobutyl, hexyl, heptyl, octyl, nonyl and 3,7-dimethyloctyl groups;

$R^2$ represents a hydrogen atom or a methyl group;

$R^3$ represents a hydrogen atom, a $C_1$-$C_5$ alkanoyl group, $C_3$-$C_5$ alkenoyl group, a cinnamoyl group, a group of formula $R^{16}$OOC(CH$_2$)$_m$CO— where $R^{16}$ represents a hydrogen atom or a $C_1$-$C_5$ alkyl group and m is an integer from 1 to 5, a cis- or trans- group of formula $R^{17}$OOC.CH═CH—CO— where $R^{17}$ represents a hydrogen atom, a $C_1$-$C_5$ alkyl group or a benzyl group, a 2-, 3- or 4-pyridinecarbonyl group or a $C_1$-$C_3$ alkyl group substituted by a group of formula —COOR$^{8a}$ where R$^{8a}$ represents a hydrogen atom, a $C_1$-$C_5$ alkyl group or an alkoxyalkyl group where both the alkoxy part and the alkyl part are $C_1$-$C_5$;

$R^4$ represents an alkyl group selected from the group consisting of methyl, ethyl, propyl, butyl, pentyl, hexyl, heptyl, octyl, 1,1,3,3-tetramethylbutyl, 1,1-dimethylbutyl and 1,1-dimethylpropyl groups;

$R^5$ represents a hydrogen atom or a methyl group;

$R^6$ and $R^7$ are independently selected from the group consisting of hydrogen atoms and $C_1$-$C_3$ alkyl groups substituted by a group of formula —COOR$^{8a}$ where R$^{8a}$ is as defined above;

Ar represents a p-phenylene group, a m-phenylene group having a methyl group at the position ortho to the position of attachment to the group of formula —(CH$_2$)$_n$—O— or a pyridine-diyl group attached to said group of formula —(CH$_2$)$_n$—O— at the 2-position and to the —CH$_2$-thiazolidine group at the 5-position;

W represents a group of formula —CH$_2$—, >C═O, >C═N—OH, >C═N—OCH$_2$COOH or >C═N—OCOR$^{18}$ where R$^{18}$ represents a $C_1$-$C_5$ alkyl group; and U represents a group of formula —CH$_2$—.

9. A compound as claimed in claim 8, in which:

$R^1$, $R^2$, $R^4$, $R^5$, Ar and U are as defined in claim 8;

$R^3$ represents a hydrogen atom, a $C_1$-$C_5$ alkanoyl group, a $C_3$-$C_5$ alkenoyl group, a cinnamoyl group, a group of formula $R^{16}$OOC(CH$_2$)$_m$CO— where $R^{16}$ and m are as defined in claim 8, a cis or trans-group of formula $R^{17}$OOC.CH═CH—CO— where $R^{17}$ is as defined in claim 8, or a 2-, 3- or 4-pyridinecarbonyl group;

$R^6$ and $R^7$ are both hydrogen atoms;

W represents a group of formula >C═NOR$^{12}$ where $R^{12}$ represents a hydrogen atom, a group of formula —(CH$_2$)$_3$COOR$^{8a}$, —CH$_2$COOR$^{8a}$, —C(CH$_3$)$_2$COOR$^{8a}$, —COCH$_2$CH$_2$COOR$^{8a}$ or —CO—CH═CH—COOR$^{8a}$ where R$^{8a}$ is as defined in claim 8, an acetyl group, a cinnamoyl group, a benzoyl group, a pyridinecarbonyl group or any one of the groups defined above for $R^3$, $R^6$ and $R^7$; and n is 1 or 2.

10. A compound as claimed in claim 8, in which:

$R^1$, $R^2$, $R^4$, $R^5$, Ar and U are as defined in claim 8;

$R^3$, $R^6$ and $R^7$ are independently selected from the group consisting of $C_1$-$C_3$ alkyl groups substituted by a group of formula —COOR$^{8a}$ where R$^{8a}$ is as defined in claim 8;

W represents a group of formula >CH$_2$, >C═O or >C═NOR$^{12}$;

$R^{12}$ represents a hydrogen atom, a group of formula —(CH$_2$)$_3$COOR$^{8a}$, —CH$_2$COOR$^{8a}$, —C(CH$_3$)$_2$COOR$^{8a}$, —COCH$_2$CH$_2$COOR$^{8a}$ or —CO—CH═CH—COOR$^{8a}$ where R$^{8a}$ is as defined in claim 8, an acetyl group, a cinnamoyl group, a benzoyl group, a pyridinecarbonyl group or any one of the groups defined above for $R^3$, $R^6$ and $R^7$; and n is 1 or 2.

11. A compound as claimed in claim 2, in which:

$R^1$ represents an alkyl group selected from the group consisting of methyl, isobutyl, hexyl, heptyl, octyl, nonyl and 3,7-dimethyloctyl groups;

$R^2$ represents a hydrogen atom or a methyl group;

$R^3$ represents a hydrogen atom, a $C_1$-$C_{10}$ alkanoyl group, a $C_3$-$C_{10}$ alkenoyl group, a $C_1$-$C_{10}$ alkanoyl or $C_3$-$C_{10}$ alkenoyl group having at least one substituent selected from the group consisting of substituents (f) as defined in claim 2, an arylcarbonyl group as defined in claim 2, a group of formula $R^{13}$—(CH$_2$)$_m$—CO— or Het—CO— where $R^{13}$, m and Het are as defined in claim 2 or a $C_1$-$C_3$ alkyl group substituted by a group of formula —COOR$^{8a}$ where R$^{8a}$ is as defined in claim 2;

$R^4$ represents an alkyl group selected from the group consisting of methyl, ethyl, propyl, butyl, pentyl, hexyl, heptyl, octyl, 1,1,3,3-tetramethylbutyl, 1,1-dimethylbutyl and 1,1-dimethylpropyl groups;

$R^5$ represents a hydrogen atom or a methyl group;

$R^6$ represents a $C_1$-$C_3$ alkyl group substituted by a group of formula —COOR$^{8a}$ where R$^{8a}$ is as defined in claim 2;

$R^7$ represents a hydrogen atom or a $C_1$-$C_3$ alkyl group substituted by a group of formula —COOR$^{8a}$ where R$^{8a}$ is as defined in claim 2;

Ar represents a p-phenylene group, a m-phenylene group having a methyl group at the position ortho to the position of attachment to the group of formula —(CH$_2$)$_n$—O— or a pyridine-diyl group attached to said group of formula —(CH$_2$)$_n$—O— at the 2-position and to the —CH$_2$-thiazolidine group at the 5-position;

W represents a group of formula >CH$_2$, >C=O or >C=NOR$^{12}$, where

R$^{12}$ represents a hydrogen atom, a group of formula —(CH$_2$)$_3$COOR$^{8a}$, —CH$_2$COOR$^{8a}$, —C(CH$_3$)$_2$COOR$^{8a}$, —COCH$_2$CH$_2$COOR$^{8a}$ or —CO—CH=CH—COOR$^{8a}$ where R$^{8a}$ is as defined in claim 2, an acetyl group, a cinnamoyl group, a benzoyl group, a pyridinecarbonyl group or a C$_1$-C$_3$ alkyl group substituted by a group of formula —COOR$^{8a}$ where R$^{8a}$ is as defined in claim 2;

U represents a group of formula —CH$_2$—; and n is 1 or 2.

12. A compound as claimed in claim 2, in which:

R$^1$ represents an alkyl group selected from the group consisting of hexyl, heptyl, octyl, nonyl and 3,7-dimethyloctyl groups;

R$^2$ represents a hydrogen atom or a methyl group;

R$^3$ represents a hydrogen atom, a C$_1$-C$_5$ alkanoyl group, C$_3$-C$_5$ alkenoyl group, a cinnamoyl group, a group of formula R$^{16}$OOC(CH$_2$)$_m$CO— where R$^{14}$ represents a hydrogen atom or a C$_1$-C$_5$ alkyl group and m is an integer from 1 to 5, a cis- or trans- group of formula R$^{17}$OOC.CH=CH—CO— where R$^{17}$ represents a hydrogen atom, C$_1$-C$_5$ alkyl group or a benzyl group, a 2-, 3- or 4-pyridinecarbonyl group or a C$_1$-C$_3$ alkyl group substituted by a group of formula —COOR$^{8a}$ where R$^{8a}$ is as defined in claim 2;

R$^4$ represents an alkyl group selected from the group consisting of methyl, ethyl, propyl, butyl, pentyl, hexyl, heptyl, octyl, 1,1,3,3-tetramethylbutyl, 1,1-dimethylbutyl and 1,1-dimethylpropyl groups;

R$^5$ represents a hydrogen atom or a methyl group;

R$^6$ and R$^7$ are independently selected from the group consisting of hydrogen atoms and C$_1$-C$_3$ alkyl groups substituted by a group of formula —COOR$^{8a}$ where R$^{8a}$ is as defined in claim 2;

Ar represents a p-phenylene group, a m-phenylene group having a methyl group at the position ortho to the position of attachment to the group of formula —(CH$_2$)$_n$—O— or a pyridine-diyl group attached to said group of formula —(CH$_2$)$_n$—O— at the 2-position and to the —CH$_2$-thiazolidine group at the 5-position;

W represents a group of formula —CH$_2$—, >C=O or >C=N—OR$^{12}$, where

R$^{12}$ represents a hydrogen atom, a group of formula —(CH$_2$)$_3$COOR$^{8a}$, —CH$_2$COOR$^{8a}$, —C(CH$_3$)$_2$COOR$^{8a}$, —COCH$_2$CH$_2$COOR$^{8a}$ or —CO—CH=CH—COOR$^{8a}$ where R$^{8a}$ is as defined in claim 2, an acetyl group, a cinnamoyl group, a benzoyl group, a pyridinecarbonyl group, a C$_1$-C$_5$ alkyl group, a C$_1$-C$_5$ alkyl group substituted by a phenyl group where the phenyl group is unsubstituted or has at least one substituent selected from the group consisting of substituents (n), or any one of the groups defined above for R$^3$, R$^6$ and R$^7$;

said substituents (n) are selected from the group consisting of C$_1$-C$_5$ alkyl groups, C$_1$-C$_5$ alkoxy groups and halogen atoms; and U represents a group of formula —CH$_2$—.

13. A compound as claimed in claim 2, in which:

R$^1$ represents an alkyl group selected from the group consisting of methyl, isobutyl, hexyl, heptyl, octyl, nonyl and 3,7-dimethyloctyl groups;

R$^2$ represents a hydrogen atom or a methyl group;

R$^3$ represents a hydrogen atom, a C$_1$-C$_5$ alkanoyl group, C$_3$-C$_5$ alkenoyl group, a cinnamoyl group, a group of formula R$^{16}$OOC(CH$_2$)$_m$CO— where R$^{16}$ represents a hydrogen atom or a C$_1$-C$_5$ alkyl group and m is an integer from 1 to 5, a cis- or trans- group of formula R$^{17}$OOC.CH=CH—CO— where R$^{17}$ represents a hydrogen atom, a C$_1$-C$_5$ alkyl group of a benzyl group, a 2-, 3- or 4-pyridinecarbonyl group or a C$_1$-C$_3$ alkyl group substituted by a group of formula —COOR$^{8a}$ where R$^{8a}$ is as defined in claim 2;

R$^4$ represents an alkyl group selected from the group consisting of hexyl, heptyl, octyl, 1,1,3,3-tetramethylbutyl, 1,1-dimethylbutyl and 1,1-dimethylpropyl groups;

R$^5$ represents a hydrogen atom or a methyl group;

R$^6$ and R$^7$ are independently selected from the group consisting of hydrogen atoms and C$_1$-C$_3$ alkyl groups substituted by a group of formula —COOR$^{8a}$ where R$^{8a}$ is as defined in claim 2;

Ar represents a p-phenylene group, a m-phenylene group having a methyl group at the position ortho to the position of attachment to the group of formula —(CH$_2$)$_n$—O— or a pyridine-diyl group attached to said group of formula —(CH$_2$)$_n$—O— at the 2-position and to the —CH$_2$-thiazolidine group at the 5-position;

W represents a group of formula —CH$_2$—, >C=O or >C=N—OR$^{12}$ where

R$^{12}$ represents a hydrogen atom, a group of formula —(CH$_2$)$_3$COOR$^{8a}$, —CH$_2$COOR$^{8a}$, —C(CH$_3$)$_2$COOR$^{8a}$, —COCH$_2$CH$_2$COOR$^{8a}$ or —CO—CH=CH—COOR$^{8a}$ where R$^{8a}$ is as defined in claim 2, an acetyl group, a cinnamoyl group, a benzoyl group, a pyridinecarbonyl group, a C$_1$-C$_5$ alkyl group, a C$_1$-C$_5$ alkyl group substituted by a phenyl group where the phenyl group is unsubstituted or has at least one substituent selected from the group consisting of substituents (n), or any one of the groups defined above for R$^3$, R$^6$ and R$^7$;

said substituents (n) are selected from the group consisting of C$_1$-C$_5$ alkyl groups, C$_1$-C$_5$ alkoxy groups and halogen atoms; and U represents a group of formula —CH$_2$—.

14. A compound as claimed in claim 2, in which:

R$^1$ represents an alkyl group selected from the group consisting of methyl, isobutyl, hexyl, heptyl, octyl, nonyl and 3,7-dimethyloctyl groups;

R$^2$ represents a hydrogen atom or a methyl group;

R$^3$ represents C$_1$-C$_3$ alkyl group substituted by a group of formula —COOR$^{8a}$, where R$^{8a}$ is as defined in claim 2;

R$^4$ represents an alkyl group selected from the group consisting of methyl, ethyl, propyl, butyl, pentyl, hexyl, heptyl, octyl, 1,1,3,3-tetramethylbutyl, 1,1-dimethylbutyl and 1,1-dimethylpropyl groups;

R$^5$ represents a hydrogen atom or a methyl group;

R$^6$ and R$^7$ are both hydrogen atoms;

Ar represents a p-phenylene group, a m-phenylene group having a methyl group at the position ortho to the position of attachment to the group of formula —(CH$_2$)$_n$—O— or a pyridine-diyl group attached to said group of formula —(CH$_2$)$_n$—O— at the 2-position and to the —CH$_2$-thiazolidine group at the 5-position;

W represents a group of formula —CH$_2$—, >C=O, >C=N—OH, or >C=N—O—(C$_1$-C$_3$ alkyl)—COOR$^{8a}$ where R$^{8a}$ is as defined in claim 2;

U represents a group of formula —CH$_2$—; and n is 1 or 2.

15. A compound as claimed in claim 2, in which:

R$^1$ represents an alkyl group selected from the group consisting of methyl, isobutyl, hexyl, heptyl, octyl, nonyl and 3,7-dimethyloctyl groups;

R$^2$ represents a hydrogen atom or a methyl group;

R$^3$ represents —CH$_2$—COO(C$_1$-C$_5$ alkyl) group;

R$^4$ represents an alkyl group selected from the group consisting of methyl, ethyl, propyl, butyl, pentyl, hexyl, heptyl, octyl, 1,1,3,3-tetramethylbutyl, 1,1-dimethylbutyl and 1,1-dimethylpropyl groups;

R$^5$ represents a hydrogen atom or a methyl group;

R$^6$ and R$^7$ are both hydrogen atoms;

Ar represents a p-phenylene group, a m-phenylene group having a methyl group at the position ortho to the position of attachment to the group of formula —(CH$_2$)$_n$—O— or a pyridine-diyl group attached to said group of formula —(CH$_2$)$_n$—O— at the 2-position and to the —CH$_2$-thiazolidine group at the 5-position;

W represents a group of formula —CH$_2$—, >C=O, >C=N—OH, or >C=N—O—(C$_1$-C$_3$ alkyl)—COO(C$_1$-C$_5$ alkyl);

U represents a group of formula —CH$_2$—; and n is 1 or 2.

16. The compound as claimed in claim 1, which is 5-[4-(6-Hydroxy-5,7,8-trimethyl-2-octylchroman-2-ylmethoxy)benzyl]thiazolidine-2,4-dione and pharmaceutically acceptable salts thereof.

17. The compound as claimed in claim 1, which is 5-{4-[6-Hydroxy-4-(E)-hydroxyimino-2,5,7,8-tetramethylchroman-2-ylmethoxy]benzyl}thiazolidine-2,4-dione and pharmaceutically acceptable salts thereof.

18. The compound as claimed in claim 1, which 5-{4-[6-Acetoxy-4-(E)-acetoxyimino-2,5,7,8-tetramethylchroman-2-ylmethoxy]benzyl}thiazolidine-2,4-dione and pharmaceutically acceptable salts thereof.

19. The compound as claimed in claim 1, which is α-{5-[4-(6-Carboxymethoxy-2,5,7,8-tetramethyl-4-oxochroman-2-ylmethoxy)benzyl]-2,4-dioxothiazolidin-3-yl}acetic acid and pharmaceutically acceptable salts thereof.

20. The compound as claimed in claim 1, which is α-{5-[4-(6-Carboxymethoxy-4-hydroxyimino-2,5,7,8-tetramethylchroman-2-ylmethoxy)benzyl]-2,4-dioxothiazolidin-3-yl}acetic acid and pharmaceutically acceptable salts thereof.

21. The compound as claimed in claim 1, which is α,α'-{5-[4-(6-Carboxymethoxy-4-hydroxyimino-2,5,7,8-tetramethylchroman-2-ylmethoxy)benzyl]-2,4-dioxothiazolidine-3,5-diyl}diacetic acid and pharmaceutically acceptable salts thereof.

22. A pharmaceutical composition for the treatment of hyperlipaemia or hyperglycaemia, comprising an effective amount of an active compound in combination with a pharmaceutically acceptable carrier or diluent, wherein the active compound is selected from the group consisting of compounds of formula (1):

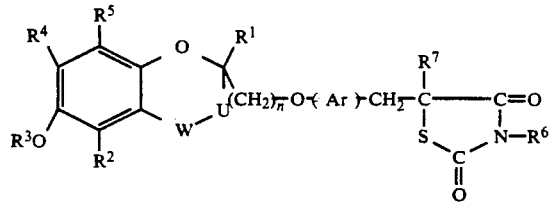

in which:

R$^1$ represents a hydrogen atom, a C$_1$-C$_{10}$ alkyl group or a C$_7$-C$_{13}$ aralkyl group;

R$^2$ represents a hydrogen atom or a C$_1$-C$_5$ alkyl group;

R$^3$ represents a hydrogen atom, a C$_1$-C$_{23}$ alkanoyl group, a C$_3$-C$_{23}$ alkenoyl group, a C$_3$-C$_{23}$ alkynoyl group, a substituted C$_1$-C$_{23}$ alkanoyl, C$_3$-C$_{23}$ alkenoyl or C$_3$-C$_{23}$ alkynoyl group having at least one substituent selected from the group consisting of substituents (a), an aromatic acyl group selected from the group consisting of benzoyl and naphthoyl, a 5 to 8-membered heterocyclic acyl group having 1 to 3 hetero atoms of N, S or O, a group of formula —SO$_3$R$^8$ where R$^8$ represents a hydrogen atom, an aralkyl group where the alkyl part is C$_1$-C$_3$ alkyl, a C$_1$-C$_5$ alkyl group or a C$_1$-C$_5$ alkyl group having at least one substituent selected from the group consisting of hydroxy groups and C$_1$-C$_5$ alkoxy groups, a C$_1$-C$_{10}$ alkyl group or a substituted C$_1$-C$_{10}$ alkyl group having at least one substituent selected from the group consisting of substituents (b);

R$^4$ represents a hydrogen atom, a C$_1$-C$_{10}$ alkyl group or a C$_1$-C$_5$ alkoxy group;

R$^5$ represents a hydrogen atom, a C$_1$-C$_5$ alkyl group or a C$_1$-C$_5$ alkoxy group;

R$^6$ and R$^7$ are independently selected for the group consisting of hydrogen atoms, C$_1$-C$_{10}$ alkyl groups and substituted C$_1$-C$_{10}$ alkyl groups having at least one substituent selected from the group consisting of substituents (b);

Ar is a divalent group selected from the group consisting of divalent carbocyclic aromatic groups, and divalent heterocyclic aromatic groups formed from a pyridine, furan, thiophene or pyrrole ring;

W represents a —CH$_2$— group, a >C=O group, a group of formula >CH—OR$^{11}$ where R$^{11}$ represents a hydrogen atom, a C$_1$-C$_{23}$ alkanoyl group, a C$_3$-C$_{23}$ alkenoyl group, a C$_3$-C$_{23}$ alkynoyl group, a substituted C$_1$-C$_{23}$ alkanoyl, C$_3$-C$_{23}$ alkenoyl or C$_3$-C$_{23}$ alkynoyl group having at least one substituent selected from the group consisting of substituents (a), an aromatic acyl group selected from the group consisting of benzoyl and napthoyl, a 5-8 membered heterocyclia acyl having 1 to 3 heteroatoms of N, S, or O, A C$_1$-C$_{10}$ alkyl group or a substituted C$_1$-C$_{10}$ alkyl group having at least one substituent selected from the group consisting of substituents (b), or a group of formula >C=N—O—R$^{12}$ in which R$^{12}$ represents a hydrogen atom, a C$_1$-C$_{10}$ alkyl group, a C$_1$-C$_{10}$ alkyl group having at least one substituent selected from the group consisting of substituents (b), a C$_1$-C$_{23}$ alkanoyl group, a C$_3$-C$_{23}$ alkenoyl group, a C$_3$-C$_{23}$ alkynoyl group, a substituted C$_1$-C$_{23}$ alkanoyl, $C_3$-$C_{23}$ alkenoyl or $C_3$-$C_{23}$ alkynoyl group having at least one substituent selected from the group consisting of substituents (a), an aromatic acyl group selected from the group consisting of benzoyl and naphthoyl or a heterocyclic acyl group having 1 to 3 hetero-atoms of N, S or O;

U represents a —$CH_2$— group; or

W and U together represent a group of formula —CH=CH—; or when W represents a carbonyl group of said group of formula $>C=N-OR^{12}$, U, $R^1$ and the carbon atom to which $R^1$ is attached together represent a group of formula —CH=C<;

n is an integer of from 1 to 3;

said aryl groups and the aryl parts of said aralkyl, aralkyloxycarbonyl, and aromatic acyloxy being $C_6$-$C_{10}$ carbocyclic aryl groups which are unsubstituted or have at least one substituent selected from the group consisting of substituents (c);

said heterocyclic groups, heterocyclic parts of said heterocyclic acyl and acyloxy groups have from 5 to 10 ring atoms, of which 1 to 5 are hetero-atoms selected from the group consisting of nitrogen, oxygen and sulfur hetero-atoms, said heterocyclic groups being unsubstituted or having at least one substituent selected from the group consisting of substituents (d); said substituents (a) being selected from the group consisting of aryl groups, carboxy groups, $C_2$-$C_6$ alkoxycarbonyl groups and aralkyloxycarbonyl groups;

said substituents (b) being selected from the group consisting of hydroxy groups, $C_1$-$C_5$ alkoxy groups, aryl groups, $C_1$-$C_{23}$ alkanoyloxy groups, $C_3$-$C_{23}$ alkenoyloxy groups, $C_3$-$C_{23}$ alkynoyloxy groups, substituted $C_1$-$C_{23}$ alkanoyloxy, $C_3$-$C_{23}$ alkenoyloxy or $C_3$-$C_{23}$ alkynoyloxy groups having at least one substituent selected from the group consisting of substituents (a), aromatic acyloxy groups, heterocyclic acyloxy groups, groups of formula —$COOR^8$ where $R^8$ is as defined above and groups of formula —$CONR^9R^{10}$ where $R^9$ and $R^{10}$ are independently selected from the group consisting of hydrogen atoms and $C_1$-$C_5$ alkyl groups or $R^9$ and $R^{10}$, together with the nitrogen atom to which they are attached, represent a heterocyclic group having from 5 to 7 ring atoms of which from 1 to 3 atoms, including said nitrogen atom, are hetero-atoms selected from the group consisting of nitrogen, oxygen and sulfur hetero-atoms, said heterocyclic group being unsubstituted, or, where said ring atoms include an additional nitrogen hetero-atom, said additional nitrogen atom being unsubstituted or having a single substituent selected from the group consisting of substituents (e);

said substituents (c) being selected from the group consisting of $C_1$-$C_5$ alkyl groups, $C_1$-$C_5$ alkoxy groups, $C_1$-$C_5$ alkyl groups having at least one halogen substituent, halogen atoms, amino groups, $C_1$-$C_5$ alkylamino groups, dialkylamino groups in which each alkyl part is $C_1$-$C_5$, nitro groups, cyano groups, groups of formula —$CONR_2$ where R represents a $C_1$-$C_5$ alkyl group or an aryl group and hydroxy groups; and said substituents (d) being selected from the group consisting of $C_1$-$C_5$ alkyl groups, $C_1$-$C_5$ alkoxy groups and doubly bonded oxygen atoms;

said substituents (e) being selected from the group consisting of $C_1$-$C_5$ alkyl groups, $C_1$-$C_5$ alkanoyl groups, $C_3$-$C_5$ alkenoykl groups and $C_3$-$C_5$ alkynoyl groups; provided that:

(α) where: $R^3$ represents said hydrogen atom, an unsubstituted $C_1$-$C_6$ alkanoyl group, an unsubstituted $C_3$-$C_6$ alkenoyl group, an unsubstituted $C_3$-$C_6$ alkynoyl group, said aromatic acyl group, said heterocyclic acyl group, an aralkanoyl group or an aralkenoyl group; and $R^6$ and $R^7$ both represent hydrogen atoms; and Ar represents a p-phenylene group; and W represents a group of formula $>CH_2$, $>C=O$ or $>CH-OR^{11x}$ (wherein $R^{11x}$ represents a hydrogen atom, an unsubstituted $C_1$-$C_6$ alkanoyl group, an unsubstituted $C_3$-$C_6$ alkenoyl group, an unsubstituted $C_3$-$C_6$ alkynoyl group, said aromatic acyl group, said heterocyclic acyl group, an aralkanoyl group or an aralkenoyl group); and U represents said group of formula $>CH_2$, then (i) when $R^1$ represents a hydrogen atom or a $C_1$-$C_5$ alkyl group, $R^4$ represents a $C_6$-$C_{10}$ alkyl group, and (ii) when $R^4$ represents a hydrogen atom, a $C_1$-$C_5$ alkyl group or a $C_1$-$C_5$ alkoxy group, $R^1$ represents a $C_6$-$C_{10}$ alkyl group or said $C_7$-$C_{13}$ aralkyl group; or (β) where: $R^1$ and $R^2$ are independently selected from the group consisting of hydrogen atoms and $C_1$-$C_5$ alkyl groups; and $R^4$ and $R^5$ are independently selected from the group consisting of hydrogen atoms, $C_1$-$C_5$ alkyl groups and $C_1$-$C_5$ alkoxy groups; and Ar represents a p-phenylene group; and W is a group of formula $>CH_2$, $>C=O$ or $>CH-OR^{11x}$ (where $R^{11x}$ is as defined above); and U represents said group of formula $>CH_2$; and n is an integer from 1 to 3, then at least one of $R^3$, $R^6$ and $R^7$ represents said alkyl or substituted alkyl group;

and pharmaceutically acceptable salts thereof.

23. A composition as claimed in claim 22, in which:

$R^1$ represents a hydrogen atom or a $C_1$-$C_{10}$ alkyl group;

$R^2$ represents a hydrogen atom or a $C_1$-$C_3$ alkyl group;

$R^3$ represents a hydrogen atom, a sulfo group, a $C_1$-$C_{10}$ alkanoyl group, a $C_3$-$C_{10}$ alkenoyl group, a substituted $C_1$-$C_{10}$ alkanoyl or $C_3$-$C_{10}$ alkenoyl group having at least one substituent selected from the group consisting of substituents (f), an arylcarbonyl group wherein the aryl part is a $C_6$-$C_{10}$ carbocyclic aryl group which is unsubstituted or has at least one substituent selected from the group consisting of substituents (g), a group of formula $R^{13}$—$(CH_2)_m$—CO—, where $R^{13}$ represents a phenyl group or a phenyl group having at least one substituent selected from the group consisting of substituents (g), and m is an integer from 1 to 5, a group of formula Het—CO—, where Het represents a heterocyclic group having 5 to 6 ring atoms, of which from 1 to 3 are hetero-atoms selected from the group consisting of nitrogen, oxygen and sulfur hetero-atoms, said heterocyclic group being unsubstituted or having at least one substituent selected from the group consisting of $C_1$–$C_5$ alkyl groups,
a $C_1$–$C_5$ alkyl group, a $C_1$–$C_5$ alkyl group substituted by a group of formula —COOR$^{8a}$, where
R$^{8a}$ represents a hydrogen atom, a $C_1$–$C_5$ alkyl group or an alkoxyalkyl group where both the alkoxy part and the alkyl part are $C_1$–$C_5$,
a $C_2$–$C_5$ hydroxyalkyl group, a $C_2$–$C_5$ alkyl group substituted by a group of formula —O—CO—R$^{53}$, where
R$^{53}$ represents a $C_1$–$C_{10}$ alkyl group, a phenyl group, a phenyl group having at least one substituent selected from the group consisting of substituents (g) or a heterocyclic group Het, as defined above,
or a $C_1$–$C_3$ alkyl group substituted by a single substituent selected from the group consisting of substituents (h);
said substituents (f) are selected from the group consisting of phenyl groups, carboxy groups, $C_2$–$C_6$ alkoxycarbonyl groups and benzyloxycarbonyl groups;
said substituents (g) are selected from the group consisting of $C_1$–$C_5$ alkyl groups, trifluoromethyl groups, $C_1$–$C_5$ alkoxy groups, halogen atoms, nitro groups, amino groups, hydroxy groups and dialkylamino groups where each alkyl part is $C_1$–$C_5$;
said substituents (h) are selected from the group consisting of alkylcarbamoyl groups where the alkyl part is $C_1$–$C_4$, dialkylcarbamoyl groups where each alkyl part is $C_1$–$C_4$, 1-pyrrolidinylcarbonyl groups, piperidinocarbonyl groups and morpholinocarbonyl groups;
R$^4$ represents a $C_1$–$C_{10}$ alkyl group or a methoxy group;
R$^5$ represents a hydrogen atom, a $C_1$–$C_5$ alkyl group or a methoxy group;
R$^6$ and R$^7$ are independently selected from the group consisting of hydrogen atoms, $C_1$–$C_5$ alkyl groups, $C_1$–$C_5$ alkyl groups substituted by a group of formula —COOR$^{8a}$ where R$^{8a}$ is as defined above, $C_2$–$C_5$ hydroxyalkyl groups, $C_1$–$C_5$ alkyl groups substituted by a $C_1$–$C_5$ alkoxy group, $C_2$–$C_5$ alkyl groups substituted by a group of formula —O—CO—R$^{53}$ where R$^{53}$ is as defined above, and $C_1$–$C_3$ alkyl groups having a single substituent selected from the group consisting of substituents (h);
Ar represents a o-phenylene, m-phenylene or p-phenylene group or a pyridine-diyl group which is attached to the part of said compound of formula (I) of formula —(CH$_2$)$_n$—O— at its 2-position and is attached to the —CH$_2$-thiazolidine group at its 5- or 6-position, said phenylene and pyridine-diyl groups being unsubstituted or having a $C_1$–$C_3$ alkyl substituent;
W represents a group of formula —CH$_2$—, >C=O, >CH—OR$^{11}$ or >C=N—OR$^{12}$ where
R$^{11}$ represents a hydrogen atom, a $C_1$–$C_{10}$ alkanoyl group, a $C_3$–$C_{10}$ alkenoyl group, a substituted $C_1$–$C_{10}$ alkanoyl or $C_3$–$C_{10}$ alkenoyl group having at least one substituent selected from the group consisting of substituents (f), an arylcarbonyl group wherein the aryl part is a $C_6$–$C_{10}$ carbocyclic aryl group which is unsubstituted or has at least one substituent selected from the group consisting of substituents (g), a group of formula R$^{13}$—(CH$_2$)$_m$—CO— where R$^{13}$ and m are as defined above or a group of formula Het—CO— where Het is as defined above, and
R$^{12}$ represents a hydrogen atom, a $C_1$–$C_5$ alkyl group, a $C_1$–$C_{10}$ alkyl group having at least one substituent selected from the group consisting of substituents (j), a $C_1$–$C_{10}$ alkanoyl group, a $C_3$–$C_{10}$ alkenoyl group, a substituted $C_1$–$C_{10}$ alkanoyl or $C_3$–$C_{10}$ alkenoyl group having at least one substituent selected from the group consisting of substituents (f), an arylcarbonyl group wherein the aryl part is a $C_6$–$C_{10}$ carbocyclic aryl group which is unsubstituted or has at least one substituent selected from the group consisting of substituents (g), or said group of formula R$^{13}$—(CH$_2$)$_m$—CO— or Het—CO—; and
said substituents (j) are selected from the group consisting of hydroxy groups, phenyl groups, phenyl groups having at least one substituent selected from the group consisting of substituents (g), $C_2$–$C_{11}$ alkanoyloxy groups, $C_2$–$C_{11}$ alkanoyloxy groups substituted by a group of formula —COOR$^{8a}$ where R$^{8a}$ is as defined above, $C_3$–$C_{11}$ alkenoyloxy groups substituted by a group of formula —COOR$^{8a}$ where R$^{8a}$ is as defined above, phenylalkenoyloxy groups where the alkenyl part is $C_2$–$C_{10}$ and the phenyl part is unsubstituted or has at least one substituent selected from the group consisting of substituents (g), benzoyloxy groups, benzoyloxy groups having at least one substituent selected from the group consisting of substituents (g), groups of formula —COOR$^{8a}$ where R$^{8a}$ is as defined above, benzyloxycarbonyl groups and groups of formula —COR$^9$R$^{10}$ where R$^9$ and R$^{10}$ are as defined above;
U represents
(i) where W represents a group of formula —CH$_2$—, >C=O, >CH$_2$OR$^{11}$ or >C=N—OR$^{12}$, a group of formula —CH$_2$—,
(ii) with W, a group of formula —CH=CH—, or
(iii) where W represents a group of formula >C=O or >C=N—OR$^{14}$, in which R$^{14}$ represents any one of the acyl groups defined for R$^{12}$, with R$^1$ and the carbon atom to which R$^1$ is attached, a group of formula —CH=C<.

24. A composition as claimed in claim 23, in which:
R$^1$, R$^2$, R$^4$, R$^5$, Ar, W and U are as defined in claim 23;
R$^6$ and R$^7$ both represent hydrogen atoms;
R$^3$ and R$^{11}$ are independently selected from the group consisting of hydrogen atoms, $C_1$–$C_{10}$ alkanoyl groups, $C_3$–$C_{10}$ alkenoyl groups, $C_1$–$C_{10}$ alkanoyl or $C_3$–$C_{10}$ alkenoyl groups having at least one substituent selected from the group consisting of substituents (f) as defined in claim 23, arylcarbonyl groups as defined in claim 23, and groups of formulae R$^{13}$—(CH$_2$)$_m$—CO— and Het—CO— where R$^{13}$, m and Het are as defined in claim 23; and
R$^{12}$ represents any one of the groups or atoms defined for R$^3$ and R$^{11}$ or a $C_1$–$C_5$ alkyl group or a $C_1$–$C_3$ alkyl group having at least one substituent selected from the group consisting of substituents (f) defined in claim 23.

25. A composition as claimed in claim 23, in which:
R$^1$, R$^2$, R$^4$, R$^5$, Ar, W and U are as defined in claim 23;
R$^3$, R$^6$, R$^7$ and R$^{12}$ are independently selected from the group consisting of hydrogen atom, $C_1$–$C_5$ alkyl groups, $C_1$-$C_5$ alkyl groups substituted by a group of formula —COOR$^{8a}$ where R$^{8a}$ is as defined in claim 23, $C_2$-$C_5$ hydroxyalkyl groups, $C_1$-$C_5$ alkyl groups substituted by a $C_1$-$C_5$ alkoxy group, $C_2$-$C_5$ alkyl groups substituted by a group of formula —O—CO—R$^{53}$ where R$^{53}$ is as defined in claim 23 and $C_1$-$C_3$ alkyl groups substituted by a single substituent selected from the group consisting of substituents (h) as defined in claim 23; and R$^{11}$ represents a hydrogen atom, an acetyl group or a benzoyl group;

R$^{12}$ represents a hydrogen atom, a $C_1$-$C_5$ alkyl group, a $C_1$-$C_{10}$ alkly group having at least one substituent selected from the group consisting of substituents (k), a $C_2$-$C_6$ alkanoyl group, a $C_2$-$C_{10}$ alkanoyl group having at least one substituent selected from the group consisting of substituents (l), a $C_3$-$C_5$ alkenoyl group, a $C_3$-$C_5$ alkenoyl group having at least one substituent selected from the group consisting of substituents (l), a benzoyl group, a benzoyl group having at least one substituent selected from the group consisting of substituents (m), a pyridinecarbonyl group, a furoyl group, a thenoyl group or a pyridinecarbonyl, furoyl or thenoyl group having at least one substituent selected from the group consisting of $C_1$-$C_5$ alkyl groups;

said substituents (k) are selected from the group consisting of hydroxy groups, phenyl groups, phenyl groups having at least one substituent selected from the group consisting of substituents (m), $C_2$-$C_5$ alkanoyloxy groups, $C_2$-$C_{10}$ alkanoyloxy or $C_3$-$C_{10}$ alkenoyloxy groups substituted by a group of formula —COOR$^{8a}$ where R$^{8a}$ is as defined in claim 23, $C_3$-$C_{10}$ alkenoyloxy groups substituted by a phenyl group where the phenyl group is unsubstituted or has at least one substituent selected from the group consisting of substituents (m), benzoyloxy groups, benzoyloxy groups having at least one substituent selected from the group consisting of substituents (m), groups of formula —COOR$^{8a}$ where R$^{8a}$ is as defined in claim 23 and substituents (h) as defined in claim 23;

said substituents (l) are selected from the group consisting of phenyl groups, carboxy groups, alkoxycarbonyl groups where the alkoxy part is $C_1$-$C_5$ and benzyloxycarbonyl groups; and said substituents (m) are selected from the group consisting of $C_1$-$C_5$ alkyl groups, $C_1$-$C_5$ alkoxy groups, halogen atoms and trifluoromethyl groups.

26. A composition as claimed in claim 22, in which:

R$^1$ represents an alkyl group selected from the group consisting of methyl, ethyl, isobutyl, pentyl, hexyl, 3,3-dimethylbutyl, heptyl, 4,4-dimethylpentyl, octyl, 5,5-dimethylhexyl, nonyl and 3,7-dimethyloctyl groups;

R$^2$ represents a hydrogen atom or a methyl group;

R$^3$ represents a hydrogen atom, a $C_1$-$C_{10}$ alkanoyl group, a $C_3$-$C_{10}$ alkenoyl group, a substituted $C_1$-$C_{10}$ alkanoyl or $C_3$-$C_{10}$ alkenoyl group having at least one substituent selected from the group consisting of substituents (f), a benzoyl group, a benzoyl group having at least one substituent selected from the group consisting of substituents (n), an aralkanoyl group of formula R$^{15}$—(CH$_2$)$_m$—CO— where R$^{15}$ represents a phenyl group or a phenyl group having at least one substituent selected from the group consisting of substituents (n), and m is an integer from 1 to 5, a pyridinecarbonyl group, a furoyl group, a thenoyl group, a $C_1$-$C_3$ alkyl group, a $C_1$-$C_3$ alkyl group substituted by a group of formula —COOR$^{8a}$ where R$^{8a}$ represents a hydrogen atom, a $C_1$-$C_5$ alkyl group or an alkoxyalkyl group where both the alkoxy part and the alkyl part are $C_1$-$C_5$, a $C_2$-$C_3$ hydroxyalkyl group, a $C_1$-$C_5$ alkyl group substituted by a $C_1$-$C_5$ alkoxy group, a $C_2$-$C_5$ alkyl group substituted by a $C_2$-$C_4$ alkanoyloxy or a benzoyloxy group or a methyl group having a single substituent selected from the group consisting of substituents (h);

said substituents (f) are selected from the group consisting of phenyl groups, carboxy groups, $C_2$-$C_6$ alkoxycarbonyl groups and benzyloxycarbonyl groups;

said substituents (n) are selected from the group consisting of $C_1$-$C_5$ alkyl groups, $C_1$-$C_5$ alkoxy groups and halogen atoms;

R$^4$ represents a $C_1$-$C_{10}$ alkyl group;

R$^5$ represents a hydrogen atom or a $C_1$-$C_3$ alkyl group;

R$^6$ and R$^7$ are independently selected from the group consisting of hydrogen atoms, $C_1$-$C_3$ alkyl groups, $C_1$-$C_3$ alkyl groups substituted by a group of formula —COOR$^{8a}$ where R$^{8a}$ is as defined above, $C_2$-$C_3$ hydroxyalkyl groups, $C_1$-$C_5$ alkyl groups substituted by a $C_1$-$C_5$ alkoxy group, $C_2$-$C_5$ alkyl groups substituted by a $C_2$-$C_4$ alkanoyloxy or a benzoyloxy group, and methyl groups substituted by a single substituent selected from the group consisting of substituents (h);

said substituents (h) are selected from the group consisting of alkylcarbamoyl groups where the alkyl part is $C_1$-$C_4$, dialkylcarbamoyl groups where each alkyl part is $C_1$-$C_4$, 1-pyrrolidinylcarbonyl groups, piperidinocarbonyl groups and morpholinocarbonyl groups;

Ar represents a o-phenylene, m-phenylene or p-phenylene group or a pyridine-diyl group which is attached to the part of said compound of formula (I) of formula —(CH$_2$)$_n$—O— at its 2-position and is attached to the —CH$_2$-thiazolidine group at its 5- or 6-position, said phenylene and pyridine-diyl groups being unsubstituted or having a methyl substituent;

W represents a group of formula —CH$_2$—, >C=O, >CH—OR$^{11}$ or >C=N—OR$^{12}$, where:

R$^{11}$ represents a hydrogen atom or any one of the acyl groups defined above for R$^3$; and R$^{12}$ represents a benzyl group, any one of the groups or atoms defined above for R$^3$, a pyridinecarbonyl group or a pyridinecarbonyl group having at least one substituent selected from the group consisting of $C_1$-$C_5$ alkyl groups;

and U represents (i) where W represents a group of formula —CH$_2$—, >C=O, >CH—OR$^{11}$ or >C=N—OR$^{12}$, a group of formula —CH$_2$—, (ii) with W, a group of formula —CH=CH—, or (iii) where W represents a group of formula >C=O, with R$^1$ and the carbon atom to which R$^1$ is attached, a group of formula —CH=C<.

27. A composition as claimed in claim 26, in which:

$R^1$, $R^2$, $R^4$, $R^5$, Ar, W and U are as defined in claim 26;

$R^6$ and $R^7$ are both hydrogen atoms;

$R^3$ and $R^{11}$ are independently selected from the group consisting of hydrogen atoms, $C_1$-$C_{10}$ alkanoyl groups, $C_3$-$C_{10}$ alkenoyl groups, $C_1$-$C_{10}$ alkanoyl or $C_3$-$C_{10}$ alkenoyl groups having at least one substituent selected from the group consisting of substituents (f) as defined in claim 26, benzoyl groups, benzoyl groups having at least one substituent selected from the group consisting of substituents (n) as defined in claim 26, groups of formula $R^{15}$—$(CH_2)_m$—CO— where $R^{15}$ and m are as defined in claim 26, pyridinecarbonyl groups, furoyl groups and thenoyl groups; and $R^{12}$ represents a hydrogen atom, a methyl group, a benzyl group, a t-butoxycarbonylmethyl group or any one of the acyl groups defined above for $R^3$ and $R^{11}$.

28. A composition as claimed in claim 26, in which:

$R^1$, $R^2$, $R^4$, $R^5$, Ar, W and U are as defined in claim 26;

$R^3$, $R^6$ and $R^7$ are independently selected from the group consisting of $C_1$-$C_3$ alkyl groups, $C_1$-$C_3$ alkyl groups substituted by a group of formula —COOR$^{8a}$ where R$^{8a}$ is as defined in claim 26, $C_2$-$C_3$ hydroxyalkyl groups, $C_1$-$C_5$alkyl groups substituted by a $C_1$-$C_5$ alkoxy group, $C_2$-$C_5$alkyl groups substituted by a $C_2$-$C_4$ alkanoyloxy or a benzoyloxy group, and methyl groups having a single substituent selected from the group consisting of substituents (h) as defined in claim 26;

$R^{11}$ represents a hydrogen atom;

$R^{12}$ represents a hydrogen atom, a $C_1$-$C_3$ alkyl group having at least one substituent selected from the group consisting of substituents (o), a $C_2$-$C_4$ alkanoyl group, a $C_2$-$C_4$ alkanoyl group substituted by a group of formula —COOR$^{8a}$ where R$^{8a}$ is as defined in claim 26, an acryloyl group, an acryloyl group having a β-substituent selected from the group consisting of substituents (f), a benzoyl group, a benzoyl group having at least one substituent selected from the group consisting of substituents (q), a pyridinecarbonyl group, a pyridinecarbonyl group having at least one substituent selected from the group consisting of $C_1$-$C_5$ alkyl groups or any one of the groups defined above for $R^3$, $R^6$ and $R^7$;

said substituents (f) are selected from the group consisting of phenyl groups, carboxy groups, $C_2$-$C_6$ alkoxycarbonyl groups and benzyloxycarbonyl groups; and said substituents (o) are selected from the group consisting of carboxy groups and alkoxycarbonyl groups where the alkoxy part is $C_1$-$C_5$;

said substituents (g) are selected from the group consisting of methyl groups, ethyl groups, methoxy groups and ethoxy groups.

29. A composition as claimed in claim 22 in which:

$R^1$ represents an alkyl group selected from the group consisting of methyl, isobutyl, hexyl, heptyl, octyl, nonyl and 3,7-dimethyloctyl groups;

$R^2$ represents a hydrogen atom or a methyl group;

$R^3$ represents a hydrogen atom, a $C_1$-$C_5$ alkanoyl group, $C_3$-$C_5$ alkenoyl group, a cinnamoyl group, a group of formula $R^{16}$OOC(CH$_2$)$_m$CO— where $R^{16}$ represents a hydrogen atom or a $C_1$-$C_5$ alkyl group and m is an integer from 1 to 5, a cis- or trans- group of formula $R^{17}$OOC.CH=CH—CO— where $R^{17}$ represents a hydrogen atom, a $C_1$-$C_5$ alkyl group or a benzyl group, a 2-, 3- or 4-pyridinecarbonyl group or a $C_1$-$C_3$ alkyl group substituted by a group of formula —COOR$^{8a}$ where R$^{8a}$ represents a hydrogen atom, a $C_1$-$C_5$ alkyl group or an alkoxyalkyl group where both the alkoxy part and the alkyl part are $C_1$-$C_5$;

$R^4$ represents an alkyl group selected from the group consisting of methyl, ethyl, propyl, butyl, pentyl, hexyl, heptyl, octyl, 1,1,3,3-tetramethylbutyl, 1,1-dimethylbutyl and 1,1-dimethylpropyl groups;

$R^5$ represents a hydrogen atom or a methyl group;

$R^6$ and $R^7$ are independently selected from the group consisting of hydrogen atoms and $C_1$-$C_3$ alkyl groups substituted by a group of formula —COOR$^{8a}$ where R$^{8a}$ is as defined above;

Ar represents a p-phenylene group, a m-phenylene group having a methyl group at the position ortho to the position of attachment to the group of formula —(CH$_2$)$_n$—O— or a pyridine-diyl group attached to said group of formula —(CH$_2$)$_n$—O— at the 2-position and to the —CH$_2$-thiazolidine group at the 5-position;

W represents a group of formula —CH$_2$—, >C=O, >C=N—OH, >C=N—OCH$_2$COOH or >C=N—OCOR$^{18}$ where $R^{18}$ represents a $C_1$-$C_5$ alkyl group; and U represents a group of formula —CH$_2$—.

30. A composition as claimed in claim 29, in which:

$R^1$, $R^2$, $R^4$, $R^5$, Ar and U are as defined in claim 29;

$R^3$ represents a hydrogen atom, a $C_1$-$C_5$ alkanoyl group, a $C_3$-$C_5$ alkenoyl group, a cinnamoyl group, a group of formula $R^{16}$OOC(CH$_2$)$_m$CO— where $R^{16}$ and m are as defined in claim 29, a cis or trans- group of formula $R^{17}$OOC.CH=CH—CO— where $R^{17}$ is as defined in claim 29, or a 2-, 3- or 4-pyridinecarbonyl group;

$R^6$ and $R^7$ are both hydrogen atoms;

W represents a group of formula >C=NOR$^{12}$ where $R^{12}$ represents a hydrogen atom, a group of formula —(CH$_2$)$_3$COOR$^{8a}$, —CH$_2$COOR$^{8a}$, —C(CH$_3$)$_2$COOR$^{8a}$, —COCH$_2$CH$_2$COOR$^{8a}$ or —CO—CH=CH—COOR$^{8a}$ where R$^{8a}$ is as defined in claim 29, an acetyl group, a cinnamoyl group, a benzoyl group, a pyridinecarbonyl group or any one of the groups defined above for $R^3$, $R^6$ and $R^7$; and n is 1 or 2.

31. A composition as claimed in claim 29, in which:

$R^1$, $R^2$, $R^4$, $R^5$, Ar and U are as defined in claim 29;

$R^3$, $R^6$ and $R^7$ are independently selected from the group consisting of $C_1$-$C_3$ alkyl groups substituted by a group of formula —COOR$^{8a}$ where R$^{8a}$ is as defined in claim 29;

W represents a group of formula >CH$_2$, >C=O or >C=NOR$^{12}$;

$R^{12}$ represents a hydrogen atom, a group of formula —(CH$_2$)$_3$COOR$^{8a}$, —CH$_2$COOR$^{8a}$, —C(CH$_3$)$_2$COOR$^{8a}$, —COCH$_2$CH$_2$COOR$^{8a}$ or —CO—CH=CH—COOR$^{8a}$ where R$^{8a}$ is as defined in claim 29, an acetyl group, a cinnamoyl group, a benzoyl group, a pyridinecarbonyl group or any one of the groups defined above for $R^3$, $R^6$ and $R^7$; and n is 1 or 2.

32. A composition as claimed in claim 23, in which:

$R^1$ represents an alkyl group selected from the group consisting of methyl, isobutyl, hexyl, heptyl, octyl, nonyl and 3,7-dimethyloctyl groups;

$R^2$ represents a hydrogen atom or a methyl group;

$R^3$ represents a hydrogen atom, a $C_1$-$C_{10}$ alkanoyl group, a $C_3$-$C_{10}$ alkenoyl group, a $C_1$-$C_{10}$ alkanoyl or $C_3$-$C_{10}$ alkenoyl group having at least one substituent selected from the group consisting of substituents (f) as defined in claim 23, an arylcarbonyl group as defined in claim 23, a group of formula $R^{13}$—$(CH_2)_m$—CO— of Het—CO— where $R^{13}$, m and Het are as defined in claim 23 or a $C_1$-$C_3$ alkyl group substituted by a group of formula —COOR$^{8a}$ where R$^{8a}$ is as defined in claim 23;

$R^4$ represents an alkyl group selected from the group consisting of methyl, ethyl, propyl, butyl, pentyl, hexyl, heptyl, octyl, 1,1,3,3-tetramethylbutyl, 1,1-dimethylbutyl and 1,1-dimethylpropyl groups;

$R^5$ represents a hydrogen atom or a methyl group;

$R^6$ represents a $C_1$-$C_3$ alkyl group substituted by a group of formula —COOR$^{8a}$ where R$^{8a}$ is as defined in claim 23;

$R^7$ represents a hydrogen atom or a $C_1$-$C_3$ alkyl group substituted by a group of formula —COOR$^{8a}$ where R$^{8a}$ is as defined in claim 23;

Ar represents a p-phenylene group, a m-phenylene group having a methyl group at the position ortho to the position of attachment to the group of formula —$(CH_2)_n$—O— or a pyridine-diyl group attached to said group of formula —$(CH_2)_n$—O— at the 2-position and to the —$CH_2$-thiazolidine group at the 5-position;

W represents a group of formula $>CH_2$, $>C=O$ or $>C=NOR^{12}$, where $R^{12}$ represents a hydrogen atom, a group of formula —$(CH_2)_3COOR^{8a}$, —$CH_2COOR^{8a}$, —$C(CH_3)_2COOR^{8a}$, —$COCH_2CH_2COOR^{8a}$ or —CO—CH=CH—COOR$^{8a}$ where R$^{8a}$ is as defined in claim 23, an acetyl group, a cinnamoyl group, a benzoyl group, a pyridinecarbonyl group or a $C_1$-$C_3$ alkyl group substituted by a group of formula —COOR$^{8a}$ where R$^{8a}$ is as defined in claim 23;

U represents a group of formula —$CH_2$—; and
n is 1 or 2.

33. A composition as claimed in claim 23, in which:

$R^1$ represents an alkyl group selected from the group consisting of hexyl, heptyl, octyl, nonyl and 3,7-dimethyloctyl groups;

$R^2$ represents a hydrogen atom or a methyl group;

$R^3$ represents a hydrogen atom, a $C_1$-$C_5$ alkanoyl group, $C_3$-$C_5$ alkenoyl group, a cinnamoyl group, a group of formula $R^{16}OOC(CH_2)_mCO$—
where $R^{16}$ represents a hydrogen atom or a $C_1$-$C_5$ alkyl group and m is an integer from 1 to 5, a cis- or trans- group of formula $R^{17}OOC.CH=CH$—CO—
where $R^{17}$ represents a hydrogen atom, $C_1$-$C_5$ alkyl group of a benzyl group, a 2-, 3- or 4-pyridinecarbonyl group or a $C_1$-$C_3$ alkyl group substituted by a group of formula —COOR$^{8a}$ where R$^{8a}$ is as defined in claim 23;

$R^4$ represents an alkyl group selected from the group consisting of methyl, ethyl, propyl, butyl, pentyl, hexyl, heptyl, octyl, 1,1,3,3-tetramethylbutyl, 1,1-dimethylbutyl and 1,1-dimethylpropyl groups;

$R^5$ represents a hydrogen atom or a methyl group;

$R^6$ and $R^7$ are independently selected from the group consisting of hydrogen atoms and $C_1$-$C_3$ alkyl groups substituted by a group of formula —COOR$^{8a}$ where R$^{8a}$ is as defined in claim 23;

Ar represents a p-phenylene group, a m-phenylene group having a methyl group at the position ortho to the position of attachment to the group of formula —$(CH_2)_n$—O— or a pyridine-diyl group attached to said group of formula —$(CH_2)_n$—O— at the 2-position and to the —$CH_2$-thiazolidine group at the 5-position;

W represents a group of formula —$CH_2$—, $>C=O$ or $>C=N$—OR$^{12}$, where $R^{12}$ represents a hydrogen atom, a group of formula —$(CH_2)_3COOR^{8a}$, —$CH_2COOR^{8a}$, —$C(CH_3)_2COOR^{8a}$, —$COCH_2CH_2COOR^{8a}$ or —CO—CH=CH—COOR$^{8a}$ where R$^{8a}$ is as defined in claim 23, an acetyl group, a cinnamoyl group, a benzoyl group, a pyridinecarbonyl group, a $C_1$-$C_5$ alkyl group, a $C_1$-$C_5$ alkyl group substituted by a phenyl group where the phenyl group is unsubstituted or has at least one substituent selected from the group consisting of substituents (n), or any one of the groups defined above for $R^3$, $R^6$ and $R^7$;

said substituents (n) are selected from the group consisting of $C_1$-$C_5$ alkyl groups, $C_1$-$C_5$ alkoxy groups and halogen atoms; and U represents a group of formula —$CH_2$—.

34. A composition as claimed in claim 23, in which:

$R^1$ represents an alkyl group selected from the group consisting of methyl, isobutyl, hexyl, heptyl, octyl, nonyl and 3,7-dimethyloctyl groups;

$R^2$ represents a hydrogen atom or a methyl group;

$R^3$ represents a hydrogen atom, a $C_1$-$C_5$ alkanoyl group, $C_3$-$C_5$ alkenoyl group, a cinnamoyl group, a group of formula $R^{16}OOC(CH_2)_mCO$—
where $R^{16}$ represents a hydrogen atom or a $C_1$-$C_5$ alkyl group and m is an integer from 1 to 5, a cis- or trans- group of formula $R^{17}OOC.CH=CH$—CO—
where $R^{17}$ represents a hydrogen atom, a $C_1$-$C_5$ alkyl group. or a benzyl group, a 2-, 3- or 4-pyridinecarbonyl group or a $C_1$-$C_3$ alkyl group substituted by a group of formula —COOR$^{8a}$ where R$^{8a}$ is as defined in claim 23;

$R^4$ represents an alkyl group selected from the group consisting of hexyl, heptyl, octyl, 1,1,3,3-tetramethylbutyl, 1,1-dimethylbutyl and 1,1-dimethylpropyl groups;

$R^5$ represents a hydrogen atom or a methyl group;

$R^6$ and $R^7$ are independently selected from the group consisting of hydrogen atoms and $C_1$-$C_3$ alkyl groups substituted by a group of formula —COOR$^{8a}$ where R$^{8a}$ is as defined in claim 23;

Ar represents a p-phenylene group, a m-phenylene group having a methyl group at the position ortho to the position of attachment to the group of formula —$(CH_2)_n$—O— or a pyridine-diyl group attached to said group of formula —$(CH_2)_n$—O— at the 2-position and to the —$CH_2$-thiazolidine group at the 5-position;

W represents a group of formula —$CH_2$—, $>C=O$ or $>C=N$—OR$^{12}$ where $R^{12}$ represents a hydrogen atom, a group of formula —$(CH_2)_3COOR^{8a}$, —$CH_2COOR^{8a}$, —$C(CH_3)_2COOR^{8a}$, —$COCH_2CH_2COOR^{8a}$ or —CO—CH=CH—COOR$^{8a}$ where R$^{8a}$ is as defined in claim 23, an acetyl group, a cinnamoyl group, a benzoyl group, a pyridinecarbonyl group, a $C_1$-$C_5$ alkyl group, a $C_1$-$C_5$ alkyl group substituted by a phenyl group where the phenyl group is unsubstituted or has at least one substituent selected from the group consisting of substituents (n), or any one of the groups defined above for $R^3$, $R^6$ and $R^7$;

said substituents (n) are selected from the group consisting of $C_1$-$C_5$ alkyl groups, $C_1$-$C_5$ alkoxy groups and halogen atoms; and U represents a group of formula —$CH_2$—.

35. A composition as claimed in claim 23, in which:

$R^1$ represents an alkyl group selected from the group consisting of methyl, isobutyl, hexyl, heptyl, octyl, nonyl and 3,7-dimethyloctyl groups;

$R^2$ represents a hydrogen atom or a methyl group;

$R^3$ represents $C_1$-$C_3$ alkyl group substituted by a group of formula —$COOR^{8a}$, where $R^{8a}$ is as defined in claim 23;

$R^4$ represents an alkyl group selected from the group consisting of methyl, ethyl, propyl, butyl, pentyl, hexyl, heptyl, octyl, 1,1,3,3-tetramethylbutyl, 1,1-dimethylbutyl and 1,1-dimethylpropyl groups;

$R^5$ represents a hydrogen atom or a methyl group;

$R^6$ and $R^7$ are both hydrogen atoms;

Ar represents a p-phenylene group, a m-phenylene group having a methyl group at the position ortho to the position of attachment to the group of formula —$(CH_2)_n$—O— or a pyridine-diyl group attached to said group of formula —$(CH_2)_n$—O— at the 2-position and to the —$CH_2$-thiazolidine group at the 5-position;

W represents a group of formula —$CH_2$—, $>C=O$, $>C=N—OH$, or $>C=N—O—(C_1$-$C_3$ alkyl)—$COOR^{8a}$ where $R^{8a}$ is as defined in claim 23;

U represents a group of formula —$CH_2$—; and

N is 1 to 2.

36. A composition as claimed in claim 23, in which:

$R^1$ represents an alkyl group selected from the group consisting of methyl, isobutyl, hexyl, heptyl, octyl, nonyl and 3,7-dimethyloctyl groups;

$R^2$ represents a hydrogen atom or a methyl group;

$R^3$ represents —$CH_2$—$COO(C_1$-$C_5$ alkyl) group;

$R^4$ represents an alkyl group selected from the group consisting of methyl, ethyl, propyl, butyl, pentyl, hexyl, heptyl, octyl, 1,1,3,3-tetramethylbutyl, 1,1-dimethylbutyl and 1,1-dimethylpropyl groups;

$R^5$ represents a hydrogen atom or a methyl group;

$R^6$ and $R^7$ are both hydrogen atoms;

Ar represents a p-phenylene group, a m-phenylene group having a methyl group at the position ortho to the position of attachment to the group of formula —$(CH_2)_n$—O— or a pyridine-diyl group attached to said group of formula —$(CH_2)_n$—O— at the 2-position and to the —$CH_2$-thiazolidine group at the 5-position;

W represents a group of formula —$CH_2$—, $>C=O$, $>C=N—OH$, or $>C=N—O—(C_1$-$C_3$ alkyl)—$COO(C_1$-$C_5$ alkyl);

U represents a group of formula —$CH_2$—; and n is 1 to 2.

37. A composition as claimed in claim 22, wherein said active compound is selected from the group consisting of:

5-[4-(6-Hydroxy-5,7,8-trimethyl-2-octylchroman-2-ylmethoxy)benzyl]thiazolidine-2,4-dione;

5-{4-[6-Hydroxy-4-(E)-hydroxyimino-2,5,7,8-tetramethylchroman-2-ylmethoxy]benzyl}thiazolidine-2,4-dione;

5-{4-[6-Acetoxy-4-(E)-acetoxyimino-2,5,7,8-tetramethylchroman-2-ylmethoxy]benzyl}thiazolidine-2,4-dione;

α-{5-[4-(6-Carboxymethoxy-2,5,7,8-tetramethyl-4-oxochroman-2-ylmethoxy)benzyl]-2,4-dioxothiazolidin-3-yl}acetic acid;

α-{5-[4-(6-Carboxymethoxy-4-hydroxyimino-2,5,7,8-tetramethylchroman-2-ylmethoxy)benzyl]-2,4-dioxothiazolidin-3-yl}acetic acid;

α,α'-{5-[4-(6-Carboxymethoxy-4-hydroxyimino-2,5,7,8-tetramethylchroman-2-ylmethoxy)benzyl]-2,4-dioxothiazolidine-3,5-diyl}diacetic acid;

and pharmaceutically acceptable salts thereof.

* * * * *